US008980898B2

(12) United States Patent
Johnson et al.

(10) Patent No.: US 8,980,898 B2
(45) Date of Patent: Mar. 17, 2015

(54) DENDRIMER LIKE AMINO AMIDES POSSESSING SODIUM CHANNEL BLOCKER ACTIVITY FOR THE TREATMENT OF DRY EYE AND OTHER MUCOSAL DISEASES

(71) Applicant: Parion Sciences, Inc., Durham, NC (US)

(72) Inventors: Michael Ross Johnson, Chapel Hill, NC (US); William Robert Thelin, Chapel Hill, NC (US); Richard C. Boucher, Chapel Hill, NC (US)

(73) Assignee: Parion Sciences, Inc., Durham, NC (US)

( * ) Notice: Subject to any disclaimer, the term of this patent is extended or adjusted under 35 U.S.C. 154(b) by 0 days.

(21) Appl. No.: 13/904,634

(22) Filed: May 29, 2013

(65) Prior Publication Data

US 2013/0324559 A1 Dec. 5, 2013

Related U.S. Application Data

(60) Provisional application No. 61/652,481, filed on May 29, 2012.

(51) Int. Cl.
| A61K 31/4965 | (2006.01) |
| C07D 241/34 | (2006.01) |
| A61K 45/06 | (2006.01) |
| C07D 241/32 | (2006.01) |
| A61K 31/497 | (2006.01) |

(52) U.S. Cl.
CPC .......... *A61K 31/4965* (2013.01); *C07D 241/34* (2013.01); *A61K 45/06* (2013.01); *C07D 241/32* (2013.01); *A61K 31/497* (2013.01)
USPC ..................................... 514/255.06; 544/407

(58) Field of Classification Search
CPC . A61K 31/4965; A61K 45/06; A61K 31/495; C07D 241/34
USPC ..................................... 514/255.06; 544/407
See application file for complete search history.

(56) References Cited

U.S. PATENT DOCUMENTS

| 6,858,614 B2 | 2/2005 | Johnson |
| 6,858,615 B2 | 2/2005 | Johnson |
| 6,903,105 B2 | 6/2005 | Johnson |
| 6,995,160 B2 | 2/2006 | Johnson |
| 7,026,325 B2 | 4/2006 | Johnson |
| 7,030,117 B2 | 4/2006 | Johnson |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,241,766 B2 | 7/2007 | Johnson |
| 7,247,636 B2 | 7/2007 | Johnson |
| 7,247,637 B2 | 7/2007 | Johnson et al. |
| 7,317,013 B2 | 1/2008 | Johnson |
| 7,332,496 B2 | 2/2008 | Johnson |
| 7,345,044 B2 | 3/2008 | Johnson |
| 7,368,447 B2 | 5/2008 | Johnson et al. |
| 7,368,450 B2 | 5/2008 | Johnson |
| 7,368,451 B2 | 5/2008 | Johnson et al. |
| 7,375,107 B2 | 5/2008 | Johnson |
| 7,388,013 B2 | 6/2008 | Johnson et al. |
| 7,399,766 B2 | 7/2008 | Johnson |
| 7,410,968 B2 | 8/2008 | Johnson et al. |
| 7,745,442 B2 | 6/2010 | Johnson et al. |
| 7,807,834 B2 | 10/2010 | Johnson et al. |
| 7,820,678 B2 | 10/2010 | Johnson |
| 7,842,697 B2 | 11/2010 | Johnson |
| 7,868,010 B2 | 1/2011 | Johnson et al. |
| 7,875,619 B2 | 1/2011 | Johnson |
| 7,956,059 B2 | 6/2011 | Johnson |
| 7,981,898 B2 | 7/2011 | Johnson et al. |
| 8,008,494 B2 | 8/2011 | Johnson |
| 8,022,210 B2 | 9/2011 | Johnson |
| 8,058,278 B2 | 11/2011 | Johnson et al. |
| 8,124,607 B2 | 2/2012 | Johnson |
| 8,143,256 B2 | 3/2012 | Johnson |
| 8,163,758 B2 | 4/2012 | Johnson et al. |
| 8,198,286 B2 | 6/2012 | Johnson |
| 8,211,895 B2 | 7/2012 | Johnson et al. |
| 8,227,474 B2 | 7/2012 | Johnson |

(Continued)

OTHER PUBLICATIONS

International Search Report and Written Opinion issued Nov. 29, 2013 in PCT/US2013/043080.
U.S. Appl. No. 14/106,156, filed Dec. 13, 2013, Johnson.
U.S. Appl. No. 14/129,734, filed Jan. 3, 2014, Johnson.
U.S. Appl. No. 14/047,281, Johnson.
U.S. Appl. No. 14/132,194, Johnson.
U.S. Appl. No. 14/106,098, filed Dec. 13, 2013, Johnson.
U.S. Appl. No. 14/106,125, filed Dec. 13, 2013, Johnson.
U.S. Appl. No. 60/495,725, filed Aug. 18, 2003, Johnson.
U.S. Appl. No. 60/495,720, filed Aug. 18, 2003, Johnson.
U.S. Appl. No. 60/495,712, filed Aug. 18, 2003, Johnson.
U.S. Appl. No. 60/602,312, filed Aug. 18, 2004, Johnson.

(Continued)

*Primary Examiner* — Raymond Henley, III
(74) *Attorney, Agent, or Firm* — Oblon, McClelland, Maier & Neustadt, L.L.P.

(57) ABSTRACT

Sodium channel blockers represented by the formula:

(I)

$$X \underset{5}{\overset{6}{\underset{}{\bigcirc}}} \underset{4}{\overset{1}{\underset{N}{\bigcirc}}} \underset{3}{\overset{2}{\underset{}{\bigcirc}}} \overset{O}{\underset{}{\parallel}} \underset{NHR^2}{\overset{NHR^1}{\underset{N=C-N}{\bigcirc}}} \overset{R^3}{\underset{R^4}{\bigcirc}}$$

are provided where the structural variables are defined herein. The invention also includes a variety of compositions, combinations and methods of treatment using these inventive sodium channel blockers.

19 Claims, 16 Drawing Sheets

(56) References Cited

U.S. PATENT DOCUMENTS

| | | | |
|---|---|---|---|
| 8,288,391 | B2 | 10/2012 | Johnson et al. |
| 8,314,105 | B2 | 11/2012 | Johnson |
| 8,324,218 | B2 | 12/2012 | Johnson |
| 8,431,579 | B2 | 4/2013 | Johnson et al. |
| 2004/0162296 | A1 | 8/2004 | Johnson et al. |
| 2005/0090505 | A1 | 4/2005 | Johnson et al. |
| 2006/0142306 | A1 | 6/2006 | Johnson |
| 2007/0021439 | A1 | 1/2007 | Johnson et al. |
| 2007/0265280 | A1 | 11/2007 | Johnson |
| 2008/0103148 | A1 | 5/2008 | Johnson |
| 2008/0167466 | A1 | 7/2008 | Johnson et al. |
| 2008/0176863 | A1 | 7/2008 | Johnson et al. |
| 2008/0200476 | A1 | 8/2008 | Johnson |
| 2008/0249109 | A1 | 10/2008 | Johnson et al. |
| 2008/0293740 | A1 | 11/2008 | Johnson et al. |
| 2009/0018144 | A1 | 1/2009 | Johnson et al. |
| 2009/0062308 | A1 | 3/2009 | Johnson |
| 2009/0104272 | A1 | 4/2009 | Boucher et al. |
| 2009/0253714 | A1 | 10/2009 | Johnson et al. |
| 2009/0324724 | A1 | 12/2009 | Johnson |
| 2010/0074881 | A1 | 3/2010 | Boucher et al. |
| 2010/0267746 | A1 | 10/2010 | Johnson et al. |
| 2011/0195973 | A1 | 8/2011 | Johnson |
| 2012/0116083 | A1 | 5/2012 | Johnson |
| 2012/0220606 | A1 | 8/2012 | Johnson et al. |
| 2013/0012692 | A1 | 1/2013 | Johnson |
| 2013/0060034 | A1 | 3/2013 | Johnson |
| 2013/0178482 | A1 | 7/2013 | Johnson |

OTHER PUBLICATIONS

U.S. Appl. No. 60/602,327, filed Aug. 18, 2004, Johnson.
U.S. Appl. No. 60/812,091, filed Jun. 9, 2006, Johnson.
U.S. Appl. No. 60/812,077, filed Jun. 9, 2006, Johnson, et al.
U.S. Appl. No. 60/812,078, filed Jun. 9, 2006, Johnson.
U.S. Appl. No. 60/842,669, filed Sep. 7, 2006, Johnson, et al.
U.S. Appl. No. 60/842,963, filed Sep. 8, 2006, Johnson, et al.
U.S. Appl. No. 60/845,171, filed Sep. 18, 2006, Johnson, et al.
U.S. Appl. No. 11/696,003, filed Apr. 3, 2007, Johnson.
U.S. Appl. No. 60/909,818, filed Apr. 3, 2007, Johnson, et al.
U.S. Appl. No. 60/909,802, filed Apr. 3, 2007, Johnson, et al.
U.S. Appl. No. 60/978,887, filed Oct. 10, 2007, Boucher, et al.
U.S. Appl. No. 60/978,874, filed Oct. 10, 2007, Boucher, et al.
U.S. Appl. No. 60/987,663, filed Nov. 13, 2007, Johnson, et al.
U.S. Appl. No. 61/013,387, filed Dec. 13, 2007, Johnson, et al.
U.S. Appl. No. 61/030,313, filed Feb. 21, 2008, Johnson.
U.S. Appl. No. 61/031,466, filed Feb. 26, 2008, Johnson.
U.S. Appl. No. 12/171,867, filed Jul. 11, 2008, Johnson, et al.
U.S. Appl. No. 12/171,897, filed Jul. 11, 2008, Johnson, et al.
U.S. Appl. No. 61/079,989, filed Jul. 11, 2008, Boucher, et al.
U.S. Appl. No. 13/904,634, filed May, 29, 2013, Johnson, et al.
U.S. Appl. No. 14/043,223, filed Oct. 1, 2013, Johnson.
U.S. Appl. No. 14/158,441, filed Jan. 17, 2014, Johnson.

DENDRIMER LIKE AMINO AMIDES POSSESSING SODIUM CHANNEL BLOCKER ACTIVITY FOR THE TREATMENT OF DRY EYE AND OTHER MUCOSAL DISEASES

CONTINUING APPLICATION INFORMATION

This application claims benefit of the filing date of Provisional Application Ser. No. 61/652,481, filed on May 29, 2012, and incorporated by reference in its entirety.

BACKGROUND OF THE INVENTION

1. Field of the Invention

The present invention relates to sodium channel blockers. The present invention also includes a variety of methods of treatment using these inventive sodium channel blockers, their pharmaceutically acceptable salt forms, which are useful as sodium channel blockers, compositions containing the same, therapeutic methods including but not limited to treating dry eye, treating Sjogren's disease-associated dry eye, promoting ocular hydration, promoting corneal hydration and the treatment of other mucousal diseases and uses for the same and processes for preparing the same. The present invention also relates to novel compounds for the treatment of dry eye, particularly including (2R,2'R)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-guanidinohexanamide) and its pharmaceutically acceptable salt forms, which are useful as sodium channel blockers, compositions containing the same, therapeutic methods including but not limited to treating dry eye, treating Sjogren's disease-associated dry eye, promoting ocular hydration, promoting corneal hydration and the treatment of other mucousal diseases and uses for the same and processes for preparing the same.

2. Description of the Background

The mucosal epithelial cells at the interface between the environment and the body have evolved a number of "innate defenses", i.e., protective mechanisms. A principal function of such innate defense is to cleanse these surfaces from microorganisms, particles and other foreign material. This process requires the presence of a layer of liquid to propel these microorganisms, particles and other foreign material away from the body to avoid colonization of microorganisms and/or tissue damage. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The critical salt transport processes that characterize a number of mucosal dysfunctions resides in the epithelial layer of the mucosal surface.

Chronic dry eye disease, also known as keratoconjunctivitis sicca, is one of the most frequently diagnosed ocular diseases, affecting more than 5 million people in the United States alone. Dry eye is characterized by inadequate aqueous tear fluid on the eyes, resulting in painful irritation, inflammation on the ocular surface, and impaired vision, and is caused by failure of lacrimal glands to secrete liquid in the face of continued $Na^+$ dependent liquid absorption on conjunctival surfaces. Dry eye is a multi-factorial disease, resulting from a common etiology of insufficient tear film, causing ocular surface damage and symptoms of ocular discomfort.

The few current therapies available, which include both immunosuppressive agents and over-the-counter tear replacements, are not sufficiently efficacious for many users or only provide transient relief from dry eye symptoms. The dry eye market is dominated by over-the-counter (OTC) tear replacements or artificial tears, estimated to be used by ~80% of dry eye patients. Artificial tears provide immediate symptomatic relief from the sensation of ocular burning and irritation by adding liquid to the ocular surface. Yet, the benefits from artificial tears are short-lived as the fluid drops are rapidly cleared from the ocular surface, providing, at most, palliative relief and requiring frequent application throughout the day.

While individuals with dry eye may not exhibit overt ocular inflammation such as red, inflamed eyes, chronic ocular inflammation is now well recognized as a significant factor perpetuating the chronic cycle of dry eye. The one approved prescription drug for the treatment of chronic dry eye is Restasis® (0.05% Cyclosporine A emulsion, Allergan), which is marketed to increase tear output "in patients whose tear production is presumed to be suppressed due to ocular inflammation associated with keratoconjunctivitis sicca." In a six month, Phase 3 pivotal trial in subjects with dry eye, Restasis statistically increased tear volume (assessed by Schirmer wetting) in 15% of the treated individuals, compared to 5% on vehicle. While the mechanism of Restasis is not fully understood, it is speculated that the inhibition of chronic ocular inflammation may, over time, restore corneal sensitivity and improve reflex tearing. However, Restasis has a low responder rate, a 3 month delay for full therapeutic benefit, and side effects, such as burning on application.

Therefore, the development of novel hydrating agents to treat dry eye would be of tremendous benefit to the therapeutic milieu. The volume of tear film on the ocular surface represents a balance between tear fluid output versus fluid loss via drainage, evaporation, or epithelial absorption. Similar to other epithelial tissues, the epithelium of the conjunctiva and cornea are capable of regulating the hydration status of the mucosal surface through active salt and water transport.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^-$ channel (ENaC) and is a key regulator of sodium (and water) absorption in numerous tissues, including the eye. ENaC is expressed on the apical surface of the corneal and conjunctival epithelia in rodents, larger mammals, and man where it functions as a critical pathway for sodium (and water) absorption (Krueger B, Schlötzer-Schrehardt U, Haerteis S, Zenkel M, Chankiewitz V E, Amann K U, Kruse F E, Korbmacher C. Four subunits ($\alpha\beta\gamma\delta$) of the epithelial sodium channel (ENaC) are expressed in the human eye in various locations. Invest Ophthalmol V is Sci. 2012; 53(2): 596-604).

In a series of in vivo bioelectric studies, Levin et al. (Levin M H, Kim J K, Hu J, Verkman A S. Potential difference measurements of ocular surface $Na^+$ absorption analyzed using an electrokinetic model. Invest Opthalmol V is Sci. 2006; 47(1):306-16) confirmed ENaC-mediated sodium transport is a substantial contributor to the ocular surface electrical potential difference Furthermore, the topical addition of the ENaC blocker amiloride produced an approximate doubling of tear volume that remained elevated for >60 minutes post-administration in rats (Yu D, Thelin W R, Rogers T D, Stuns M J, Randell S H, Grubb B R, Boucher R C.

Regional differences in rat conjunctival ion transport activities. Am J Physiol Cell Physiol. 2012; 303(7):C767-80.) and rabbits (Hara S, Hazama A, Miyake M, Kojima T, Sasaki Y, Shimazaki J, Dogru M and Tsubota K. The Effect of Topical Amiloride Eye Drops on Tear Quantity in Rabbits. Molecular Vision 2010; 16:2279-2285).

Taken together, these data provide an important proof-of-concept that the inhibition of ENaC will increase tear volume. The inhibition of ENaC in the eye is predicted to preserve lacrimal secretions and maintain hydration on the ocular surface. Because ENaC is positioned on the apical surface of the epithelium, i.e. the mucosal surface-environmental interface, to inhibit ENaC mediated Na$^+$ and liquid absorption, an ENaC blocker of the amiloride class (which blocks from the extracellular domain of ENaC) must be delivered to the mucosal surface and, importantly, be maintained at this site, to achieve therapeutic utility. The present invention describes diseases characterized by too little liquid on mucosal surfaces and "topical" sodium channel blockers designed to exhibit the increased potency, reduced mucosal absorption, and slow dissociation ("unbinding" or detachment) from ENaC required for therapy of these diseases.

The use of ENaC blockers has been reported for a variety of diseases which are ameliorated by increased mucosal hydration. In particular, the use of ENaC blockers in the treatment of respiratory diseases such as chronic bronchitis (CB), cystic fibrosis (CF), and COPD, which reflect the body's failure to clear mucus normally from the lungs and ultimately result in chronic airway infection, has been reported. See, *Evidence for airway surface dehydration as the initiating event in CF airway disease*, R. C. Boucher, Journal of Internal Medicine, Vol. 261, Issue 1, January 2007, pages 5-16; and *Cystic fibrosis: a disease of vulnerability to airway surface dehydration*, R. C. Boucher, Trends in Molecular Medicine, Vol. 13, Issue 6, June 2007, pages 231-240.

Data indicate that the initiating problem in both chronic bronchitis and cystic fibrosis is the failure to clear mucus from airway surfaces. The failure to clear mucus reflects an imbalance in the quantities of mucus as airway surface liquid (ASL) on airway surfaces. This imbalance results in a relative reduction in ASL which leads to mucus concentration, reduction in the lubricant activity of the periciliary liquid (PCL), mucus adherence to the airway surface, and failure to clear mucus via ciliary activity to the mouth. The reduction in mucus clearance leads to chronic bacterial colonization of mucus adherent to airway surfaces. The chronic retention of bacteria, inability of local antimicrobial substances to kill mucus-entrapped bacteria on a chronic basis, and the consequent chronic inflammatory response to this type of surface infection, are manifest in chronic bronchitis and cystic fibrosis.

Chronic obstructive pulmonary diseases are characterized by dehydration of airway surfaces and the retention of mucous secretions in the lungs. Examples of such diseases include cystic fibrosis, chronic bronchitis, and primary or secondary ciliary dyskinesia. Such diseases affect approximately 15 million patients in the United States, and are the sixth leading cause of death. Other airway or pulmonary diseases characterized by the accumulation of retained mucous secretions include sinusitis (an inflammation of the paranasal sinuses associated with upper respiratory infection) and pneumonia.

Chronic bronchitis (CB), including the most common lethal genetic form of chronic bronchitis, cystic fibrosis (CF), are diseases that reflect the body's failure to clear mucus normally from the lungs, which ultimately produces chronic airways infection. In the normal lung, the primary defense against chronic intrapulmonary airways infection (chronic bronchitis) is mediated by the continuous clearance of mucus from bronchial airway surfaces. This function in health effectively removes from the lung potentially noxious toxins and pathogens. Recent data indicate that the initiating problem, i.e., the "basic defect," in both CB and CF is the failure to clear mucus from airway surfaces. The failure to clear mucus reflects an imbalance between the amount of liquid and mucin on airway surfaces. This "airway surface liquid" (ASL) is primarily composed of salt and water in proportions similar to plasma (i.e., isotonic). Mucin macromolecules organize into a well-defined "mucus layer" which normally traps inhaled bacteria and is transported out of the lung via the actions of cilia which beat in a watery, low viscosity solution termed the "periciliary liquid" (PCL). In the disease state, there is an imbalance in the quantities of mucus as ASL on airway surfaces. This results in a relative reduction in ASL which leads to mucus concentration, reduction in the lubricant activity of the PCL, and a failure to clear mucus via ciliary activity to the mouth. The reduction in mechanical clearance of mucus from the lung leads to chronic bacterial colonization of mucus adherent to airway surfaces. It is the chronic retention of bacteria, the failure of local antimicrobial substances to kill mucus-entrapped bacteria on a chronic basis, and the consequent chronic inflammatory responses of the body to this type of surface infection, that lead to the syndromes of CB and CF.

The current afflicted population in the U.S. is 12,000,000 patients with the acquired (primarily from cigarette smoke exposure) form of chronic bronchitis and approximately 30,000 patients with the genetic form, cystic fibrosis. Approximately equal numbers of both populations are present in Europe. In Asia, there is little CF but the incidence of CB is high and, like the rest of the world, is increasing.

There is currently a large, unmet medical need for products that specifically treat CB and CF at the level of the basic defect that cause these diseases. The current therapies for chronic bronchitis and cystic fibrosis focus on treating the symptoms and/or the late effects of these diseases. Thus, for chronic bronchitis, β-agonists, inhaled steroids, anti-cholinergic agents, and oral theophyllines and phosphodiesterase inhibitors are all in development. However, none of these drugs treat effectively the fundamental problem of the failure to clear mucus from the lung. Similarly, in cystic fibrosis, the same spectrum of pharmacologic agents is used. These strategies have been complemented by more recent strategies designed to clear the CF lung of the DNA ("Pulmozyme"; Genentech) that has been deposited in the lung by neutrophils that have futilely attempted to kill the bacteria that grow in adherent mucus masses and through the use of inhaled antibiotics ("TOBI") designed to augment the lungs' own killing mechanisms to rid the adherent mucus plaques of bacteria. A general principle of the body is that if the initiating lesion is not treated, in this case mucus retention/obstruction, bacterial infections became chronic and increasingly refractory to antimicrobial therapy. Thus, a major unmet therapeutic need for both CB and CF lung diseases is an effective means of re-hydrating airway mucus (i.e., restoring/expanding the volume of the ASL) and promoting its clearance, with bacteria, from the lung.

R. C. Boucher, in U.S. Pat. No. 6,264,975, describes the use of pyrazinoylguanidine sodium channel blockers for hydrating mucosal surfaces. These compounds, typified by the well-known diuretics amiloride, benzamil, and phenamil, are effective. However, these compounds suffer from the significant disadvantage that they are (1) relatively impotent, which is important because the mass of drug that can be inhaled by the lung is limited; (2) rapidly absorbed, which limits the half-life of the drug on the mucosal surface; and (3) are freely dissociable from ENaC. The sum of these disadvantages embodied in these well-known diuretics produces compounds with insufficient potency and/or effective half-life on mucosal surfaces to have therapeutic benefit for hydrating mucosal surfaces.

R. C. Boucher, in U.S. Pat. No. 6,926,911, suggests the use of the relatively impotent sodium channel blockers such as amiloride, with osmolytes for the treatment of airway diseases. This combination gives no practical advantage over either treatment alone and is clinically not useful (see Donaldson et al, N Eng J Med 2006; 353:241-250). Amiloride was found to block the water permeability of airways and negate the potential benefit of concurrent use of hypertonic saline and amiloride.

U.S. Pat. No. 5,817,028 to Anderson describes a method for the provocation of air passage narrowing (for evaluating susceptibility to asthma) and/or the induction of sputum in subjects via the inhalation of mannitol. It is suggested that the same technique can be used to induce sputum and promote mucociliary clearance. Substances suggested include sodium chloride, potassium chloride, mannitol and dextrose.

Clearly, what is needed are drugs that are more effective at restoring the clearance of mucus from the lungs of patients with CB/CF. The value of these new therapies will be reflected in improvements in the quality and duration of life for both the CF and the CB populations.

Other mucosal surfaces in and on the body exhibit subtle differences in the normal physiology of the protective surface liquids on their surfaces but the pathophysiology of disease reflects a common theme, i.e., too little protective surface liquid. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity.

In rhinosinusitis, there is an imbalance, as in CB, between mucin secretion and relative ASL depletion. Finally, in the gastrointestinal tract, failure to secrete Cl— (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

The published literature includes a number of patent applications and granted patents to Parion Sciences Inc., directed toward pyrazinoylguanidine analogs as sodium channel blockers. Examples of such publications include PCT Publication Nos. WO2007146867, WO2003/070182, WO2003/070184, WO2004/073629, WO2005/025496, WO2005/016879, WO2005/018644, WO2006/022935, WO2006/023573, WO2006/023617, WO2007/018640, WO2007146870, WO2007/146869, WO2008030217, WO2008/031028, WO2008/031048, WO2013/003386, WO2013/003444, and U.S. Pat. Nos. 6,858,614, 6,858,615, 6,903,105, 6,995,160, 7,026,325, 7,030,117, 7,064,129, 7,186,833, 7,189,719, 7,192,958, 7,192,959, 7,192,960, 7,241,766, 7,247,636, 7,247,637, 7,317,013, 7,332,496, 7,368,447, 7,368,450, 7,368,451, 7,375,102, 7,375,107, 7,388,013, 7,399,766, 7,410,968, 7,807,834, 7,820,678, 7,842,697, 7,868,010, 7,956,059, 7,981,898, 8,008,494, 8,022,210, 8,058,278, 8,124,607, 8,143,256, 8,163,758, 8,198,286, 8,211,895, 8,198,286, 8,227,474, and 8,324,218.

There remains a need for novel sodium channel blocking compounds with enhanced potency and effectiveness on mucosal tissues, especially ocular tissues. There also remains the need for novel sodium channel blocking compounds that provide therapeutic effect, but minimize or eliminate the onset or progression of hyperkalemia in recipients.

SUMMARY OF THE INVENTION

It is an object of the present invention to provide compounds that are more potent and/or absorbed less rapidly from mucosal surfaces, such as ocular surfaces, and/or are less reversible as compared to known compounds.

It is another aspect of the present invention to provide compounds that are more potent and/or absorbed less rapidly and/or exhibit less reversibility, as compared to compounds such as amilorde, benzamil, and phenamil. Therefore, the compounds will give a prolonged pharmacodynamic half-life on mucosal surfaces as compared to known compounds.

It is another object of the present invention to provide compounds which (1) are absorbed less rapidly from mucosal surfaces, especially ocular surfaces, as compared to known compounds and (2) when absorbed from mucosal surfaces after administration to the these surfaces, are excreted mainly non-renally in order to minimize the chances of hyperkalemia.

It is another object of the present invention to provide compounds which are (1) absorbed less rapidly from mucosal surfaces, especially ocular surfaces, as compared to known compounds and (2) are converted in vivo into metabolic derivatives thereof which have reduced efficacy in blocking sodium channels as compared to the administered parent compound in order to minimize the chances of hyperkalemia.

It is another object of the present invention to provide compounds that are more potent and/or absorbed less rapidly and/or exhibit less reversibility, as compared to compounds such as amiloride, benzamil, and phenamil. Therefore, such compounds will give a prolonged pharmacodynamic half-life on mucosal surfaces as compared to previous compounds.

It is another object of the present invention to provide compounds that are metabolically stable. Therefore, such compounds will give a prolonged pharmacodynamic half-life on mucosal surfaces as compared to previous compounds.

It is another object of the present invention to provide methods of treatment that take advantage of the pharmacological properties of the compounds described above.

In particular, it is an object of the present invention to provide methods of treatment which rely on rehydration of mucosal surfaces.

In particular, it is an object of the present invention to provide methods of treating dry eye and related ocular diseases.

The objects of the present invention may be accomplished with a class of pyrazinoylguanidine represented by a compound of formula (I):

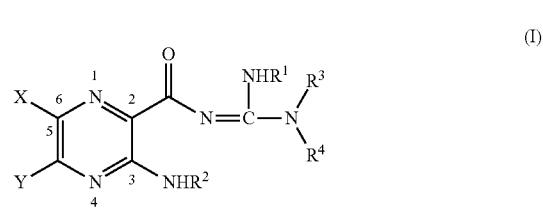

and includes racemates, enantiomers, diastereomers, tautomers, polymorphs, pseudopolymorphs and pharmaceutically acceptable salts, thereof, wherein:

X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;

Y is hydrogen, hydroxyl, mercapto, lower alkoxy, lower alkyl-thio, halogen, lower alkyl, unsubstituted or substituted mononuclear aryl, or $-N(R^2)_2$;

$R^1$ is hydrogen or lower alkyl;

each $R^2$ is, independently, $-R^7$, $-(CH_2)_m-OR^8$, $-(CH_2)_m-NR^7R^{10}$, $-(CH_2)_n(CHOR^8)(CHOR^8)_n-CH_2OR^8$, $-(CH_2CH_2O)_m-R^8$, $-(CH_2CH_2O)_m-CH_2CH_2NR^7R^{10}$, $-(CH_2)_n-C(=O)NR^7R^{10}$, $-(CH_2)_n-(Z)_g-R^7$, $-(CH_2)_m-NR^{10}-CH_2(CHOR^8)(CHOR^8)_n-CH_2OR^8$, $-(CH_2)-CO_2R^7$, or

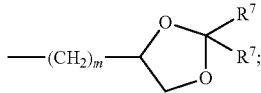

$R^3$ and $R^4$ are each, independently, hydrogen, lower alkyl, hydroxyl-lower alkyl, phenyl, (phenyl)-lower alkyl, (halophenyl)-lower alkyl, ((lower-alkyl)phenyl)-lower-alkyl, ((lower-alkoxy)phenyl))-lower alkyl, (naphthyl)-lower alkyl, or (pyridyl)-lower alkyl, or a group represented by formula A or formula B, with the proviso that at least one of $R^3$ and $R^4$ is a group represented by the formula A or formula B;

$-(C(R^L)_2)_o-x-(C(R^L)_2)_p A^1$      formula A:

$-(C(R^L)_2)_o-x-(C(R^L)_2)_p A^2$      formula B:

$A^1$ is a $C_6-C_{15}$-membered aromatic carbocycle substituted with at least one $R^5$ and the remaining substituents are $R^6$;

$A^2$ is a six to fifteen-membered aromatic heterocycle substituted with at least one $R^5$ and the remaining substituents are $R^6$ wherein said aromatic heterocycle comprises 1-4 heteroatoms selected from the group consisting of O, N, and S;

each $R^L$ is, independently, $-R^7$, $-(CH_2)_n-OR^8$, $-O-(CH_2)_m-OR^8$, $-(CH_2)_n-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

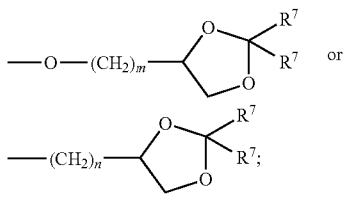

each o is, independently, an integer from 0 to 10;
each p is, independently, an integer from 0 to 10;
with the proviso that the sum of o and p in each contiguous chain is from 1 to 10;

each x is, independently, O, $NR^{10}$, C(=O), CHOH, $C(=N-R^{10})$, $CHNR^7R^{10}$, or a single bond;

each $R^5$ is, independently, -Link-$(CH_2)_m$-CAP, -Link-$(CH_2)_n(CHOR^8)(CHOR^8)_n$-CAP, -Link-$(CH_2CH_2O)_m$-CH_2-CAP, -Link-$(CH_2CH_2O)_m$-CH_2CH_2-CAP, -Link-$(CH_2)_m$-$(Z)_g$-CAP, -Link-$(CH_2)_n(Z)_g$-$(CH_2)_m$-CAP, -Link-$(CH_2)_n$-$NR^{13}$-$CH_2(CHOR^8)(CHOR^8)_n$-CAP, -Link-$(CH_2)_n$-$(CHOR^8)_m CH_2$-$NR^{13}$-$(Z)_g$-CAP, -Link-$(CH_2)_n NR^{13}$-$(CH_2)_m (CHOR^8)_n CH_2 NR^{13}$-$(Z)_g$-CAP, -Link-$(CH_2)_m$-$(Z)_g$-$(CH_2)_m$-CAP, -Link-NH-C(=O)-NH-$(CH_2)_m$-CAP, -Link-$(CH_2)_m$-C(=O)$NR^{13}$-$(CH_2)_m$-CAP, -Link-$(CH_2)_n$-$(Z)_g$-$(CH_2)_m$-$(Z)_g$-CAP, or -Link-$Z_g$-$(CH_2)_m$-Het-$(CH_2)_m$-CAP;

each $R^6$ is, independently, hydrogen, lower alkyl, phenyl, substituted phenyl o-$CH_2(CHOR^8)_m$-$CH_2OR^8$, $-OR^{11}$, $-N(R^7)_2$, $-(CH_2)_m-OR^8$, $-O-(CH_2)_m-OR^B$, $-(CH_2)_m-NR^7R^{10}$, $-O-(CH_2)_m-NR^7R^{10}$, $-(CH_2)_n(CHOR^8)(CHOR^8)_n-CH_2OR^8$, $-O-(CH_2)_m(CHOR^8)(CHOR^8)_n-CH_2OR^8$, $-(CH_2CH_2O)_m-R^8$, $-O-(CH_2CH_2O)_m-R^8$, $-(CH_2CH_2O)_m-CH_2CH_2NR^7R^{10}$, $-O-(CH_2CH_2O)_m-CH_2CH_2NR^7R^{10}$, $-(CH_2)_n-C(=O)NR^7R^{10}$, $-O-(CH_2)_m-C(=O)NR^7R^{10}$, $-(CH_2)_n-(Z)_g-R^7$, $-O-(CH_2)_m-(Z)_g-R^7$, $-(CH_2)_n-NR^{10}-CH_2(CHOR^8)(CHOR^8)_n-CH_2OR^8$, $-O-(CH_2)_m-NR^{10}-CH_2(CHOR^8)(CHOR^8)_n-CH_2OR^8$, $-(CH_2)_n-CO_2R^7$, $-O-(CH_2)_m-CO_2R^7$, $-OSO_3H$, $-O$-glucuronide, $-O$-glucose,

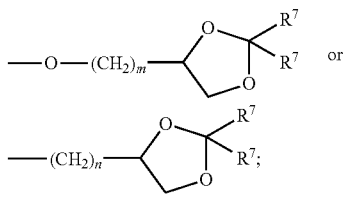

wherein when two $R^6$ are $-OR^{11}$ and are located adjacent to each other on the aromatic carbocycle or aromatic heterocycle, the two $OR^{11}$ may form a methylenedioxy group;

each $R^7$ is, independently, hydrogen, lower alkyl, phenyl, substituted phenyl or $-CH_2(CHOR^8)_m-CH_2OR^8$;

each $R^8$ is, independently, hydrogen, lower alkyl, $-C(=O)-R^{11}$, glucuronide, 2-tetrahydropyranyl, or

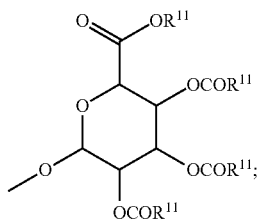

each $R^9$ is, independently, $-CO_2R^7$, $-CON(R^7)_2$, $-SO_2CH_3$, $-C(=O)R^7$, $-CO_2R^{13}$, $-CON(R^{13})_2$, $-SO_2CH_2R^{13}$, or $-C(=O)R^{13}$;

each $R^{10}$ is, independently, $-H$, $-SO_2CH_3$, $-CO_2R^7$, $-C(=O)NR^7R^9$, $-C(=O)R^7$, or $-CH_2-(CHOH)_n-CH_2OH$;

each Z is, independently, $-(CHOH)-$, $-C(=O)-$, $-(CHNR^7R^{10})-$, $-(C=NR^{10})-$, $-NR^{10}-$, $-(CH_2)_n-$, $-(CHNR^{13}R^{13})-$, $-(C=NR^{13})-$, or $-NR^{13}-$;

each $R^{11}$ is, independently, hydrogen, lower alkyl, phenyl lower alkyl or substituted phenyl lower alkyl;

each $R^{12}$ is, independently, $-SO_2CH_3$, $-CO_2R^7$, $-C(=O)NR^7R^9$, $-C(=O)R^7$, $-CH_2(CHOH)_n-CH_2OH$, $-CO_2R^7$, $-C(=O)NR^7R^7$, or $-C(=O)R^7$;

each $R^{13}$ is, independently, hydrogen, lower alkoxy, $R^{10}$, $R^{11}$, $R^{12}$, $-OR^7$, $-(CH_2)_m-NR^7R^{10}$, $-(CH_2)_m-NR^7R^7$, $-(CH_2)_m-NR^{11}R^{11}$, $-(CH_2)_m-(NR^{11}R^{11}R^{11})^+$, $-(CH_2)_m-(CHOR^8)_m-(CH_2)_mNR^{11}R^{11}$, $-(CH_2)_m-(CHOR^8)_m-(CH_2)_mNR^7R^{10}$, $-(CH_2)_m-NR^{10}R^{10}$, $-(CH_2)_m-(CHOR^8)_m-(CH_2)_m-(NR^{11}R^{11}R^{11})^+$, $-(CH_2)_m-(CHOR^8)_m-(CH_2)_mNR^7R^7$,

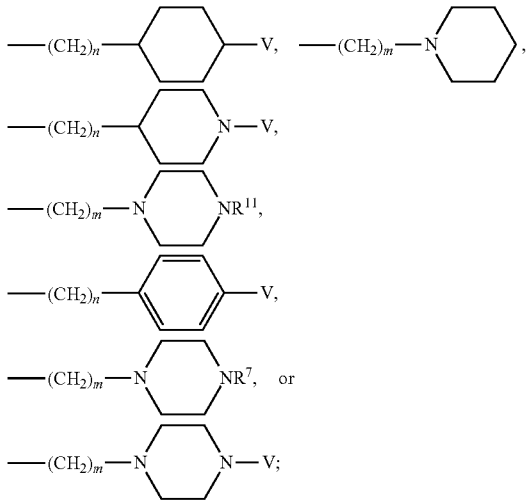

with the proviso that in the moiety $-NR^{13}R^{13}$, the two $R^{13}$ along with the nitrogen to which they are attached may, optionally, form a ring selected from:

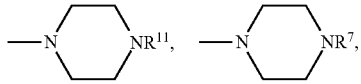

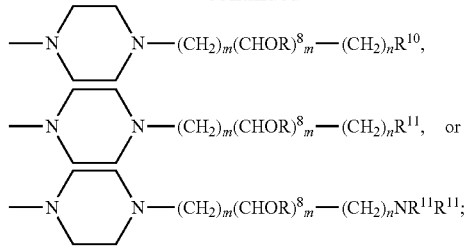

each V is, independently, $-(CH_2)_m-NR^7R^{10}$, $-(CH_2)_m-NR^7R^7$, $-(CH_2)_m-(NR^{11}R^{11}R^{11})^+$, $-(CH_2)_n-(CHOR^8)_m-(CH_2)_mNR^7R^{10}$, $-(CH_2)_n-NR^{10}R^{10}$, $-(CH_2)_n-(CHOR^8)_m-(CH_2)_mNR^7R^7$, $-(CH_2)_n-(CHOR^8)_m-(CH_2)_m-(NR^{11}R^{11}R^{11})^+$ with the proviso that when V is attached directly to a nitrogen atom, then V can also be, independently, $R^7$, $R^{10}$, or $(R^{11})_2$;

each $R^{14}$ is, independently, H, $R^{12}$, $-(CH_2)_n-SO_2CH_3$, $-(CH_2)_n-CO_2R^{13}$, $-(CH_2)_n-C(=O)NR^{13}R^{13}$, $-(CH_2)_n-C(=O)R^{13}$, $-(CH_2)_n-(CHOH)_n-CH_2OH$, $-NH-(CH_2)_n-SO_2CH_3$, $-NH-(CH_2)_n-C(=O)R^{11}$, $-NH-C(=O)-NH-C(=O)R^{11}$, $-C(=O)NR^{13}R^{13}$, $-OR^{11}$, $-NH-(CH_2)_n-R^{10}$, $-Br$, $-Cl$, $-I$, $SO_2NHR^{11}$, $-NHR^{13}$, $-NH-C(=O)-NR^{13}R^{13}$, $-(CH_2)_n-NHR^{13}$, or $-NH-(CH_2)_n-C(=O)-R^{13}$;

each g is, independently, an integer from 1 to 6;
each m is, independently, an integer from 1 to 7;
each n is, independently, an integer from 0 to 7;
each -Het- is, independently, $-N(R^7)-$, $-N(R^{10})-$, $-S-$, $-SO-$, $-SO_2-$; $-O-$, $-SO_2NH-$, $-NHSO_2-$, $-NR^7CO-$, $-CONR^7-$, $-N(R^{13})-$, $-SO_2NR^{13}-$, $-NR^{13}CO-$, or $-CONR^{13}-$;

each Link is, independently, $-O-$, $-(CH_2)_n-$, $-O(CH_2)_m-$, $-NR^{13}-C(=O)-NR^{13}-$, $-NR^{13}-C(=O)-(CH_2)_m-$, $-C(=O)NR^{13}-(CH_2)_m-$, $-(CH_2)_n-(Z)_g-(CH_2)_n-$, $-S-$, $-SO-$, $-SO_2-$, $-SO_2NR^7-$, $-SO_2NR^{10}-$, or -Het-;

each CAP is, independently

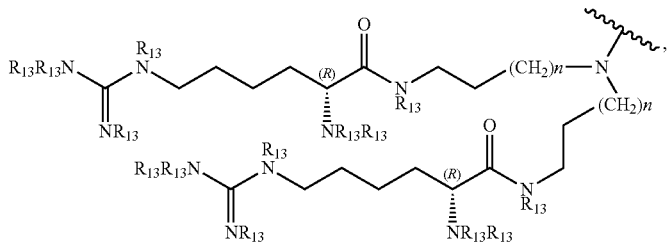

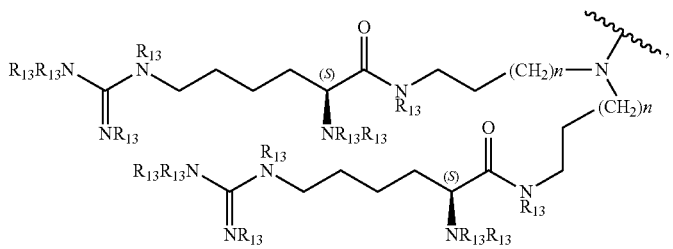

-continued
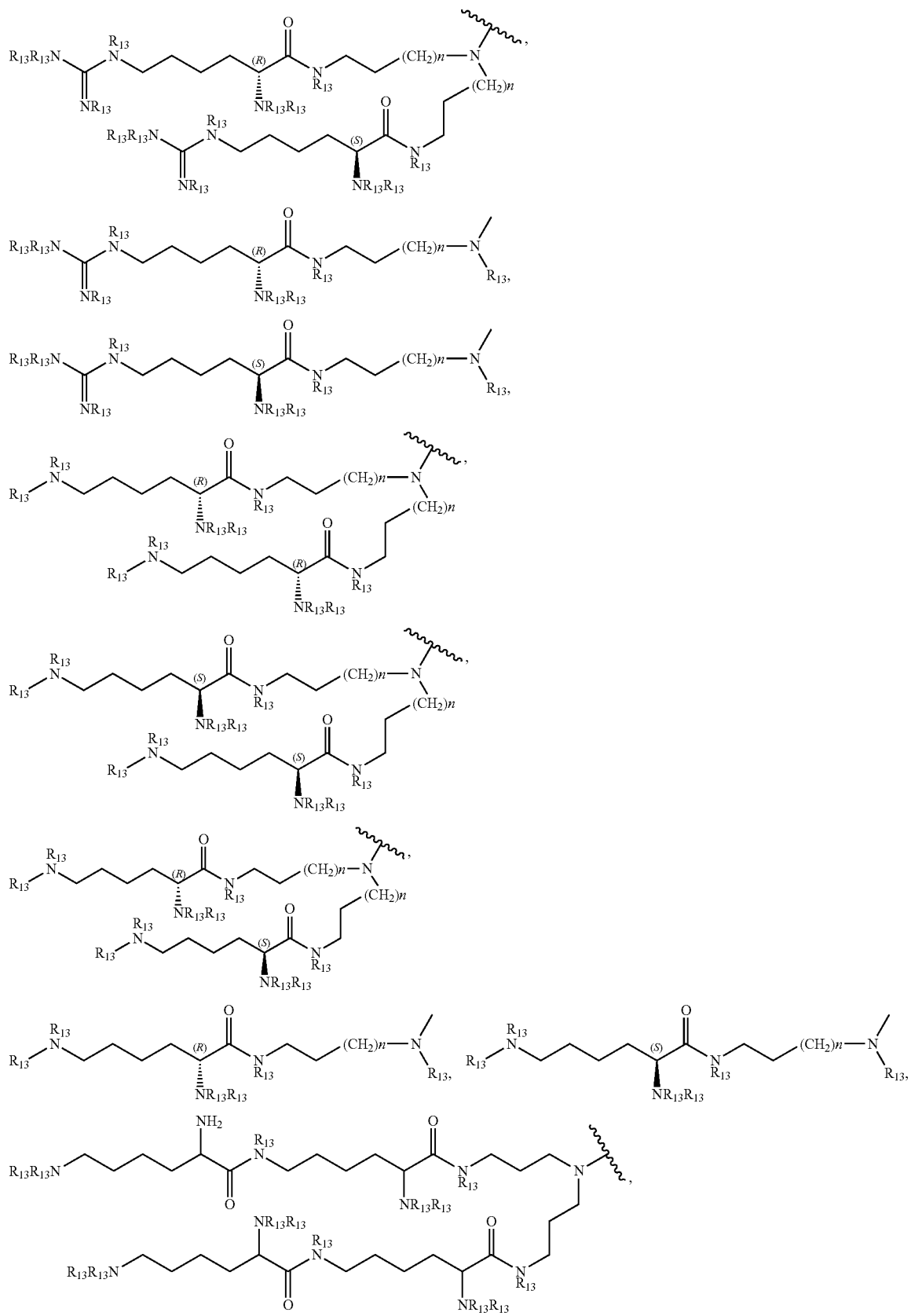

-continued
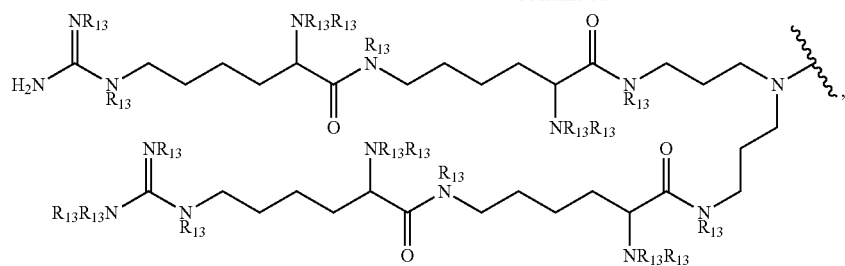
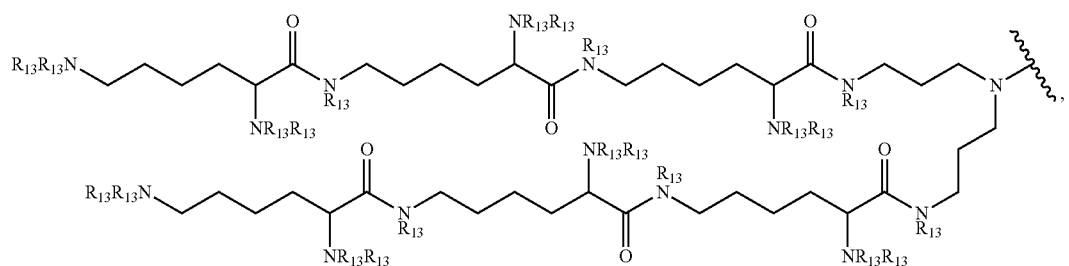
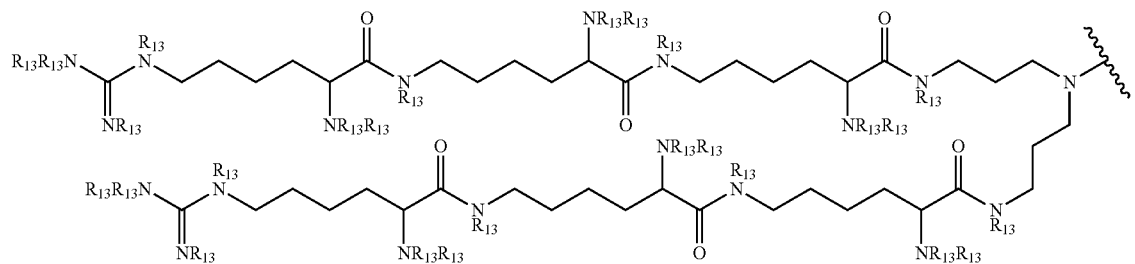
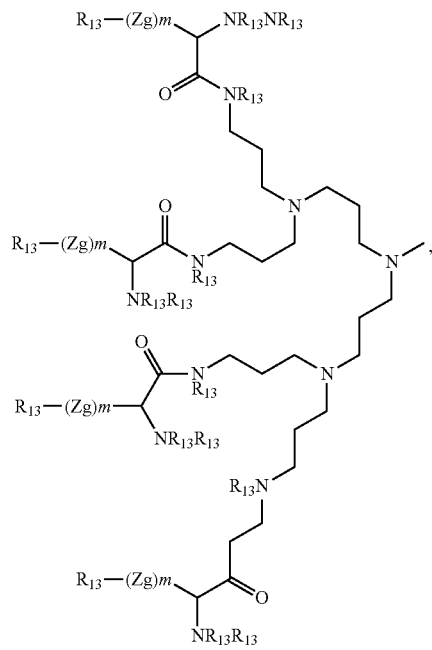

-continued

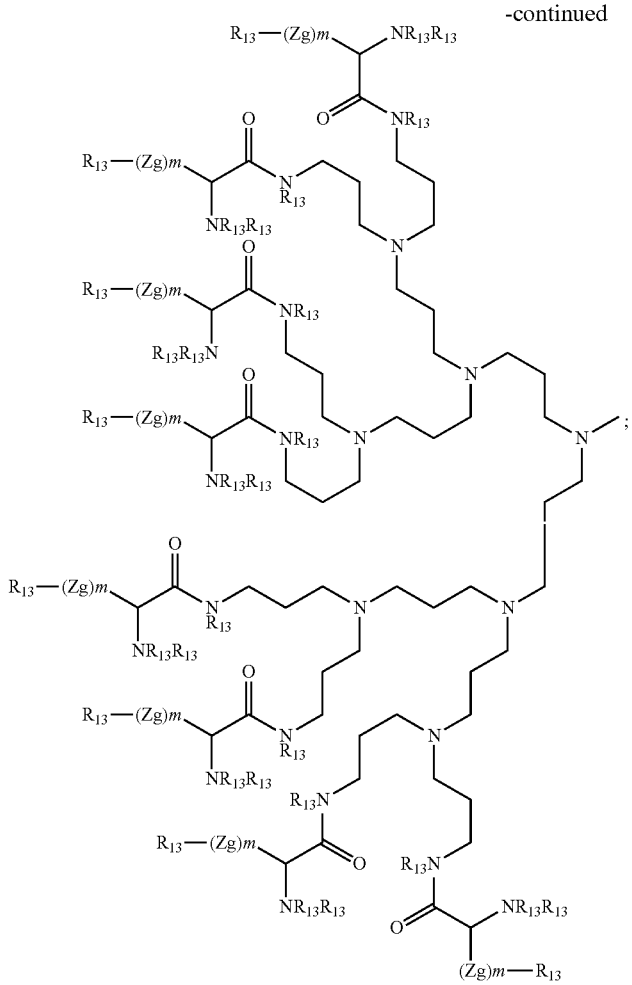

with the proviso that when any —CHOR$^8$— or —CH$_2$OR$^8$ groups are located 1,2- or 1,3- with respect to each other, the R$^8$ groups may, optionally, be taken together to form a cyclic mono- or di-substituted 1,3-dioxane or 1,3-dioxolane.

The present also provides pharmaceutical compositions which comprise a compound described herein.

The present invention also provides a method of promoting hydration of mucosal surfaces, comprising:
administering an effective amount of a compound described herein to a mucosal surface of a subject.

The present invention also provides a method of restoring mucosal defense, comprising:
topically administering an effective amount of compound described herein to a mucosal surface of a subject in need thereof.

The present invention also provides a method of blocking ENaC, comprising:
contacting sodium channels with an effective amount of a compound represented by described herein.

The present invention also provides a method of promoting mucus clearance in mucosal surfaces, comprising:
administering an effective amount of a compound represented described herein to a mucosal surface of a subject.

The present invention also provides a method of treating dry eye, comprising:
administering an effective amount of a compound described herein to the eye of the subject in need thereof.

The present invention also provides a method of treating Sjogren's disease-associated dry eye, comprising:
administering an effective amount of a compound described herein to the eye of the subject in need thereof.

The present invention also provides a method of treating eye inflammation caused by dry eye, comprising:
administering an effective amount of a compound described herein to the eye of the subject in need thereof.

The present invention also provides a method of promoting ocular hydration, comprising:
administering an effective amount of a compound described herein to the eye of the subject.

The present invention also provides a method of promoting corneal hydration, comprising:
administering an effective amount of a compound described herein to the eye of the subject.

The present invention also provides a method of treating chronic bronchitis, comprising:
administering an effective amount of a compound described herein to a subject in need thereof.

The present invention also provides a method of treating cystic fibrosis, comprising:
administering an effective amount of compound described herein to a subject in need thereof.

The present invention also provides a method of treating rhinosinusitis, comprising:
administering an effective amount of a compound described herein to a subject in need thereof.

The present invention also provides a method of treating nasal dehydration, comprising:

administering an effective amount of a compound described herein to the nasal passages of a subject in need thereof.

In a specific embodiment, the nasal dehydration is brought on by administering dry oxygen to the subject.

The present invention also provides a method of treating sinusitis, comprising:

administering an effective amount of a compound described herein to a subject in need thereof.

The present invention also provides a method of treating pneumonia, comprising:

administering an effective amount of a compound described herein to a subject in need thereof.

The present invention also provides a method of treating ventilator-induced pneumonia, comprising:

administering an effective compound described herein to a subject by means of a ventilator.

The present invention also provides a method of treating asthma, comprising:

administering an effective amount of a compound described herein to a subject in need thereof.

The present invention also provides a method of treating primary ciliary dyskinesia, comprising:

administering an effective amount of a compound described herein to a subject in need thereof.

The present invention also provides a method of treating otitis media, comprising:

administering an effective amount of a compound described herein to a subject in need thereof.

The present invention also provides a method of inducing sputum for diagnostic purposes, comprising:

administering an effective amount of compound described herein to a subject in need thereof.

The present invention also provides a method of treating chronic obstructive pulmonary disease, comprising:

administering an effective amount of a compound described herein to a subject in need thereof.

The present invention also provides a method of treating emphysema, comprising:

administering an effective amount of a compound described herein to a subject in need thereof.

The present invention also provides a method of treating Sjögren's disease, comprising:

administering an effective amount of compound described herein to a subject in need thereof.

The present invention also provides a method of treating vaginal dryness, comprising:

administering an effective amount of a compound described herein to the vaginal tract of a subject in need thereof.

The present invention also provides a method of treating dry skin, comprising:

administering an effective amount of a compound described herein to the skin of a subject in need thereof.

The present invention also provides a method of treating dry mouth (xerostomia), comprising:

administering an effective amount of compound described herein to the mouth of the subject in need thereof.

The present invention also provides a method of treating distal intestinal obstruction syndrome, comprising:

administering an effective amount of compound described herein to a subject in need thereof.

The present invention also provides a method of treating esophagitis, comprising:

administering an effective amount of a compound described herein to a subject in need thereof.

The present invention also provides a method of treating bronchiectasis, comprising:

administering an effective amount of a compound described herein to a subject in need thereof.

The present invention also provides a method of treating constipation, comprising:

administering an effective amount of a compound described herein to a subject in need thereof. In one embodiment of this method, the compound is administered either orally or via a suppository or enema.

The present invention also provides a method of treating chronic diverticulitis comprising:

administering an effective amount of a compound described herein to a subject in need thereof.

It is an object of the present invention to provide treatments comprising the use of osmolytes together with sodium channel blockers of formula (I) that are more potent, more specific, and/or absorbed less rapidly from mucosal surfaces, and/or are less reversible as compared to compounds such as amiloride, benzamil, and phenamil.

It is another aspect of the present invention to provide treatments using sodium channel blockers of formula (I) that are more potent and/or absorbed less rapidly and/or exhibit less reversibility, as compared to compounds such as amiloride, benzamil, and phenamil when administered with an osmotic enhancer. Therefore, such sodium channel blockers when used in conjunction with osmolytes will give a prolonged pharmacodynamic half-life on mucosal surfaces as compared to either compound used alone.

It is another object of the present invention to provide treatments using sodium channel blockers of formula (I) and osmolytes together which are absorbed less rapidly from mucosal surfaces, especially airway surfaces, as compared to compounds such as amiloride, benzamil, and phenamil It is another object of the invention to provide compositions which contain sodium channel blockers of formula (I) and osmolytes.

The objects of the invention may be accomplished with a method of treating a disease ameliorated by increased mucociliary clearance and mucosal hydration comprising administering an effective amount of a compound of formula (I) as defined herein and an osmolyte to a subject to a subject in need of increased mucociliary clearance and mucosal hydration.

The objects of the invention may also be accomplished with a method of inducing sputum for diagnostic purposes, comprising administering an effective amount of a compound of formula (I) as defined herein and an osmolyte to a subject in need thereof.

The objects of the invention may also be accomplished with a method of treating anthrax, comprising administering an effective amount of a compound of formula (I) as defined herein and an osmolyte to a subject in need thereof.

The objects of the invention may also be accomplished with a method of prophylactic, post-exposure prophylactic, preventive or therapeutic treatment against diseases or conditions caused by pathogens, particularly pathogens which may be used in bioterrorism, comprising administering an effective amount of a compound of formula (I) to a subject in need thereof.

The objects of the invention may also be accomplished with a composition, comprising a compound of formula (I) as defined herein and an osmolyte as defined herein.

BRIEF DESCRIPTION OF THE DRAWINGS

A more complete appreciation of the invention and many of the advantages thereof may be readily obtained by reference to the information herein in conjunction with the following figures.

DETAILED DESCRIPTION OF THE INVENTION

Figure 1:
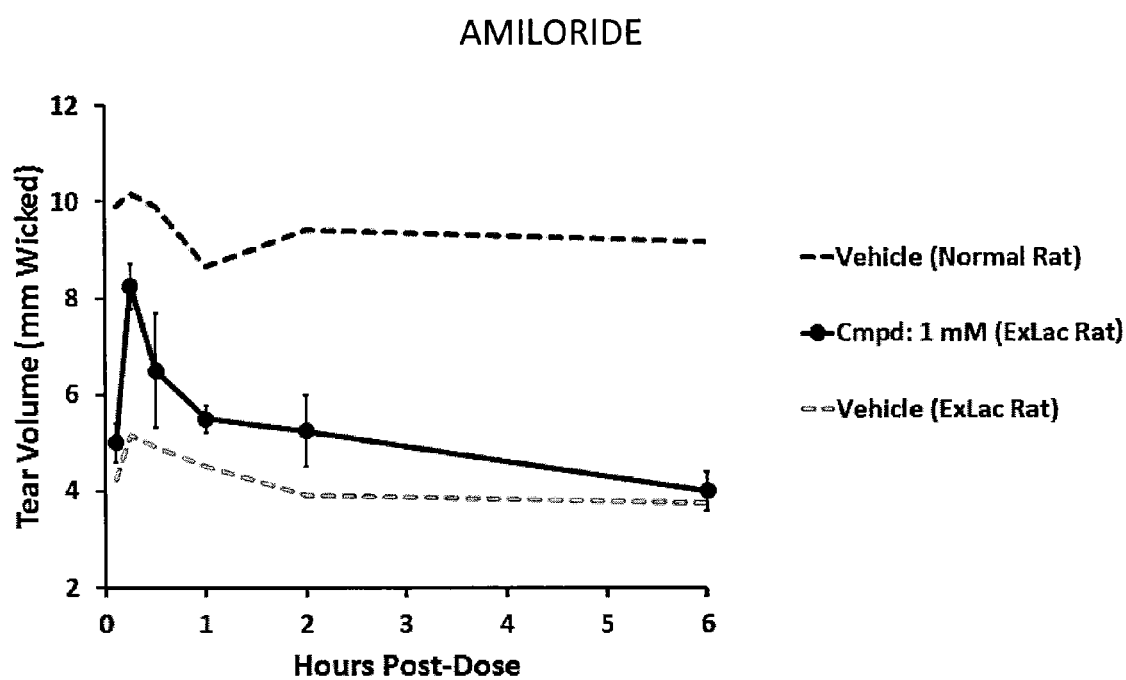
FIG. 1: Tear volume assessments over 6 hours in ExLac rats with Amiloride. Tear volume from ExLac and Normal rats treated with a vehicle are shown for comparison. Error bars are standard error.
Figure 2:
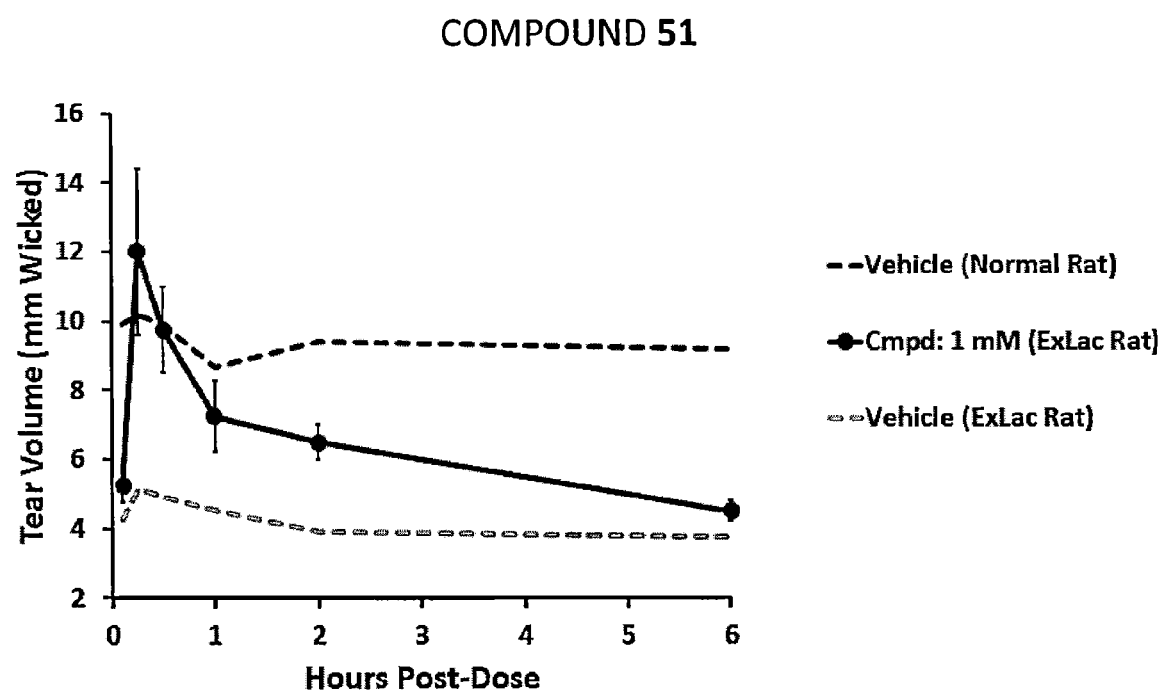
FIG. 2: Tear volume assessments over 6 hours in ExLac rats with Compound 51. Tear volume from ExLac and Normal rats treated with a vehicle are shown for comparison. Error bars are standard error.
Figure 3:
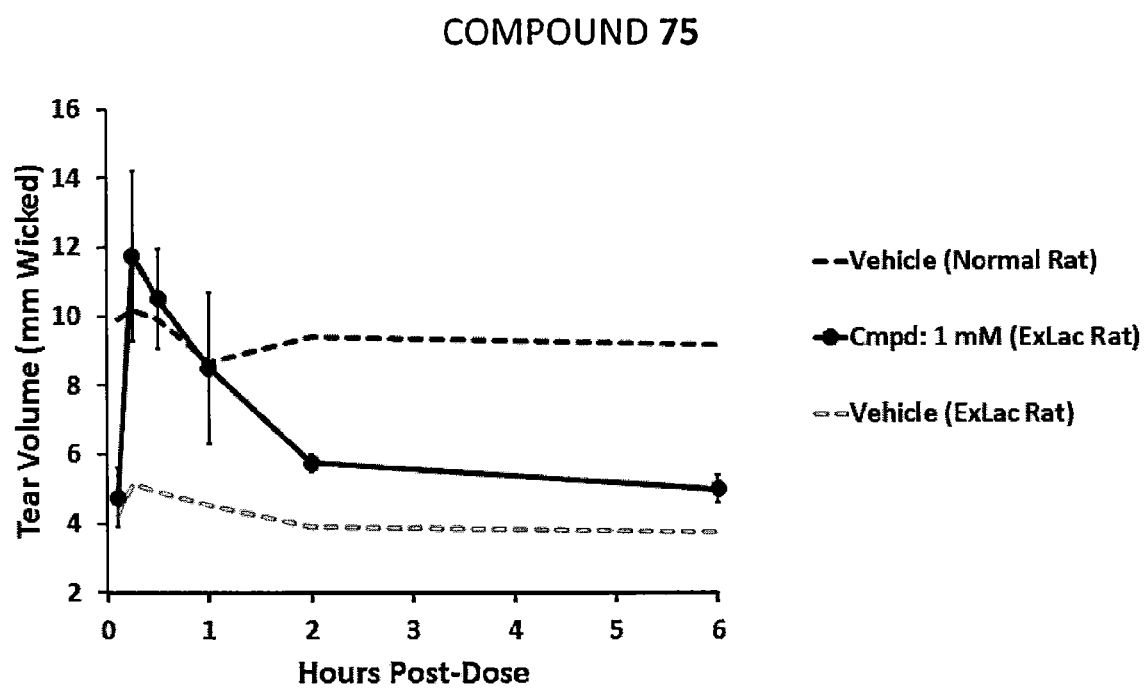
FIG. 3: Tear volume assessments over 6 hours in ExLac rats with Compound 75. Tear volume from ExLac and Normal rats treated with a vehicle are shown for comparison. Error bars are standard error.
Figure 4:
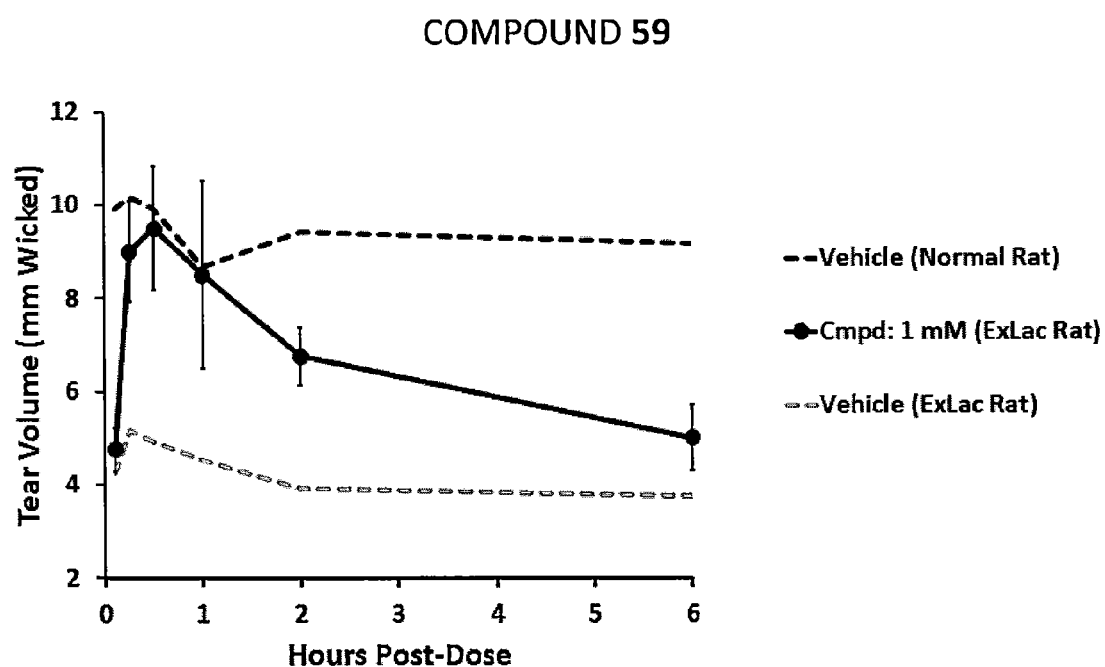
FIG. 4: Tear volume assessments over 6 hours in ExLac rats with Compound P-59. Tear volume from ExLac and Normal rats treated with a vehicle are shown for comparison. Error bars are standard error.
Figure 5:
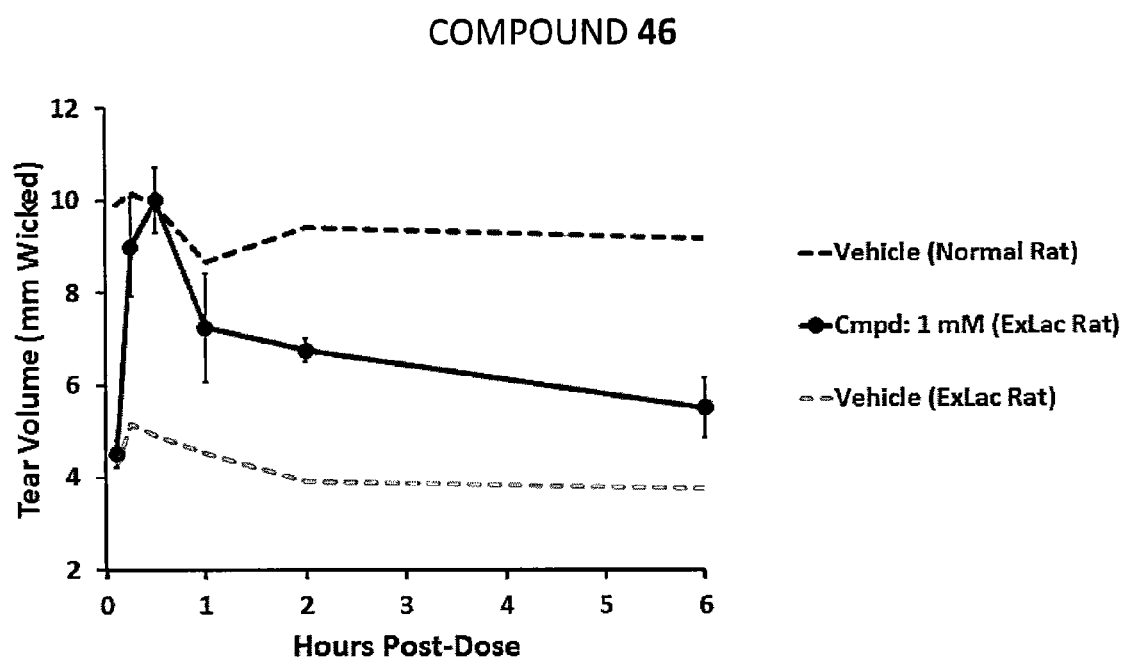
FIG. 5: Tear volume assessments over 6 hours in ExLac rats with Compound 46. Tear volume from ExLac and Normal rats treated with a vehicle are shown for comparison. Error bars are standard error.
Figure 6:
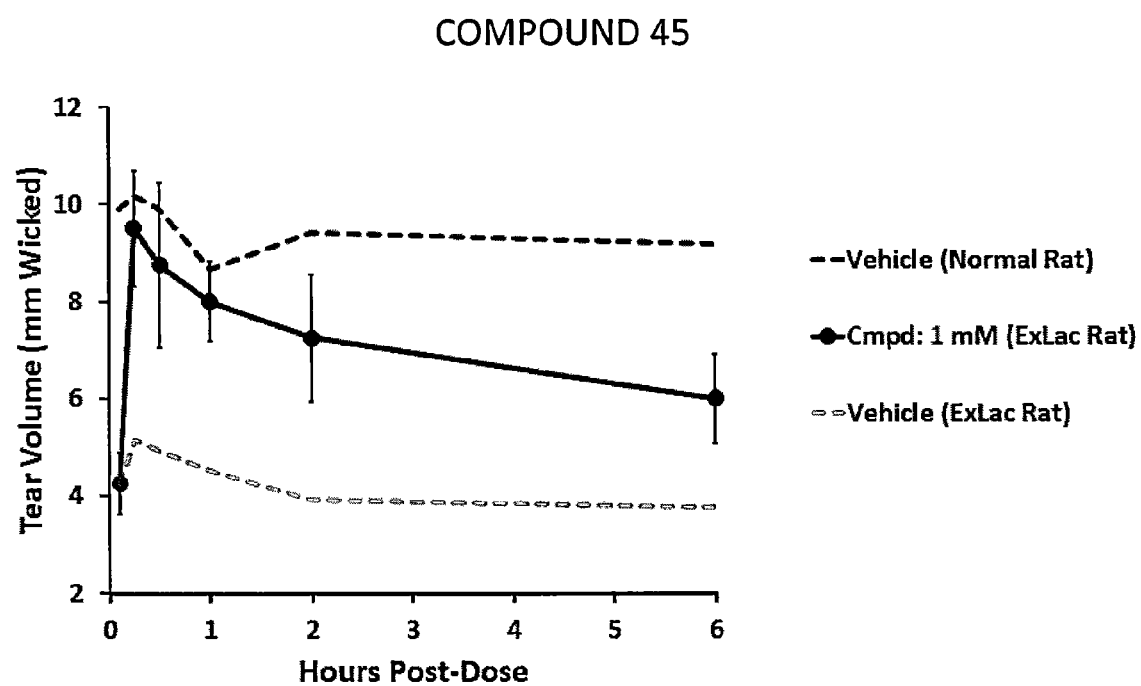
FIG. 6: Tear volume assessments over 6 hours in ExLac rats with Compound 45. Tear volume from ExLac and Normal rats treated with a vehicle are shown for comparison. Error bars are standard error.
Figure 7:
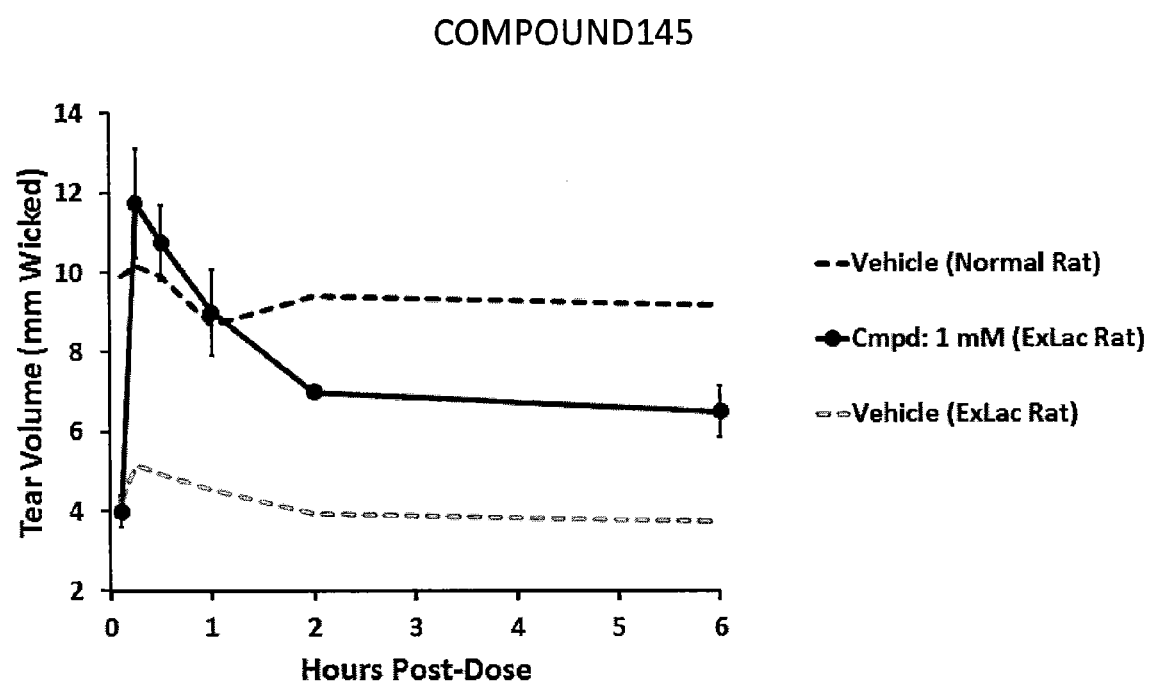
FIG. 7: Tear volume assessments over 6 hours in ExLac rats with Compound 145. Tear volume from ExLac and Normal rats treated with a vehicle are shown for comparison. Error bars are standard error.
Figure 8:
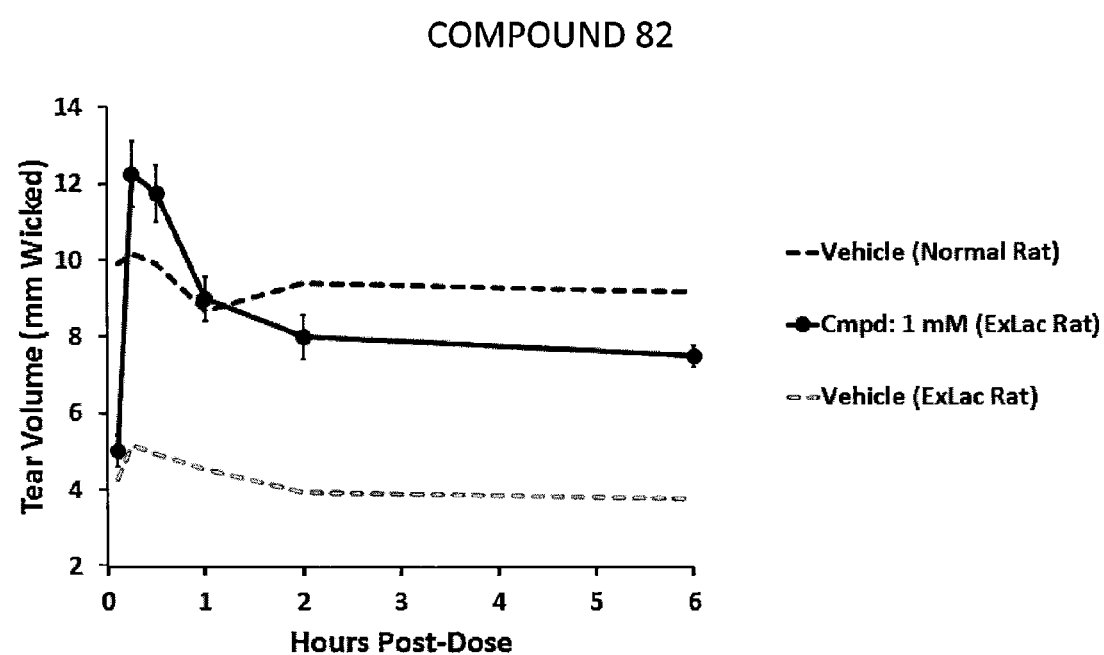
FIG. 8: Tear volume assessments over 6 hours in ExLac rats with Compound 82. Tear volume from ExLac and Normal rats treated with a vehicle are shown for comparison. Error bars are standard error.
Figure 9:
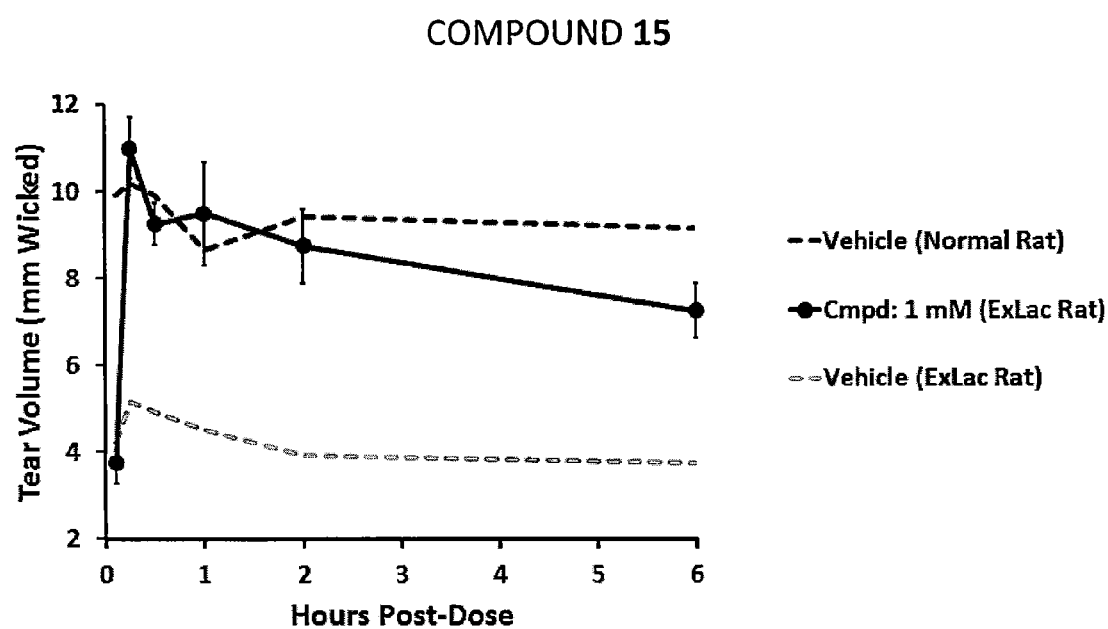
FIG. 9: Tear volume assessments over 6 hours in ExLac rats with Compound 15. Tear volume from ExLac and Normal rats treated with a vehicle are shown for comparison. Error bars are standard error.
Figure 10:
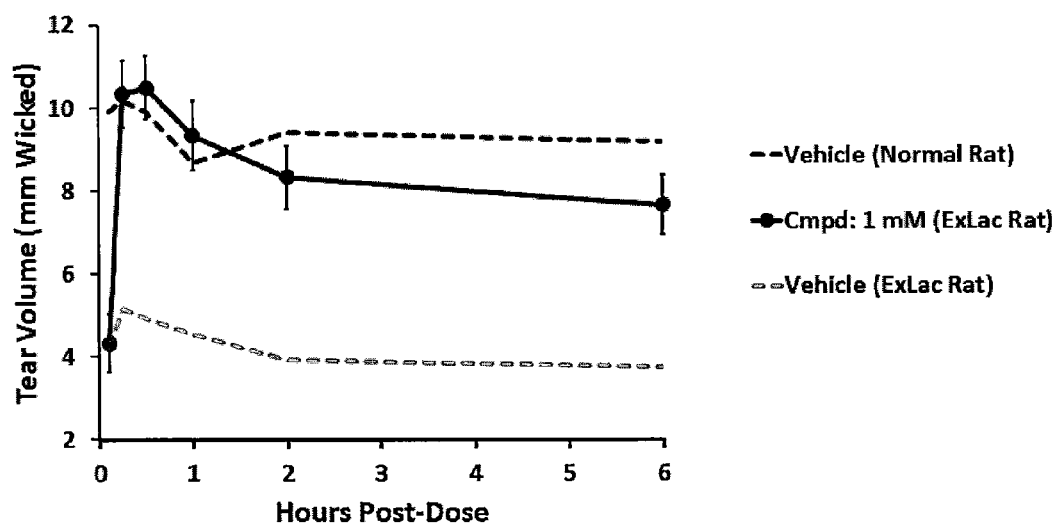
FIG. 10: Tear volume assessments over 6 hours in ExLac rats with Compound 9. Tear volume from ExLac and Normal rats treated with a vehicle are shown for comparison. Error bars are standard error.
Figure 11:
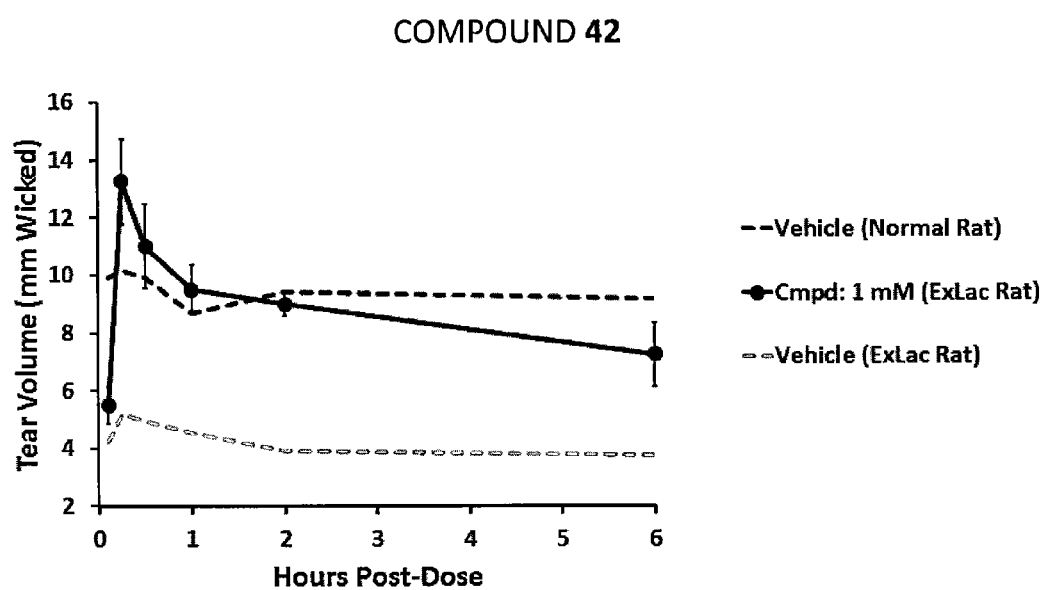
FIG. 11: Tear volume assessments over 6 hours in ExLac rats with Compound 42. Tear volume from ExLac and Normal rats treated with a vehicle are shown for comparison. Error bars are standard error.
Figure 12:
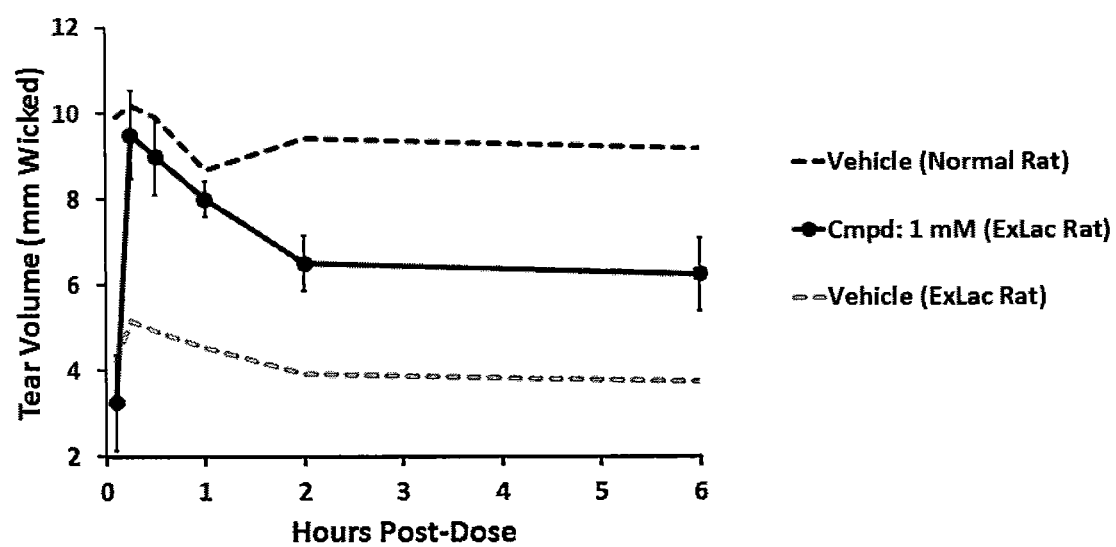
FIG. 12: Tear volume assessments over 6 hours in ExLac rats with Compound 116. Tear volume from ExLac and Normal rats treated with a vehicle are shown for comparison. Error bars are standard error.
Figure 13:
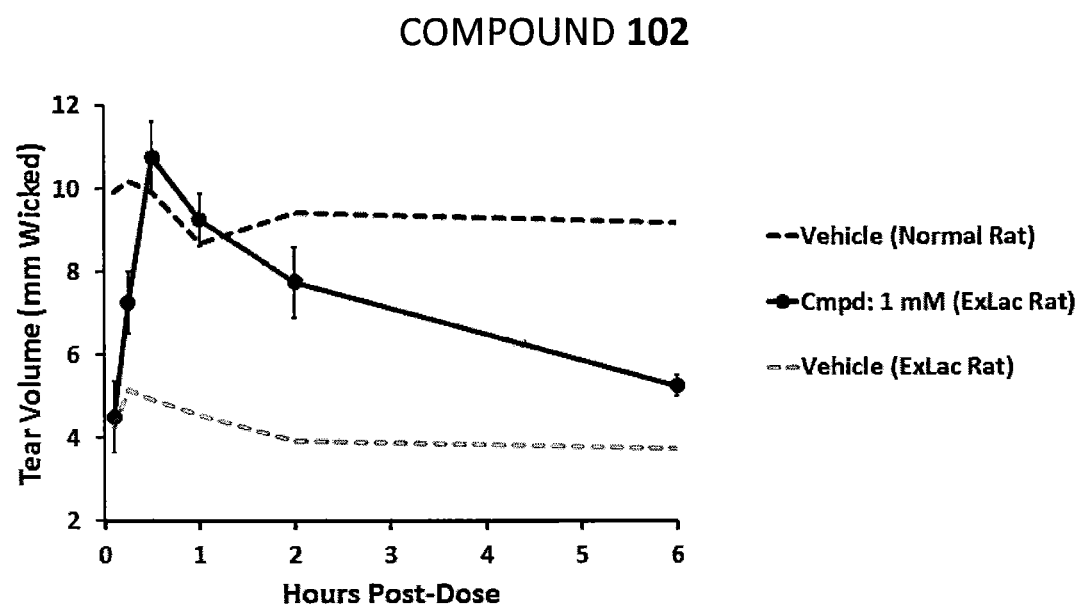
FIG. 13: Tear volume assessments over 6 hours in ExLac rats with Compound 102. Tear volume from ExLac and Normal rats treated with a vehicle are shown for comparison. Error bars are standard error.
Figure 14:
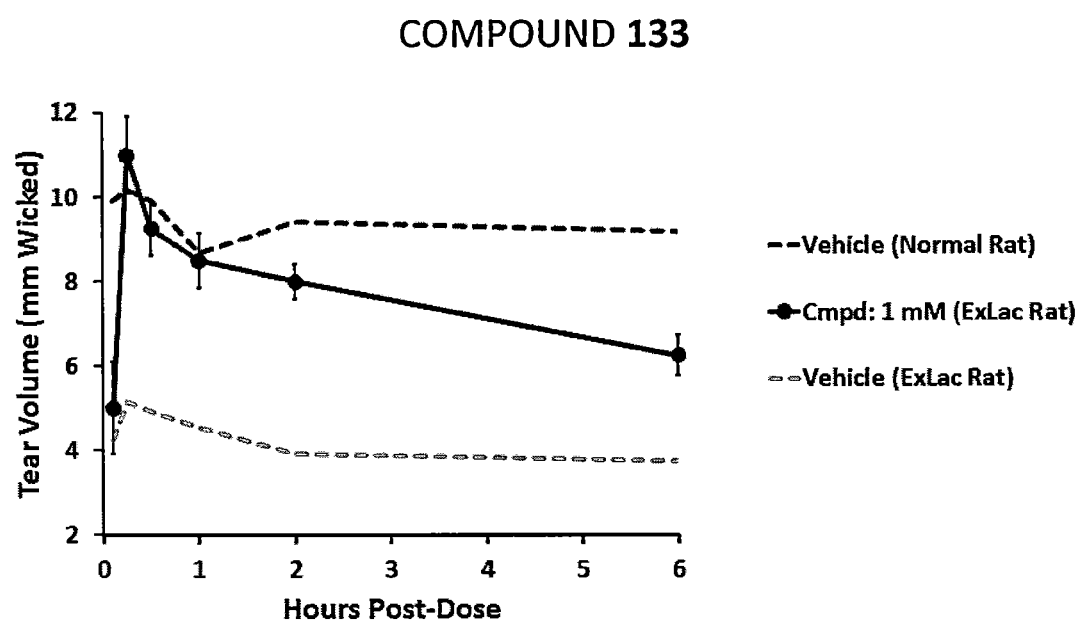
FIG. 14: Tear volume assessments over 6 hours in ExLac rats with Compound 133. Tear volume from ExLac and Normal rats treated with a vehicle are shown for comparison. Error bars are standard error.
Figure 15:
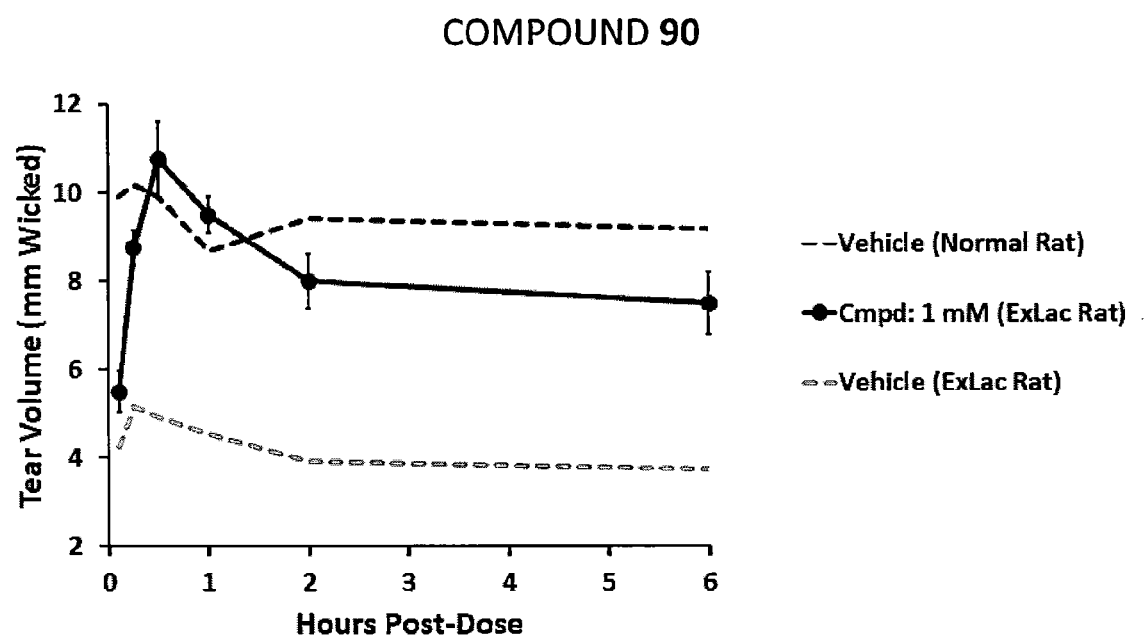
FIG. 15: Tear volume assessments over 6 hours in ExLac rats with Compound 90. Tear volume from ExLac and Normal rats treated with a vehicle are shown for comparison. Error bars are standard error.

As used herein, the following terms are defined as indicated.

"A compound of the invention" means a compound of Formula I or a salt, particularly a pharmaceutically acceptable salt thereof.

"A compound of Formula I" means a compound having the structural formula designated herein as Formula I. Compounds of Formula I include solvates and hydrates (i.e., adducts of a compound of Formula I with a solvent). In those embodiments wherein a compound of Formula I includes one or more chiral centers, the phrase is intended to encompass each individual stereoisomer including optical isomers (enantiomers and diastereomers) and geometric isomers (cis-/trans-isomerism) and mixtures of stereoisomers. In addition, compounds of Formula I also include tautomers of the depicted formula (s).

Throughout the description and examples, compounds are named using standard IUPAC naming principles, where possible, including the use of the ChemDraw Ultra 11.0 software program for naming compounds, sold by CambridgeSoft Corp./PerkinElmer.

In some chemical structure representations where carbon atoms do not have a sufficient number of attached variables depicted to produce a valence of four, the remaining carbon substituents needed to provide a valence of four should be assumed to be hydrogen. Similarly, in some chemical structures where a bond is drawn without specifying the terminal group, such bond is indicative of a methyl (Me, —$CH_3$) group, as is conventional in the art.

The present invention is based on the discovery that the compounds of formula (I) are more potent and/or absorbed less rapidly from mucosal surfaces, and/or are less reversible as compared to known compounds.

The present invention is also based on the discovery that the compounds of formula (I) are more potent and/or absorbed less rapidly and/or exhibit less reversibility, as compared to compounds such as amilorde, benzamil, and phenamil. Therefore, the compounds will give a prolonged pharmacodynamic half-life on mucosal surfaces as compared to known compounds.

The present invention is also based on the discovery that certain compounds embraced by formula (I) (1) are absorbed less rapidly from mucosal surfaces, especially ocular surfaces, as compared to known compounds and (2) when absorbed from musosal surfaces after administration to the mucosal surfaces, are excreated mainly non-renally in order to minimize the chances of hyperkalemia. The present invention is also based on the discovery that certain compounds embraced by formula (I) (1) are absorbed less rapidly from mucosal surfaces, especially ocular surfaces, as compared to known compounds and (2) are converted in vivo into metabolic derivitives thereof which have reduced efficacy in blocking sodium channels as compared to the administered parent compound in order to minimize the chances of hyperkalemia.

The present invention is also based on the discovery that certain compounds embraced by formula (I) (1) are absorbed less rapidly from mucosal surfaces, especially ocular surfaces, as compared to known compounds and (2) are not converted in vivo into metabolic derivitives thereof which have enhanced or similar efficacy in blocking sodium channels as compared to the administered parent compound in order to minimize the chances of hyperkalemia The present invention is also based on the discovery that certain compounds embraced by formula (I) provide methods of treatment that take advantage of the pharmacological properties of the compounds described above.

In particular, the present invention is also based on the discovery that certain compounds embraced by formula (I) rehydrate mucosal surfaces.

In particular, the present invention is also based on the discovery that certain compounds embraced by formula (I) are useful in treating dry eye and related ocular diseases.

In the compounds represented by formula (I), X may be hydrogen, halogen, trifluoromethyl, lower alkyl, lower cycloalkyl, unsubstituted or substituted phenyl, lower alkyl-thio, phenyl-lower alkyl-thio, lower alkyl-sulfonyl, or phenyl-lower alkyl-sulfonyl. Halogen is preferred.

Examples of halogen include fluorine, chlorine, bromine, and iodine. Chlorine and bromine are the preferred halogens. Chlorine is particularly preferred. This description is applicable to the term "halogen" as used throughout the present disclosure.

As used herein, the term "lower alkyl" means an alkyl group having less than 8 carbon atoms. This range includes all specific values of carbon atoms and subranges there between, such as 1, 2, 3, 4, 5, 6, and 7 carbon atoms. The term "alkyl" embraces all types of such groups, e.g., linear, branched, and cyclic alkyl groups. This description is applicable to the term "lower alkyl" as used throughout the present disclosure. Examples of suitable lower alkyl groups include methyl, ethyl, propyl, cyclopropyl, butyl, isobutyl, etc.

Substituents for the phenyl group include halogens. Particularly preferred halogen substituents are chlorine and bromine.

Y may be hydrogen, hydroxyl, mercapto, lower alkoxy, lower alkyl-thio, halogen, lower alkyl, lower cycloalkyl, mononuclear aryl, or —N($R^2$)$_2$. The alkyl moiety of the lower alkoxy groups is the same as described above. Examples of mononuclear aryl include phenyl groups. The phenyl group may be unsubstituted or substituted as described above. The preferred identity of Y is —N($R^2$)$_2$. Particularly preferred are such compounds where each $R^2$ is hydrogen.

$R^1$ may be hydrogen or lower alkyl. Hydrogen is preferred for $R^1$.

Each $R^2$ may be, independently, —$R^7$, —(CH$_2$)$_m$—OR$^8$, —(CH$_2$)$_m$—NR$^7$R$^{10}$, —(CH$_2$)$_n$(CHOR$^8$)(CHOR$^8$)$_n$—CH$_2$OR$^8$, —(CH$_2$CH$_2$O)$_m$—R$^8$, —(CH$_2$CH$_2$O)$_m$—CH$_2$CH$_2$NR$^7$R$^{10}$, —(CH$_2$)$_n$—C(=O)NR$^7$R$^{10}$, —(CH$_2$)$_n$—(Z)$_g$—R$^7$, —(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, or

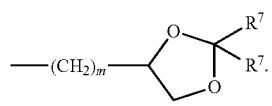

Hydrogen and lower alkyl, particularly C$_1$-C$_3$ alkyl, are preferred for $R^2$. Hydrogen is particularly preferred.

$R^3$ and $R^4$ may be, independently, hydrogen, lower alkyl, hydroxyl-lower alkyl, phenyl, (phenyl)-lower alkyl, (halophenyl)-lower alkyl, ((lower-alkyl)phenyl)-lower-alkyl), (lower-alkoxyphenyl)-lower alkyl, (naphthyl)-lower alkyl, (pyridyl)-lower alkyl or a group represented by —(C(R$^L$)$_2$)$_o$-x-(C(R$^L$)$_2$)$_p$A$^1$ or —(C(R$^L$)$_2$)$_o$-x-(C(R$^L$)$_2$)$_p$A$^2$, provided that at least one of $R^3$ and $R^4$ is a group represented by —(C(R$^L$)$_2$)$_o$-x-(C(R$^L$)$_2$)$_p$A$^1$ or —(C(R$^L$)$_2$)$_o$-x-(C(R$^L$)$_2$)$_p$A$^2$.

Preferred compounds are those where one of $R^3$ and $R^4$ is hydrogen and the other is represented by —(C(R$^L$)$_2$)$_o$-x-(C(R$^L$)$_2$)$_p$A$^1$ or —(C(R$^L$)$_2$)$_o$-x-(C(R$^L$)$_2$)$_p$A$^2$. In a particularly preferred aspect one of $R^3$ and $R^4$ is hydrogen and the other of $R^3$ or $R^4$ is represented by —(C(R$^L$)$_2$)$_o$-x-(C(R$^L$)$_2$)$_p$A$^1$. In another particularly preferred aspect one of $R^3$ and $R^4$ is hydrogen and the other of $R^3$ or $R^4$ is represented by —(C(R$^L$)$_2$)$_o$-x-(C(R$^L$)$_2$)$_p$A$^2$.

A moiety —(C(R$^L$)$_2$)$_o$-x-(C(R$^L$)$_2$)$_p$— defines an alkylene group bonded to the group A$^1$ or A$^2$. The variables o and p may each, independently, be an integer from 0 to 10, subject to the proviso that the sum of o and p in the chain is from 1 to 10. Thus, o and p may each be 0, 1, 2, 3, 4, 5, 6, 7, 8, 9, or 10. Preferably, the sum of o and p is from 2 to 6. In a particularly preferred embodiment, the sum of o and p is 4.

The linking group in the alkylene chain, x, may be, independently, O, NR$^{10}$, C(=O), CHOH, C(=N—R$^{10}$), CHNR$^7$R$^{10}$, or a single bond;

Therefore, when x is a single bond, the alkylene chain bonded to the ring is represented by the formula —(C(R$^L$)$_2$)$_{o+p}$—, in which the sum o+p is from 1 to 10.

Each R$^L$ may be, independently, —R$^7$, —(CH$_2$)$_n$—OR$^8$, —O—(CH$_2$)$_n$—OR$^8$, —(CH$_2$)$_n$—NR$^7$R$^{10}$, —O—(CH$_2$)$_m$—NR$^7$R$^{10}$, —(CH$_2$)$_n$(CHOR$^8$)(CHOR$^8$)$_n$—CH$_2$OR$^8$, —O—(CH$_2$)$_m$(CHOR$^8$)(CHOR$^8$)$_n$—CH$_2$OR$^8$, —(CH$_2$CH$_2$O)$_m$—R$^8$, —O—(CH$_2$CH$_2$O)$_m$—R$^8$, —(CH$_2$CH$_2$O)$_m$—CH$_2$CH$_2$NR$^7$R$^{10}$, —O—(CH$_2$CH$_2$O)$_m$—CH$_2$CH$_2$NR$^7$R$^{10}$, —(CH$_2$)$_n$—C(=O)NR$^7$R$^{10}$, —O—(CH$_2$)$_m$—C(=O)NR$^7$R$^{10}$, —(CH$_2$)$_n$—(Z)$_g$—R$^7$, —O—(CH$_2$)$_m$—(Z)$_g$—R$^7$, —(CH$_2$)$_n$—NR$^{10}$—CH$_2$(CHOR$^8$)(CHOR$^8$)$_n$—CH$_2$OR$^8$, —O—(CH$_2$)$_m$—NR$^{10}$—CH$_2$(CHOR$^8$)(CHOR$^8$)$_n$—CH$_2$OR$^8$, —(CH$_2$)$_n$—CO$_2$R$^7$, —O—(CH$_2$)$_m$—CO$_2$R$^7$, —OSO$_3$H, —O-glucuronide, —O-glucose,

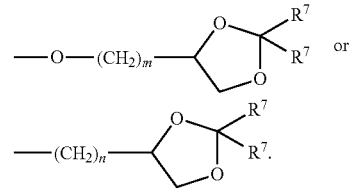

The term —O-glucuronide, unless otherwise specified, means a group represented by

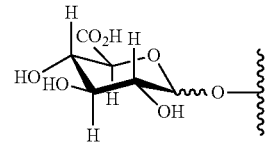

wherein the ~~o means the glycosidic linkage can be above or below the plane of the ring.

The term —O-glucose, unless otherwise specified, means a group represented by

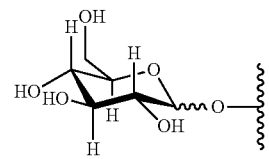

wherein the ~~o means the glycosidic linkage can be above or below the plane of the ring.

The preferred $R^L$ groups include —H, —OH, —N($R^7$)$_2$, especially where each $R^7$ is hydrogen.

In the alkylene chain in —(C($R^L$)$_2$)$_o$-x-(C($R^L$)$_2$)$_p$$A^1$ or —(C($R^L$)$_2$)$_o$-x-(C($R^L$)$_2$)$_p$$A^2$, it is preferred that when one $R^L$ group bonded to a carbon atoms is other than hydrogen, then the other $R^L$ bonded to that carbon atom is hydrogen, i.e., the formula —CHR$^L$—. It is also preferred that at most two $R^L$ groups in an alkylene chain are other than hydrogen, wherein the other $R^L$ groups in the chain are hydrogens. Even more preferably, only one $R^L$ group in an alkylene chain is other than hydrogen, wherein the other $R^L$ groups in the chain are hydrogens. In these embodiments, it is preferable that x is a single bond.

In another particular embodiment of the invention, all of the $R^L$ groups in the alkylene chain are hydrogen. In these embodiments, the alkylene chain is represented by the formula —(CH$_2$)$_o$-x-(CH$_2$)$_p$—.

$A^1$ is a $C_6$-$C_{15}$-membered aromatic carbocycle substituted with at least one $R^5$ and the remaining substituents are $R^6$. The term aromatic is well known term of chemical art and designates conjugated systems of 4n'+2 electrons that are within a ring system, that is with 6, 10, 14, etc. π-electrons wherein, according to the rule of Huckel, n' is 1, 2, 3, etc. The 4n'+2 electrons may be in any size ring including those with partial saturation so long as the electrons are conjugated. For instance, but not by way of limitation, 5H-cyclohepta-1,3,5-triene, benzene, naphthalene, 1,2,3,4-tetrahydronaphthalene etc. would all be considered aromatic.

The $C_6$-$C_{15}$ aromatic carbocycle may be monocyclic, bicyclic, or tricyclic and may include partially saturated rings. Non-limiting examples of these aromatic carbocycles comprise benzene, 5H-cyclohepta-1,3,5-triene, naphthalene, phenanthrene, azulene, anthracene, 1,2,3,4-tetrahydronapthalene, 1,2-dihydronapthalene, indene, 5H-dibenzo[a,d]cycloheptene, etc.

The $C_6$-$C_{15}$ aromatic carbocycle may be attached to the —(C($R^L$)$_2$)$_o$-x-(C($R^L$)$_2$)$_p$-moiety through any ring carbon atom as appropriate, unless otherwise specified. Therefore, when partially saturated bicyclic aromatic is 1,2-dihydronapthalene, it may be 1,2-dihydronapthalen-1-yl, 1,2-dihydronapthalen-3-yl, 1,2-dihydronapthalen-5-yl, etc. In a preferred embodiment $A^1$ is phenyl, indenyl, napthalenyl, 1,2-dihydronapthalenyl, 1,2,3,4-tetrahydronapthalenyl, anthracenyl, fluorenyl, phenanthrenyl, azulenyl, cyclohepta-1,3,5-trienyl or 5H-dibenzo[a,d]cycloheptenyl. In another preferred embodiment, $A^1$ is napthalen-1-yl. In another preferred embodiment, $A^1$ is napthalen-2-yl.

In another preferred embodiment, $A^1$ is

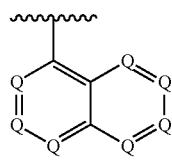

wherein each Q is, independently, C—H, C—$R^5$, or C—$R^6$, with the proviso that at least one Q is C—$R^5$. Therefore, Q may be 1, 2, 3, 4, 5, or 6 C—H. Therefore, Q may be 1, 2, 3, 4, 5, or 6 C—$R^6$. In a particularly preferred embodiment, each $R^6$ is H.

In another preferred embodiment, $A^1$ is

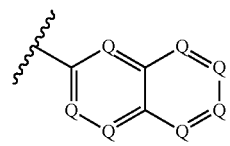

wherein each Q is, independently, C—H, C—$R^5$, C—$R^6$, with the proviso that at least one Q is C—$R^5$. Therefore, Q may be 1, 2, 3, 4, 5, or 6 C—H. Therefore, Q may be 1, 2, 3, 4, 5, or 6 C—$R^6$. In a particularly preferred embodiment, each $R^6$ is H.

In another preferred embodiment, $A^1$ is

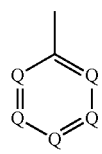

wherein each Q is, independently, C—H, C—$R^5$, or C—$R^6$, with the proviso that at least one Q is C—$R^5$. Therefore, Q may be 1, 2, 3, or 4 C—H. Therefore, Q may be 1, 2, 3, or 4 C—$R^6$. In a particularly preferred embodiment, each $R^6$ is H.

In a particularly preferred embodiment, $A^1$ is

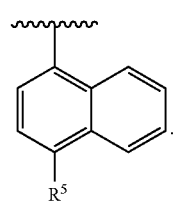

In another particularly preferred embodiment, $A^1$ is

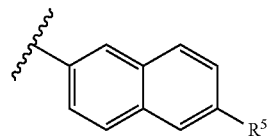

In another particularly preferred embodiment, $A^1$ is

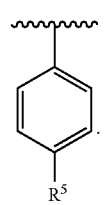

$A^2$ is a six to fifteen-membered aromatic heterocycle substituted with at least one $R^5$ and the remaining substituents are $R^6$ wherein the aromatic heterocycle comprises 1-4 heteroatoms selected from the group consisting of O, N, and S.

The six to fifteen-membered aromatic heterocycle may be monocyclic, bicyclic, or tricyclic and may include partially saturated rings. Non limiting examples of these aromatic heterocycles include pyridine, pyrazine, triazine, 1H-azepine, benzo[b]furan, benzo[b]thiophene, isobenzofuran, isobenzothiophene, 2,3-dihydrobenzo[b]furan, benzo[b] thiophene, 2,3-dihydrobenzo[b]thiophene, indolizine, indole, isoindole benzoxazole, benzimidazole, indazole, benzisoxazole, benzisothizole, benzopyrazole, benzoxadiazole, benzothiadiazole, benzotriazole, purine, quinoline, 1,2,3,4-tetrahydroquinoline, 3,4-dihydro-2H-chromene, 3,4-dihydro-2H-thiochromene, isoquinoline, cinnoline, quinolizine, phthalazine, quinoxaline, quinazoline, naphthiridine, pteridine, benzopyrane, pyrrolopyridine, pyrrolopyrazine, imidazopyrdine, pyrrolopyrazine, thienopyrazine, furopyrazine, isothiazolopyrazine, thiazolopyrazine, isoxazolopyrazine, oxazolopyrazine, pyrazolopyrazine, imidazopyrazine, pyrrolopyrimidine, thienopyrimidine, furopyrimidine, isothiazolopyrimidine, thiazolopyrimidine, isoxazolopyrimidine, oxazolopyrimidine, pyrazolopyrimidine, imidazopyrimidine, pyrrolopyridazine, thienopyridazine, furopyridazine, isothiazolopyridazine, thiazolopyridazine, oxazolopyridazine, thiadiazolopyrazine, oxadiazolopyrimidine, thiadiazolopyrimidine, oxadiazolopyridazine, thiazolopyridazine, imidazooxazole, imidazothiazole, imidazoimidazole, isoxazolotriazine, isothiazolotriazine, oxazolotriazine, thiazolotriazine, carbazole, acridine, phenazine, phenothiazine, phenooxazine, and 5H-dibenz[b,f] azepine, 10,11-dihydro-5H-dibenz[b,f]azepine, etc.

The six to fifteen-membered aromatic heterocycle may be attached to the —$(C(R^L)_2)_o$-x-$(C(R^L)_2)_p$— moiety through any ring carbon atom or ring nitrogen atom so long as a quanternary nitrogen atom is not formed by the attachment. Therefore, when partially saturated aromatic heterocycle is 1H-azepine, it may be 1H-azepin-1-yl, 1H-azepin-2-yl, 1H-azepin-3-yl, etc. Preferred aromatic heterocycles are indolizinyl, indolyl, isoindolyl, indolinyl, benzo[b]furanyl, 2,3-dihydrobenzo[b]furanyl, benzo[b]thiophenyl, 2,3-dihydrobenzo[b]thiophenyl, indazolyl, benzimidazolyl, benzthiazolyl, purinyl, quinolinyl, 1,2,3,4-tetrahydroquinolinyl, 3,4-dihydro-2H-chromenyl, 3,4-dihydro-2H-thiochromenyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, dibenzofuranyl, dibenzothiophenyl, 1H-azepinyl, 5H-dibenz[b,f]azepinyl, are 10,11-dihydro-5H-dibenz[b,f]azepinyl.

In another preferred embodiment, $A^2$ is

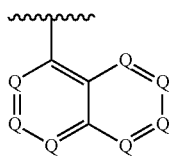

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. Therefore, in any one ring, each Q may be 1, 2, or 3 nitrogen atoms. In a preferred embodiment, only one Q in each ring is nitrogen. In another preferred embodiment, only a single Q is nitrogen. Optionally, 1, 2, 3, 4, or 5 Q may be C—$R^6$. Optionally, Q may be 1, 2, 3, 4, or 5 C—H. In a particularly preferred embodiment, each $R^6$ is H.

In another preferred embodiment, $A^2$ is

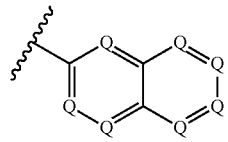

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. Therefore, in any one ring, each Q may be 1, 2, or 3 nitrogen atoms. In a preferred embodiment, only one Q in each ring is nitrogen. In another preferred embodiment, only a single Q is nitrogen. Optionally, 1, 2, 3, 4, or 5 Q may be C—H. Optionally, 1, 2, 3, 4, or 5 Q may be C—$R^6$. In a particularly preferred embodiment, each $R^6$ is H.

In another preferred embodiment, $A^2$ is

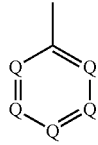

wherein each Q is, independently, C—H, C—$R^5$, C—$R^6$, or a nitrogen atom, with the proviso that at least one Q is nitrogen and one Q is C—$R^5$, and at most three Q in a ring are nitrogen atoms. Therefore, each Q may be 1, 2, or 3 nitrogen atoms. In a preferred embodiment, only one Q in each ring is nitrogen. In another preferred embodiment, only a single Q is nitrogen. Optionally, 1, 2, or 3, Q may be C—$R^6$. Optionally, Q may be 1, 2, or 3 C—H. In a particularly preferred embodiment, each $R^6$ is H.

Each $R^5$ is, independently, -Link-$(CH_2)_m$-CAP, -Link-$(CH_2)_n(CHOR^8)(CHOR^8)_n$-CAP, -Link-$(CH_2CH_2O)_m$—$CH_2$-CAP, -Link-$(CH_2CH_2O)_m$—$CH_2CH_2$-CAP, -Link-$(CH_2)_m$—$(Z)_g$-CAP, -Link-$(CH_2)_n(Z)_g$—$(CH_2)_m$-CAP, -Link-$(CH_2)_n$—$NR^{13}$—$CH_2(CHOR^8)(CHOR^8)_n$-CAP, -Link-$(CH_2)_n$—$(CHOR^8)_mCH_2$—$NR^{13}$—$(Z)_g$-CAP, -Link-$(CH_2)_nNR^{13}$—$(CH_2)_m(CHOR^8)_nCH_2NR^{13}$—$(Z)_g$-CAP, -Link-$(CH_2)_m$—$(Z)_g$—$(CH_2)_m$-CAP, -Link-NH—C(=O)—NH—$(CH_2)_m$-CAP, -Link-$(CH_2)_m$—C(=O)$NR^{13}$—$(CH_2)_m$-CAP, -Link-$(CH_2)_n$—$(Z)_g$—$(CH_2)_m$—$(Z)_g$-CAP, or -Link-$Z_g$—$(CH_2)_m$-Het-$(CH_2)_m$-CAP;

In a preferred embodiment, $R^5$ is -Link-$(CH_2)_m$-CAP.

In another preferred embodiment $R^5$ is one of the following:

-Link-$(CH_2)_n(CHOR^8)(CHOR^8)_n$-CAP, -Link-$(CH_2CH_2O)_m$—$CH_2$-CAP, -Link-$(CH_2CH_2O)_m$—$CH_2CH_2$-CAP, -Link-$(CH_2)_m$—$(Z)_g$-CAP, -Link-$(CH_2)_n(Z)_g$—$(CH_2)_m$-CAP In another preferred embodiment $R^5$ is one of the following: -Link-$(CH_2)_n$—$NR^{13}$—$CH_2(CHOR^8)(CHOR^8)_n$-CAP, -Link-$(CH_2)_n$—$(CHOR^8)_mCH_2$—$NR^{13}$—$(Z)_g$-CAP, -Link-$(CH_2)_nNR^{13}$—$(CH_2)_m(CHOR^8)_nCH_2NR^{13}$—$(Z)_g$-CAP, -Link-$(CH_2)_m$—$(Z)_g$—$(CH_2)_m$-CAP, -Link-NH—C(=O)—NH—$(CH_2)_m$-CAP, -Link-$(CH_2)_m$—C(=O)$NR^{13}$—$(CH_2)_m$-CAP, -Link-$(CH_2)_n$—$(Z)_g$—$(CH_2)_m$—$(Z)_g$-CAP, or -Link-$Z_g$—$(CH_2)_m$-Het-$(CH_2)_m$-CAP;

In a particularly preferred embodiment, $R^5$ is
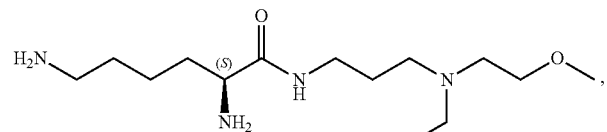
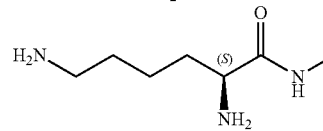
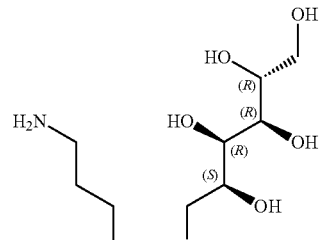
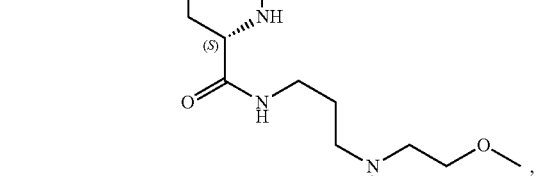
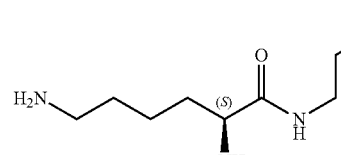
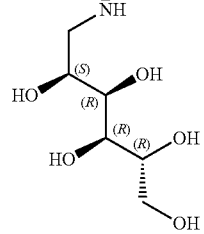
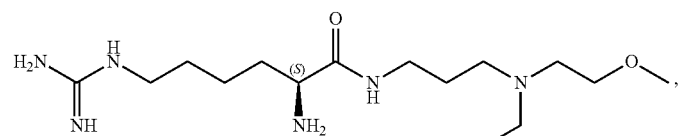
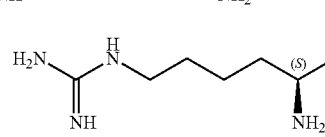
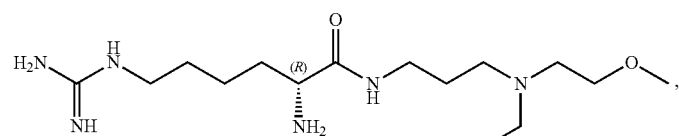
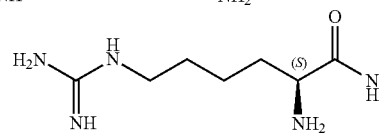

-continued
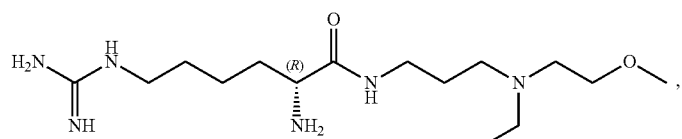
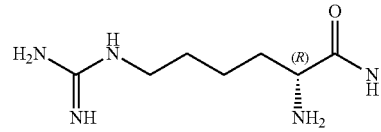
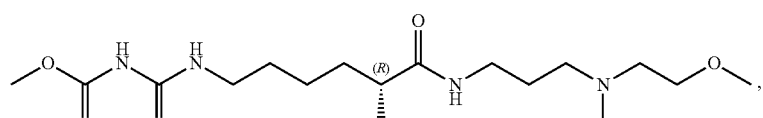
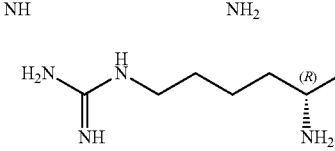
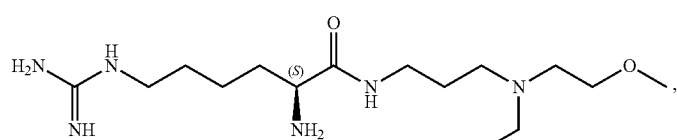
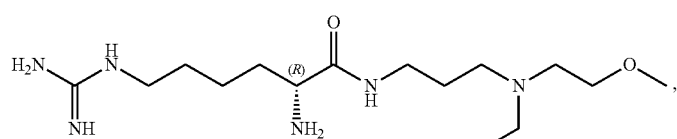
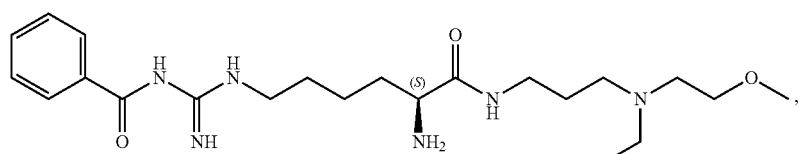
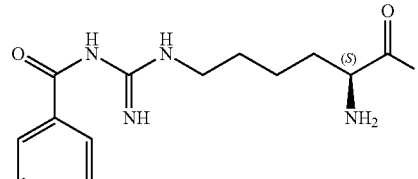
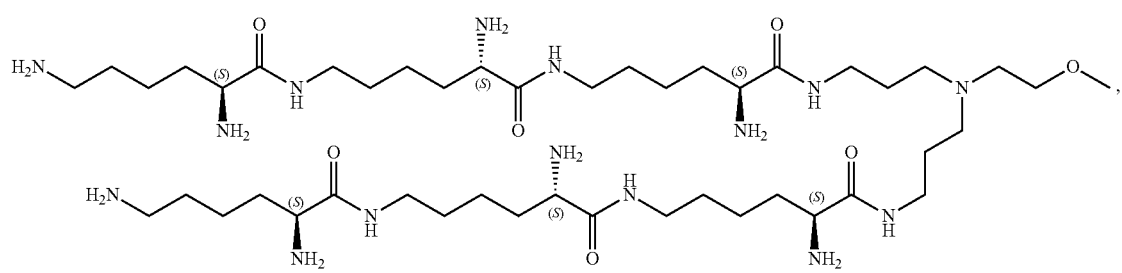

-continued
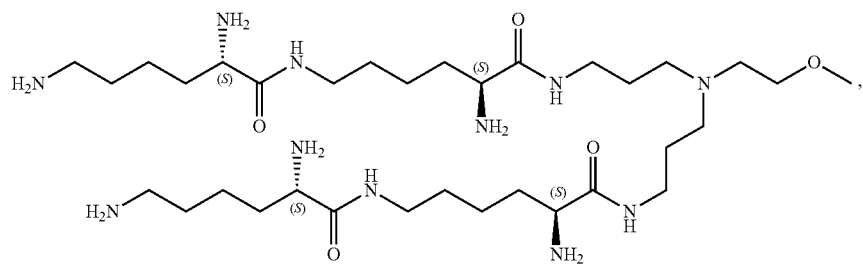
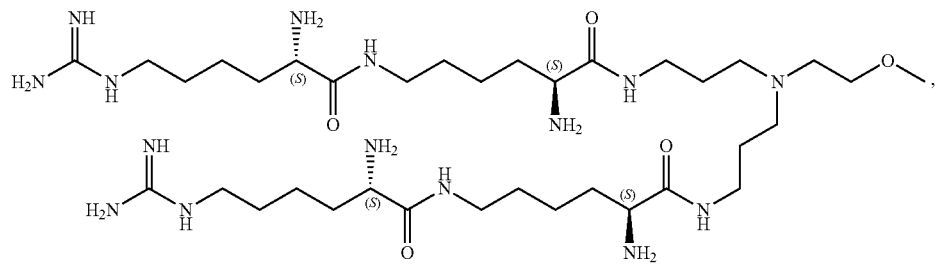
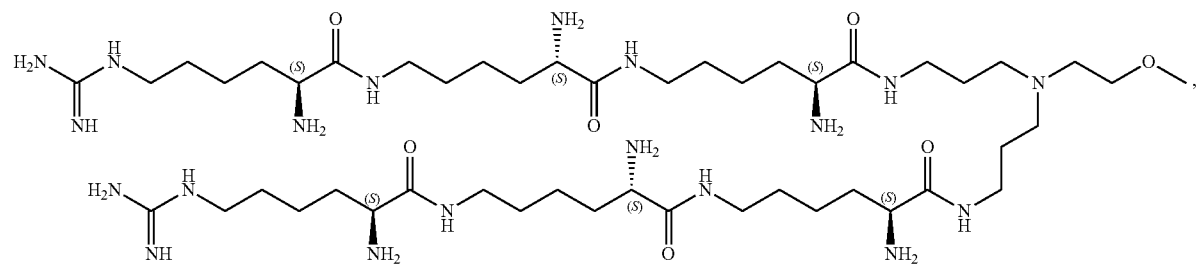
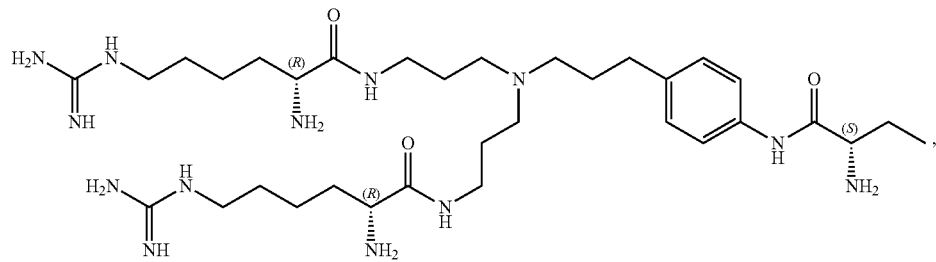
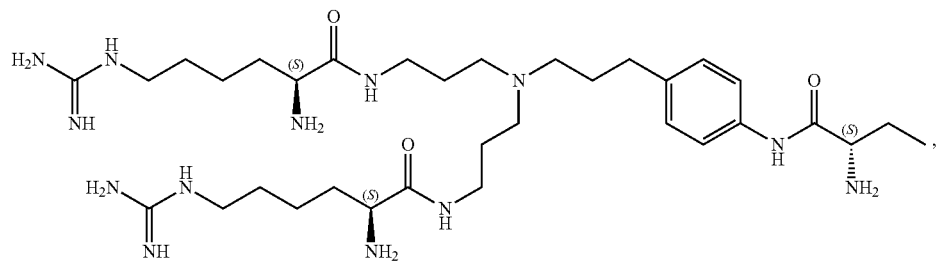

-continued
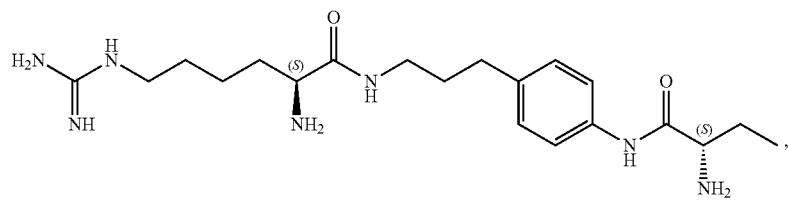
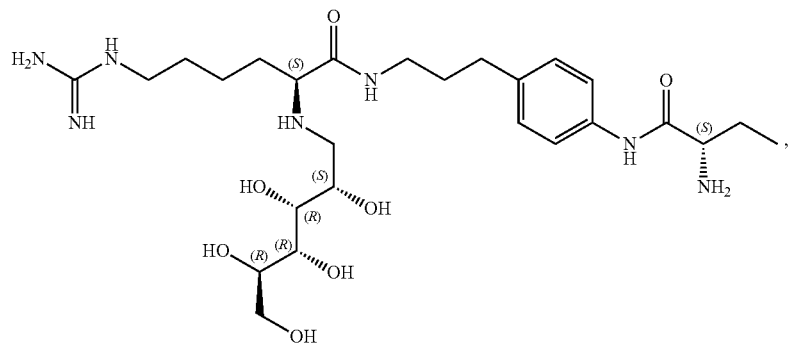
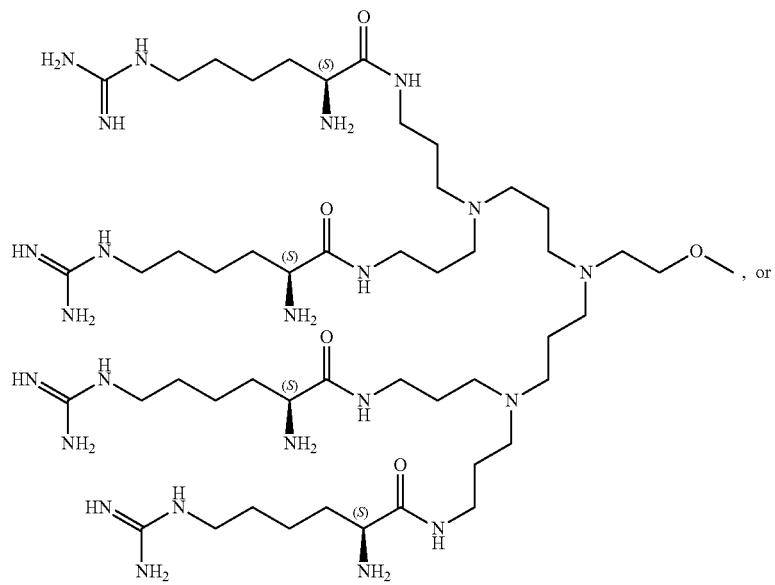

-continued

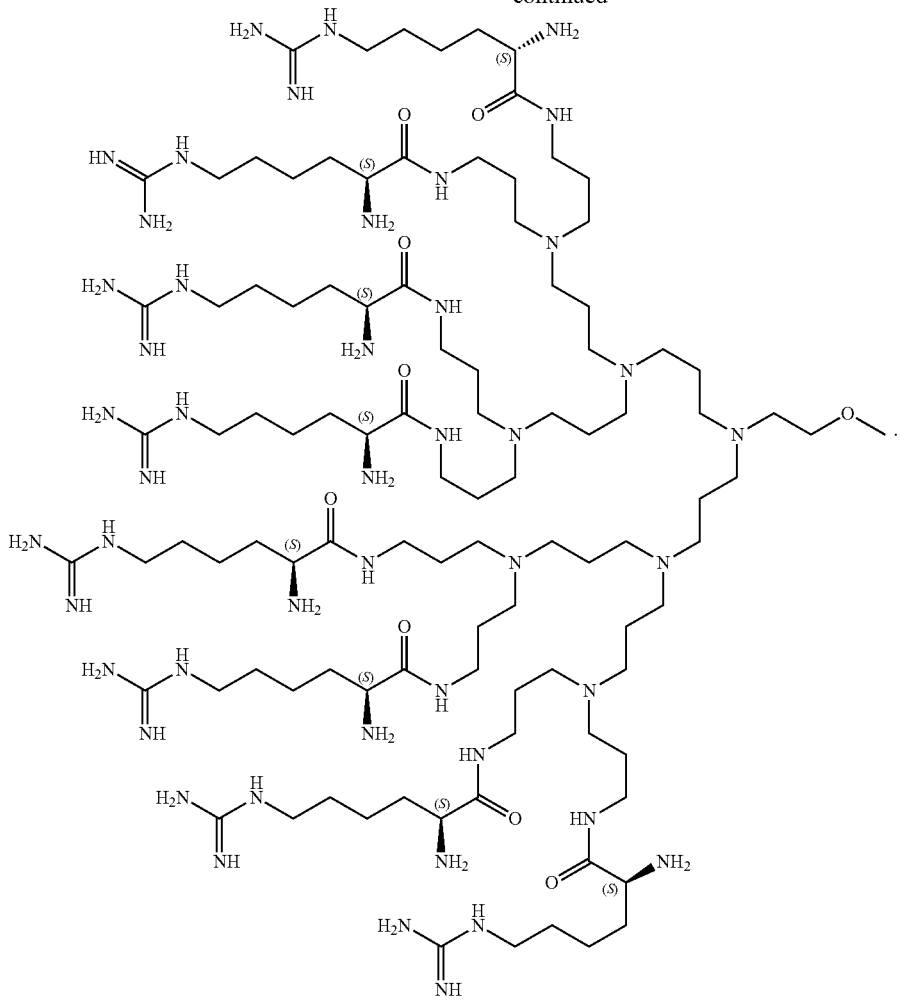

Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, $R^9$ contains a $R^{13}$ substituent. $R^{13}$ can contain an $R^{10}$ substituent and $R^{10}$ can contain a $R^9$ substituent. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, $R^9$, $R^{13}$ and $R^{10}$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, $R^9$ will occur 0 to 8 times in a given embodiment, $R^{13}$ will occur 0 to 6 times in a given embodiment and $R^{10}$ will occur 0 to 6 times in a given embodiment. Even more typically yet, $R^9$ will occur 0 to 6 times in a given embodiment, $R^{13}$ will occur 0 to 4 times in a given embodiment and $R^{10}$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Each -Het- is, independently, —N($R^7$)—), —N($R^{10}$)—, —S—, —SO—, —SO$_2$—; —O—, —SO$_2$NH—, —NHSO$_2$—, —NR$^7$CO—, —CONR$^7$—, —N($R^{13}$)—, —SO$_2$NR$^{13}$—, —NR$^{13}$CO—, or —CONR$^{13}$—. In a preferred embodiment, -Het- is —O—, —N($R^7$)—, or —N($R^{10}$)—. Most preferably, -Het- is —O—.

Each -Link- is, independently, —O—, —(CH$_2$)$_n$—, —O(CH$_2$)$_n$—, —NR$^{13}$—C(=O)—NR$^{13}$—, —NR$^{13}$—C(=O)—(CH$_2$)$_m$—, —C(=O)NR$^{13}$—(CH$_2$)$_m^-$, —(CH$_2$)$_n$—(Z)$_g$—(CH$_2$)$_n^-$, —S—, —SO—, —SO$_2$—, —SO$_2$NR$^7$—, —SO$_2$NR$^{10}$—, or -Het-. In a preferred embodiment, -Link- is —O—, —(CH$_2$)$_n$—, —NR$^{13}$—C(=O)—(CH$_2$)$_m$—, or —C(=O)NR$^{13}$—(CH$_2$)$_m^-$.

Each -CAP is, independently, each CAP is,
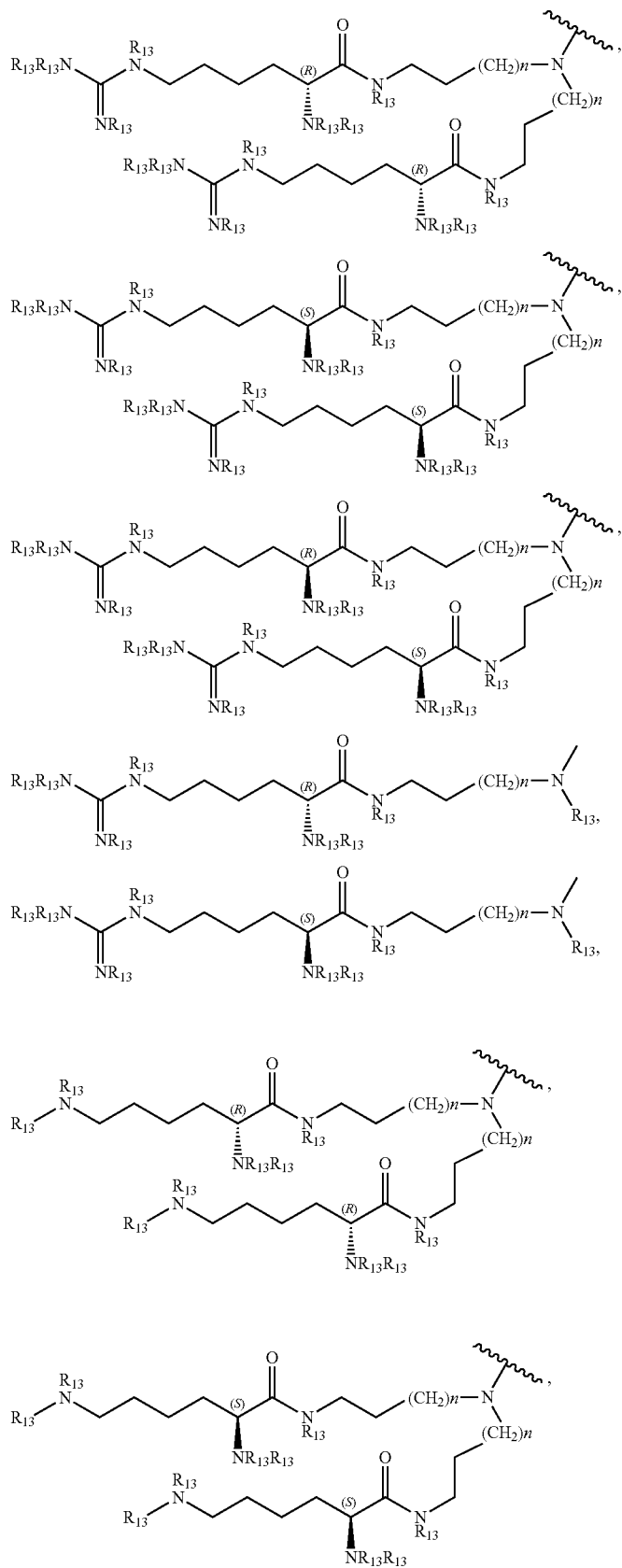

-continued
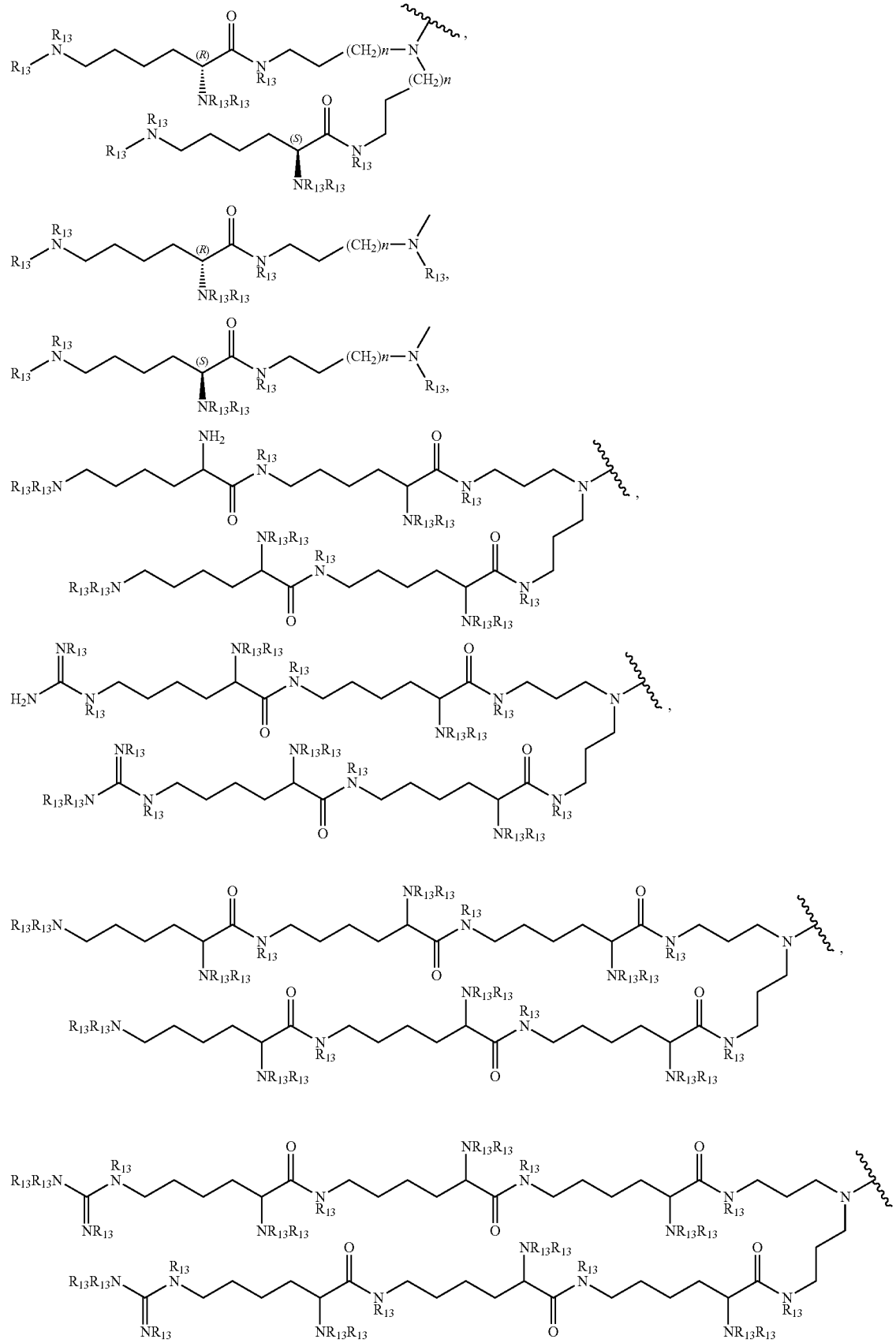

-continued
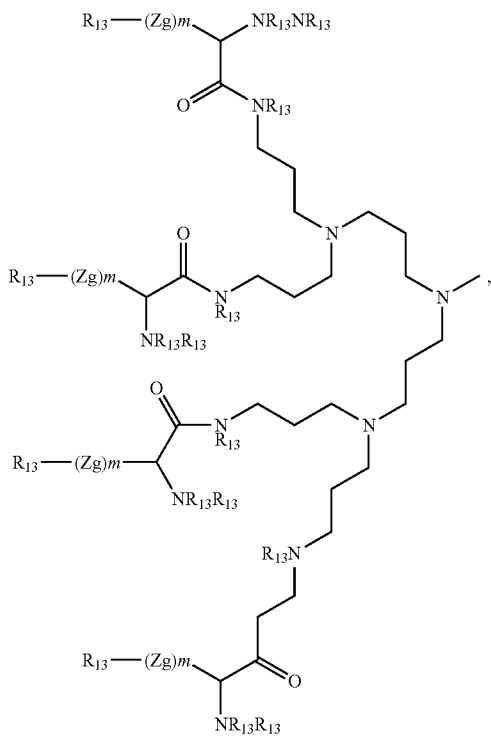
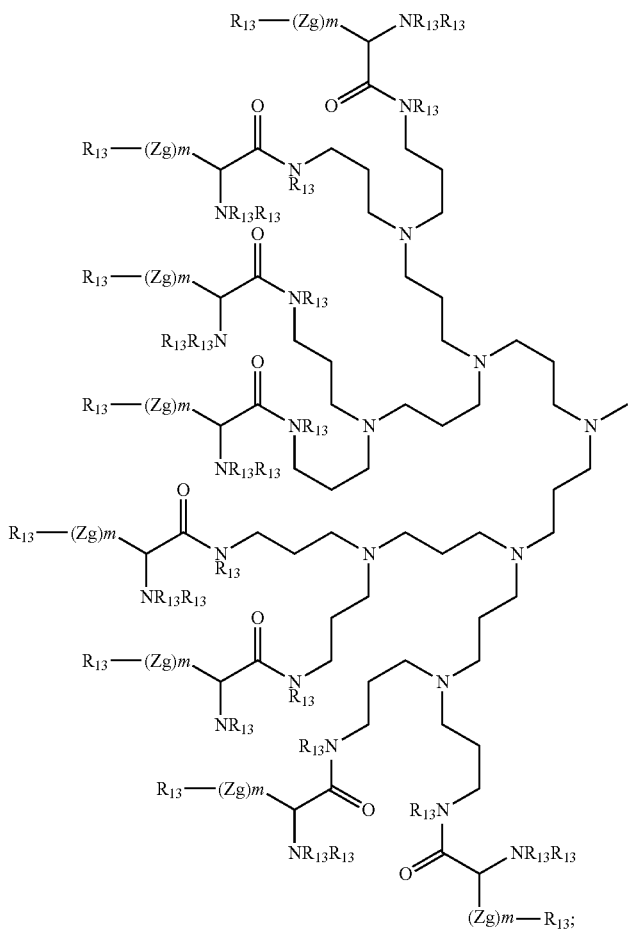

In a preferred embodiment, CAP is

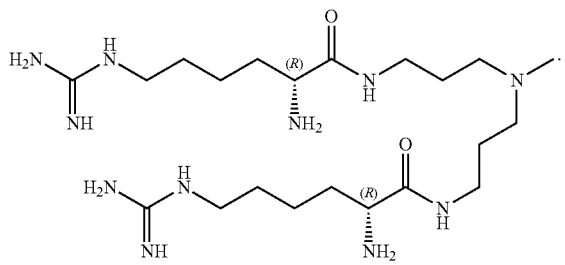

Each Ar is, independently, phenyl, substituted phenyl, wherein the substituents of the substituted phenyl are 1-3 substituents independently selected from the group consisting of OH, $OCH_3$, $NR^{13}R^{13}$, Cl, F, and $CH_3$, or heteroaryl.

Examples of heteroaryl include pyridinyl, pyrazinyl, furanyl, thienyl, tetrazolyl, thiazolidinedionyl, imidazoyl, pyrrolyl, quinolinyl, indolyl, adeninyl, pyrazolyl, thiazolyl, isoxazolyl, benzimidazolyl, purinyl, isoquinolinyl, pyridazinyl, pyrimidinyl, 1,2,3-triazinyl, 1,2,4-triazinyl, 1,3,5-triazinyl, cinnolinyl, phthalazinyl, quinazolinyl, quinoxalinyl, and pterdinyl groups.

Each W is, independently, thiazolidinedione, oxazolidinedione, heteroaryl-$C(=O)N$ $R^{13}R^{13}$, —CN, —O—C$(=S)NR^{13}R^{13}$, —$(Z)_gR^{13}$, —$CR^{10}((Z)_gR^{13})((Z)_gR^{13})$, —C(=O)OAr, —C(=O)N $R^{13}$Ar, imidazoline, tetrazole, tetrazole amide, —$SO_2NHR^{13}$, —$SO_2NH$—$C(R^{13}R^{13})$—$(Z)_g$—$R^{13}$, a cyclic sugar or oligosaccharide, a cyclic amino sugar, oligosaccharide,

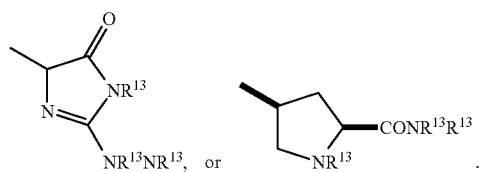

There is at least one $R^5$ on $A^1$ and $A^2$ and the remaining substituents are $R^6$. Each $R^6$ is, independently, $R^5$, —$R^7$, —$OR^{11}$, —$N(R^7)_2$, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n$(CHOR$^8$)(CHOR$^8$)$_n$—$CH_2OR^8$, —O—$(CH_2)_m$(CHOR$^8$)(CHOR$^8$)$_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C$(=O)NR^7R^{10}$, —O—$(CH_2)_m$—C$(=O)NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2$(CHOR$^8$)(CHOR$^8$)$_n$—$CH_2OR^8$, —O—$(CH_2)_m$—$NR^{10}$—$CH_2$(CHOR$^8$)(CHOR$^8$)$_n$—$CH_2OR^8$, —$(CH_2)_n$—$CO_2R^7$, —O—$(CH_2)_m$—$CO_2R^7$, —$OSO_3H$, —O-glucuronide, —O-glucose,

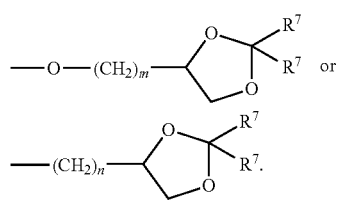

When two $R^6$ are —$OR^{11}$ and are located adjacent to each other on the aromatic carbocycle or aromatic heterocycle, the two $OR^{11}$ may form a methylenedioxy group; i.e., a group of the formula —O—$CH_2$—O—.

In addition, one or more of the $R^6$ groups can be one of the $R^5$ groups which fall within the broad definition of $R^6$ set forth above.

$R^6$ may be hydrogen. Therefore, provided that the aromatic carbocycle or aromatic heterocycle is substituted with $R^5$, the remaining $R^6$ may be hydrogen. Preferably, at most, 3 of the $R^6$ groups are other than hydrogen. More preferably, provided that the aromatic carbocycle or aromatic heterocycle is substituted with $R^5$, then $R^6$ is H.

Each g is, independently, an integer from 1 to 6. Therefore, each g may be 1, 2, 3, 4, 5, or 6.

Each m is an integer from 1 to 7. Therefore, each m may be 1, 2, 3, 4, 5, 6, or 7.

Each n is an integer from 0 to 7. Therefore, each n may be 0, 1, 2, 3, 4, 5, 6, or 7.

Each Z is, independently, —(CHOH)—, —C(=O)—, —(CHNR$^7$R$^{10}$)—, —(C=NR$^{10}$)—, —NR$^{10}$—, —(CH$_2$)$_n$—, —(CHNR$^{13}$R$^{13}$)—, —(C=NR$^{13}$)—, or —NR$^{13}$—. As designated by $(Z)_g$ in certain embodiments, Z may occur one, two, three, four, five or six times and each occurrence of Z is, independently, —(CHOH)—, —C(=O)—, —(CHNR$^7$R$^{10}$)—, —(C=NR$^{10}$)—, —(CH$_2$)$_n$—, —(CHNR$^{13}$R$^{13}$)—, —(C=NR$^{13}$)—, or —NR$^{13}$—. Therefore, by way of example and not by way of limitation, $(Z)_g$ can be —(CHOH)—(CHNR$^7$R$^{10}$)—, —(CHOH)—(CHNR$^7$R$^{10}$)—C(=O)—, —(CHOH)—(CHNR$^7$R$^{10}$)—C(=O)—(CH$_2$)$_n$—, —(CHOH)—(CHNR$^7$R$^{10}$)—C(=O)—(CH$_2$)$_n$—(CHNR$^{13}$R$^{13}$)—, —(CHOH)—(CHNR$^7$R$^{10}$)—C(=O)—(CH$_2$)$_n$—(CHNR$^{13}$R$^{13}$)—C(=O)—, and the like.

In any variable containing —CHOR$^8$— or —CH$_2$OR$^8$ groups, when any —CHOR$^8$— or —CH$_2$OR$^8$ groups are located 1,2- or 1,3- with respect to each other, the R$^8$ groups may, optionally, be taken together to form a cyclic mono- or di-substituted 1,3-dioxane or 1,3-dioxolane.

More specific examples of suitable compounds represented by formula (I) are shown in formula II below wherein $A^1$ is defined as above:

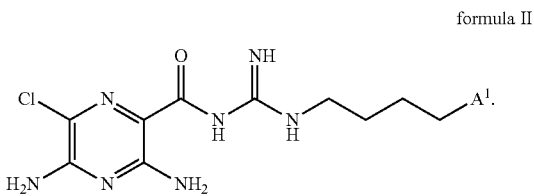

formula II

In a preferred aspect of formula II, $A^1$ is selected from phenyl, indenyl, napthalenyl, 1,2-dihydronapthalenyl, 1,2,3,4-tetrahydronapthalenyl, anthracenyl, fluorenyl, phenanthrenyl, azulenyl, cyclohepta-1,3,5-trienyl or 5H-dibenzo[a,d]cycloheptenyl.

In another preferred aspect of formula II, $A^1$ is

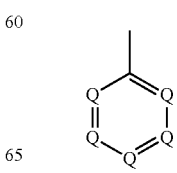

wherein each Q is, independently, C—H, C—R⁵, or C—R⁶, with the proviso that at least one Q is C—R⁵. Preferably, 4 Q are C—H. Preferably, each R⁶ is H. Preferably, R⁵ is -Link-(CH$_2$)$_n$-CAP, -Link-(CH$_2$)$_n$(CHOR⁸)(CHOR⁸)$_n$-CAP, -Link-(CH$_2$CH$_2$O)$_m$—CH$_2$-CAP, -Link-(CH$_2$CH$_2$O)$_m$—CH$_2$CH$_2$-CAP, -Link-(CH$_2$)$_m$—(Z)$_g$-CAP, -Link-(CH$_2$)$_n$(Z)$_g$—(CH$_2$)$_m$-CAP, -Link-(CH$_2$)$_n$—NR¹³—CH$_2$(CHOR⁸)(CHOR⁸)$_n$-CAP, -Link-(CH$_2$)$_n$—(CHOR⁸)$_m$CH$_2$—NR¹³—(Z)$_g$-CAP, -Link-(CH$_2$)$_n$NR¹³—(CH$_2$)$_m$(CHOR⁸)$_n$CH$_2$NR¹³—(Z)$_g$-CAP, -Link-(CH$_2$)$_m$—(Z)$_g$—(CH$_2$)$_m$-CAP, -Link-NH—C(═O)—NH—(CH$_2$)$_m$-CAP, -Link-(CH$_2$)$_m$—C(═O)NR¹³—(CH$_2$)$_m$-CAP, -Link-(CH$_2$)$_n$—(Z)$_g$—(CH$_2$)$_m$—(Z)$_g$-CAP, or -Link-Z$_g$—(CH$_2$)$_m$-Het-(CH$_2$)$_m$-CAP;

Most preferably, R⁵ is

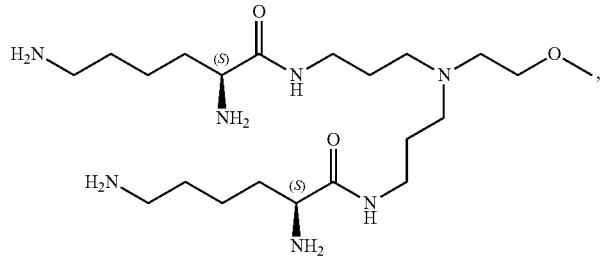

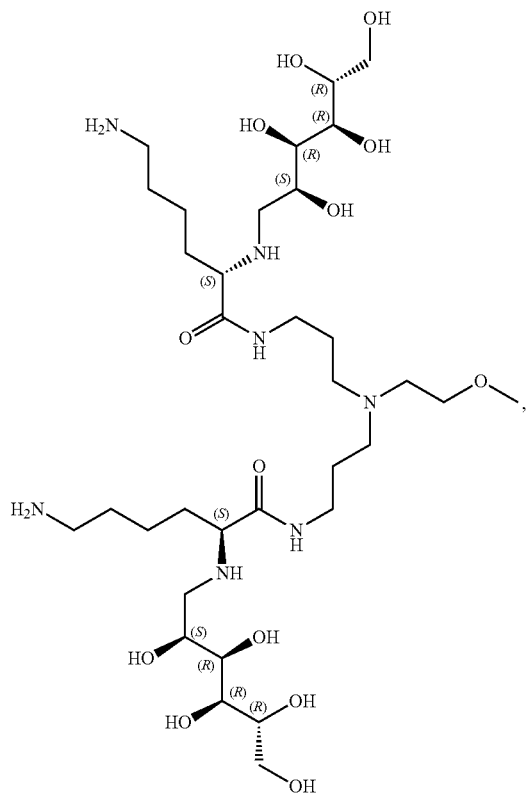

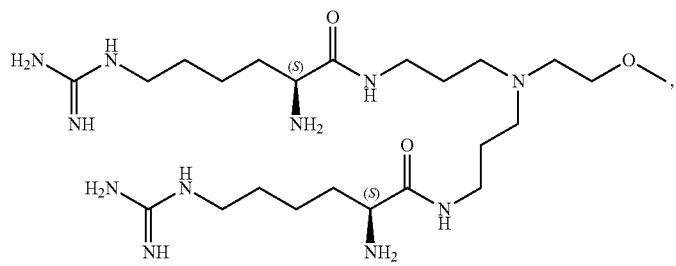

-continued
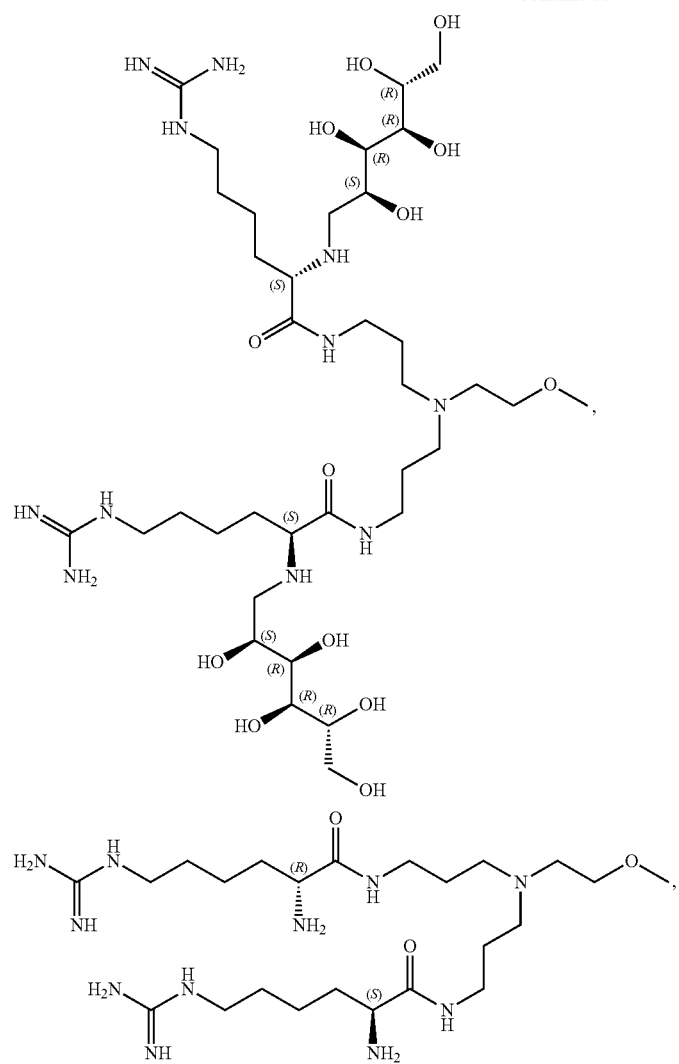
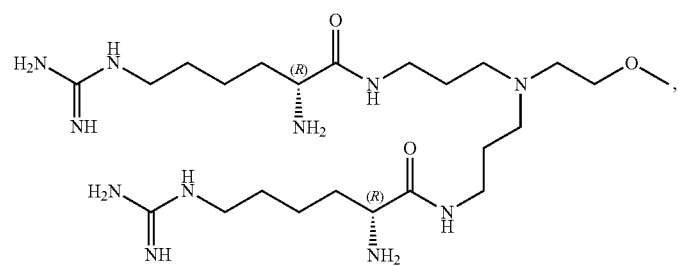
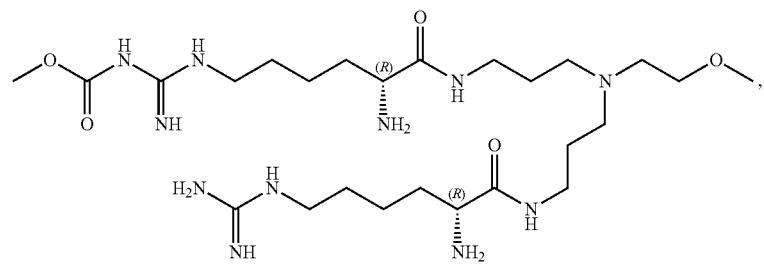

-continued
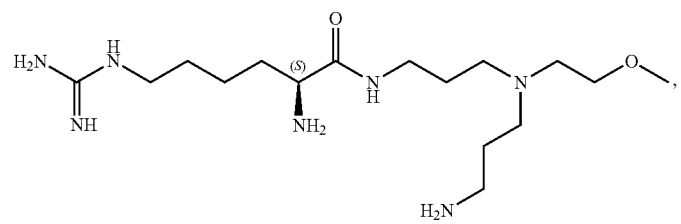
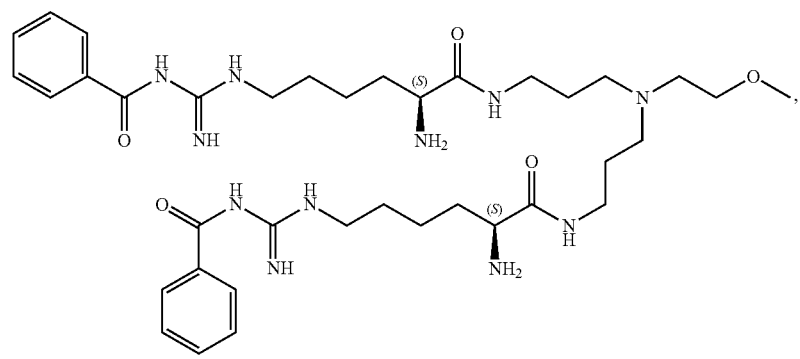
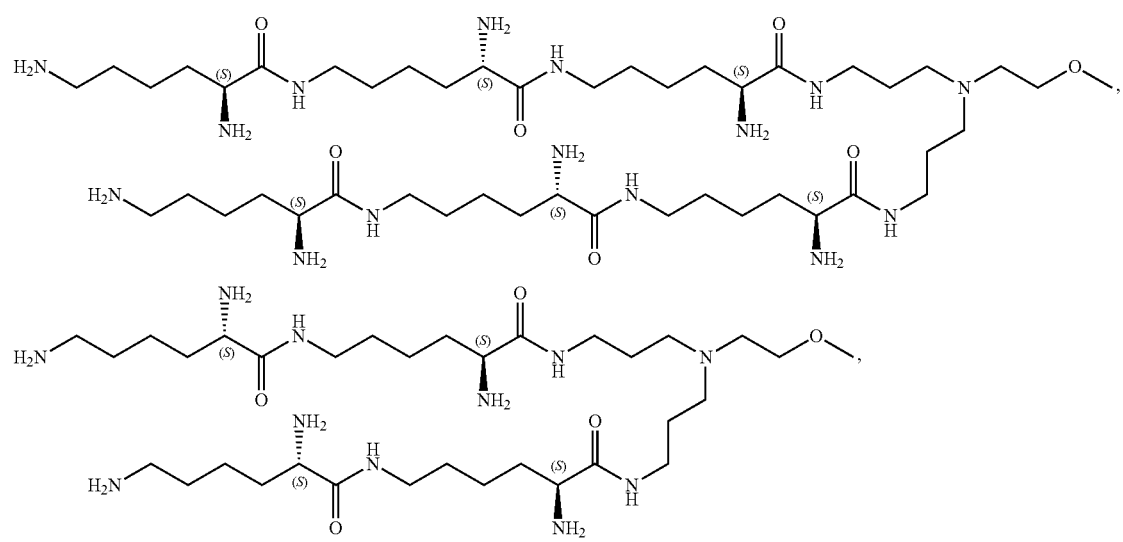
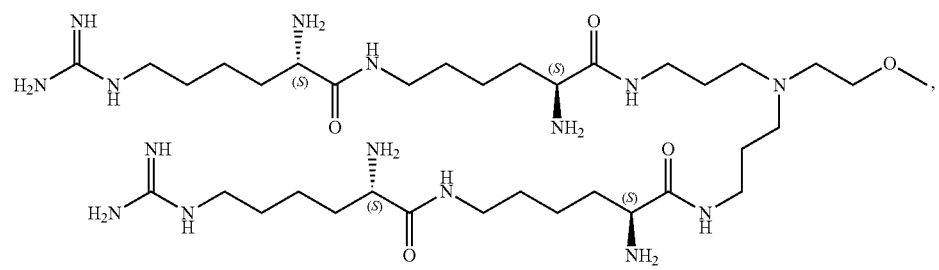
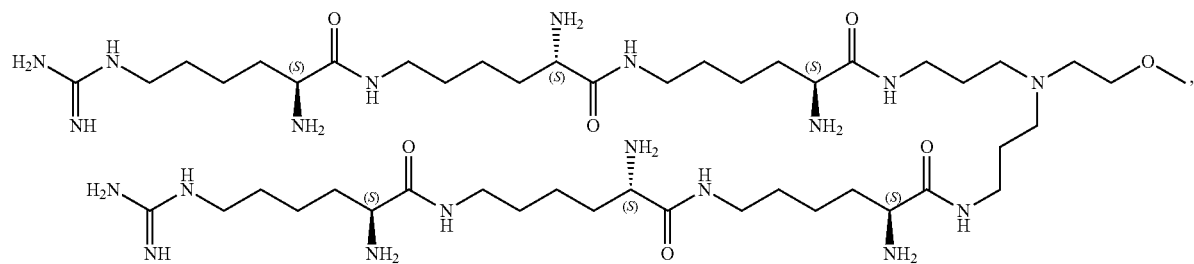

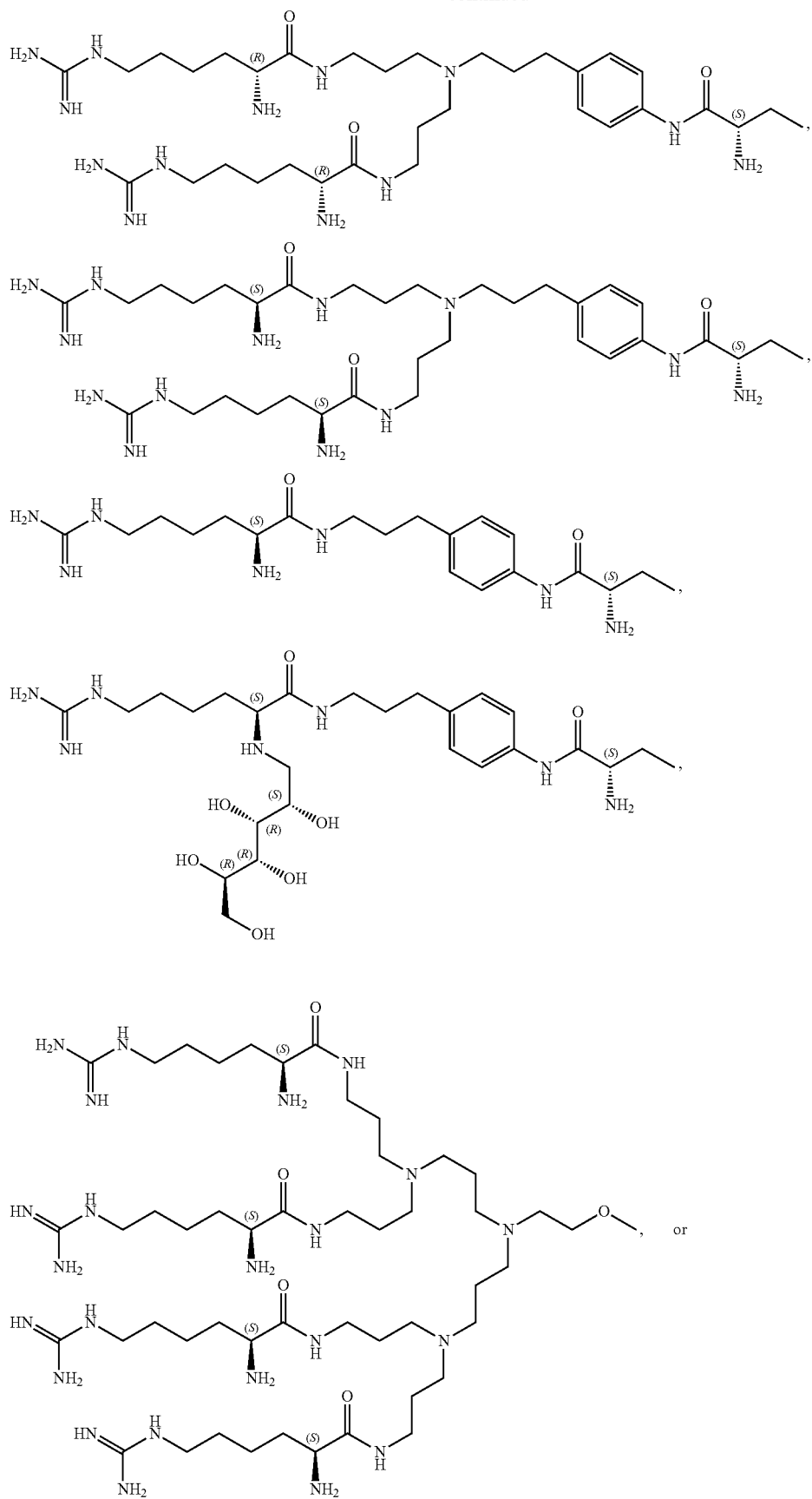

-continued

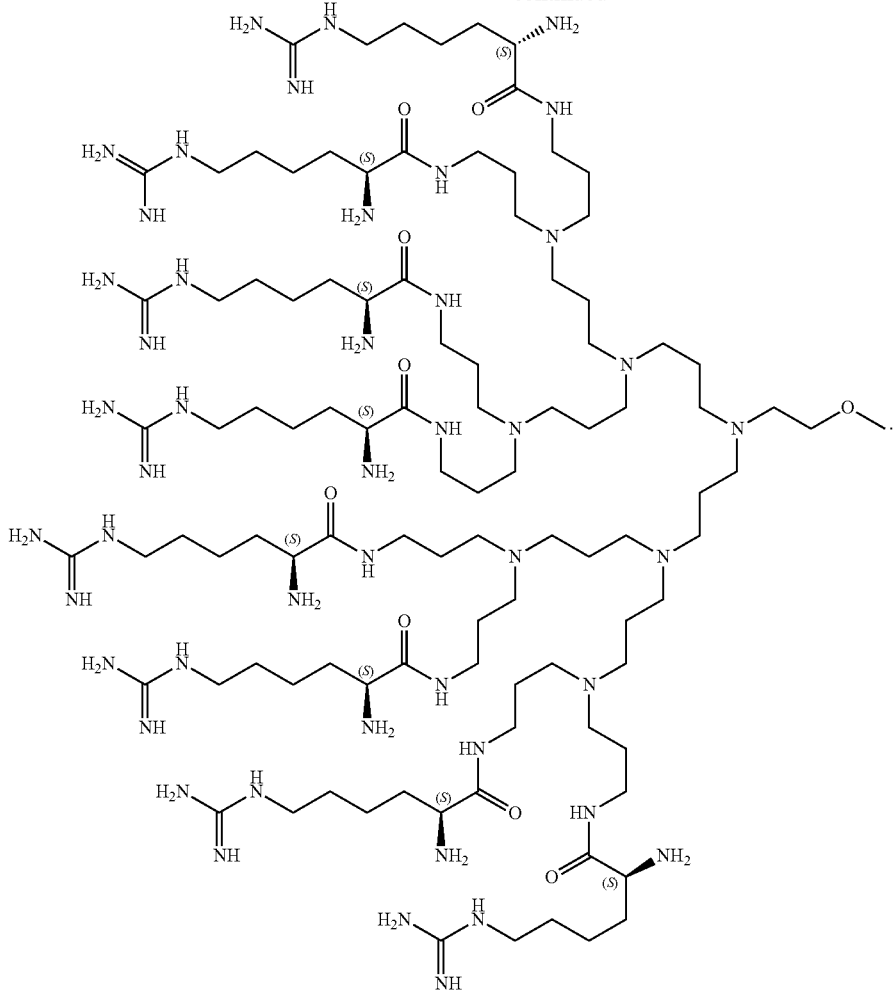

and four Q are C—H.
In another preferred aspect of formula II, $A^1$ is

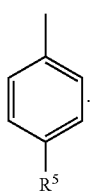

Preferably, $R^5$ is -Link-$(CH_2)_m$-CAP, -Link-$(CH_2)_n(CHOR^8)$ $(CHOR^8)_n$-CAP, -Link-$(CH_2CH_2O)_m$—$CH_2$-CAP, -Link-$(CH_2CH_2O)_m$—$CH_2CH_2$-CAP, -Link-$(CH_2)_m$—$(Z)_g$-CAP, -Link-$(CH_2)_n(Z)_g$—$(CH_2)_m$-CAP, -Link-$(CH_2)_n$—$NR^{13}$—$CH_2(CHOR^8)(CHOR^8)_n$-CAP, -Link-$(CH_2)_n$—$(CHOR^8)_mCH_2$—$NR^{13}$—$(Z)_g$-CAP, -Link-$(CH_2)_nNR^{13}$—$(CH_2)_m(CHOR^8)_nCH_2NR^{13}$—$(Z)_g$-CAP, -Link-$(CH_2)_m$—$(Z)_g$—$(CH_2)_m$-CAP, -Link-NH—C(=O)—NH—$(CH_2)_m$-CAP, -Link-$(CH_2)_m$—C(=O)$NR^{13}$—$(CH_2)_m$-CAP, -Link-$(CH_2)_n(Z)_g$—$(CH_2)_m$—$(Z)_g$-CAP, or -Link-$Z_g$—$(CH_2)_m$-Het-$(CH_2)_m$-CAP;

Most preferably, $R^5$ is

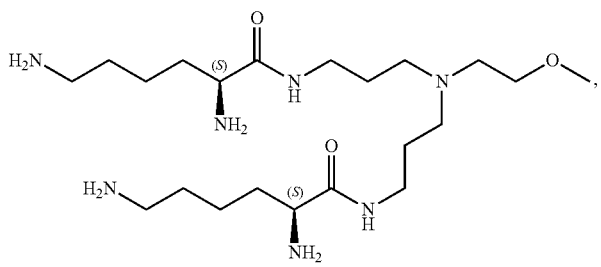

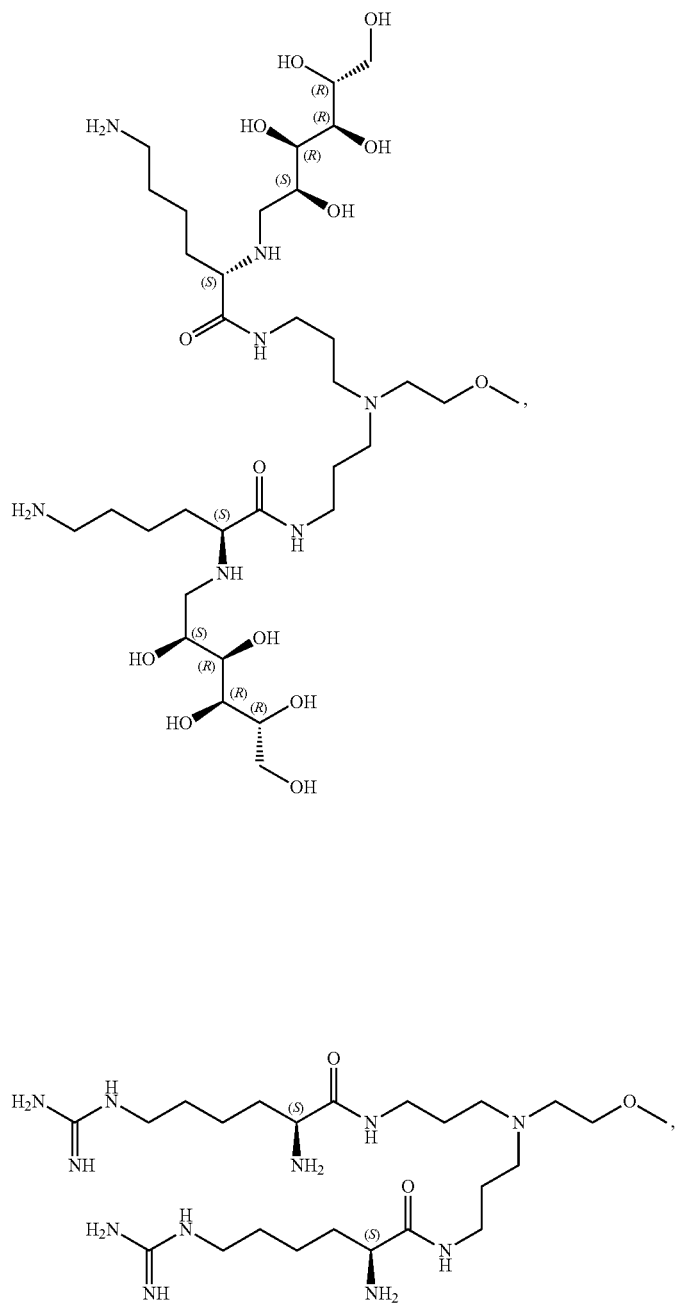

-continued
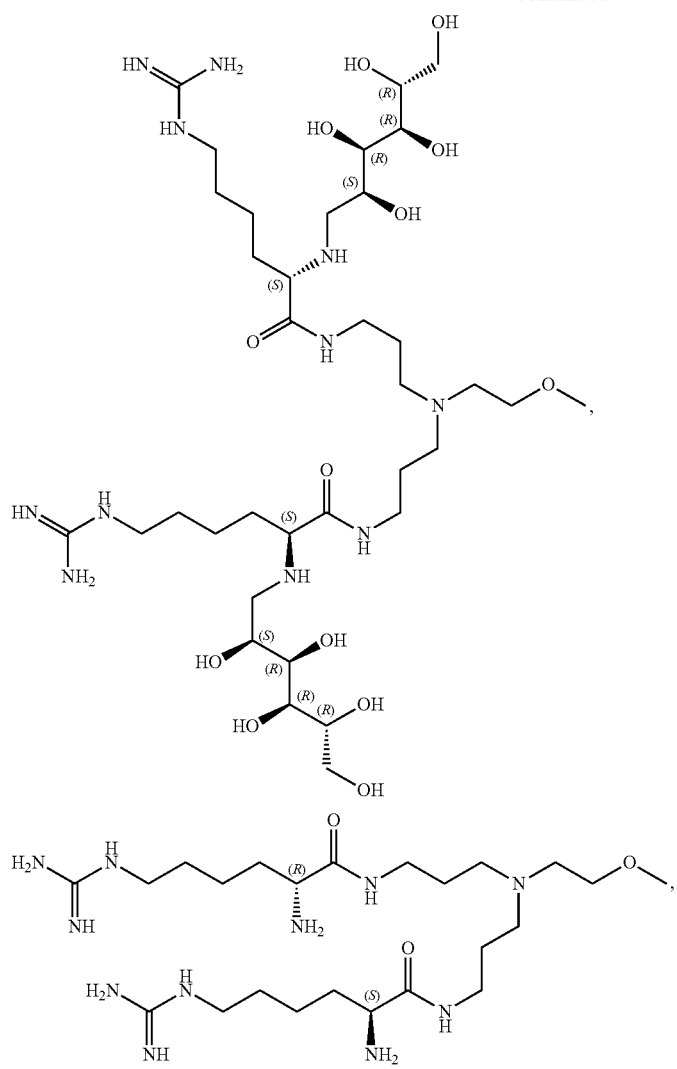
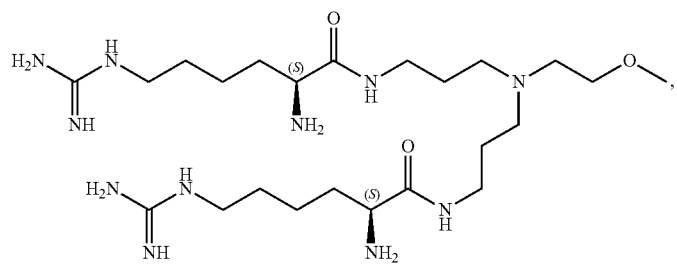
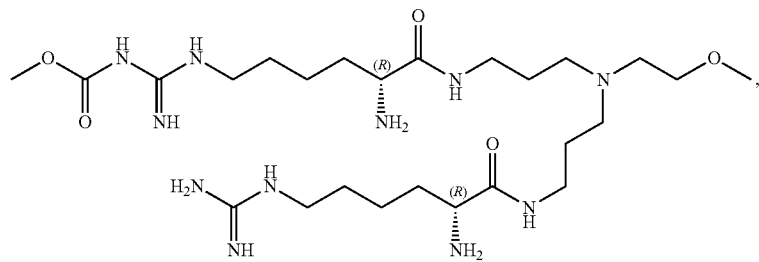

-continued
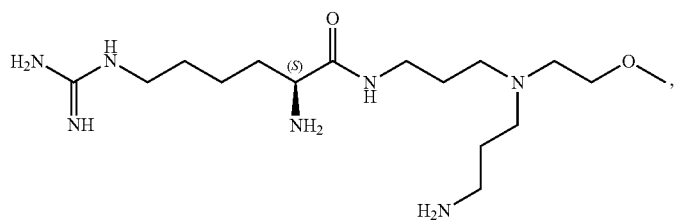
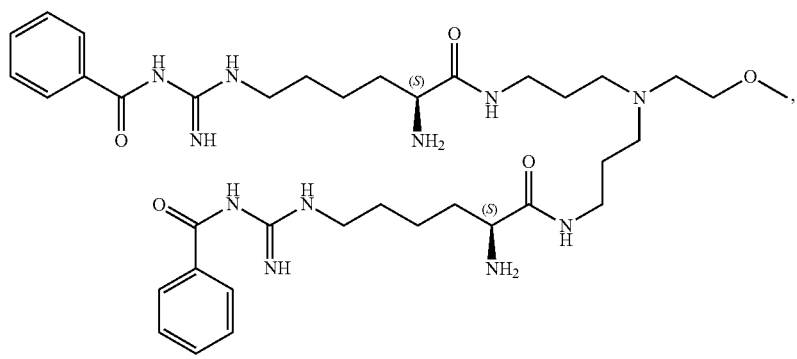
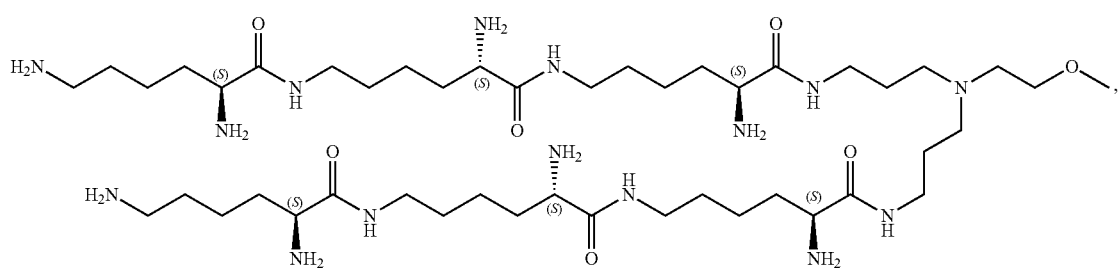
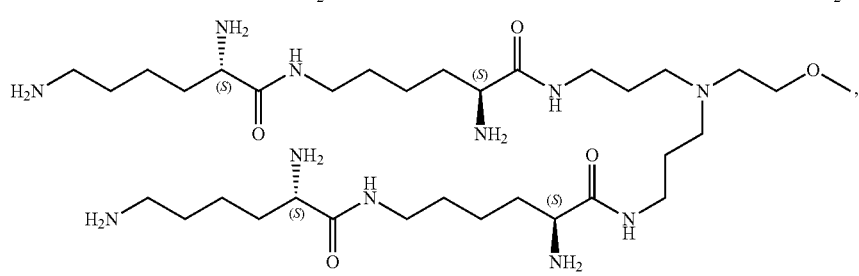
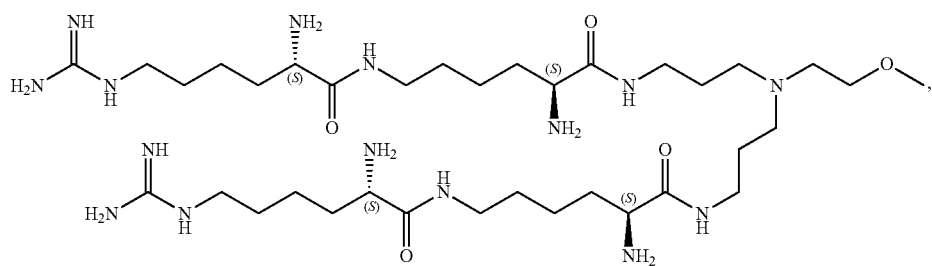
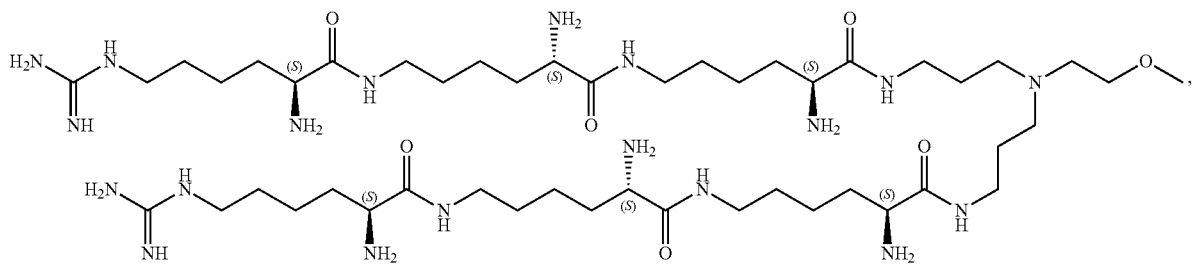

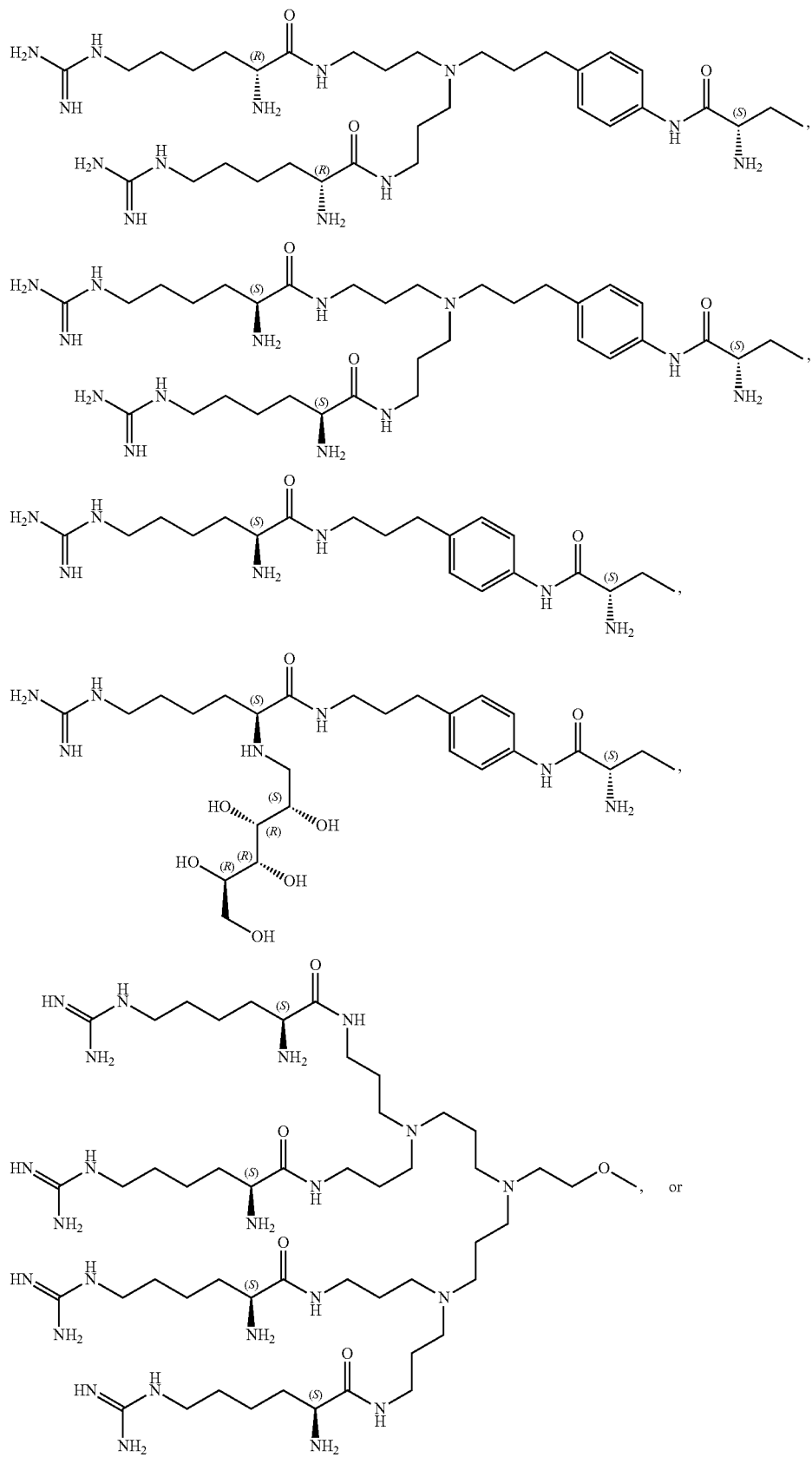

-continued
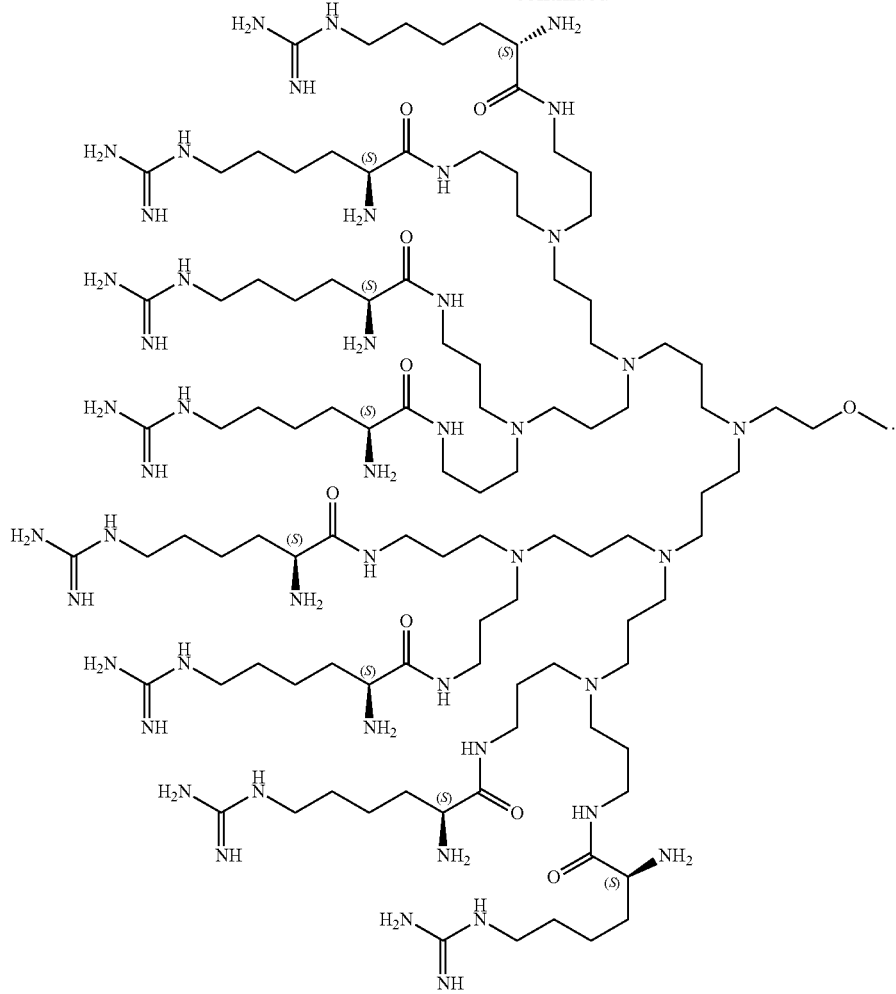
In a particularly preferred embodiment, the compounds of formula I, formula II, or formula III are:
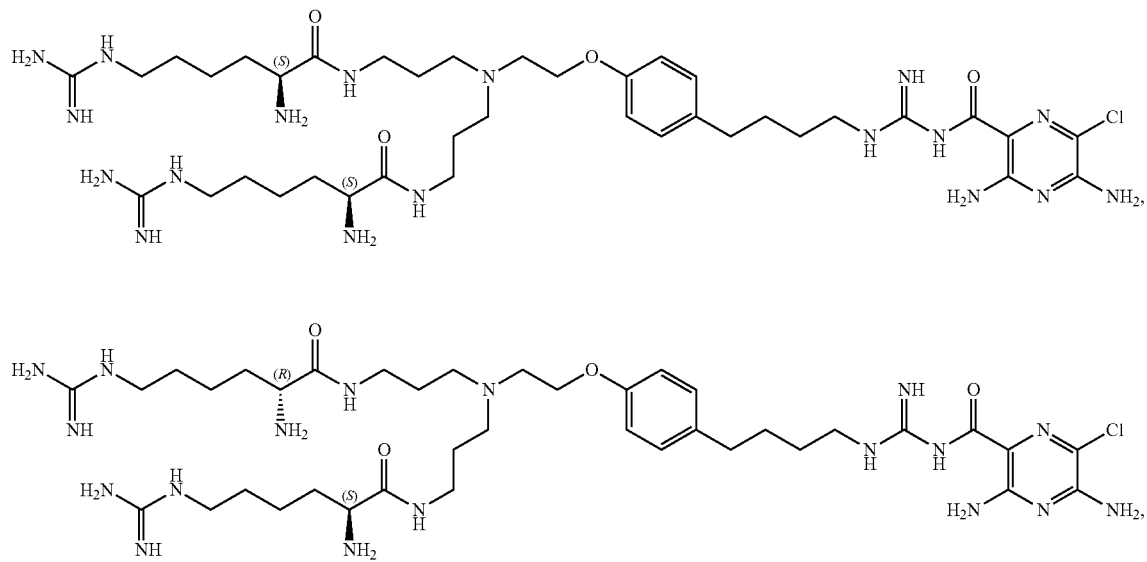

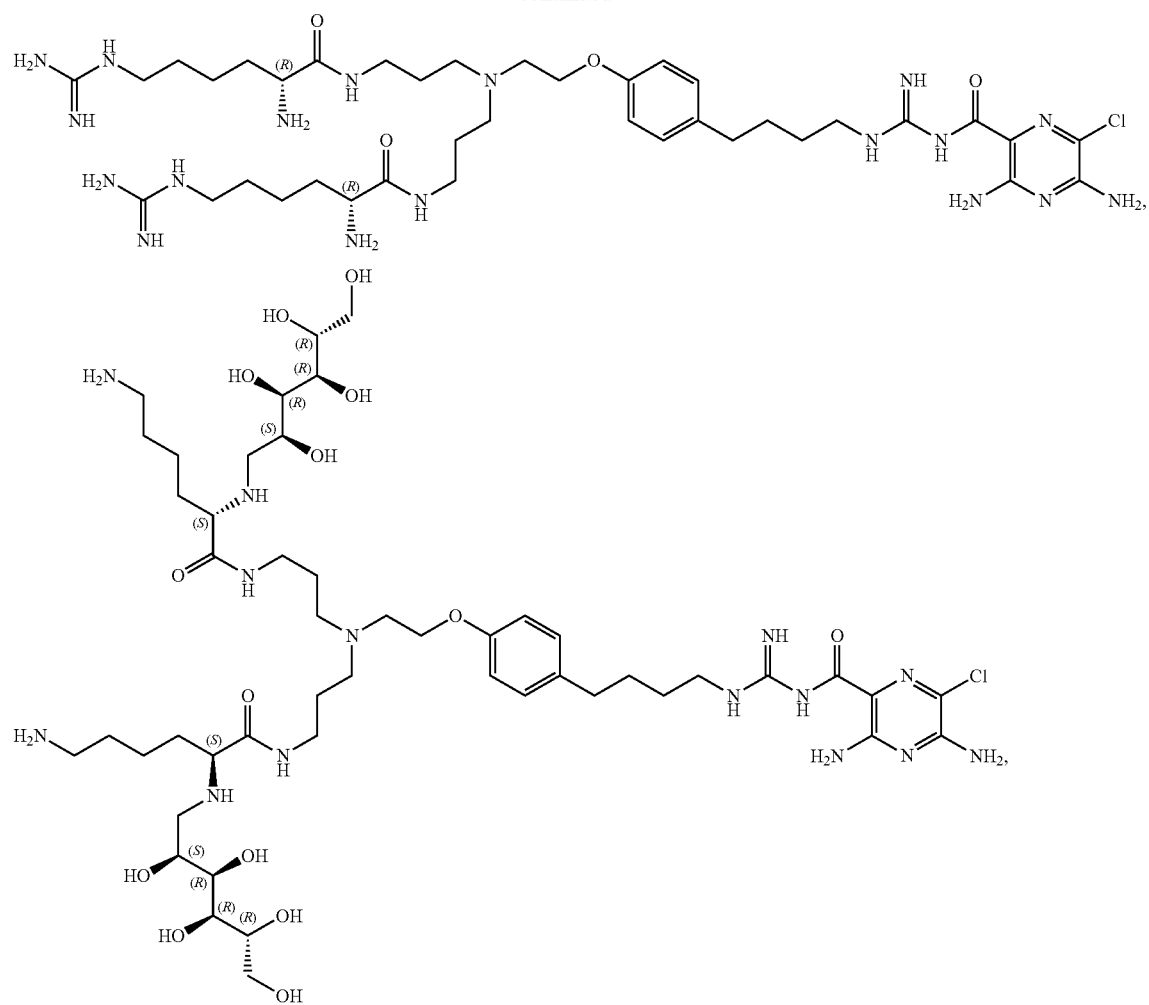
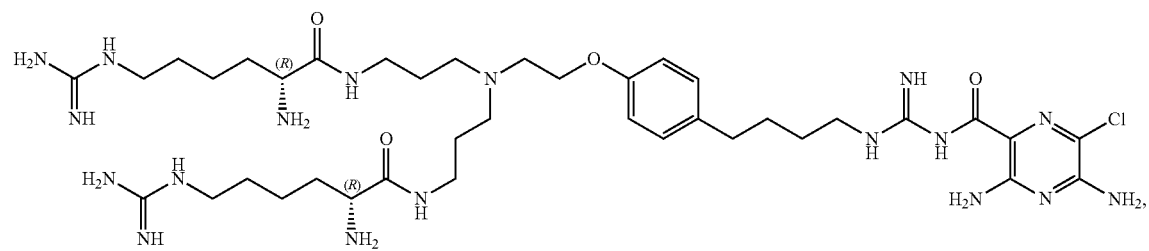

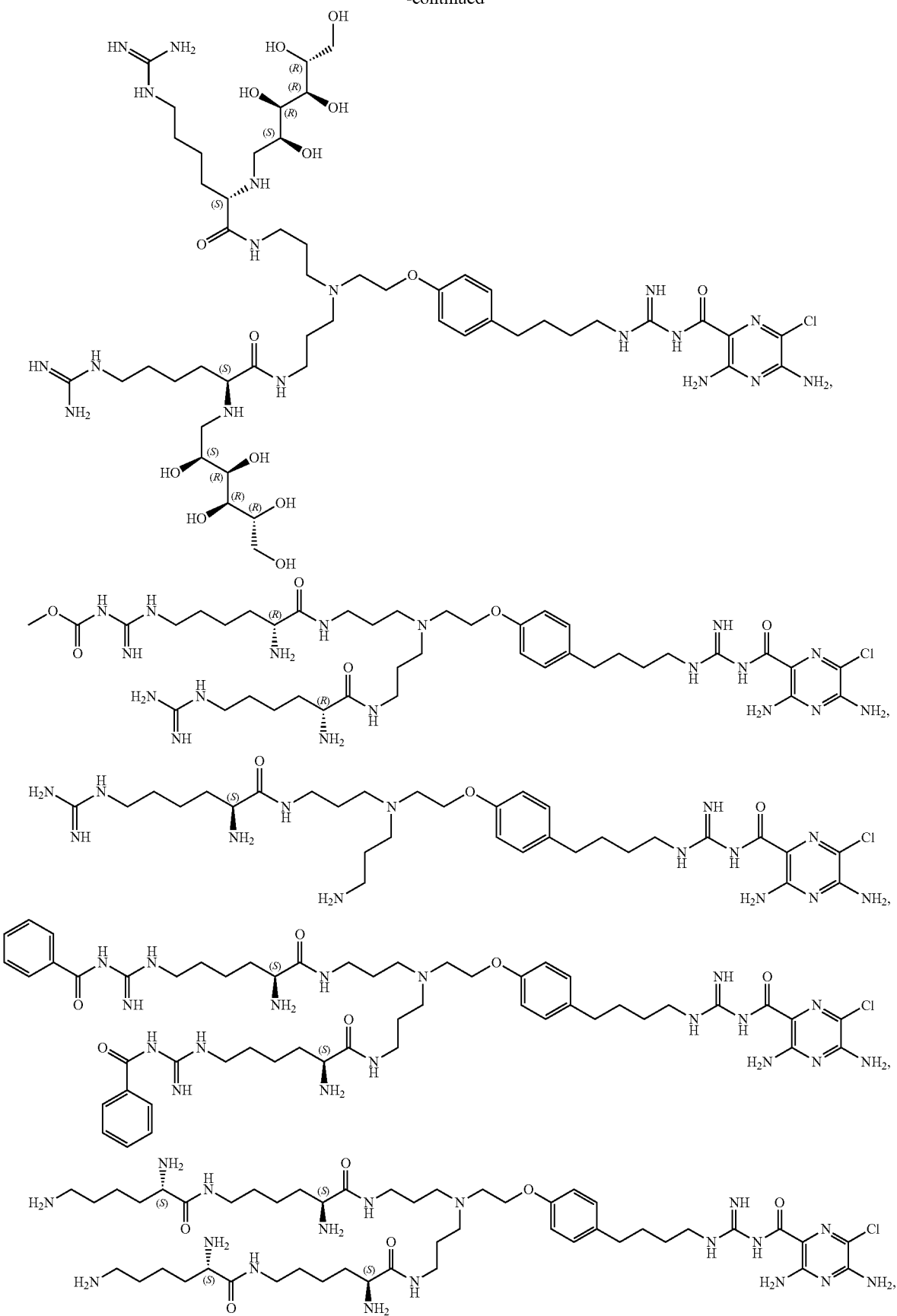

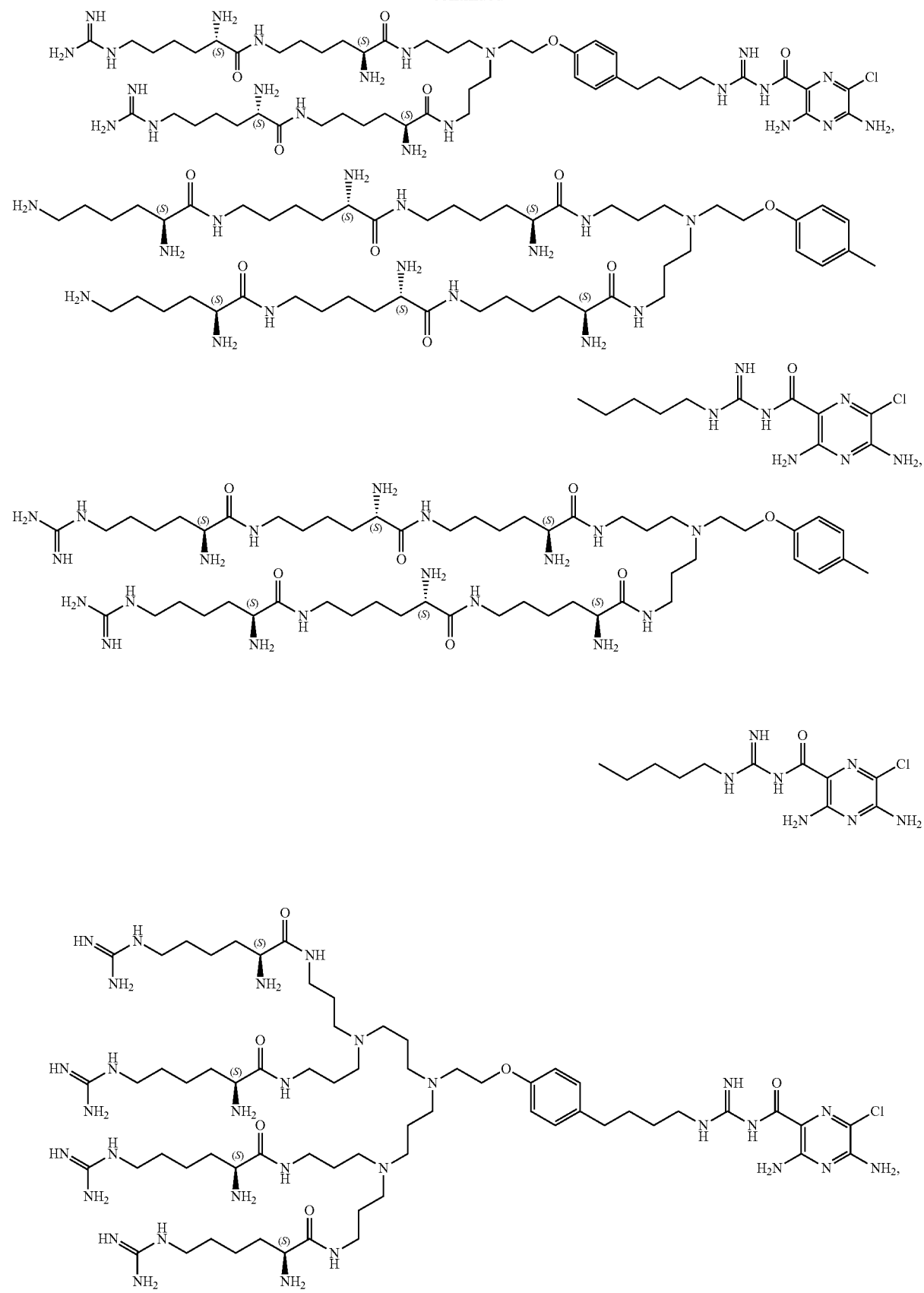

-continued

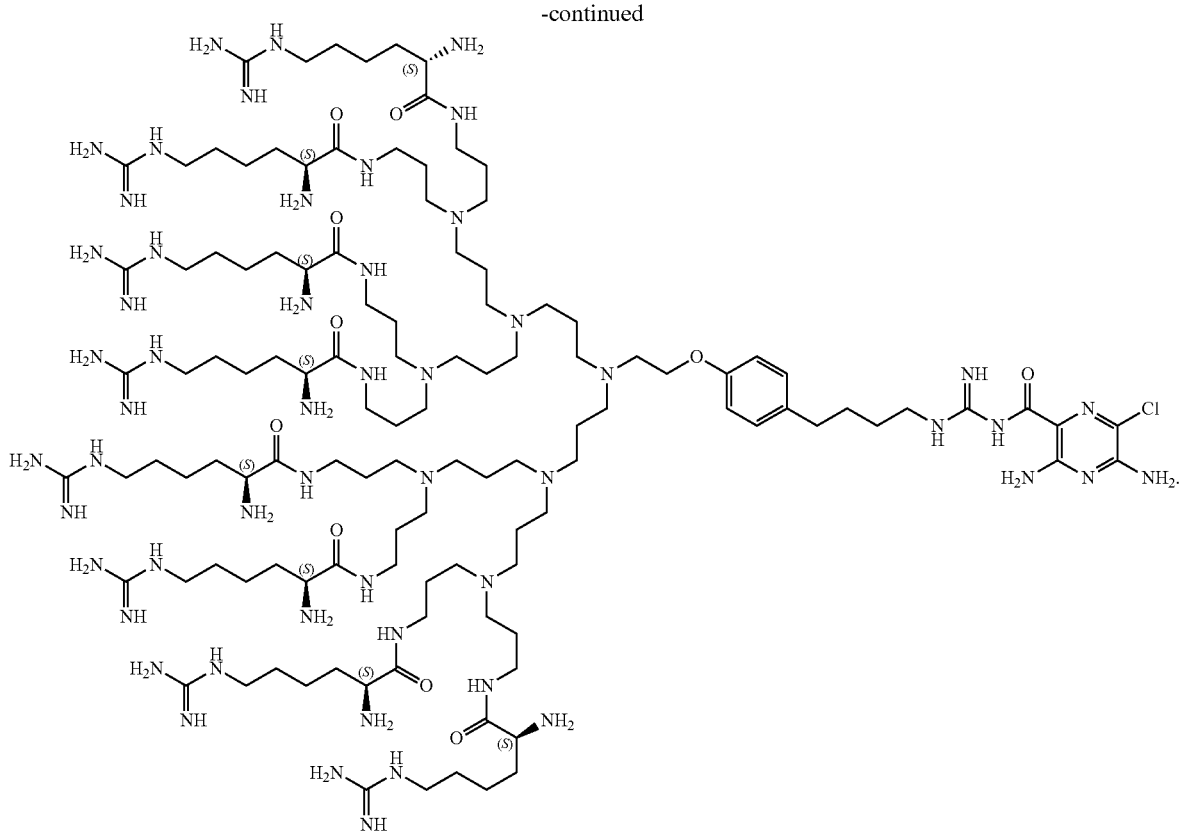

The compounds described herein may be prepared and used as the free base. Alternatively, the compounds may be prepared and used as a pharmaceutically acceptable salt. Pharmaceutically acceptable salts are salts that retain or enhance the desired biological activity of the parent compound and do not impart undesired toxicological effects. Examples of such salts are (a) acid addition salts formed with inorganic acids, for example, hydrochloric acid, hydrobromic acid, sulfuric acid, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid and the like; and (c) salts formed from elemental anions for example, chlorine, bromine, and iodine.

It is to be noted that all enantiomers, diastereomers, and racemic mixtures, tautomers, polymorphs, pseudopolymorphs and pharmaceutically acceptable salts of compounds within the scope of formula (I), formula II, or formula III are embraced by the present invention. All mixtures of such enantiomers and diastereomers are within the scope of the present invention.

A compound of formula I-III and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of formula I-III and their pharmaceutically acceptable salts.

A compound of formula I-III and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of formula I-III and their pharmaceutically acceptable salts.

The compounds of formula I-III may exist in different tautomeric forms. One skilled in the art will recognize that amidines, amides, guanidines, ureas, thioureas, heterocycles and the like can exist in tautomeric forms. By way of example and not by way of limitation, compounds of formula I-III can exist in various tautomeric forms as shown below:

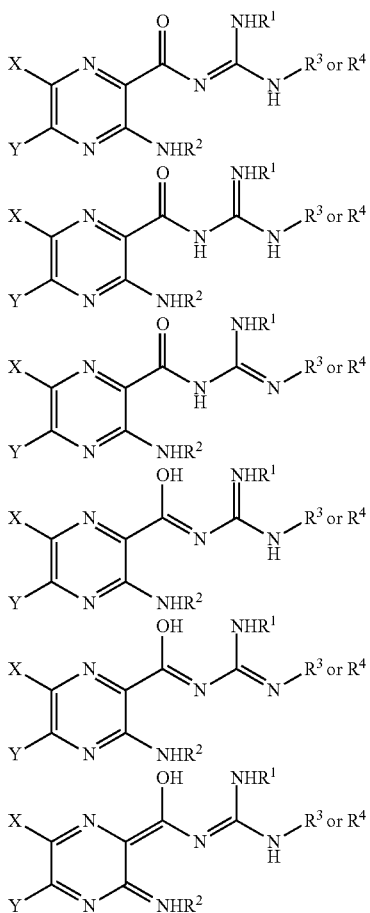

All possible tautomeric forms of the amidines, amides, guanidines, ureas, thioureas, heterocycles and the like of all of the embodiments of formula I-III are within the scope of the instant invention.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

Without being limited to any particular theory, it is believed that the compounds of formula (I), formula II, or formula III function in vivo as sodium channel blockers. By blocking epithelial sodium channels present in mucosal surfaces the compounds of formula (I), formula II, or formula III reduce the absorption of water by the mucosal surfaces. This effect increases the volume of protective liquids on mucosal surfaces, rebalances the system, and thus treats disease.

The present invention also provides methods of treatment that take advantage of the properties of the compounds described herein as discussed above. The present invention may be used to hydrate mucosal surfaces including ocular surfaces or surfaces of the eye, airway surfaces, gastrointestinal surfaces, oral surfaces, genito-urethral surfaces, the inner ear and the middle ear. The active compounds disclosed herein may be administered in an effective amount to mucosal surfaces by any suitable means, including topically, orally, rectally, vaginally, ocularly and dermally, etc. For example, for the treatment of constipation, the active compounds may be administered orally or rectally to the gastrointestinal mucosal surface. The active compound may be combined with a pharmaceutically acceptable carrier in any suitable form, such as sterile physiological or dilute saline or topical solution, as a droplet, tablet or the like for oral administration, as a suppository for rectal or genito-urethral administration, etc. Excipients may be included in the formulation to enhance the solubility of the active compounds, as desired. Thus, subjects that may be treated by the methods of the present invention include, but are not limited to, patients afflicted with chronic dry eye, Sjögren's disease, dry mouth (xerostomia), vaginal dryness, cystic fibrosis, primary ciliary dyskinesia, chronic bronchitis, bronchiectasis chronic obstructive airway disease, artificially ventilated patients, patients with acute pneumonia, etc.

The present invention may be used to obtain a sputum sample from a patient by administering the active compounds to at least one lung of a patient, and then inducing or collecting a sputum sample from that patient. Typically, the invention will be administered to respiratory mucosal surfaces via aerosol (liquid or dry powders) or lavage.

Subjects that may be treated by the method of the present invention also include patients being administered supplemental oxygen nasally (a regimen that tends to dry the airway surfaces); patients afflicted with an allergic disease or response (e.g., an allergic response to pollen, dust, animal hair or particles, insects or insect particles, etc.) that affects nasal airway surfaces; patients afflicted with a bacterial infection e.g., staphylococcus infections such as *Staphylococcus aureus* infections, *Hemophilus influenza* infections, *Streptococcus pneumoniae* infections, *Pseudomonas aeuriginosa* infections, etc.) of the nasal airway surfaces; patients afflicted with an inflammatory disease that affects nasal airway surfaces; or patients afflicted with sinusitis (wherein the active agent or agents are administered to promote drainage of congested mucous secretions in the sinuses by administering an amount effective to promote drainage of congested fluid in the sinuses), or combined, rhinosinusitis. The invention may be administered to rhino-sinal surfaces by topical delivery, including aerosols and drops.

The present invention is concerned primarily with the treatment of human subjects, but may also be employed for the treatment of other mammalian subjects, such as dogs and cats, for veterinary purposes.

As discussed above, the compounds used to prepare the compositions of the present invention may be in the form of a pharmaceutically acceptable free base. Because the free base of the compound is generally less soluble in aqueous solutions than the salt, free base compositions are employed to provide more sustained release of active agent to the lungs. An active agent present in the lungs in particulate form which has not dissolved into solution is not available to induce a physiological response, but serves as a depot of bioavailable drug which gradually dissolves into solution.

Another aspect of the present invention is a pharmaceutical composition, comprising a compound of formula (I) in a pharmaceutically acceptable carrier (e.g., an aqueous carrier solution). In general, the compound of formula (I) is included in the composition in an amount effective to inhibit the reabsorption of water by mucosal surfaces.

Pharmaceutically acceptable carriers for ophthalmic indications include solutions, emulsions, suspensions, and sustained release forms including, but not limited to, dissolvable inserts, plugs, or contact lenses. Pharmaceutically acceptable carriers include, but are not limited to buffers (including phosphate, citrate, bicarbonate, and borate); tonicity adjusting agents (sodium chloride, potassium chloride, Mannitol, dextrose); viscosity enhancing agents (carboxymethyl cellulose, glycerol). Pharmaceutically acceptable carriers can be sterile or preserved with agents including, but not limited to benzalkonium chloride.

Without being limited to any particular theory, it is believed that sodium channel blockers of the present invention block epithelial sodium channels present in mucosal surfaces. The sodium channel blocker described herein reduces the absorption of salt and water by the mucosal surfaces. This effect increases the volume of protective liquids on mucosal surfaces, rebalances the system, and thus treats disease.

Uses

The compounds of the invention exhibit activity as sodium channel blockers. Without being bound by any particular theory, it is believed that the compounds of the invention may function in vivo by blocking epithelial sodium channels present in mucosal surfaces and thereby reduce the absorption of water by the mucosal surfaces. This effect increases the volume of protective liquids on mucosal surfaces, and rebalances the system.

As a consequence, the compounds of the invention are useful as medicaments, particularly for the treatment of clinical conditions for which a sodium channel blocker may be indicated. Sodium channel blockers may be indicated for the treatment of conditions which are ameliorated by increased mucosal hydration in mucosal surfaces other than pulmonary mucosal surfaces. Examples of such conditions include dry mouth (xerostomia), dry skin, vaginal dryness, sinusitis, rhinosinusitis, nasal dehydration, including nasal dehydration brought on by administering dry oxygen, dry eye, Sjogren's disease, otitis media, primary ciliary dyskinesia, distal intestinal obstruction syndrome, esophagitis, constipation, and chronic diverticulitis. The compounds of the invention can also be used for promoting ocular or corneal hydration.

Other conditions that may benefit from treatment with a sodium channel blocker include pulmonary conditions, such as diseases associated with reversible or irreversible airway obstruction, chronic obstructive pulmonary disease (COPD), including acute exacerbations of COPD, asthma, bronchiectasis (including bronchiectasis due to conditions other than cystic fibrosis), acute bronchitis, chronic bronchitis, post-viral cough, cystic fibrosis, emphysema, pneumonia, panbronchiolitis, and transplant-associated bronchiolitis, including lung- and bone marrow-transplant associated bronchiolitis, in a human in need thereof. The compounds of the invention may also be useful for treating ventilator-associated tracheobronchitis and/or preventing ventilator-associated pneumonia in ventilated patients. The present invention comprises methods for treating each of these conditions in a mammal in need thereof, preferably in a human in need thereof, each method comprising administering to said mammal a pharmaceutically effective amount of a compound of the present invention, or a pharmaceutically acceptable salt thereof. Also provided are (a) a method for reducing exacerbations of COPD in a mammal in need thereof; (b) a method for reducing exacerbations of CF in a mammal in need thereof, (c) a method of improving lung function (FEV1) in a mammal in need thereof, (d) a method of improving lung function (FEV1) in a mammal experiencing COPD, (e) a method of improving lung function (FEV1) in a mammal experiencing CF, (f) a method of reducing airway infections in a mammal in need thereof.

Also provided is a method of stimulating, enhancing or improving mucociliary clearance in a mammal, the method comprising administering to a mammal in need thereof a pharmaceutically effective amount of a compound of formula (I), or a pharmaceutically acceptable salt thereof. Mucociliary clearance will be understood to include the natural mucociliary actions involved in the transfer or clearance of mucus in the airways, including the self-clearing mechanisms of the bronchi. Therefore, also provided is a method of improving mucus clearance in the airways of a mammal in need thereof.

The compounds of the present invention may also be useful in methods for obtaining a sputum sample from a human. The method may be carried out by administering a compound of the invention to at least one lung of the patient, and then inducing and collecting a sputum sample from that human.

Accordingly, in one aspect, the present invention provides a method for the treatment of a condition in a mammal, such as a human, for which a sodium channel blocker is indicated.

In other embodiments, the present invention provides each of the methods described herein with the additional benefit of minimizing or eliminating hyperkalemia in the recipient of the method. Also provided are embodiments comprising each of the methods described herein wherein an improved therapeutic index is achieved.

The terms "treat", "treating" and "treatment", as used herein refers to reversing, alleviating, inhibiting the progress of, or preventing the disorder or condition or one or more symptoms of such disorder or condition.

All therapeutic methods described herein are carried out by administering an effective amount of a compound of the invention, a compound of Formula I or a pharmaceutically acceptable salt thereof, to a subject (typically mammal and preferably human) in need of treatment.

In one embodiment the invention provides a method for the treatment of a condition which is ameliorated by increased mucosal hydration in a mammal, particularly a human in need thereof. In one embodiment the invention provides a method for the treatment of a disease associated with reversible or irreversible airway obstruction in a mammal, particularly a human, in need thereof. In one particular embodiment the present invention provides a method for the treatment of chronic obstructive pulmonary disease (COPD) in a mammal, particularly a human in need thereof. In one particular embodiment the present invention provides a method for reducing the frequency, severity or duration of acute exacerbation of COPD or for the treatment of one or more symptoms of acute exacerbation of COPD in a mammal, particularly a human in need thereof. In one embodiment the invention provides a method for the treatment of asthma in a mammal, particularly a human, in need thereof. In one embodiment the invention provides a method for the treatment of bronchiectasis (including bronchiectasis due to conditions other than cystic fibrosis) in a mammal, particularly a human, in need thereof. In one embodiment the invention provides a method for the treatment of bronchitis, including acute and chronic bronchitis in a mammal, particularly a human, in need thereof. In one embodiment the invention provides a method for the treatment of post-viral cough in a mammal, particularly a human, in need thereof. In one embodiment the invention provides a method for the treatment of cystic fibrosis in a mammal, particularly a human, in need thereof. In one embodiment the invention provides a method for the treatment of emphysema in a mammal, particularly a human in need thereof. In one embodiment the invention provides a method for the treatment of pneumonia in a mammal, particularly a human in need thereof. In one embodiment the invention provides a method for the treatment of panbronchiolitis in a mammal, particularly a human in need thereof. In one embodiment the invention provides a method for the treatment of transplant-associated bronchiolitis, including lung- and bone marrow-transplant associated bronchiolitis in a mammal, particularly a human, in need thereof. In one embodiment the invention provides a method for treating ventilator-associated tracheobronchitis and/or preventing ventilator-associated pneumonia in a ventilated human in need thereof.

In one embodiment the invention provides a method for the treatment of dry mouth (xerostomia) in a mammal, particularly a human in need thereof. In one embodiment the invention provides a method for the treatment of dry skin in a mammal, particularly a human in need thereof. In one embodiment the invention provides a method for the treatment of vaginal dryness in a mammal, particularly a human in need thereof. In one embodiment the invention provides a method for the treatment of sinusitis, rhinosinusitis, or nasal dehydration, including nasal dehydration brought on by administering dry oxygen, in a mammal, particularly a human in need thereof. In one embodiment the invention provides a method for the treatment of dry eye, or Sjogren's disease, or promoting ocular or corneal hydration in a mammal, particularly a human in need thereof. In one embodiment the invention provides a method for the treatment of otitis media in a mammal, particularly a human in need thereof. In one embodiment the invention provides a method for the treatment of primary ciliary dyskinesia, in a mammal, particularly a human in need thereof. In one embodiment the invention provides a method for the treatment of distal intestinal obstruction syndrome, esophagitis, constipation, or chronic diverticulitis in a mammal, particularly a human in need thereof.

There is also provided a compound of the invention for use in medical therapy, particularly for use in the treatment of condition in a mammal, such as a human, for which a sodium channel blocker is indicated. All therapeutic uses described herein are carried out by administering an effective amount of a compound of the invention to the subject in need of treatment. In one embodiment there is provided a compound of the invention for use in the treatment of a pulmonary condition such as a disease associated with reversible or irreversible airway obstruction in a mammal, particularly a human, in need thereof. In one particular embodiment there is provided a compound of the invention for use in the treatment of chronic obstructive pulmonary disease (COPD) in a mammal, particularly a human in need thereof. In one embodiment, there is provided a compound of the invention for use in reducing the frequency, severity or duration of acute exacerbation of COPD or for the treatment of one or more symptoms of acute exacerbation of COPD, in a mammal, particularly a human, in need thereof. In one embodiment there is provided a compound of the invention for use in the treatment of asthma in a mammal, particularly a human, in need thereof. In one embodiment there is provided a compound for use in the treatment of bronchiectasis, including bronchiectasis due to conditions other than cystic fibrosis, or bronchitis, including acute bronchitis and chronic bronchitis, in a mammal, particularly a human, in need thereof. In one embodiment there is provided a compound for use in the treatment of post-viral cough, in a mammal, particularly a human, in need thereof. In one embodiment there is provided a compound for use in the treatment of cystic fibrosis in a mammal, particularly a human in need thereof. In one embodiment there is provided a compound of the invention for use in the treatment of emphysema in a mammal, particularly a human, in need thereof. In one embodiment there is provided a compound of the invention for use in the treatment of pneumonia in a mammal, particularly a human, in need thereof. In one embodiment there is provided a compound of the invention for use in the treatment of panbronchiolitis or transplant-associated bronchiolitis, including lung- and bone marrow-transplant associated bronchiolitis in a mammal, particularly a human, in need thereof. In one embodiment there is provided a compound of the invention for use in the treatment of ventilator-associated tracheobronchitis or preventing ventilator-associated pneumonia in a ventilated human in need thereof.

In one embodiment there is provided a compound of the invention for use in the treatment of a condition ameliorated by increased mucosal hydration in mucosal surfaces of a mammal, particularly a human, in need thereof. In one embodiment there is provided a compound for use in the treatment of dry mouth (xerostomia) in a mammal, particularly a human, in need thereof. In one embodiment there is provided a compound for use in the treatment of dry skin in a mammal, particularly a human, in need thereof. In one embodiment there is provided a compound for use in the treatment of vaginal dryness in a mammal, particularly a human in need thereof. In one embodiment there is provided a compound of the invention for use in the treatment of sinusitis, rhinosinusitis, or nasal dehydration, including nasal dehydration brought on by administering dry oxygen in a mammal, particularly a human, in need thereof. In one embodiment there is provided a compound of the invention for use in the treatment of dry eye, or Sjogren's disease or promoting ocular or corneal hydration in a mammal, particularly a human, in need thereof. In one embodiment there is provided a compound of the invention for use in the treatment of otitis media in a mammal, particularly a human, in need thereof. In one embodiment there is provided a compound of the invention for use in the treatment of primary ciliary dyskinesia in a mammal, particularly a human, in need thereof. In one embodiment there is provided a compound of the invention for use in the treatment of distal intestinal obstruction syndrome, esophagitis, constipation, or chronic diverticulitis in a mammal, particularly a human, in need thereof.

The present invention also provides the use of a compound of the invention in the manufacture of a medicament for the treatment of a condition in a mammal, such as a human, for which a sodium channel blocker is indicated. In one embodiment is provided the use of a compound of the invention in the manufacture of a medicament for the treatment of diseases associated with reversible or irreversible airway obstruction, chronic obstructive pulmonary disease (COPD), acute exacerbations of COPD, asthma, bronchiectasis (including bronchiectasis due to conditions other than cystic fibrosis), bronchitis (including acute bronchitis and chronic bronchitis), post-viral cough, cystic fibrosis, emphysema, pneumonia, panbronchiolitis, transplant-associated bronchiolitis, (including lung- and bone marrow-transplant associated bronchiolitis), ventilator-associated tracheobronchitis or preventing ventilator-associated pneumonia.

In one particular embodiment is provided the use of a compound of the invention in the manufacture of a medicament for the treatment of a condition ameliorated by increased mucosal hydration in mucosal surfaces, treatment of dry mouth (xerostomia), dry skin, vaginal dryness, sinusitis, rhinosinusitis, nasal dehydration, including nasal dehydration brought on by administering dry oxygen, treatment of dry eye, Sjogren's disease, promoting ocular or corneal hydration, treatment of otitis media, primary ciliary dyskinesia, distal intestinal obstruction syndrome, esophagitis, constipation, or chronic diverticulitis The terms "effective amount", "pharmaceutically effective amount", "effective dose", and "pharmaceutically effective dose" as used herein, refer to an amount of compound of the invention which is sufficient in the subject to which it is administered, to elicit the biological or medical response of a cell culture, tissue, system, or mammal (including human) that is being sought, for instance by a researcher or clinician. The term also includes within its scope, amounts effective to enhance normal physiological function. In one embodiment, the effective amount is the amount needed to provide a desired level of drug in the secretions and tissues of the airways and lungs, or alternatively, in the bloodstream of a subject to be treated to give an anticipated physiological response or desired biological effect when such a composition is administered by inhalation. For example an effective amount of a compound of the invention for the treatment of a condition for which a sodium channel blocker is indicated is sufficient in the subject to which it is administered to treat the particular condition. In one embodiment an effective amount is an amount of a compound of the invention which is sufficient for the treatment of COPD or cystic fibrosis in a human.

The precise effective amount of the compounds of the invention will depend on a number of factors including but not limited to the species, age and weight of the subject being treated, the precise condition requiring treatment and its severity, the bioavailability, potency, and other properties of the specific compound being administered, the nature of the formulation, the route of administration, and the delivery device, and will ultimately be at the discretion of the attendant physician or veterinarian. Further guidance with respect to appropriate dose may be found in considering conventional dosing of other sodium channel blockers, such as amiloride, with due consideration also being given to any differences in potency between amiloride and the compounds of the present invention.

A pharmaceutically effective dose administered topically to the ocular surfaces of a subject (e.g., by applied as a topical eye drop) of a compound of the invention for treatment of a 70 kg human may be in the range of from about 0.01 to about 1000 µg.

A pharmaceutically effective dose administered topically to the airway surfaces of a subject (e.g., by inhalation) of a compound of the invention for treatment of a 70 kg human may be in the range of from about 0.1 to about 1000 µg. Typically, the daily dose administered topically to the airway surfaces will be an amount sufficient to achieve dissolved concentration of active agent on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter. The selection of the specific dose for a patient will be determined by the attendant physician, clinician or veterinarian of ordinary skill in the art based upon a number of factors including those noted above. In one particular embodiment the dose of a compound of the invention for the treatment of a 70 kg human will be in the range of from about 0.1 to about 1,000 µg. In one embodiment, the dose of a compound of the invention for the treatment of a 70 kg human will be in the range of from about 0.5 to about 50 µg. In another embodiment, the pharmaceutically effective dose will be from about 1 to about 10 µg. In another embodiment, the pharmaceutically effective dose will be from about 10 µg to about 40 µg. In a further embodiment, the pharmaceutically effective dose will be from about 15 µg to about 30 µg. The foregoing suggested doses may be adjusted using conventional dose calculations if the compound is administered via a different route. Determination of an appropriate dose for administration by other routes is within the skill of those in the art in light of the foregoing description and the general knowledge in the art. These doses and solutions will range from about 0.00001% to 10% on a weight per volume (w/v) basis.

Delivery of an effective amount of a compound of the invention may entail delivery of a single dosage form or multiple unit doses which may be delivered contemporaneously or separate in time over a designated period, such as 24 hours. A dose of a compound of the invention (alone or in the form of a composition comprising the same) may be administered from one to ten times per day. Typically, a compound of the invention (alone or in the form of a composition comprising the same) will be administered four, three, two, or once per day (24 hours).

The compounds of formula (I) of the present invention are also useful for treating airborne infections. Examples of airborne infections include, for example, RSV. The compounds of formula (I) of the present invention are also useful for treating an anthrax infection. The present invention relates to the use of the compounds of formula (I) of the present invention for prophylactic, post-exposure prophylactic, preventive or therapeutic treatment against diseases or conditions caused by pathogens. In a preferred embodiment, the present invention relates to the use of the compounds of formula (I) for prophylactic, post-exposure prophylactic, preventive or therapeutic treatment against diseases or conditions caused by pathogens which may be used in bioterrorism.

In recent years, a variety of research programs and biodefense measures have been put into place to deal with concerns about the use of biological agents in acts of terrorism. These measures are intended to address concerns regarding bioterrorism or the use of microorganisms or biological toxins to kill people, spread fear, and disrupt society. For example, the National Institute of Allergy and Infectious Diseases (NIAID) has developed a Strategic Plan for Biodefense Research which outlines plans for addressing research needs in the broad area of bioterrorism and emerging and reemerging infectious diseases. According to the plan, the deliberate exposure of the civilian population of the United States to *Bacillus anthracis* spores revealed a gap in the nation's overall preparedness against bioterrorism. Moreover, the report details that these attacks uncovered an unmet need for tests to rapidly diagnose, vaccines and immunotherapies to prevent, and drugs and biologics to cure disease caused by agents of bioterrorism.

Much of the focus of the various research efforts has been directed to studying the biology of the pathogens identified as potentially dangerous as bioterrorism agents, studying the host response against such agents, developing vaccines against infectious diseases, evaluating the therapeutics currently available and under investigation against such agents, and developing diagnostics to identify signs and symptoms of threatening agents. Such efforts are laudable but, given the large number of pathogens which have been identified as potentially available for bioterrorism, these efforts have not yet been able to provide satisfactory responses for all possible bioterrorism threats. Additionally, many of the pathogens identified as potentially dangerous as agents of bioterrorism do not provide adequate economic incentives for the development of therapeutic or preventive measures by industry. Moreover, even if preventive measures such as vaccines were available for each pathogen which may be used in bioterrorism, the cost of administering all such vaccines to the general population is prohibitive.

Until convenient and effective treatments are available against every bioterrorism threat, there exists a strong need for preventative, prophylactic or therapeutic treatments which can prevent or reduce the risk of infection from pathogenic agents.

The present invention provides such methods of prophylactic treatment. In one aspect, a prophylactic treatment method is provided comprising administering a prophylactically effective amount of the compounds of formula (I) to an individual in need of prophylactic treatment against infection from one or more airborne pathogens. A particular example of an airborne pathogen is anthrax.

In another aspect, a prophylactic treatment method is provided for reducing the risk of infection from an airborne pathogen which can cause a disease in a human, said method comprising administering an effective amount of the compounds of formula (I) to the lungs of the human who may be at risk of infection from the airborne pathogen but is asymptomatic for the disease, wherein the effective amount of a sodium channel blocker and osmolye are sufficient to reduce the risk of infection in the human. A particular example of an airborne pathogen is anthrax.

In another aspect, a post-exposure prophylactic treatment or therapeutic treatment method is provided for treating infection from an airborne pathogen comprising administering an effective amount of the compounds of formula (I) to the lungs of an individual in need of such treatment against infection from an airborne pathogen. The pathogens which may be protected against by the prophylactic post exposure, rescue and therapeutic treatment methods of the invention include any pathogens which may enter the body through the mouth, nose or nasal airways, thus proceeding into the lungs. Typically, the pathogens will be airborne pathogens, either naturally occurring or by aerosolization. The pathogens may be naturally occurring or may have been introduced into the environment intentionally after aerosolization or other method of introducing the pathogens into the environment. Many pathogens which are not naturally transmitted in the air have been or may be aerosolized for use in bioterrorism. The pathogens for which the treatment of the invention may be useful includes, but is not limited to, category A, B and C priority pathogens as set forth by the NIAID. These categories correspond generally to the lists compiled by the Centers for Disease Control and Prevention (CDC). As set up by the CDC, Category A agents are those that can be easily disseminated or transmitted person-to-person, cause high mortality, with potential for major public health impact. Category B agents are next in priority and include those that are moderately easy to disseminate and cause moderate morbidity and low mortality. Category C consists of emerging pathogens that could be engineered for mass dissemination in the future because of their availability, ease of production and dissemination and potential for high morbidity and mortality. Particular examples of these pathogens are anthrax and plague. Additional pathogens which may be protected against or the infection risk therefrom reduced include influenza viruses, rhinoviruses, adenoviruses and respiratory syncytial viruses, and the like. A further pathogen which may be protected against is the coronavirus which is believed to cause severe acute respiratory syndrome (SARS).

The present invention also relates to the use of sodium channel blockers of Formula I, or a pharmaceutically acceptable salt thereof, for preventing, mitigating, and/or treating deterministic health effects to the respiratory tract caused by exposure to radiological materials, particularly respirable aerosols containing radionuclides from nuclear attacks, such as detonation of radiological dispersal devices (RDD), or accidents, such as nuclear power plant disasters. As such, provided herein is a method for preventing, mitigating, and/or treating deterministic health effects to the respiratory tract and/or other bodily organs caused by respirable aerosols containing radionuclides in a recipient in need thereof, including in a human in need thereof, said method comprising administering to said human an effective amount of a compound of Formula (I), or a pharmaceutically acceptable salt thereof.

A major concern associated with consequence management planning for exposures of members of the public to respirable aerosols containing radionuclides from nuclear attacks, such as detonation of radiological dispersal devices (RDD), or accidents, such as nuclear power plant disasters is how to prevent, mitigate or treat potential deterministic health effects to the respiratory tract, primarily the lung. It is necessary to have drugs, techniques and procedures, and trained personnel prepared to manage and treat such highly internally contaminated individuals.

Research has been conducted to determine ways in which to prevent, mitigate or treat potential damage to the respiratory tract and various organs in the body that is caused by internally deposited radionuclides. To date, most of the research attention has focused on strategies designed to mitigate health effects from internally deposited radionuclides by accelerating their excretion or removal. These strategies have focused on soluble chemical forms that are capable of reaching the blood stream and are deposited at remote systemic sites specific to a given radioelement. Such approaches will not work in cases where the deposited radionuclide is in relatively insoluble form. Studies have shown that many, if not most of the physicochemical forms of dispersed radionuclides from RDDs, will be in relatively insoluble form.

The only method known to effectively reduce the radiation dose to the lungs from inhaled insoluble radioactive aerosols is bronchoalveolar lavage or BAL. This technique, which was adapted from that already in use for the treatment of patients with alveolar proteinosis, has been shown to be a safe, repeatable procedure, even when performed over an extended period of time. Although there are variations in procedure, the basic method for BAL is to anaesthetize the subject, followed by the slow introduction of isotonic saline into a single lobe of the lung until the function residual capacity is reached. Additional volumes are then added and drained by gravity.

The results of studies using BAL on animals indicate that about 40% of the deep lung content can be removed by a reasonable sequence of BALs. In some studies, there was considerable variability among animals in the amount of radionuclide recovered. The reasons for the variability are currently not understood.

Further, based on a study on animals, it is believed that a significant dose reduction from BAL therapy results in mitigation of health effects due to inhalation of insoluble radionuclides. In the study, adult dogs inhaled insoluble $^{144}$Ce-FAP particles. Two groups of dogs were given lung contents of $^{144}$Ce known to cause radiation pneumonitis and pulmonary fibrosis (about 2 MBq/kg body mass), with one group being treated with 10 unilateral lavages between 2 and 56 days after exposure, the other untreated. A third group was exposed at a level of $^{144}$Ce comparable to that seen in the BAL-treated group after treatment (about 1 MBq/kg), but these animals were untreated. All animals were allowed to live their lifespans, which extended to 16 years. Because there is variability in initial lung content of $^{144}$Ce among the dogs in each group, the dose rates and cumulative doses for each group overlap. Nevertheless, the effect of BAL in reducing the risk from pneumonitis/fibrosis was evident from the survival curves. In the untreated dogs with lung contents of 1.5-2.5 MBq/kg, the mean survival time was 370±65 d. For the treated dogs, the mean survival was 1270±240 d, which was statistically significantly different. The third group, which received lung contents of $^{144}$Ce of 0.6-1.4 MBq had a mean survival time of 1800±230, which was not statistically different from the treated group. Equally important to the increased survival, the dogs in the high-dose untreated group died from deterministic effects to lung (pneumonitis/fibrosis) while the treated dogs did not. Instead, the treated dogs, like the dogs in the low-dose untreated group, mostly had lung tumors (hemangiosarcoma or carcinoma). Therefore, the reduction in dose resulting from BAL treatment appears to have produced biological effects in lung that were predictable based on the radiation doses that the lungs received.

Based on these results, it is believed that decreasing the residual radiological dose further by any method or combination of methods for enhancing the clearance of particles from the lung would further decrease the probability of health effects to lung. However, BAL is a procedure that has many drawbacks. BAL is a highly invasive procedure that must be performed at specialized medical centers by trained pulmonologists. As such, a BAL procedure is expensive. Given the drawbacks of BAL, it is not a treatment option that would be readily and immediately available to persons in need of accelerated removal of radioactive particles, for example, in the event of a nuclear attack. In the event of a nuclear attack or a nuclear accident, immediate and relatively easily administered treatment for persons who have been exposed or who are at risk of being exposed is needed. Sodium channel blockers administered as an inhalation aerosol have been shown to restore hydration of airway surfaces. Such hydration of airway surfaces aids in clearing accumulated mucus secretions and associated particulate matter from the lung. As such, without being bound by any particular theory, it is believed that sodium channel blockers can be used to accelerate the removal of radioactive particles from airway passages.

As discussed above, the greatest risk to the lungs following a radiological attack, such as a dirty bomb, results from the inhalation and retention of insoluble radioactive particles. As a result of radioactive particle retention, the cumulative exposure to the lung is significantly increased, ultimately resulting in pulmonary fibrosis/pneumonitis and potentially death. Insoluble particles cannot be systemically cleared by chelating agents because these particles are not in solution. To date, the physical removal of particulate matter through BAL is the only therapeutic regimen shown to be effective at mitigating radiation-induced lung disease. As discussed above, BAL is not a realistic treatment solution for reducing the effects of radioactive particles that have been inhaled into the body. As such, it is desirable to provide a therapeutic regimen that effectively aids in clearing radioactive particles from airway passages and that, unlike BAL, is relatively simple to administer and scalable in a large-scale radiation exposure scenario. In addition, it is also desirable that the therapeutic regimen be readily available to a number of people in a relatively short period of time.

In an aspect of the present invention, a method for preventing, mitigating, and/or treating deterministic health effects to the respiratory tract and/or other bodily organs caused by respirable aerosols containing radionuclides comprises administering an effective amount of a sodium channel blocker of Formula I or a pharmaceutically acceptable salt thereof to an individual in need. In a feature of this aspect, the sodium channel blocker is administered in conjunction with an osmolyte. With further regard to this feature, the osmolyte is hypertonic saline (HS). In a further feature, the sodium channel blocker and the osmolyte are administered in conjunction with an ion transport modulator. With further regard to this feature, the ion transport modulator may be selected from the group consisting of β-agonists, CFTR potentiators, purinergic receptor agonists, lubiprostones, and protease inhibitors. In another feature of this aspect, the radionuclides are selected from the group consisting of Colbalt-60, Cesium-137, Iridium-192, Radium-226, Phospohrus-32, Strontium-89 and 90, Iodine-125, Thallium-201, Lead-210, Thorium-234, Uranium-238, Plutonium, Cobalt-58, Chromium-51, Americium, and Curium. In a further feature, the radionuclides are from a radioactive disposal device. In yet another feature, the sodium channel blocker or pharmaceutically acceptable salt thereof is administered in an aerosol suspension of respirable particles which the individual inhales. In an additional feature, the sodium channel blocker or a pharmaceutically acceptable salt thereof is administered post-exposure to the radionuclides.

Compositions

While it is possible for a compound of the invention to be administered alone, in some embodiments it is preferable to present it in the form of a composition, particularly a pharmaceutical composition (formulation). Thus, in another aspect, the invention provides compositions, and particularly pharmaceutical compositions (such as an inhalable pharmaceutical composition) comprising a pharmaceutically effective amount of a compound of the invention as an active ingredient, and a pharmaceutically acceptable excipient, diluent or carrier. The term "active ingredient" as employed herein refers to any compound of the invention or combination of two or more compounds of the invention in a pharmaceutical composition. Also provided are specific embodiments in which a pharmaceutical composition comprises a pharmaceutically effective amount of a compound of Formula (I), independently or in combination, and a pharmaceutically acceptable excipient, diluent or carrier.

Also provided is a kit comprising i) a pharmaceutically effective amount of a compound of Formula (I), or a pharmaceutically acceptable salt thereof; ii) one or more pharmaceutically acceptable excipients, carriers, or diluents; iii) instructions for administering the compound of group i) and the excipients, carriers, or diluents of group ii) to a subject in need thereof; and; iv) a container. A subject in need thereof includes any subject in need of the methods of treatment described herein.

In one embodiment a kit comprises i) from about 10 µg to about 40 µg of a compound of Formula (I), or a pharmaceutically acceptable salt thereof, per dose; ii) from about 1 to about 5 mL of diluent per dose; iii) instructions for administering the compound of group i) and the diluent of group ii) to a subject in need thereof; and; iv) a container. In a further embodiment, the diluent is from about 1 to about 5 mL of a saline solution, as described herein, per dose.

Also provided is a kit comprising i) a solution comprising a pharmaceutically effective amount of a compound of Formula (I), or a pharmaceutically acceptable salt thereof; dissolved in a pharmaceutically acceptable diluent; iii) instructions for administering the solution of group i) to a subject in need thereof; and iii) a container.

Also provided is a kit comprising i) a solution comprising from about 10 µg to about 40 µg of a compound of Formula (I), or a pharmaceutically acceptable salt thereof; dissolved in a pharmaceutically acceptable diluent; iii) instructions for administering the solution of group i) to a subject in need thereof; and iii) a container. In a further embodiment, the diluent is from about 1 to about 5 mL of a saline solution, as described herein, per dose.

For each of the kits described above there is an additional embodiment in which the diluent is hypertonic saline.

The pharmaceutically acceptable excipient(s), diluent(s) or carrier(s) must be acceptable in the sense of being compatible with the other ingredients of the formulation and not deleterious to the recipient thereof. Generally, the pharmaceutically acceptable excipient(s), diluent(s) or carrier(s) employed in the pharmaceutical formulation are "non-toxic" meaning that it/they is/are deemed safe for consumption in the amount delivered in the formulation and "inert" meaning that it/they does/do not appreciable react with or result in an undesired effect on the therapeutic activity of the active ingredient(s). Pharmaceutically acceptable excipients, diluents and carriers are conventional in the art and may be selected using conventional techniques, based upon the desired route of administration. See, REMINGTON'S, PHARMACEUTICAL SCIENCES, Lippincott Williams & Wilkins; 21$^{st}$ Ed (May 1, 2005). Preferably, the pharmaceutically acceptable excipient(s), diluent(s) or carrier(s) are Generally Regarded As Safe (GRAS) according to the FDA.

Pharmaceutical compositions according to the invention include those suitable for oral administration; parenteral administration, including subcutaneous, intradermal, intramuscular, intravenous and intraarticular; topical administration, including topical administration to the skin, eyes, ears, etc; vaginal or rectal administration; and administration to the respiratory tract, including the nasal cavities and sinuses, oral and extrathoracic airways, and the lungs, including by use of aerosols which may be delivered by means of various types of dry powder inhalers, pressurized metered dose inhalers, soft-mist inhalers, nebulizers, or insufflators. The most suitable route of administration may depend upon, several factors including the patient and the condition or disorder being treated.

The formulations may be presented in unit dosage form or in bulk form as for example in the case of formulations to be metered by an inhaler and may be prepared by any of the methods well known in the art of pharmacy. Generally, the methods include the step of bringing the active ingredient into association with the carrier, diluent or excipient and optionally one or more accessory ingredients. In general the formulations are prepared by uniformly and intimately bringing into association the active ingredient with one or more liquid carriers, diluents or excipients or finely divided solid carriers, diluents or excipients, or both, and then, if necessary, shaping the product into the desired formulation.

Pharmaceutical compositions for topical administration may be formulated as ointments, creams, suspensions, lotions, powders, solutions, pastes, gels, sprays, aerosols or oils. Compositions designed for the treatment of the eyes or other external tissues, for example the mouth and skin, may be applied as a topical ointment, cream or eye drops. When formulated as an ointment, the active ingredient may be employed with either a paraffinic or a water-miscible ointment base. Alternatively, the active ingredient may be formulated in a cream with an oil-in-water cream base or a water-in-oil base.

Other compositions designed for topical administration to the eyes or ears include eye drops and ear drops wherein the active ingredient is dissolved or suspended in a suitable carrier, such as for example an aqueous solvent, including saline.

Formulations suitable for oral administration may be presented as discrete units such as capsules, cachets or tablets, each containing a predetermined amount of the active ingredient; as a powder or granules; as a solution or suspension in an aqueous liquid or a non-aqueous liquid; or as an oil-in-water liquid emulsion or a water-in-oil liquid emulsion. The active ingredient may also be presented as a sachet, bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binders, lubricant, inert diluent, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example saline or water-for-injection, immediately prior to use. Extemporaneous injection solutions and suspensions may be prepared from sterile powders, granules and tablets of the kind previously described.

Oral fluids such as solutions, syrups and elixirs can be prepared in dosage unit form so that a given quantity contains a predetermined amount of the active ingredient. Syrups can be prepared by dissolving the active ingredient in a suitably flavored aqueous solution, while elixirs are prepared through the use of a pharmaceutically acceptable alcoholic vehicle. Suspensions can be formulated by dispersing the active ingredient in a pharmaceutically acceptable vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be incorporated into oral liquid compositions.

Liposome delivery systems such as small unilamellar vesicles, large unilamellar vesicles and multilamellar vesicles may also be employed as delivery means for the compounds of the invention. Liposomes may be formed from a variety of phospholipids such as cholesterol, stearylamine and phosphatidylcholines.

Compositions designed for nasal administration include aerosols, solutions, suspensions, sprays, mists and drops. Aerosolable formulations for nasal administration may be formulated in much the same ways as aerosolable formulations for inhalation with the condition that particles of non-respirable size will be preferred in formulations for nasal administration. Typically, particles of about 5 microns in size, up to the size of visible droplets may be employed. Thus, for nasal administration, a particle size in the range of 10-500 μm may be used to ensure retention in the nasal cavity.

Transdermal patches may also be employed, which are designed to remain in contact with the epidermis of the patient for an extended period of time and promote the absorption of the active ingredient there through.

Compositions for vaginal or rectal administration include ointments, creams, suppositories and enemas, all of which may be formulated using conventional techniques.

In one preferred embodiment, the composition is an inhalable pharmaceutical composition which is suitable for inhalation and delivery to the endobronchial space. Typically, such composition is in the form of an aerosol comprising particles for delivery using a nebulizer, pressurized metered dose inhaler (MDI), softmist inhaler, or dry powder inhaler (DPI). The aerosol formulation used in the methods of the present invention may be a liquid (e.g., solution) suitable for administration by a nebulizer, softmist inhaler, or MDI, or a dry powder suitable for administration by an MDI or DPI.

Aerosols used to administer medicaments to the respiratory tract are typically polydisperse; that is they are comprised of particles of many different sizes. The particle size distribution is typically described by the Mass Median Aerodynamic Diameter (MMAD) and the Geometric Standard Deviation (GSD). For optimum drug delivery to the endobronchial space the MMAD is in the range from about 1 to about 10 μm and preferably from about 1 to about 5 μm, and the GSD is less than 3, and preferably less than about 2. Aerosols having a MMAD above 10 μm are generally too large when inhaled to reach the lungs. Aerosols with a GSD greater than about 3 are not preferred for lung delivery as they deliver a high percentage of the medicament to the oral cavity. To achieve these particle sizes in powder formulation, the particles of the active ingredient may be size reduced using conventional techniques such as micronisation or spray drying. Non-limiting examples of other processes or techniques that can be used to produce respirable particles include spray drying, precipitation, supercritical fluid, and freeze drying. The desired fraction may be separated out by air classification or sieving. In one embodiment, the particles will be crystalline. For liquid formulations, the particle size is determined by the selection of a particular model of nebulizer, softmist inhaler, or MDI.

Aerosol particle size distributions are determined using devices well known in the art. For example a multi-stage Anderson cascade impactor or other suitable method such as those specifically cited within the US Pharmacopoeia Chapter 601 as characterizing devices for aerosols emitted from metered-dose and dry powder inhalers.

Dry powder compositions for topical delivery to the lung by inhalation may be formulated without excipient or carrier and instead including only the active ingredients in a dry powder form having a suitable particle size for inhalation. Dry powder compositions may also contain a mix of the active ingredient and a suitable powder base (carrier/diluent/excipient substance) such as mono-, di- or poly-saccharides (e.g., lactose or starch). Lactose is typically the preferred excipient for dry powder formulations. When a solid excipient such as lactose is employed, generally the particle size of the excipient will be much greater than the active ingredient to aid the dispersion of the formulation in the inhaler.

Non-limiting examples of dry powder inhalers include reservoir multi-dose inhalers, pre-metered multi-dose inhalers, capsule-based inhalers and single-dose disposable inhalers. A reservoir inhaler contains a large number of doses (e.g. 60) in one container. Prior to inhalation, the patient actuates the inhaler which causes the inhaler to meter one dose of medicament from the reservoir and prepare it for inhalation. Examples of reservoir DPIs include but are not limited to the Turbohaler® by AstraZeneca and the ClickHaler® by Vectura.

In a pre-metered multi-dose inhaler, each individual dose has been manufactured in a separate container, and actuation of the inhaler prior to inhalation causes a new dose of drug to be released from its container and prepared for inhalation. Examples of multidose DPI inhalers include but are not limited to Diskus® by GSK, Gyrohaler® by Vectura, and Prohaler® by Valois. During inhalation, the inspiratory flow of the patient accelerates the powder out of the device and into the oral cavity. For a capsule inhaler, the formulation is in a capsule and stored outside the inhaler. The patient puts a capsule in the inhaler, actuates the inhaler (punctures the capsule), then inhales. Examples include the Rotohaler™ (GlaxoSmithKline), Spinhaler™ (Novartis), HandiHaler™ (IB), TurboSpin™ (PH&T). With single-dose disposable inhalers, the patient actuates the inhaler to prepare it for inhalation, inhales, then disposes of the inhaler and packaging. Examples include the Twincer™ (U Groningen), One-Dose™ (GFE), and Manta Inhaler™ (Manta Devices).

Generally, dry powder inhalers utilize turbulent flow characteristics of the powder path to cause the excipient-drug aggregates to disperse, and the particles of active ingredient are deposited in the lungs. However, certain dry powder inhalers utilize a cyclone dispersion chamber to produce particles of the desired respirable size. In a cyclone dispersion chamber, the drug enters a coin shaped dispersion chamber tangentially so that the air path and drug move along the outer circular wall. As the drug formulation moves along this circular wall it bounces around and agglomerates are broken apart by impact forces. The air path spirals towards the center of the chamber exiting vertically. Particles that have small enough aerodynamic sizes can follow the air path and exit the chamber. In effect, the dispersion chamber works like a small jet mill. Depending on the specifics of the formulation, large lactose particles may be added to the formulation to aid in the dispersion through impact with the API particles.

The Twincer™ single-dose disposable inhaler appears to operate using a coin-shaped cyclone dispersion chamber referred to as an "air classifier." See, U.S. Published Patent Application No. 2006/0237010 to Rijksuniversiteit Groningen. Papers published by the University of Groningen, have stated that a 60 mg dose of pure micronized colistin sulfomethate could be effectively delivered as an inhalable dry powder utilizing this technology.

In preferred embodiments, the aerosol formulation is delivered as a dry powder using a dry powder inhaler wherein the particles emitted from the inhaler have an MMAD in the range of about 1 μm to about 5 μm and a GSD about less than 2.

Examples of suitable dry powder inhalers and dry powder dispersion devices for use in the delivery of compounds and compositions according to the present invention include but are not limited to those disclosed in U.S. Pat. No. 7,520,278; U.S. Pat. No. 7,322,354; U.S. Pat. No. 7,246,617; U.S. Pat. No. 7,231,920; U.S. Pat. No. 7,219,665; U.S. Pat. No. 7,207,330; U.S. Pat. No. 6,880,555; U.S. Pat. No. 5,522,385; U.S. Pat. No. 6,845,772; U.S. Pat. No. 6,637,431; U.S. Pat. No. 6,329,034; U.S. Pat. No. 5,458,135; U.S. Pat. No. 4,805,811; and U.S. Published Patent Application No. 2006/0237010.

In one embodiment, the pharmaceutical formulation according to the invention is a dry powder for inhalation which is formulated for delivery by a Diskus®-type device. The Diskus® device comprises an elongate strip formed from a base sheet having a plurality of recesses spaced along its length and a lid sheet hermetically but peelably sealed thereto to define a plurality of containers, each container having therein an inhalable formulation containing a predetermined amount of active ingredient either alone or in admixture with one or more carriers or excipients (e.g., lactose) and/or other therapeutically active agents. Preferably, the strip is sufficiently flexible to be wound into a roll. The lid sheet and base sheet will preferably have leading end portions which are not sealed to one another and at least one of the leading end portions is constructed to be attached to a winding means. Also, preferably the hermetic seal between the base and lid sheets extends over their whole width. To prepare the dose for inhalation, the lid sheet may preferably be peeled from the base sheet in a longitudinal direction from a first end of the base sheet.

In one embodiment, the pharmaceutical formulation according to the invention is a dry powder for inhalation which is formulated for delivery using a single-dose disposable inhaler, and particularly the Twincer™ inhaler. The Twincer™ inhaler comprises a foil laminate blister with one or more recesses and a lid sheet hermetically but peelably sealed thereto to define a plurality of containers. Each container has therein an inhalable formulation containing a predetermined amount of active ingredient(s) either alone or in admixture with one or more carriers or excipeints (e.g., lactose). The lid sheet will preferably have a leading end portion which is constructed to project from the body of the inhaler. The patient would operate the device and thereby administer the aerosol formulation by 1) removing the outer packaging overwrap, 2) pulling the foil tab to uncover the drug in the blister and 3) inhaling the drug from the blister.

In another embodiment, the pharmaceutical formulation according to the invention is a dry powder for inhalation wherein the dry powder is formulated into microparticles as described in PCT Publication No. WO2009/015286 or WO2007/114881, both to NexBio. Such microparticles are generally formed by adding a counterion to a solution containing a compound of the invention in a solvent, adding an antisolvent to the solution; and gradually cooling the solution to a temperature below about 25° C., to form a composition containing microparticles comprising the compound. The microparticles comprising the compound may then be separated from the solution by any suitable means such as sedimentation, filtration or lyophillization. Suitable counterions, solvents and antisolvents for preparing microparticles of the compounds of the invention are described in WO2009/015286.

In another embodiment, a pharmaceutical composition according to the invention is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234 and U.S. Pat. No. 7,108,159. In a preferred embodiment, a compound of the invention is delivered as a dry powder using a metered dose inhaler wherein the emitted particles have an MMAD that is in the range of about 1 μm to about 5 μm and a GSD that is less than about 2 μm.

Liquid aerosol formulations for delivery to the endobronchial space or lung by inhalation may for example be formulated as aqueous solutions or suspensions or as aerosols delivered from pressurized packs, such as metered dose inhalers, with the use of suitable liquefied propellants, softmist inhalers, or nebulizers. Such aerosol compositions suitable for inhalation can be either a suspension or a solution and generally contain the active ingredient(s) together with a pharmaceutically acceptable carrier or diluent (e.g., water (distilled or sterile), saline, hypertonic saline, or ethanol) and optionally one or more other therapeutically active agents.

Aerosol compositions for delivery by pressurized metered dose inhalers typically further comprise a pharmaceutically acceptable propellant. Examples of such propellants include fluorocarbon or hydrogen-containing chlorofluorocarbon or mixtures thereof, particularly hydrofluoroalkanes, e.g., dichlorodifluoromethane, trichlorofluoromethane, dichlorotetrafluoroethane, especially 1,1,1,2-tetrafluoroethane, 1,1,1,2,3,3,3,-heptafluoro-n-propane or a mixture thereof. The aerosol composition may be excipient free or may optionally contain additional formulation excipients well known in the art such as surfactants e.g., oleic acid or lecithin and cosolvents e.g., ethanol. Pressurized formulations will generally be retained in a canister (e.g., an aluminum canister) closed with a valve (e.g., a metering valve) and fitted into an actuator provided with a mouthpiece.

In another embodiment, a pharmaceutical composition according to the invention is delivered as a liquid using a metered dose inhaler. Non-limiting examples of metered dose inhalers and devices include those disclosed in U.S. Pat. Nos. 6,253,762, 6,413,497, 7,601,336, 7,481,995, 6,743,413, and 7,105,152. In a preferred embodiment, a compound of the invention is delivered as a dry powder using a metered dose inhaler wherein the emitted particles have an MMAD that is in the range of about 1 μm to about 5 μm and a GSD that is less than about 2.

In one embodiment the aerosol formulation is suitable for aerosolization by a jet nebulizer, or ultrasonic nebulizer including static and vibrating porous plate nebulizers. Liquid aerosol formulations for nebulization may be generated by solubilizing or reconstituting a solid particle formulation or may be formulated with an aqueous vehicle with the addition of agents such as acid or alkali, buffer salts, and isotonicity adjusting agents. They may be sterilized by in-process techniques such as filtration, or terminal processes such as heating in an autoclave or gamma irradiation. They may also be presented in non-sterile form.

Patients can be sensitive to the pH, osmolality, and ionic content of a nebulized solution. Therefore these parameters should be adjusted to be compatible with the active ingredient and tolerable to patients. The most preferred solution or suspension of active ingredient will contain a chloride concentration >30 mM at pH 4.5-7.4, preferably 5.0-5.5, and an osmolality of from about 800-1600 mOsm/kg. The pH of the solution can be controlled by either titration with common acids (hydrochloric acid or sulfuric acid, for example) or bases (sodium hydroxide, for example) or via the use of buffers. Commonly used buffers include citrate buffers, acetate buffers, and phosphate buffers. Buffer strengths can range from 2 mM to 50 mM.

Such formulations may be administered using commercially available nebulizers or other atomizer that can break the formulation into particles or droplets suitable for deposition in the respiratory tract. Non-limiting examples of nebulizers which may be employed for the aerosol delivery of a composition of the invention include pneumatic jet nebulizers, vented or breath enhanced jet nebulizers, or ultrasonic nebulizers including static or vibrating porous plate nebulizers.

A jet nebulizer utilizes a high velocity stream of air blasting up through a column of water to generate droplets. Particles unsuitable for inhalation impact on walls or aerodynamic baffles. A vented or breath enhanced nebulizer works in essentially the same way as a jet nebulizer except that inhaled air passes through the primary droplet generation area to increase the output rate of the nebulizer while the patient inhales.

In an ultrasonic nebulizer, vibration of a piezoelectric crystal creates surface instabilities in the drug reservoir that cause droplets to be formed. In porous plate nebulizers pressure fields generated by sonic energy force liquid through the mesh pores where it breaks into droplets by Rayleigh breakup. The sonic energy may be supplied by a vibrating horn or plate driven by a piezoelectric crystal, or by the mesh itself vibrating. Non-limiting examples of atomizers include any single or twin fluid atomizer or nozzle that produces droplets of an appropriate size. A single fluid atomizer works by forcing a liquid through one or more holes, where the jet of liquid breaks up into droplets. Twin fluid atomizers work by either forcing both a gas and liquid through one or more holes, or by impinging a jet of liquid against another jet of either liquid or gas.

The choice of nebulizer which aerosolizes the aerosol formulation is important in the administration of the active ingredient(s). Different nebulizers have differing efficiencies based their design and operation principle and are sensitive to the physical and chemical properties of the formulation. For example, two formulations with different surface tensions may have different particle size distributions. Additionally, formulation properties such as pH, osmolality, and permeant ion content can affect tolerability of the medication, so preferred embodiments conform to certain ranges of these properties.

In a preferred embodiment, the formulation for nebulization is delivered to the endobronchial space as an aerosol having an MMAD between about 1 µm and about 5 µm and a GSD less than 2 using an appropriate nebulizer. To be optimally effective and to avoid upper respiratory and systemic side effects, the aerosol should not have a MMAD greater than about 5 µm and should not have a GSD greater than about 2. If an aerosol has an MMAD larger than about 5 µm or a GSD greater than about 2 µm.a large percentage of the dose may be deposited in the upper airways decreasing the amount of drug delivered to the desired site in the lower respiratory tract. If the MMAD of the aerosol is smaller than about 1 µm then a large percentage of the particles may remain suspended in the inhaled air and may then be exhaled during expiration.

The compounds of the invention may also be administered by transbronchoscopic lavage.

In another aspect, the invention provides a method of promoting hydration of mucosal surfaces or restoring mucosal defense in a human in need thereof, comprising administering to the human a pharmaceutical composition comprising a compound of the invention, wherein said compound is administered in an effective amount. In one preferred embodiment, the method comprises administering the pharmaceutical composition as an inhalable composition comprising an amount of a compound of the invention that is sufficient to achieve dissolved concentration of the compound on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter.

In another aspect, the invention provides a method of treating any one of: a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, and ventilator-associated tracheobronchitis or preventing ventilator-associated pneumonia in a human in need thereof, comprising administering to the human a pharmaceutical composition comprising a compound of the invention, wherein said compound is administered in an effective amount. In one preferred embodiment, the method comprises administering the pharmaceutical composition as an inhalable composition comprising an amount of a compound of the invention that is sufficient to achieve dissolved concentration of the compound on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter.

In another aspect, the invention provides a method of treating any one of dry mouth (xerostomia), dry skin, vaginal dryness, sinusitis, rhinosinusitis, or nasal dehydration, including nasal dehydration brought on by administering dry oxygen, dry eye, Sjogren's disease-associated dry eye, promoting ocular or corneal hydration, treating distal intestinal obstruction syndrome, treating otitis media, primary ciliary diskinesia, distal intestinal obstruction syndrome, esophagitis, constipation, or chronic diverticulitis in a human in need thereof, comprising administering to the human a pharmaceutical composition comprising a compound of the invention, wherein said compound is administered in an effective amount.

Preferred unit dosage formulations for the compounds of the invention are those containing an effective amount of the active ingredient or an appropriate fraction thereof.

It should be understood that in addition to the ingredients particularly mentioned above, the formulations of this invention may include other agents conventional in the art having regard to the type of formulation in question for example those suitable for oral administration may include flavoring agents.

The compositions of the present invention may be formulated for immediate, controlled or sustained release as desired for the particular condition being treated and the desired route of administration. For example, a controlled release formulation for oral administration may be desired for the treatment of constipation in order to maximize delivery of the active agent to colon. Such formulations and suitable excipients for the same are well known in the art of pharmacy. Because the free base of the compound is generally less soluble in aqueous solutions than the salt, compositions comprising a free base of a compound of Formula I may be employed to provide more sustained release of active agent delivered by inhalation to the lungs. An active agent present in the lungs in particulate form which has not dissolved into solution is not available to induce a physiological response, but serves as a depot of bioavailable drug which gradually dissolves into solution. As another example, a formulation may employ both a free base and salt form of a compound of the invention to provide both immediate release and sustained release of the active ingredient for dissolution into the mucus secretions of, for example, the nose.

ENaC blockers described in this invention can be administered by topical administration to the eyes of a patient in need of such treatment. ENaC blockers of Formula I are administered to the ocular surface of a subject, in an amount effective to reduce dry eye symptoms and to improve hydration of the tear film. Preferably, ENaC blockers are administered as a liquid or gel suspension in the form of drops, spray or gel. Alternatively, ENaC blockers can be applied to the eye via liposomes. ENaC blockers can also be contained within, carried by, or attached to contact lenses, punctual plugs or other compatible controlled release materials, which are placed on the eye. ENaC blockers can also be contained within a swab or sponge which can be applied to the ocular surface. ENaC blockers can also be contained within a liquid spray which can be applied to the ocular surface. Another embodiment of the present invention involves an injection of ENaC blockers directly into the lacrimal tissues or onto the eye surface.

The topical solution containing ENaC blockers can contain a physiologically compatible vehicle, as those skilled in the ophthalmic art can select using conventional criteria. The ophthalmic vehicles include, but are not limited to, saline solution, water polyethers such as polyethylene glycol, polyvinyls such as polyvinyl alcohol and povidone, cellulose derivatives such as methylcellulose and hydroxypropyl methylcellulose, polycarbophil, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

The topical formulation optionally includes a preservative, such as benzalkonium chloride and other inactive ingredients such as EDTA. The pH of the formulation is adjusted by adding any physiologically and ophthamologically acceptable pH adjusting acids, bases or buffers to within the range of about 4.5 to 7.5; preferably 5 to 7. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. Salts and buffers include citrate/dextrose, sodium bicarbonate, ammonium chloride and mixtures of the aforementioned acids and bases.

The osmotic pressure of the topical formulation of ENaC blockers is generally from about 200 to about 400 milliosmolar (mOsM), more preferably from 260 to 340 mOsM. The osmotic pressure can be adjusted by using appropriate amounts of physiologically and ophthamologically acceptable ionic or non-ionic agents. Sodium chloride is a preferred ionic agent, and the amount of sodium chloride ranges from about 0.01% to about 1% (w/v), and preferably from about 0.05% to about 0.85% (w/v). Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can be used in addition to or instead of sodium chloride to achieve osmolality within the above-stated range. Further, non-ionic agents such as mannitol, dextrose, sorbitol, glucose and the like can also be used to adjust the osmolality.

The concentration of ENaC blockers included in the topical formulation is an amount sufficient to reduce dry eye symptoms and/or improve hydration of the tear film. This formulation is preferably an aqueous solution of ENaC blockers and is in the range of 0.0001-0.3%, preferably 0.001% to 0.1%, more preferably 0.003-0.05%, and most preferably about 0.03% (w/v). "About" as used herein, refers to ±15% of the recited value. The formulation optionally includes a preservative, such as benzalkonium chloride (0.003% w/v) and inactive ingredients: edetate sodium, purified water, sodium chloride, sodium phosphate monobasic, sodium hydroxide, and/or hydrochloric acid to adjust the pH to about 4-8.

The daily topical dose to reduce dry eye symptoms and improve tear film composition can be divided among one or several unit dose administrations. The total daily dose for ENaC blockers, for example, can range from one drop (about 50 μl), one to four times a day, depending upon the age and condition of the subject. A preferred regimen for ENaC blockers is one drop of 0.03% (w/v) solution, about one to two times a day.

Liquid pharmaceutical compositions of ENaC blockers for producing eye drops can be prepared by combining ENaC blockers with a suitable vehicle, such as sterile pyrogen free water or sterile saline by techniques known to those skilled in the art.

Combinations

The compounds of the invention may be formulated and/or used in combination with other therapeutically active agents. Examples of other therapeutically active agents which may be formulated or used in combination with the compounds of the invention include but are not limited to osmolytes, anti-inflammatory agents, anticholinergic agents, β-agonists (including selective $β_2$-agonists), P2Y2 receptor agonists, peroxisome proliferator-activated receptor (PPAR) delta agonists, other epithelial sodium channel blockers (ENaC receptor blockers), cystic fibrosis transmembrane conductance regulator (CFTR) modulators, kinase inhibitors, antiinfective agents, antihistamines, non-antibiotic anti-inflammatory macrolides, elastase and protease inhibitors, and mucus or mucin modifying agents, such as surfactants.

The present invention thus provides, as another aspect, a composition comprising an effective amount of a compound of the invention and one or more other therapeutically active agents selected from osmolytes, anti-inflammatory agents, anticholinergic agents, β-agonists (including selective $β_2$-agonists), P2Y2 receptor agonists, PPAR delta agonists, ENaC receptor blockers, cystic fibrosis transmembrane conductance regulator (CFTR) modulators, kinase inhibitors, antiinfective agents, antihistamines, non-antibiotic anti-inflammatory macrolides, elastase and protease inhibitors, and mucus or mucin modifying agents, such as surfactants. Use of the compounds of the invention in combination with one or more other therapeutically active agents (particularly osmolytes) may lower the dose of the compound of the invention that is required to sufficiently hydrate mucosal surfaces, thereby reducing the potential for undesired side-effects attributable to systemic blocking of sodium channels such as for example in the kidneys.

"Osmolytes" according to the present invention are molecules or compounds that are osmotically active. "Osmotically active" molecules and compounds are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Suitable osmolytes include ionic osmolytes (i.e., salts), and non-ionic osmolytes (i.e., sugars, sugar alcohols, and organic osmolytes). In general, osmolytes (both ionic and non-ionic) used in combination with the compounds of the invention are preferably osmolytes that do not promote, or in fact deter or retard bacterial growth. Osmolytes suitable for use in the present invention may be in racemic form or in the form of an enantiomer, diastereomer, tautomer, polymorph or pseudopolymorph.

Examples of ionic osmolytes useful in the present invention include any salt of a pharmaceutically acceptable anion and a pharmaceutically acceptable cation. Preferably, either (or both) of the anion and cation are osmotically active and not subject to rapid active transport, in relation to the airway surfaces to which they are administered. Such compounds include but are not limited to anions and cations that are contained in FDA approved commercially marketed salts, see, e.g., *Remington: The Science and Practice of Pharmacy*, Vol. II, pg. 1457 (19$^{th}$ Ed. 1995), and can be used in any combination as known in the art.

Specific examples of pharmaceutically acceptable osmotically active anions include but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrte, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Preferred anions include chloride, sulfate, nitrate, gluconate, iodide, bicarbonate, bromide, and phosphate.

Specific examples of pharmaceutically acceptable osmotically active cations include but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like; and metallic cations such as aluminum, calcium, lithium, magnesium, potassium, sodium, zinc, iron, ammonium, and the like. Preferred organic cations include 3-carbon, 4-carbon, 5-carbon and 6-carbon organic cations. Preferred cations include sodium, potassium, choline, lithium, meglumine, D-lysine, ammonium, magnesium, and calcium.

Specific examples of ionic osmolytes that may be used in combination with a compound of the invention include but are not limited to, sodium chloride (particularly hypertonic saline), potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, and combinations of any two or more of the foregoing. In one embodiment, the present invention provides a combination of a compound of the invention and two different osmotically active salts. When different salts are used, one of the anion or cation may be the same among the differing salts. Hypertonic saline is a preferred ionic osmolyte for use in combination with the compounds of the invention.

Non-ionic osmolytes include sugars, sugar-alcohols, and organic osmolytes. Sugars and sugar-alcohols useful as osmolytes in the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol are also suitable for the present invention. For example, glucose, when reduced, becomes sorbitol; an osmolyte within the scope of the invention. Accordingly, sorbitol and other reduced forms of sugar/sugar alcohols (e.g., mannitol, dulcitol, arabitol) are suitable osmolytes for use in the present invention. Mannitol is a preferred non-ionic osmolyte for use in combination with the compounds of the invention.

"Organic osmolytes" is generally used to refer to molecules that control intracellular osmolality in the kidney. See e.g., J. S. Handler et al., *Comp. Biochem. Physiol*, 117, 301-306 (1997); M. Burg, *Am. J. Physiol.* 268, F983-F996 (1995). Organic osmolytes include but are not limited to three major classes of compounds: polyols (polyhydric alcohols), methylamines, and amino acids. Suitable polyol organic osmolytes include but are not limited to, inositol, myo-inositol, and sorbitol. Suitable methylamine organic osmolytes include but are not limited to, choline, betaine, carnitine (L-, D- and DL forms), phosphorylcholine, lyso-phosphorylcholine, glycerophosphorylcholine, creatine, and creatine phosphate. Suitable amino acid organic osmolytes include but are not limited to, the D- and L-forms of glycine, alanine, glutamine, glutamate, aspartate, proline and taurine. Additional organic osmolytes suitable for use in the present invention include tihulose and sarcosine. Mammalian organic osmolytes are preferred, with human organic osmolytes being most preferred. However, certain organic osmolytes are of bacterial, yeast, and marine animal origin, and these compounds may also be employed in the present invention.

Osmolyte precursors may be used in combination with the compounds of the invention An "osmolyte precursor" as used herein refers to a compound which is converted into an osmolyte by a metabolic step, either catabolic or anabolic. Examples of osmolyte precursors include but are not limited to, glucose, glucose polymers, glycerol, choline, phosphatidylcholine, lyso-phosphatidylcholine and inorganic phosphates, which are precursors of polyols and methylamines. Precursors of amino acid osmolytes include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Chemically modified osmolytes or osmolyte precursors may also be employed. Such chemical modifications involve linking the osmolyte (or precursor) to an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., *J. Med. Chem.* 19:113-117 (1976); Bodor, N. et al., *J. Pharm. Sci.* 67:1045-1050 (1978); Bodor, N. et al., *J. Med. Chem.* 26:313-318 (1983); Bodor, N. et al., *J. Pharm. Sci.* 75:29-35 (1986).

Preferred osmolytes for use in combination with the compounds of the invention include sodium chloride, particular hypertonic saline, and mannitol.

For the formulation of 7% and >7% hypertonic saline, formulations containing bicarbonate anions may be particularly useful, especially for respiratory disorders with cystic fibrosis transmembrane conductance regulator (CFTR) dysfunction such as CF or COPD. Recent findings indicate that, although the relative ratio of $HCO_3^-$ conductance/$Cl^-$ conductance is between 0.1 and 0.2 for single CFTR channels activated with cAMP and ATP, the ratio in the sweat duct can range from virtually 0 to almost 1.0, depending on conditions of stimulation. That is, combining cAMP+cGMP+α-ketoglutarate can yield CFTR $HCO_3^-$ conductance almost equal to that of $Cl^-$ conductance (Quiton et al. Physiology, Vol. 22, No. 3, 212-225, June 2007). Furthermore, formulations of 7% and >7% hypertonic saline containing bicarbonate anions may be particularly useful due to better control of the pH in the airway surface liquid. First, it has shown that that airway acidification occurs in CF (Tate et al. 2002) and that absent CFTR-dependent bicarbonate secretion can lead to an impaired capacity to respond to airway conditions associated with acidification of airway surface liquid layer (Coakley et al. 2003). Second, addition of HS solution without bicarbonate to the surface of the lung may further dilute the bicarbonate concentrations, and potentially reduce the pH or the ability to respond to airway acidification within the airway surface liquid layer. Therefore addition of bicarbonate anions to HS may help maintain or improve the pH of airway surface liquid layer in CF patients.

Due to this evidence, inclusion of bicarbonate anion in the formulation of 7% or >7% hypertonic saline administered by the method of this invention would be particularly useful. Formulations containing up to 30 to 200 mM concentrations of bicarbonate anions are of particular interest for 7% or >7% HS solutions.

Hypertonic saline is understood to have a salt concentration greater than that of normal saline, i.e. greater than 9 g/L or 0.9% w/v, and hypotonic saline has a salt concentration less than that of normal saline. Hypotonic saline solutions useful in the formulations and methods of treatment herein may have a salt concentration from about 1% to about 23.4% (w/v). In one embodiment the hypertonic saline solution has a salt concentration from about 60 g/L (6% w/v) to about 100 g/L (10% w/v). In another embodiment, the saline solution has a salt concentration from about 70 g/L (7% w/v) to about 100 g/L (10% w/v). In further embodiments, the saline solution has salt concentrations of a) from about 0.5 g/L (0.05% w/v) to about 70 g/L (7% w/v); b) from about 1 g/L (0.1% w/v) to about 60 g/L (6% w/v); c) from about 1 g/L (0.1% w/v) to about 50 g/L (5% w/v); d) from about 1 g/L (0.1% w/v) to about 40 g/L (4% w/v); e) from about 1 g/L (0.1% w/v) to about 30 g/L (3% w/v); and f) from about 1 g/L (0.1% w/v) to about 20 g/L (2% w/v).

Specific concentrations of saline solutions useful in the formulations and methods of treatment herein include, independently, those having salt concentrations of 1 g/L (0.1% w/v), 2 g/L (0.2% w/v), 3 g/L (0.3% w/v), 4 g/L (0.4% w/v), 5 g/L (0.5% w/v), 6 g/L (0.6% w/v), 7 g/L (0.7% w/v), 8 g/L (0.8% w/v), 9 g/L (0.9% w/v), 10 g/L (1% w/v), 20 g/L (2% w/v), 30 g/L (3% w/v), 40 g/L (4% w/v), 50 g/L (5% w/v), 60 g/L (6% w/v), 70 g/L (7% w/v), 80 g/L (8% w/v), 90 g/L (9% w/v), 100 g/L (10% w/v), 110 g/L (11% w/v), 120 g/L (12% w/v), 130 g/L (13% w/v), 140 g/L (14% w/v), and 150 g/L (15% w/v). Saline concentrations between each of these listed concentrations/percentages may also be used, such as saline of 1.7 g/L (0.17% w/v), 28 g/L (2.8% w/v), 35 g/L (3.5% w/v), and 45 g/L (4.5% w/v). Each of the ranges and specific concentrations of saline may be used with the formulations, methods of treatment, regimens, and kits described herein.

Also intended within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., J. Med. Chem. 19:113-117 (1976); Bodor, N. et al., J. Pharm. Sci. 67:1045-1050 (1978); Bodor, N. et al., J. Med. Chem. 26:313-318 (1983); Bodor, N. et al., J. Pharm. Sci. 75:29-35 (1986), each incorporated herein by reference.

Suitable anti-inflammatory agents for use in combination with the compounds of the invention include corticosteroids and non-steroidal anti-inflammatory drugs (NSAIDs), particularly phosphodiesterase (PDE) inhibitors. Examples of corticosteroids for use in the present invention include oral or inhaled corticosteroids or prodrugs thereof. Specific examples include but are not limited to ciclesonide, desisobutyryl-ciclesonide, budesonide, flunisolide, mometasone and esters thereof (e.g., mometasone furoate), fluticasone propionate, fluticasone furoate, beclomethasone, methyl prednisolone, prednisolone, dexamethasone, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g., the 17-propionate ester or the 17,21-dipropionate ester, fluoromethyl ester, triamcinolone acetonide, rofleponide, or any combination or subset thereof. Preferred corticosteroids for formulation or use in combination with the compounds of the invention are selected from ciclesonide, desisobutyryl-ciclesonide, budesonide, mometasone, fluticasone propionate, and fluticasone furoate, or any combination or subset thereof.

NSAIDs for use in the present invention include but are not limited to sodium cromoglycate, nedocromil sodium, phosphodiesterase (PDE) inhibitors (e.g., theophylline, aminophylline, PDE4 inhibitors, mixed PDE3/PDE4 inhibitors or mixed PDE4/PDE7 inhibitors), leukotriene antagonists, inhibitors of leukotriene synthesis (e.g., 5 LO and FLAP inhibitors), nitric oxide synthase (iNOS) inhibitors, protease inhibitors (e.g., tryptase inhibitors, neutrophil elastase inhibitors, and metalloprotease inhibitors) β2-integrin antagonists and adenosine receptor agonists or antagonists (e.g., adenosine 2a agonists), cytokine antagonists (e.g., chemokine antagonists) or inhibitors of cytokine synthesis (e.g., prostaglandin D2 (CRTh2) receptor antagonists). Examples of leukotriene modifiers suitable for administration by the method of this invention include monteleukast, zileuton and zafirlukast.

The PDE4 inhibitor, mixed PDE3/PDE4 inhibitor or mixed PDE4/PDE7 inhibitor may be any compound that is known to inhibit the PDE4 enzyme or which is discovered to act as a PDE4 inhibitor, and which are selective PDE4 inhibitors (i.e., compounds which do not appreciably inhibit other members of the PDE family). Examples of specific PDE4 inhibitors for formulation and use in combination with the compounds of the present invention include but are not limited to roflumilast, pumafentrine, arofylline, cilomilast, tofimilast, oglemilast, tolafentrine, piclamilast, ibudilast, apremilast, 2-[4-[6,7-diethoxy-2,3-bis(hydroxymethyl)-1-naphthalenyl]-2-pyridinyl]-4-(3-pyridinyl)-1(2H)-phthalazinone (T2585), N-(3,5-dichloro-4-pyridinyl)-1-[(4-fluorophenyl)methyl]-5-hydroxy-α-oxo-1H-indole-3-acetamide (AWD-12-281, 4-[(2R)-2-[3-(cyclopentyloxy)-4-methoxyphenyl]-2-phenylethyl]-pyridine (CDP-840), 2-[4-[[[[2-(1,3-benzodioxol-5-yloxy)-3-pyridinyl]carbonyl]amino]methyl]-3-fluorophenoxy]-(2R)-propanoic acid (CP-671305), N-(4,6-dimethyl-2-pyrimidinyl)-4-[4,5,6,7-tetrahydro-2-(4-methoxy-3-methylphenyl)-5-(4-methyl-1-piperazinyl)-1H-indol-1-yl]-benzenesulfonamide, (2E)-2-butenedioate (YM-393059), 9-[(2-fluorophenyl)methyl]-N-methyl-2-(trifluoromethyl)-9H-purin-6-amine (NCS-613), N-(2,5-dichloro-3-pyridinyl)-8-methoxy-5-quinolinecarboxamide (D-4418), N-[(3R)-9-amino-3,4,6,7-tetrahydro-4-oxo-1-phenylpyrrolo[3,2,1-][1,4]benzodiazepin-3-yl]-3H-purin-6-amine (PD-168787), 3-[[3-(cyclopentyloxy)-4-methoxyphenyl]methyl]-N-ethyl-8-(1-methylethyl)-3H-purin-6-amine hydrochloride (V-11294A), N-(3,5-dichloro-1-oxido-4-pyridinyl)-8-methoxy-2-(trifluoromethyl)-5-quinolinecarboxamide (Sch351591), 5-[3-(cyclopentyloxy)-4-methoxyphenyl]-3-[(3-methylphenyl)methyl]-(3S,5S)-2-piperidinone (HT-0712), 5-(2-((1R,4R)-4-amino-1-(3-(cyclopenyloxy)-4-methyoxyphenyl)cyclohexyl)ethynyl)-pyrimidine-2-amine, cis-[4-cyano-4-(3-cyclopropylmethoxy-4-difluoromethoxy phenyl) cyclohexan-1-ol], and 4-[6,7-diethoxy-2,3-bis (hydroxymethyl)-1-naphthalenyl]-1-(2-methoxyethyl)-2 (1H)-pyridinone (T-440), and any combination or subset thereof.

Leukotriene antagonists and inhibitors of leukotriene synthesis include zafirlukast, montelukast sodium, zileuton, and pranlukast.

Anticholinergic agents for formulation or use in combination with the compounds of the invention include but are not limited to muscarinic receptor antagonists, particularly including pan antagonists and antagonists of the $M_3$ receptors. Exemplary compounds include the alkaloids of the belladonna plants, such as atropine, scopolamine, homatropine, hyoscyamine, and the various forms including salts thereof (e.g., anhydrous atropine atropine sulfate, atropine oxide or HCl, methylatropine nitrate, homatropine hydrobromide, homatropine methyl bromide, hyoscyamine hydrobromide, hyoscyamine sulfate, scopolamine hydrobromide, scopolamine methyl bromide), or any combination or subset thereof.

Additional anticholinergics for formulation and use in combination with the methantheline, propantheline bromide, anisotropine methyl bromide or Valpin 50, aclidinium bromide, glycopyrrolate (Robinul), isopropamide iodide, mepenzolate bromide, tridihexethyl chloride, hexocyclium methylsulfate, cyclopentolate HCl, tropicamide, trihexyphenidyl CCl, pirenzepine, telenzepine, and methoctramine, or any combination or subset thereof.

Preferred anticholinergics for formulation and use in combination with the compounds of the invention include ipratropium (bromide), oxitropium (bromide) and tiotropium (bromide), or any combination or subset thereof.

Examples of β-agonists for formulation and use in combination with the compounds of the invention include but are not limited to salmeterol, R-salmeterol, and xinafoate salts thereof, albuterol or R-albuterol (free base or sulfate), levalbuterol, salbutamol, formoterol (fumarate), fenoterol, procaterol, pirbuterol, metaprterenol, terbutaline and salts thereof, and any combination or subset thereof.

P2Y2 receptor agonists for formulation and use in combination with the compounds of the invention may be employed in an amount effective to stimulate chloride and water secretion by airway surfaces, particularly nasal airway surfaces. Suitable P2Y2 receptor agonists are known in the art and are described for example, in columns 9-10 of U.S. Pat. No. 6,264,975, and also U.S. Pat. Nos. 5,656,256 and 5,292,498.

$P2Y_2$ agonists that can be administered by the methods of this invention include $P2Y_2$ receptor agonists such as ATP, UTP, UTP-.gamma.-S and dinucleotide $P2Y_2$ receptor agonists (e.g. denufosol or diquafosol) or a pharmaceutically acceptable salt thereof. The $P2Y_2$ receptor agonist is typically included in an amount effective to stimulate chloride and water secretion by airway surfaces, particularly nasal airway surfaces. Suitable $P2Y_2$ receptor agonists are described in, but are not limited to, U.S. Pat. No. 6,264,975, U.S. Pat. No. 5,656,256, U.S. Pat. No. 5,292,498, U.S. Pat. No. 6,348,589, U.S. Pat. No. 6,818,629, U.S. Pat. No. 6,977,246, U.S. Pat. No. 7,223,744, U.S. Pat. No. 7,531,525 and U.S. Pat. AP. 2009/0306009 each of which is incorporated herein by reference.

Combination therapies and formulations herein can include adenosine 2b (A2b) agonists, also, including BAY 60-6583, NECA (N-ethylcarboxamidoadenosine), (5)-PHP-NECA, LUF-5835 and LUF-5845. A2b agonists that may be used are described by Volpini et al., *Journal of Medicinal Chemistry* 45 (15): 3271-9 (2002); Volpini et al., *Current Pharmaceutical Design* 8 (26): 2285-98 (2002); Baraldi et al., *Journal of Medicinal Chemistry* 47 (6): Cacciari et al., 1434-47 (2004); *Mini Reviews in Medicinal Chemistry* 5 (12): 1053-60 (December 2005); Baraldi et al., *Current Medicinal Chemistry* 13 (28): 3467-82 (2006); Beukers et al., *Medicinal Research Reviews* 26 (5): 667-98 (September 2006); Elzein et al., *Bioorganic & Medicinal Chemistry Letters* 16 (2): 302-6 (January 2006); Carotti, et al., *Journal of Medicinal Chemistry* 49 (1): 282-99 (January 2006); Tabrizi et al., *Bioorganic & Medicinal Chemistry* 16 (5): 2419-30 (March 2008); and Stefanachi, et al., *Bioorganic & Medicinal Chemistry* 16 (6): 2852-69 (March 2008).

Examples of other ENaC receptor blockers for formulation and use in combination with the compounds of the invention include but are not limited to amiloride and derivatives thereof such as those compounds described in U.S. Pat. No. 6,858,615, and PCT Publication Nos. WO2003/070182, WO2004/073629, WO2005/018644, WO2006/022935, WO2007/018640, and WO2007/146869, all to Parion Sciences, Inc.

Small molecule ENaC blockers are capable of directly preventing sodium transport through the ENaC channel pore. ENaC blocker that can be administered in the combinations herein include, but are not limited to, amiloride, benzamil, phenamil, and amiloride analogues as exemplified by U.S. Pat. No. 6,858,614, U.S. Pat. No. 6,858,615, U.S. Pat. No. 6,903,105, U.S. Pat. No. 6,995,160, U.S. Pat. No. 7,026,325, U.S. Pat. No. 7,030,117, U.S. Pat. No. 7,064,129, U.S. Pat. No. 7,186,833, U.S. Pat. No. 7,189,719, U.S. Pat. No. 7,192, 958, U.S. Pat. No. 7,192,959, U.S. Pat. No. 7,241,766, U.S. Pat. No. 7,247,636, U.S. Pat. No. 7,247,637, U.S. Pat. No. 7,317,013, U.S. Pat. No. 7,332,496, U.S. Pat. No. 7,345,044, U.S. Pat. No. 7,368,447, U.S. Pat. No. 7,368,450, U.S. Pat. No. 7,368,451, U.S. Pat. No. 7,375,107, U.S. Pat. No. 7,399,766, U.S. Pat. No. 7,410,968, U.S. Pat. No. 7,820,678, U.S. Pat. No. 7,842,697, U.S. Pat. No. 7,868,010, U.S. Pat. No. 7,875,619.

ENaC proteolysis is well described to increase sodium transport through ENaC. Protease inhibitors block the activity of endogenous airway proteases, thereby preventing ENaC cleavage and activation. Proteases that cleave ENaC include furin, meprin, matriptase, trypsin, channel associated proteases (CAPs), and neutrophil elastases. Protease inhibitors that can inhibit the proteolytic activity of these proteases that can be administered in the combinations herein include, but are not limited to, camostat, prostasin, furin, aprotinin, leupeptin, and trypsin inhibitors.

Combinations herein may include one or more suitable nucleic acid (or polynucleic acid), including but not limited to antisense oligonucleotide, siRNA, miRNA, miRNA mimic, antagomir, ribozyme, aptamer, and decoy oligonucleotide nucleic acids. See, e.g., US Patent Application Publication No. 20100316628. In general, such nucleic acids may be from 17 or 19 nucleotides in length, up to 23, 25 or 27 nucleotides in length, or more. Examples include, but are not limited to, those described in U.S. Pat. No. 7,517,865 and US Patent Applications Nos. 20100215588; 20100316628; 20110008366; and 20110104255. In general, the siRNAs are from 17 or 19 nucleotides in length, up to 23, 25 or 27 nucleotides in length, or more.

CFTR activity modulating compounds that can be administered in the combinations of this invention include, but are not limited to, compounds described in US 2009/0246137 A1, US 2009/0253736 A1, US 2010/0227888 A1, U.S. Pat. No. 7,645,789, US 2009/0246820 A1, US 2009/0221597 A1, US 2010/0184739 A1, US 2010/0130547 A1, US 2010/0168094 A1 and issued U.S. Pat. No. 7,553,855; U.S. Pat. No. 7,772,259 B2, U.S. Pat. No. 7,405,233 B2, US 2009/0203752, U.S. Pat. No. 7,499,570.

Mucus or mucin modifying agents useful in the combinations and methods herein include reducing agents, surfactants and detergents, expectorants, and deoxyribonuclease agents.

Mucin proteins are organized into high molecular weight polymers via the formation of covalent (disulfide) and non-covalent bonds. Disruption of the covalent bonds with reducing agents is a well-established method to reduce the viscoelastic properties of mucus in vitro and is predicted to minimize mucus adhesiveness and improve clearance in vivo. Reducing agents are well known to decrease mucus viscosity in vitro and commonly used as an aid to processing sputum samples[8]. Examples of reducing agents include sulfide containing molecules or phosphines capable of reducing protein di-sulfide bonds including, but not limited to, N-acetyl cysteine, N-acystelyn, carbocysteine, glutathione, dithiothreitol, thioredoxin containing proteins, and tris(2-carboxyethyl) phosphine.

N-acetyl cysteine (NAC) is approved for use in conjunction with chest physiotherapy to loosen viscid or thickened airway mucus [12]. Clinical studies evaluating the effects of oral or inhaled NAC in CF and COPD have reported improvements in the rheologic properties of mucus and trends toward improvements in lung function and decreases in pulmonary exacerbations[9]. However, the preponderance of clinical data suggests that NAC is at best a marginally effective therapeutic agent for treating airway mucus obstruction when administered orally or by inhalation. A recent Cochrane review of the existing clinical literature on the use of NAC found no evidence to support the efficacy of NAC for CF[10]. The marginal clinical benefit of NAC reflects:

NAC is a relative inefficient reducing agent which is only partially active on the airway surface. Very high concentrations of NAC (200 mM or 3.26%) are required to fully reduce Muc5B, a major gel-forming airway mucin, in vitro. Furthermore, in the pH environment of the airway surface (measured in the range of pH 6.0 to 7.2 in CF and COPD airways)[11], NAC exists only partially in its reactive state as a negatively charge thiolate. Thus, in the clinic, NAC is administered at very high concentrations. However, it is predicted that current aerosol devices will not be able to achieve therapeutic concentrations of even a 20% Mucomyst solution on distal airway surfaces within the relatively short time domains (7.5-15 minutes) typically used.

In non-clinical studies, $^{14}$C-labled NAC, administered by inhalation, exhibits rapid elimination from the lungs with a half-life ranging from 6 to 36 minutes[12]

NAC is administered as a highly concentrated, hypertonic inhalation solution (20% or 1.22 molar) and has been reported to cause bronchoconstriction and cough. In many cases, it is recommended that NAC be administered with a bronchodilator to improve the tolerability of this agent.

Thus, reducing agents such as NAC are not well suited for bolus aerosol administration. However, it is anticipated that delivery of reducing agents by pulmonary aerosol infusion would increase the effectiveness, while allowing for a decrease in the concentration of reducing agent in the inhalation solution (predicted to increase tolerability).

Surfactants and detergents are spreading agents shown to decrease mucus viscoelasticity, improving mucus clearability. Examples of surfactants include DPPC, PF, palmitic acid, palmitoyl-oleoylphosphatidylglycerol, surfactant proteins (e.g. SP-A, B, or C), or may be animal derived (e.g. from cow or calf lung lavage or extracted from minced pig lung) or combinations thereof. See, e.g., U.S. Pat. Nos. 7,897,577; 5,876,970; 5,614,216; 5,100,806; and 4,312,860. Examples of surfactant products include Exosurf, Pumactant, KL-4, Venticute, Alveofact, Curosurf, Infasurf, and Survanta. Examples of detergents include, but are not limited to, Tween-80 and triton-X 100.

Any suitable expectorant can be used, including but not limited to guaifenesin (see, e.g., U.S. Pat. No. 7,345,051). Any suitable deoxyribonuclease can be used, including but not limited to Dornase Alpha. (see, e.g., U.S. Pat. No. 7,482,024).

Examples of kinase inhibitors include inhibitors of NFkB, PI3K (phosphatidylinositol 3-kinase), p38-MAP kinase and Rho kinase.

Antiinfective agents for formulation and use in combination with the compounds of the invention include antivirals and antibiotics. Examples of suitable antivirals include Tamiflu® and Relenza®. Examples of suitable antibiotics include but are not limited to aztreonam (arginine or lysine), fosfomycin, and aminoglycosides such as tobramycin, or any combination or subset thereof. Additional antiinfective agents that may be used herein include aminoglycosides, Daptomycin, Fluoroquinolones, Ketolides, Carbapenems, Cephalosporins, Erythromycin, Linezolid, Penicillins, Azithromycin, Clindamycin, Oxazolidinones, Tetracyclines, and Vancomycin.

Examples of useful carbapenam antibiotics are impenam, panipenam, meropenam, biapenam, MK-826, DA-1131, ER-35786, lenapenam, S-4661, CS-834 (prodrug of R-95867), KR-21056 (prodrug of KR-21012), L-084 (prodrug of LJC 11036) and CXA-101.

Antihistamines (i.e., H1-receptor antagonists) for formulation and use in combination with the compounds of the invention include but are not limited to: ethanolamines such as diphenhydramine HCl, carbinoxamine maleate, doxylamine, clemastine fumarate, diphenylhydramine HCl and dimenhydrinate; ethylenediamines such as pyrilamine maleate (metpyramine), tripelennamine HCl, tripelennamine citrate, and antazoline; alkylamines such as pheniramine, chlorpheniramine, bromopheniramine, dexchlorpheniramine, triprolidine and acrivastine; pyridines such as methapyrilene, piperazines such as hydroxyzine HCl, hydroxyzine pamoate, cyclizine HCl, cyclizine lactate, meclizine HCl and cetirizine HCl; piperidines such as astemisole, levocabastine HCl, loratadine, descarboethoxy loratadine, terfenadine, and fexofenadine HCl; tri- and tetracyclics such as promethazine, chlorpromethazine trimeprazine and azatadine; and azelastine HCl, or any combination or subset thereof.

Examples of other classes of therapeutic agents suitable for use in the combinations and methods herein include antivirals such as ribavirin, anti-fungal agents such as amphotericin, intraconazol and voriconazol, anti-rejection drugs such as cyclosporine, tacrolimus and sirolimus, immunomodulatory agents including steroids such as dexamethasone, anti-inflammatory agents including but not limited to cyclooxygenase inhibitors, cytokine inhibitors, JAK inhibitors, and inhibitors of T-cell function, bronchodilators including but not limited to anticholinergic agents such as atrovent, siRNAs, gene therapy vectors, aptamers, endothelin-receptor antagonists, alpha-1-antitrypsin and prostacyclins.

Examples of other classes of agents suitable for use in the combinations and methods herein include viscosity enhancing or water retaining agents such as hyaluronic acid or carboxymethylcellulose, hormones including estrogen or testosterone, and other agents used to treat dry eye disease including autologous serum and tear substitutes.

In the above-described methods of treatment and uses, a compound of the invention may be employed alone, or in combination with one or more other therapeutically active agents. Typically, any therapeutically active agent that has a therapeutic effect in the disease or condition being treated with the compound of the invention may be utilized in combination with the compounds of the invention, provided that the particular therapeutically active agent is compatible with therapy employing a compound of the invention. Typical therapeutically active agents which are suitable for use in combination with the compounds of the invention include agents described above.

In one preferred embodiment, the compounds of the invention are used in combination with one or more osmolytes, particularly hypertonic saline or mannitol.

In another aspect, the invention provides methods for treatment and uses as described above, which comprise administering an effective amount of a compound of the invention and at least one other therapeutically active agent. The compounds of the invention and at least one additional therapeutically active agent may be employed in combination concomitantly or sequentially in any therapeutically appropriate combination. The administration of a compound of the invention with one or more other therapeutically active agents may be by administration concomitantly in 1) a unitary pharmaceutical composition, such as the compositions described above, or 2) separate pharmaceutical compositions each including one or more of the component active ingredients. The components of the combination may be administered separately in a sequential manner wherein the compound of the invention is administered first and the other therapeutically active agent is administered second or vice versa.

In the embodiments wherein the compound of the invention is administered in combination with one or more osmolytes, the administration of each component is preferably concomitant, and may be in a unitary composition or separate compositions. In one embodiment, the compound of the invention and one or more osmolytes are administered concomitantly by transbrochoscopic lavage. In another embodiment, the compound of the invention and one or more osmolytes are administered concomitantly by inhalation.

When a compound of the invention is used in combination with another therapeutically active agent, the dose of each compound may differ from that when the compound of the invention is used alone. Appropriate doses will be readily determined by one of ordinary skill in the art. The appropriate dose of the compound of the invention, the other therapeutically active agent(s) and the relative timings of administration will be selected in order to achieve the desired combined therapeutic effect, and are within the expertise and discretion of the attendant physician, clinician or veterinarian.

The compounds of formula I-III may be synthesized according to procedures known in the art. A representative synthetic procedure is shown in the scheme below:

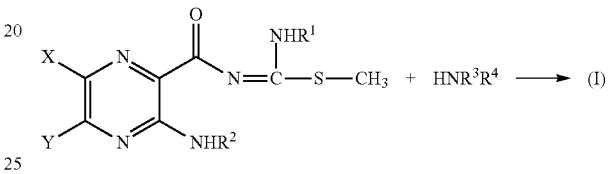

These procedures are described in, for example, E. J. Cragoe, "The Synthesis of Amiloride and Its Analogs" (Chapter 3) in *Amiloride and Its Analogs*, pp. 25-36, incorporated herein by reference. Other methods of preparing the compounds are described in, for example, U.S. Pat. No. 3,313,813, incorporated herein by reference. See in particular Methods A, B, C, and D described in U.S. Pat. No. 3,313,813. Additional methods of preparing intermediates used in the preparation of compounds of the instant invention are disclosed in U.S. Pat. No. 7,064,129, U.S. Pat. No. 6,858,615, U.S. Pat. No. 6,903,105, WO 2004/073629, WO 2007/146869, and WO 2007/018640, each of which is expressly incorporated by reference.

Several assays may be used to characterize the compounds of the present invention. Representative assays are discussed below.

Animal Models of Dry Eye Disease (1) In Vitro Measure of Sodium Channel Blocking Activity One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. This assay is described in detail in Hirsh, A. J., Zhang, J., Zamurs, A., et al. Pharmacological properties of N-(3,5-diamino-6-chloropyrazine-2-carbonyl)-N'-4-[4-(2,3-dihydroxypropoxy)phenyl]butyl-guanidine methanesulfonate (552-02), a novel epithelial sodium channel blocker with potential clinical efficacy for CF lung disease. *J. Pharmacol. Exp. Ther.* 2008; 325(1): 77-88.

Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Ussing chambers. All test drug additions are to the lumenal bath with half-log dose addition protocols (from $1\times10^{-11}$ M to $3\times10^{-5}$M), and the cumulative change in $I_{SC}$ (inhibition) recorded. All drugs are prepared in dimethyl sulfoxide as stock solutions at a concentration of $1\times10^{-2}$M and stored at $-20°$ C. Eight preparations are typically run in parallel; two preparations per run incorporate amiloride and/or benzamil as positive controls. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls. The potency of the sodium channel blocking activity of representative compounds relative to amiloride in freshly excised cells from canine airways is shown in Table 1.

TABLE 1

Potency of sodium channel blocking activity of Formula I compounds.

| Compound | Potency of Sodium Channel Blockade In Canine Cells ($IC_{50}$) |
|---|---|
| Amiloride | 781.0 |
| 30 | 33.1 |
| 35 | 13.8 |
| 45 | 2.1 |
| 15 | 4.6 |
| 42 | 24.6 |
| 9 | 3.2 |
| 51 | 6.6 |
| 59 | 41.3 |
| 145 | 7.3 |
| 82 | 4.6 |

(2) Pharmacological Effects of Compounds on Tear Volume in an Animal Model of Dry Eye Disease In Vivo.

The effects of compounds on tear volume was assessed in a rat model of dry eye disease in which Sprague Dawley rats undergo surgical lacrimal gland excision (ExLac Model) to reduce normal tear volume. The lacrimal excision reduces normal tear volume by ~50% (Table 2).

Both the ipsilateral and contralateral eyes were dosed with 5 µl of test article solution. Tear production was measured using the ZoneQuick cotton thread with impregnated phenol red dye. The folded end of the thread was held in the lateral-ventral conjunctival cul-de-sac for 10 seconds. The length of tear wicking onto the thread was determined by measuring the length of the thread that changes color from yellow to red. Use of a stereomicroscope was assist in the accurate measurement (recorded in millimeters) of the wicking/color change. Tear volume was assessed pre-dose, and 15, 30, 60, 120, and 360 minute post-dose. The change in ocular hydration produced by representative compounds in ExLac rats relative to amiloride is shown in Table 2 and FIGS. 1-16. For reference, the effect of a saline vehicle is shown for ExLac rats and normal (no lacrimal excision surgery) rats.

TABLE 2

Ocular hydrating activity of Formula I componds.

| Compound | Rat Model | 6 h Ocular Hydration ($AUC_{0-6}$) |
|---|---|---|
| Vehicle | ExLac | 24.2 |
| Amiloride | ExLac | 30.4 |
| 51 | ExLac | 38.0 |
| 75 | ExLac | 38.2 |
| 59 | ExLac | 39.7 |
| 46 | ExLac | 39.9 |
| 116 | ExLac | 40.9 |
| 45 | ExLac | 42.3 |
| 102 | ExLac | 43.2 |
| 145 | ExLac | 44.7 |
| 133 | ExLac | 45.7 |

TABLE 2-continued

Ocular hydrating activity of Formula I componds.

| Compound | Rat Model | 6 h Ocular Hydration ($AUC_{0-6}$) |
|---|---|---|
| 90 | ExLac | 49.0 |
| 82 | ExLac | 49.8 |
| 15 | ExLac | 50.2 |
| 9 | ExLac | 50.2 |
| 42 | ExLac | 52.3 |
| Vehicle | Normal | 58.1 |

(3) Confocal Microscopy Assay of Amiloride Congener Transport

Figure 16:
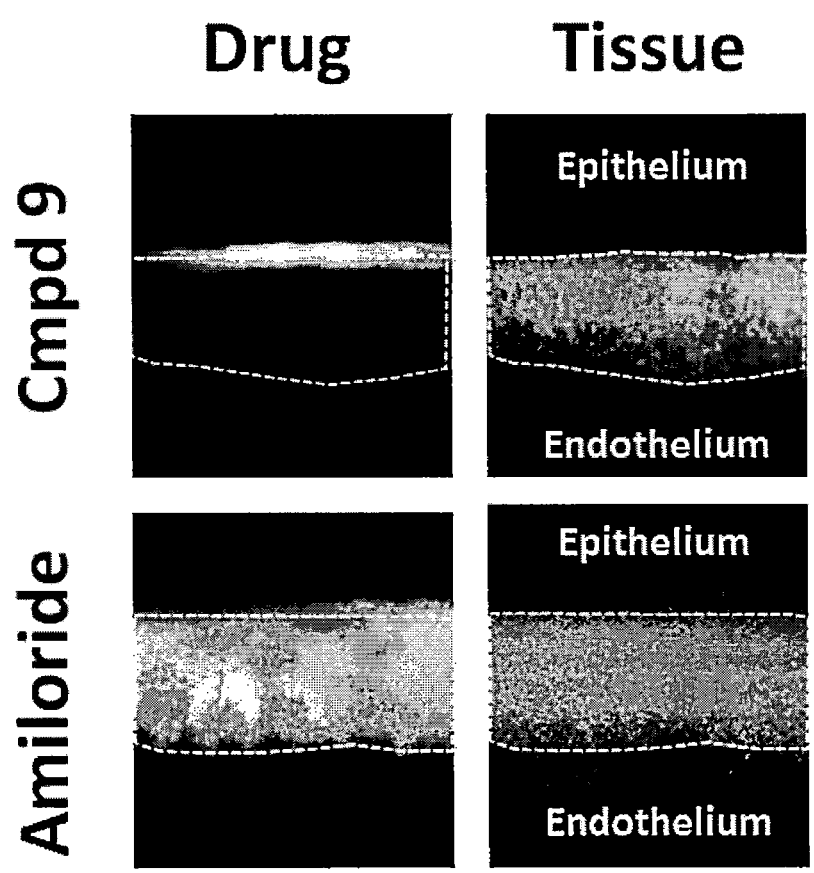
FIG. 16: Confocal images showing the x-z reconstruction of mouse corneas imaged as either the corneal cells (Calcein labeled) or the treatment drug (amiloride or Compound 9) taken one hour after application to the corneal epithelium.

Virtually all amiloride-like molecules fluoresce in the ultraviolet range. This property of these molecules may be used to directly measure cellular update using confocal microscopy. Corneal cells were labeled using calcein-AM dye by incubating with corneas for 45 minutes at 37 C in DMEM media. Equimolar concentrations of 2 microliters of compound 9 or amiloride were placed on the apical (epithelial) surface of mouse corneas for one hour at 37 C. Serial x-y images were obtained one hour post-drug addition by confocal microsopy. The data shown in FIG. 16, show a x-z image of the corneas made up from the composite of the x-y image stack. FIG. 16 shows that amiloride can fully penetrate the cornea is one hour post-administration, but Compound 9 remains associated with the apical (epithelial) surface.

(4) In Vitro Drug Metabolism

The metabolic stability of 9 and 15 was assessed in plasma (rat, rabbit, dog and human) and hepatocytes (rat and dog). Compounds were added either directly to plasma or to hepatocyte suspensions at a final concentration of 2.5 or 10 µM, respectively, and incubated at 37° C. for up to six hours. Aliquots were removed at various time points and quenched. The amount of parent compound was quantified via UPLC-fluorescence analysis. The amount of parent compound remaining was calculated based on the total peak area at the time of sampling divided by the total peak area at initiation. The results presented in Tables 3 and 4 show that 9 was stable towards metabolic hydrolysis in both plasma and hepatocytes among the species evaluated, whereas, 15 was rapidly metabolized in both plasma and hepatocytes. These results confirm that the 15 with amide linkages in the naturally occurring S configuration is susceptible to enzymatic hydrolysis, whereas, the amide linkages in the R configuration are stable towards hydrolysis.

TABLE 3

Plasma Stability of Compounds

| Matrix | Compound 9 | Compound 15 |
|---|---|---|
| Rat | 87% | 10% |
| Rabbit | 89% | 8.7% |
| Dog | 103% | 18% |
| Human | 101% | 7.6% |

TABLE 4

Hepatocyte Stability of Compounds

| Matrix | Compound 9 | Compound 15 | Compound 45 |
|---|---|---|---|
| Rat | 100% | 14% | 83% |
| Dog | 94% | 19% | 75% |

(5) In Vitro Assays of Compound Metabolism

Airway epithelial cells have the capacity to metabolize drugs during the process of transepithelial absorption. Further, although less likely, it is possible that drugs can be metabolized on airway epithelial surfaces by specific ectoenzyme activities. Perhaps more likely as an ecto-surface event, compounds may be metabolized by the infected secretions that occupy the airway lumens of patients with lung disease, e.g. cystic fibrosis. Thus, a series of assays is performed to characterize the compound metabolism that results from the interaction of test compounds with human airway epithelia and/or human airway epithelial lumenal products.

In the first series of assays, the interaction of test compounds in KBR as an "ASL" stimulant are applied to the apical surface of human airway epithelial cells grown in the T-Col insert system. For most compounds, metabolism (generation of new species) is tested for using high performance liquid chromatography (HPLC) to resolve chemical species and the endogenous fluorescence properties of these compounds to estimate the relative quantities of test compound and novel metabolites. For a typical assay, a test solution (25 µl KBR, containing 10 µM test compound) is placed on the epithelial lumenal surface. Sequential 5 to 10 µl samples are obtained from the lumenal and serosal compartments for HPLC analysis of (1) the mass of test compound permeating from the lumenal to serosal bath and (2) the potential formation of metabolites from the parent compound. In instances where the fluorescence properties of the test molecule are not adequate for such characterizations, radiolabeled compounds are used for these assays. From the HPLC data, the rate of disappearance and/or formation of novel metabolite compounds on the lumenal surface and the appearance of test compound and/or novel metabolite in the basolateral solution is quantitated. The data relating the chromatographic mobility of potential novel metabolites with reference to the parent compound are also quantitated.

To analyze the potential metabolism of test compounds by CF sputum, a "representative" mixture of expectorated CF sputum obtained from 10 CF patients (under IRB approval) has been collected. The sputum has been be solubilized in a 1:5 mixture of KBR solution with vigorous vortexing, following which the mixture was split into a "neat" sputum aliquot and an aliquot subjected to ultracentrifugation so that a "supernatant" aliquot was obtained (neat=cellular; supernatant=liquid phase). Typical studies of compound metabolism by CF sputum involve the addition of known masses of test compound to "neat" CF sputum and aliquots of CF sputum "supernatant" incubated at 37° C., followed by sequential sampling of aliquots from each sputum type for characterization of compound stability/metabolism by HPLC analysis as described above. As above, analysis of compound disappearance, rates of formation of novel metabolities, and HPLC mobilities of novel metabolites are then performed.

(6) Pharmacological Effects and Mechanism of Action of the Drug in Animals

The effect of compounds for enhancing mucociliary clearance (MCC) can be measured using an in vivo model described by Sabater et al., Journal of Applied Physiology, 1999, pp. 2191-2196, incorporated herein by reference.

Methods

Animal Preparation:

Adult ewes (ranging in weight from 25 to 35 kg) were restrained in an upright position in a specialized body harness adapted to a modified shopping cart. The animals' heads were immobilized and local anesthesia of the nasal passage was induced with 2% lidocaine. The animals were then nasally intubated with a 7.5 mm internal diameter endotracheal tube (ETT). The cuff of the ETT was placed just below the vocal cords and its position was verified with a flexible bronchoscope. After intubation the animals were allowed to equilibrate for approximately 20 minutes prior to initiating measurements of mucociliary clearance.

Administration of Radio-Aerosol:

Aerosols of $^{99m}$Tc-Human serum albumin (3.1 mg/ml; containing approximately 20 mCi) were generated using a Raindrop Nebulizer which produces a droplet with a median aerodynamic diameter of 3.6 µm. The nebulizer was connected to a dosimetry system consisting of a solenoid valve and a source of compressed air (20 psi). The output of the nebulizer was directed into a plastic T connector; one end of which was connected to the endotracheal tube, the other was connected to a piston respirator. The system was activated for one second at the onset of the respirator's inspiratory cycle. The respirator was set at a tidal volume of 500 mL, an inspiratory to expiratory ratio of 1:1, and at a rate of 20 breaths per minute to maximize the central airway deposition. The sheep breathed the radio-labeled aerosol for 5 minutes. A gamma camera was used to measure the clearance of $^{99m}$Tc-Human serum albumin from the airways. The camera was positioned above the animal's back with the sheep in a natural upright position supported in a cart so that the field of image was perpendicular to the animal's spinal cord. External radio-labeled markers were placed on the sheep to ensure proper alignment under the gamma camera. All images were stored in a computer integrated with the gamma camera. A region of interest was traced over the image corresponding to the right lung of the sheep and the counts were recorded. The counts were corrected for decay and expressed as percentage of radioactivity present in the initial baseline image. The left lung was excluded from the analysis because its outlines are superimposed over the stomach and counts can be swallowed and enter the stomach as radio-labeled mucus.

Treatment Protocol (Assessment of Activity at t-zero):

A baseline deposition image was obtained immediately after radio-aerosol administration. At time zero, after acquisition of the baseline image, vehicle control (distilled water), positive control (amiloride), or experimental compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were extubated immediately following delivery of the total dose in order to prevent false elevations in counts caused by aspiration of excess radio-tracer from the ETT. Serial images of the lung were obtained at 15-minute intervals during the first 2 hours after dosing and hourly for the next 6 hours after dosing for a total observation period of 8 hours. A washout period of at least 7 days separated dosing sessions with different experimental agents.

Treatment Protocol (Assessment of Activity at t-4 Hours):

The following variation of the standard protocol was used to assess the durability of response following a single exposure to vehicle control (distilled water), positive control compounds (amiloride or benzamil), or investigational agents. At time zero, vehicle control (distilled water), positive control (amiloride), or investigational compounds were aerosolized from a 4 ml volume using a Pari LC JetPlus nebulizer to free-breathing animals. The nebulizer was driven by compressed air with a flow of 8 liters per minute. The time to deliver the solution was 10 to 12 minutes. Animals were restrained in an upright position in a specialized body harness for 4 hours. At the end of the 4-hour period animals received a single dose of aerosolized $^{99m}$Tc-Human serum albumin (3.1 mg/ml; containing approximately 20 mCi) from a Raindrop Nebulizer. Animals were extubated immediately following delivery of the total dose of radio-tracer. A baseline deposition image was obtained immediately after radio-aerosol administration. Serial images of the lung were obtained at 15-minute intervals during the first 2 hours after administration of the radio-tracer (representing hours 4 through 6 after drug administration) and hourly for the next 2 hours after dosing for a total observation period of 4 hours. A washout period of at least 7 days separated dosing sessions with different experimental agents.

Statistics:

Data were analyzed using SYSTAT for Windows, version 5. Data were analyzed using a two-way repeated ANOVA (to assess overall effects), followed by a paried t-test to identify differences between specific pairs. Significance was accepted when P was less than or equal to 0.05. Slope values (calculated from data collected during the initial 45 minutes after dosing in the t-zero assessment) for mean MCC curves were calculated using linear least square regression to assess differences in the initial rates during the rapid clearance phase.

EXAMPLES

Having generally described this invention, a further understanding can be obtained by reference to certain specific examples which are provided herein for purposes of illustration only and are not intended to be limiting unless otherwise specified.

Preparation of Sodium Channel Blockers

Materials and methods. The present invention also provides processes for preparing the compounds of the invention and to the synthetic intermediates useful in such processes, as described in detail below.

Certain abbreviations and acronyms are used in describing the synthetic processes and experimental details. Although most of these would be understood by one skilled in the art, the following table contains a list of many of these abbreviations and acronyms.

Abbreviation Meaning
AcOH Acetic Acid
AIBN AzobisisobutyroInitrile
DIAD Diisopropyl azidocarboxylate
DIPEA N,N-Diisopropylethylamine
DCE dichloroethane
DCM dichloromethane
DMF dimethylformamide
Et Ethyl
EtOAc or EA ethyl acetate
EtOH Ethanol
Abbreviation Meaning
ESI electrospray ionization
HATU 2-(1H-7-Azabenzotriazol-1-yl)-1,1,3,3-tetramethyl uronium hexafluorophosphate
HPLC High performance liquid chromatography
iPrOH Isopropyl alcohol
i.t. or IT intratracheal
Me Methyl
MeOH methanol
m/z or m/e mass to charge ratio
MH$^+$ mass plus 1
MH$^-$ mass minus 1
MIC minimal inhibitory concentration
MS or ms mass spectrum
rt or r.t. room temperature
$R_f$ Retardation factor
t-Bu tert-butyl
THF tetrahydrofuran
TLC or tlc thin layer chromatography
δ parts per million down field from tetramethylsilane
Cbz Benzyloxycarbonyl, i.e. —(CO)O-benzyl
AUC Area under the curve or peak
MTBE Methyl tertiary butyl ether
$t_R$ Retention time
GC-MS Gas chromatography-mass spectrometry
wt % Percent by weight
h Hours
min Minutes
MHz megahertz
TFA Trifluoroacetic acid
UV Ultraviolet
Abbreviation Meaning
Boc tert-butyloxycarbonyl
DIAD Diisopropyl azodicarboxylate
AcOH Acetic Acid
DIPEA N,N-Diisopropylethylamine or Hünig's base
Ph$_3$P Triphenylphosine The compounds of Formula I may be synthesized using techniques known in the art. A representative synthetic procedure is illustrated in Scheme 1 below.

Scheme 1. Preparation of the hydrochloride salt of (2R,2'R)-N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-guanidinohexanamide) (9).

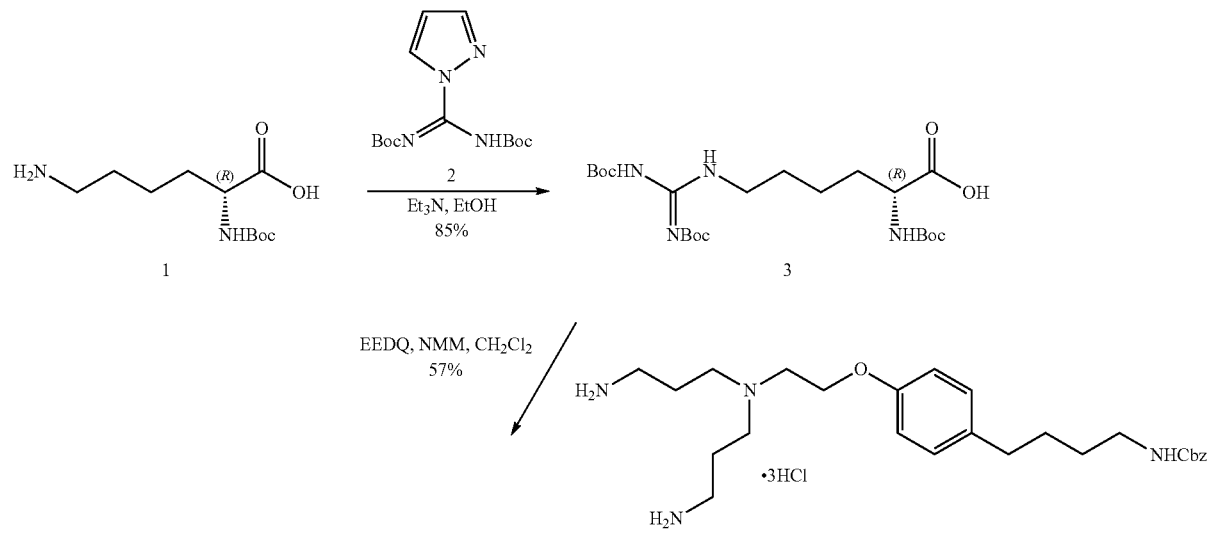

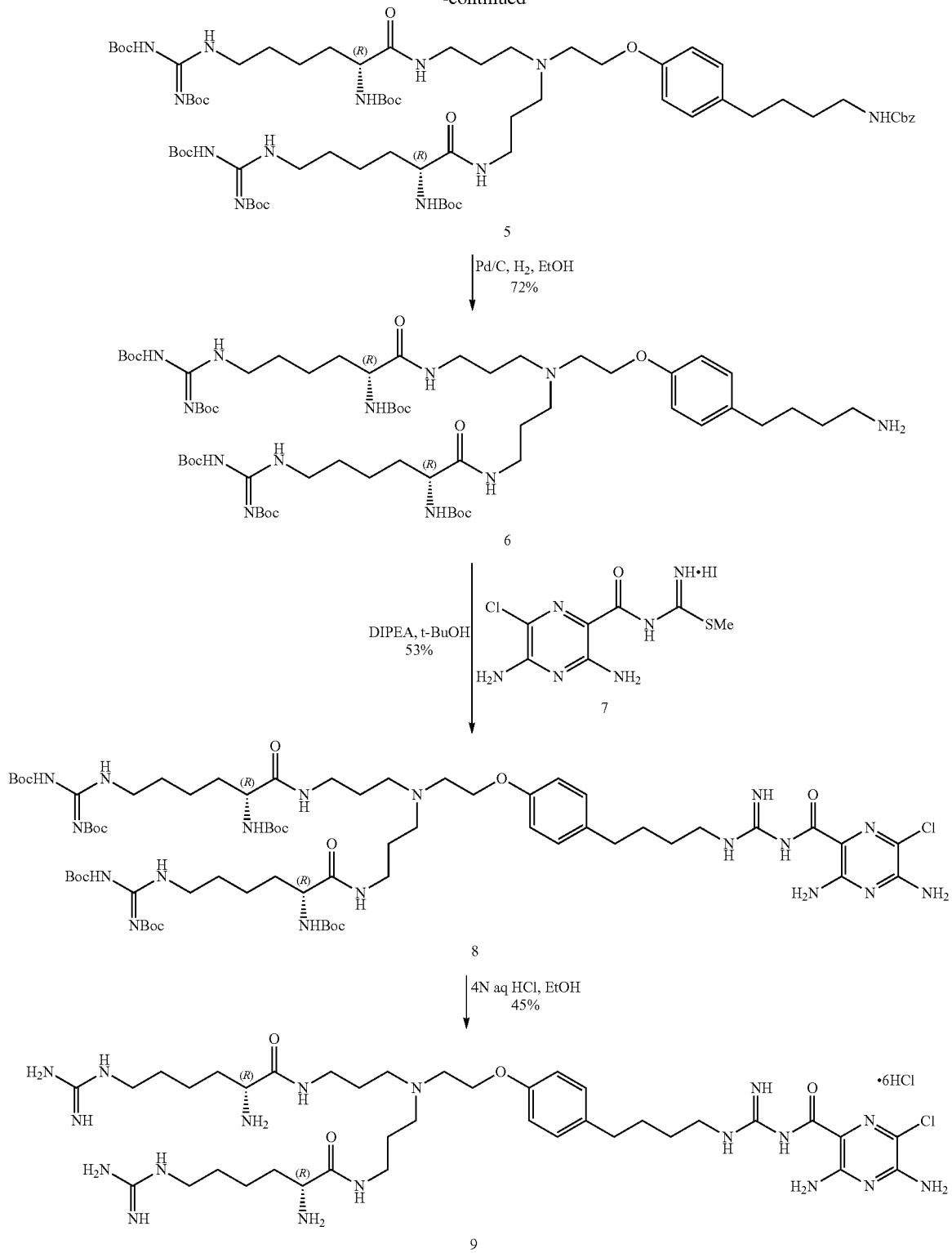

Preparation of (R)-6-(2,3-bis(tert-butoxycarbonyl) guanidino)-2-((tertbutoxycarbonyl)amino) hexanoic acid (3)

To a solution of N-α-Boc-D-lysine (13.0 g, 52.7 mmol) in EtOH (290 mL) was added N,N'-bis-Boc-1-guanylpyrazole (16.3 g, 52.7 mmol) and triethyl amine (10.6 g, 105 mmol). The reaction mixture was stirred at room temperature for 6 h. Solvent was removed and the residue was purified by column chromatography (silica gel, 10:1 CH$_2$Cl$_2$/MeOH) to afford a pyrazole salt (25.0 g) as colorless oil. The salt was dissolved in 1 N NaOH (300 mL) and neutralized with 1 N HCl (305 mL) The resulting precipitate was filtered out and dried, to afford compound 3 (22.0 g, 85%) as a white solid: $^1$H NMR (400 MHz, CDCl$_3$) δ 11.48 (br s, 1H), 8.35 (br s, 1H), 5.23 (d, J=7.5 Hz, 1H), 4.23 (br s, 1H), 3.48-3.25 (m, 2H), 1.96-1.50 (m, 6H), 1.51 (s, 9H), 1.49 (s, 9H), 1.43 (s, 9H).

Preparation of Compound 5

To a solution of amino acid 3 (3.00 g, 6.14 mmol) in CH$_2$Cl$_2$ (100 mL) was added EEDQ (3.17 g, 12.8 mmol) and NMM (4.90 g, 49.1 mmol). The reaction mixture was stirred at room temperature for 10 min and then bis-amine 4 (1.73 g, 3.07 mmol) was added. The resulting mixture was stirred at room temperature for 24 h. Amino acid 3 (900 mg, 1.84 mmol) was added and the reaction mixture was stirred for additional 16 h. Solvent was removed and the residue was purified by column chromatography (silica gel, 10:1 CH$_2$Cl$_2$/EtOAc, 10:1 CH$_2$Cl$_2$/MeOH) to afford amide 5 (2.30 g, 57%) as a colorless solid: $^1$H NMR (400 MHz, CD$_3$OD) δ 7.38-7.24 (m, 5H), 7.06 (d, J=8.4 Hz, 2H), 6.82 (d, J=8.4 Hz, 2H), 5.05 (s, 2H), 4.09-3.92 (m, 4H), 3.68 (t, J=4.8 Hz, 4H), 3.58 (t, J=6.3 Hz, 1H), 3.28-3.21 (m, 4H), 3.14-3.07 (m, 2H), 2.89-2.83 (m, 2H) 2.64-2.50 (m, 6H), 2.43 (br s, 4H), 2.27 (s, 3H), 1.77-1.65 (m, 6H), 1.64-1.54 (m, 6H), 1.52 (s, 18H), 1.46 (s, 18H), 1.42 (s, 18H).

Preparation of Compound 6

A suspension of compound 5 (2.30 g, 1.64 mmol) and 10% Pd/C (1.50 g) in EtOH (10 mL) was subjected to hydrogenation conditions (1 atm) for 4 h at room temperature. The reaction mixture was filtered through celite and washed with EtOH. The filtrate was concentrated to afford an amine (2.10 g) as colorless oil. The crude was purified by column chromatography (silica gel, 8:1 CH$_2$Cl$_2$/MeOH) to afford amine 6 (1.50 g, 72%) as colorless oil: $^1$H NMR (400 MHz, CD$_3$OD) δ 7.08 (d, J=8.5 Hz, 2H), 6.83 (d, J=8.5 Hz, 2H), 4.15-3.88 (m, 4H), 3.28-3.21 (m, 8H), 2.84 (t, J=5.5 Hz, 2H), 2.78 (t, J=7.4 Hz, 2H), 2.58 (t, J=7.2 Hz, 6H), 1.84-1.52 (m, 20H), 1.52 (s, 18H), 1.46 (s, 18H), 1.43 (s, 18H).

Preparation of Compound 8

To a solution of amine 6 (9.00 g, 7.12 mmol) and methyl 3,5-diamino-6-chloropyrazine-2-carbonylcarbamimidothioate hydroiodic acid salt (7, 4.43 g, 11.3 mmol) in t-BuOH (90 mL) was added DIPEA (7.36 g, 56.9 mmol) at room temperature. The reaction mixture was heated at 70° C. in a sealed tube for 2 h, then cooled to room temperature, and concentrated in vacuum. The residue was purified by column chromatography (silica gel, 10:1 CH$_2$Cl$_2$/MeOH, 5:1:0.1 CHCl$_3$/MeOH/NH$_4$OH) to afford compound 8 (5.60 g, 53%) as a yellow solid: $^1$H NMR (400 MHz, CD$_3$OD) δ 7.10 (d, J=8.7 Hz, 2H), 6.84 (d, J=8.7 Hz, 1H), 4.06-3.94 (m, 4H), 3.29-3.20 (m, 6H), 2.87-2.80 (m, 2H), 2.64-2.53 (m, 6H), 1.78-1.64 (m, 12H), 1.65-1.51 (m, 12H), 1.52 (s, 18H), 1.47 (s, 18H), 1.41 (s, 18H).

Preparation of the hydrochloride salt of (2R,2'R)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-guanidinohexanamide) compound 9

To a solution of compound 8 (5.60 g, 0.81 mmol) in EtOH (20 mL) was added 4 N aq HCl (120 mL) at room temperature and the reaction mixture was stirred for 4 h at room temperature. The reaction mixture was concentrated in vacuum and the residue was purified by reverse phase column chromatography and lyophilized to afford hydrochloric acid salt 9 (1.5 g, 45%) as a yellow hygroscopic solid: $^1$H NMR (400 MHz, D$_2$O) δ 7.22 (d, J=8.2 Hz, 1H), 6.91 (d, J=8.2 Hz, 1H), 4.28 (br s, 2H), 3.89 (t, J=6.8 Hz, 2H), 3.60 (br s, 2H), 3.37-3.23 (m, 10H), 3.08 (t, J=7.2 Hz, 4H), 2.59 (br s, 2H), 2.05-1.93 (m, 4H), 1.86-1.75 (m, 4H), 1.66 (br s, 4H), 1.58-1.47 (m, 4H), 1.39-1.27 (m, 4H).

Scheme 2. Preparation of the hydrochloride salt of (2R,2'R)-N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-guanidinohexanamide) (15)

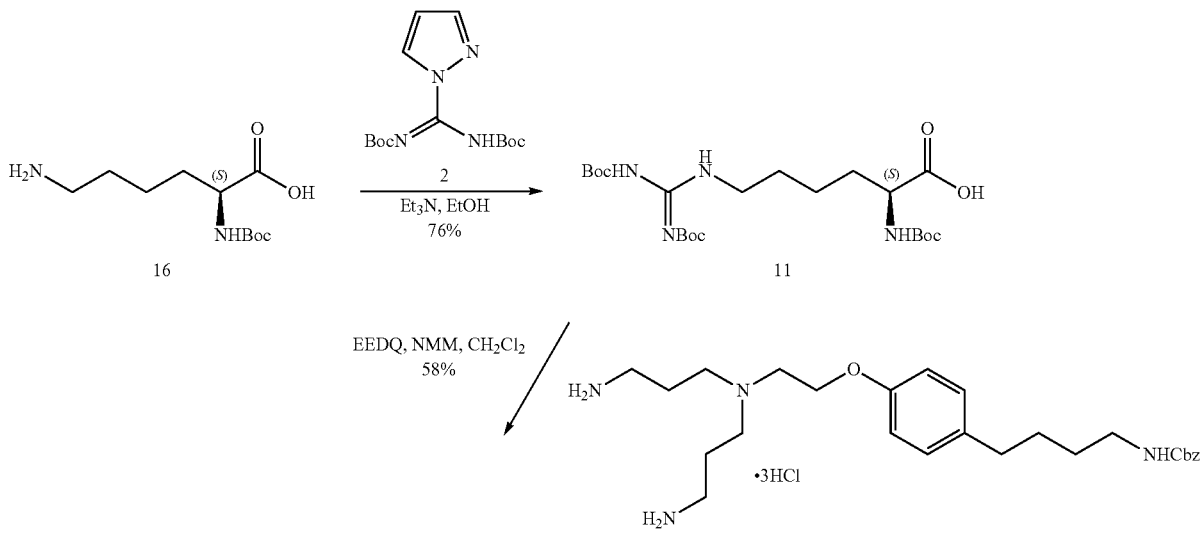

-continued
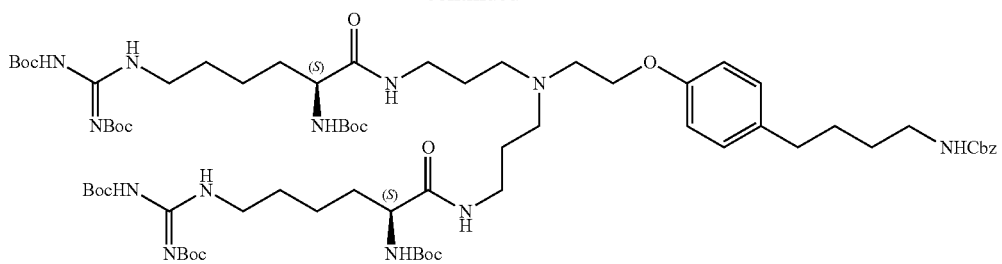
12
↓ Pd/C, H₂
EtOH/AcOH
75%
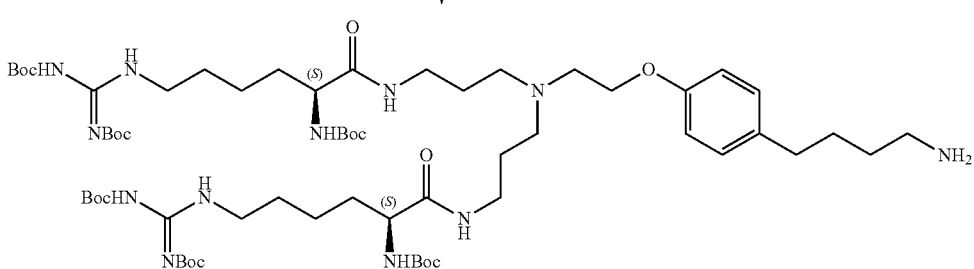
13
↓ DIPEA, t-BuOH
47%
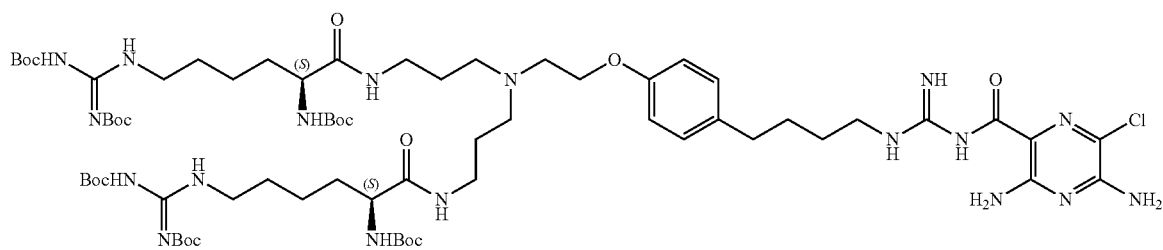
14
↓ 4N aq HCl, EtOH
40%
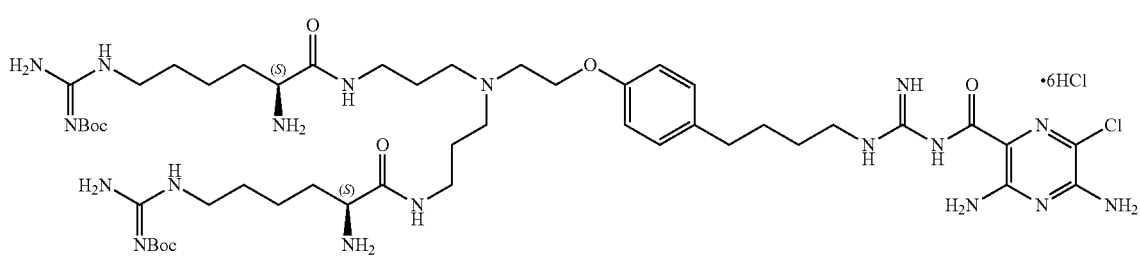
15

Preparation of (S)-6-(2,3-bis(tert-butoxycarbonyl) guanidino)-2-((tertbutoxycarbonyl)amino) hexanoic acid (11)

To a solution of N-α-Boc-L-lysine (1.00 g, 4.06 mmol) 16 in EtOH (30 mL) was added N,N'-bis-Boc-1-guanylpyrazole (1.36 g, 4.38 mmol) 2 and triethyl amine (810 mg, 8.12 mmol). The reaction mixture was stirred at room temperature for 6 h. Solvent was removed and the residue was purified by column chromatography (silica gel, 10:1 $CH_2Cl_2$/MeOH) to afford a pyrazole salt (1.98 g) as colorless oil. The salt was dissolved in 1 N NaOH (100 mL) and neutralized with 1 N HCl (105 mL) The resulting precipitate was filtered out and dried, to afford compound 11 (1.50 g, 76%) as a white solid: $^1$H NMR (300 MHz, $CDCl_3$) δ 11.47 (br s, 1H), 8.37 (br s, 1H), 5.22 (d, J=7.5 Hz, 1H), 4.26 (br s, 1H), 3.49-3.29 (m, 2H), 1.98-1.51 (m, 6H), 1.50 (s, 9H), 1.49 (s, 9H), 1.44 (s, 9H).

Preparation of Compound 12

To a solution of amino acid 11 (6.00 g, 12.0 mmol) in $CH_2Cl_2$ (150 mL) was added EEDQ (5.00 g, 20.2 mmol) and NMM (10.0 g, 99.0 mmol). The reaction mixture was stirred at room temperature for 10 min and then bis-amine 4 (3.40 g, 6.00 mmol) was added. The resulting mixture was stirred at room temperature for 48 h. Solvent was removed and the residue was purified by column chromatography (silica gel, 10:1 $CH_2Cl_2$/EtOAc, 10:1 $CH_2Cl_2$/MeOH) to afford amide 12 (4.98 g, 58%) as a colorless solid: $^1$H NMR (300 MHz, $CD_3OD$) δ 7.33-7.31 (m, 5H), 7.06 (d, J=8.1 Hz, 1H), 6.82 (d, J=8.1 Hz, 1H), 5.05 (s, 2H), 4.10-4.01 (m, 4H), 3.35-3.23 (m, 8H), 3.11 (t, J=6.9 Hz, 2H), 2.85 (t, J=5.4 Hz, 2H), 2.44-2.41 (m, 6H), 1.72-1.51 (m, 20H), 1.51 (s, 18H), 1.46 (s, 18H), 1.43 (s, 18H).

Preparation of Compound 13

A suspension of compound 12 (4.95 g, 3.54 mmol) and 10% Pd/C (2.50 g) in EtOH/AcOH (150 mL/5.0 mL) was subjected to hydrogenation conditions (1 atm) for 16 h at room temperature. The reaction mixture was filtered through celite and washed with EtOH. The filtrate was concentrated to afford an acid salt (4.80 g) as colorless oil. The salt was neutralized with satd $Na_2CO_3$ and purified by column chromatography (silica gel, 8:1 $CH_2Cl_2$/MeOH) to afford free base 13 (3.35 g, 75%) as colorless oil: $^1$H NMR (300 MHz, $CD_3OD$) δ 7.08 (d, J=8.4 Hz, 1H), 6.82 (d, J=8.4 Hz, 1H), 4.05-4.01 (m, 4H), 3.31-3.23 (m, 8H), 2.84 (t, J=5.4 Hz, 2H), 2.73 (t, J=6.9 Hz, 2H), 2.61-2.55 (m, 6H), 1.72-1.52 (m, 20H), 1.51 (s, 18H), 1.46 (s, 18H), 1.43 (s, 18H).

Preparation of Compound 14

To a solution of amine 13 (3.30 g, 2.61 mmol) and methyl 3,5-diamino-6-chloropyrazine-2-carbonylcarbamimidothioate hydroiodic acid salt (7, 1.62 g, 4.18 mmol) in t-BuOH (80 mL) was added DIPEA (2.70 g, 20.8 mmol) at room temperature. The reaction mixture was heated at 70° C. in a sealed tube for 2 h, then cooled to room temperature, and concentrated in vacuum. The residue was purified by column chromatography (silica gel, 10:1 $CH_2Cl_2$/MeOH, 5:1:0.1 $CHCl_3$/MeOH/$NH_4OH$) to afford compound 14 (1.78 g, 47%) as a yellow solid: $^1$H NMR (300 MHz, $CD_3OD$) δ 7.10 (d, J=8.4 Hz, 1H), 6.85 (d, J=8.4 Hz, 1H), 4.05-3.99 (m, 4H), 3.31-3.23 (m, 10H), 2.86 (t, J=5.4 Hz, 2H), 2.62-2.58 (m, 6H), 1.70-1.52 (m, 20H), 1.51 (s, 18H), 1.48 (s, 18H), 1.46 (s, 18H).

Preparation of Compound 15

To a solution of compound 14 (1.20 g, 0.813 mmol) in EtOH (5 mL) was added 4 N aq HCl (25 mL) at room temperature and the reaction mixture was stirred for 4 h at room temperature. The reaction mixture was concentrated in vacuum and the residue was purified by reverse phase column chromatography and lyophilized to afford hydrochloric acid salt 15 (356 mg, 40%) as a yellow hygroscopic solid: $^1$H NMR (300 MHz, $D_2O$) δ 7.12 (d, J=8.4 Hz, 1H), 6.81 (d, J=8.4 Hz, 1H), 4.18 (br s, 2H), 3.79 (t, J=4.9 Hz, 2H), 3.50 (br s, 2H), 3.24-3.20 (m, 10H), 2.98 (t, J=6.9 Hz, 2H), 2.50 (br s, 2H), 1.92-1.87 (m, 4H), 1.74-1.67 (m, 4H), 1.45 (br s, 4H), 1.28-1.21 (m, 4H).

Scheme 3. Preparation of Intermediate 4

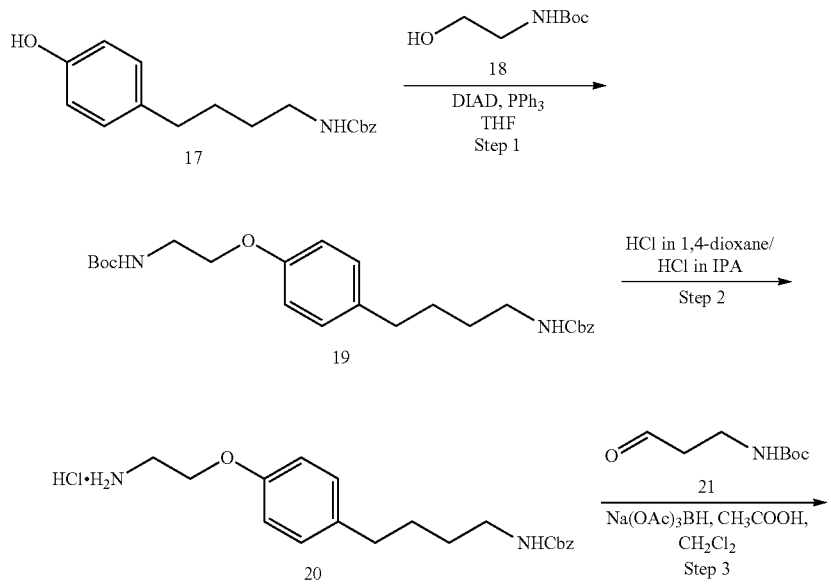

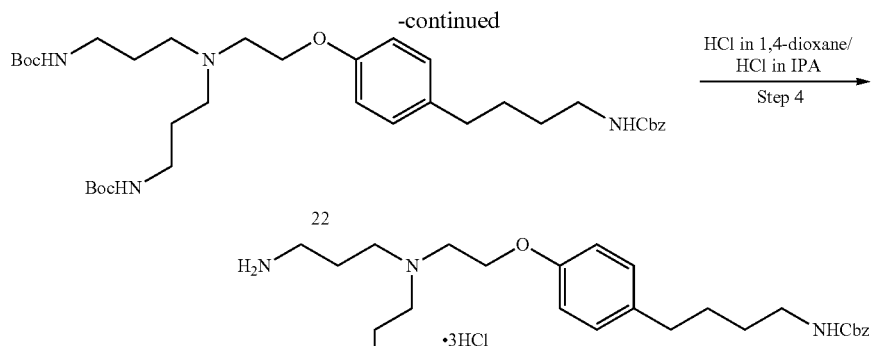

General Description for the Preparation of the hydrochloride salt of benzyl 4-(4-(2-(bis(3-aminopropyl)amino)ethoxy)phenyl)butylcarbamate (4)

All non-aqueous reactions were carried out under an atmosphere of either nitrogen or argon. Reagents and solvents were used as received from suppliers. Deionized water (DI water) was used for workups and to prepare diluted solutions. Thin-layer chromatography (TLC) was performed using Merck silica-gel plates and visualized by UV light (254 nm) or appropriate stain. $^1$H NMR and $^{13}$C NMR spectra were obtained on a Bruker AVANCE-400 Ultra Shield spectrometer at 400 MHz for proton and 100 MHz for carbon, using $CDCl_3$, $D_2O$, or DMSO-$d_6$ as the solvents. The mass spectra were obtained on an Agilent spectrometer using electrospray or atmospheric-pressure chemical ionization (APCI).

Step 1. Preparation of 5

A stirred solution of benzyl [4-(4-hydroxyphenyl)butyl] carbamate (17, 500 g, 1670 mmol, 1.0 equiv), tert-butyl (2-hydroxyethyl)carbamate (18, 350.0 g, 2170 mmol, 1.3 equiv), and PPh$_3$ (568.0 g, 2170 mmol, 1.3 equiv, AVRA) in THF (7500 mL, 15 vol, Finar lot) was charged with DIAD (438.0 g, 2170 mmol, 1.3 equiv, AVRA) dropwise at 0° C. over 30 min, and stirred at room temperature for 16 h. The progress of the reaction was monitored by TLC analysis (7:3 hexanes:EtOAc), which confirmed the presence of ≈10% compound 17. 18 (81 g, 503 mmol, 0.3 equiv), PPh$_3$ (132 g, 503 mmol, 0.3 equiv), and DIAD (102 g, 503 mmol, 0.3 equiv) were added at <10° C. and the mixture was stirred at room temperature for 16 h. Having confirmed the complete consumption of compound 17, the solvent was evaporated under vacuum to afford crude 19 (2.50 kg, crude), which was used as produced in the next step.

Step 2. Preparation of 20

A stirred solution of 19 (2500 g) and HCl in dioxane (10,000 mL, Durga) was stirred at room temperature for 3-4 h. The progress of the reaction was monitored by TLC (30% EtOAc:hexanes). After completion of the reaction, the solvent was evaporated under vacuum to ⅓ volume. The resulting solid was triturated with MTBE (5000 mL, Savla Chemicals) and the precipitate was filtered and dried under vacuum to afford 20 (370.0 g, 58%) as a white solid.

Step 3. Preparation of 22

Preparation of 20 Free Base

Compound 20 (140.0 g) was dissolved in DI water (1500 mL) and the pH was adjusted to ≈9 using solid Na$_2$CO$_3$ (Finar Reagents). The aqueous layer was extracted with CH$_2$Cl$_2$ (3×500 mL, MSN lot). The combined organic layers were dried over anhydrous Na$_2$SO$_4$ and evaporated under vacuum to afford the free base of 20 [75 g, 60%].

Reductive Amination

A stirred solution of 20 free base [75 g, 219 mmol, 1.0 equiv] and 21 (95.0 g, 549 mmol, 2.5 equiv) in CH$_2$Cl$_2$ (1500 mL, MSN) was charged with CH$_3$COOH (13.0 g, 219 mmol, 1.0 equiv, S.D. Fine-Chem) and stirred for 30 min at room temperature, then cooled to 0-5° C. Na(OAc)$_3$BH (140.0 g, 660 mmol, Aldrich lot) was added portionwise over 30 min, and the mixture was stirred at room temperature for 16 h. The progress of the reaction was monitored by TLC (9.5:0.5 CH$_2$Cl$_2$:MeOH, 2 runs). After the reaction was complete, the reaction mixture was quenched with aqueous 1 N NaOH solution, adjusting the pH to ≈9. The layers were separated and the aqueous layer was extracted with CH$_2$Cl$_2$ (2×500 mL, MSN). The combined organic layers were washed with water (1×300 mL), dried over anhydrous Na$_2$SO$_4$, and evaporated under vacuum to afford crude 22 (160.0 g) as a thick, light green liquid. The crude was purified by column chromatography (silica gel, 100-200 mesh, 4.9:0.1, CH$_2$Cl$_2$:MeOH as eluent, 2 purifications) to give pure 22 [61 g, 42%] as a pale yellow liquid.

Step 4. Preparation of 4

A mixture of 22 [130.0 g, 198 mmol] and HCl in IPA (≈20%, 650 mL, Durga Industries) was stirred for 3 h. The progress of the reaction was monitored by TLC (9.5:0.5, CH$_2$Cl$_2$:MeOH). After the completion of the reaction, the solvent was evaporated to ⅓ volume and MTBE (650 mL, Savla Chemicals) was added. A thick solid was precipitated; the solvent was decanted. The mixture was solvent-swapped with toluene (2×500 mL) and MTBE (2×1000 mL, Savla Chemicals) and dried under vacuum. The resulting sticky solid was stirred in MTBE (1000 mL) for 1 h, the solvent was decanted, and the product was dried under vacuum to afford 4 (94.0 g, 84%, AMRI) as a highly hygroscopic, off-white solid.

Step 5. Preparation of 18

A stirred solution of 2-aminoethanol (200.0 g, 3274.3 mmol, 1.0 equiv) and TEA (497.0 g, 4911.4 mmol, 1.5 equiv) in $CH_2Cl_2$ (2400 mL, 12 vol, MSN) was charged with $(Boc)_2O$ (856.0 g, 3926.1 mmol, 1.2 equiv, Globe Chemie) at 0-5° C., and was stirred at room temperature for 2 h, monitoring the progress of the reaction by TLC (9:1, $CH_2Cl_2$: MeOH). After the complete consumption of the 2-aminoethanol, DI water (2500 mL) was added and the mixture was stirred for 10 min. The two layers were separated and the organic layer was washed with 0.2 N HCl (3000 mL) and DI water (1000 mL), dried over anhydrous $Na_2SO_4$, and evaporated under vacuum to afford 18 (482 g, 91%) as a pale green liquid.

Step 6. Preparation of 23

A stirred solution of 3-aminopropanol (250 g, 3334 mmol, 1.0 equiv, Alfa Aesar) and TEA (505 g, 5000 mmol, 1.5 equiv, AVRA) in $CH_2Cl_2$ (3000 mL, 12 vol, MSN 1) was charged with $(Boc)_2O$ (872 g, 4000 mmol, 1.2 equiv, Globe Chemie lot) at 0-5° C., and was stirred at room temperature for 2 h, monitoring the progress of the reaction by TLC (9:1, $CH_2Cl_2$: MeOH). After the completion of the reaction, water (3000 mL) was added and the mixture was stirred for 10 min. The layers were separated and the organic layer was washed with 0.2 N HCl (3000 mL) and DI water (1000 mL), dried over anhydrous $Na_2SO_4$, and evaporated under vacuum to afford Boc-aminopropanol 23 (588 g, 100%) as a pale green liquid.

Step 7. Preparation of 21

A stirred solution of 23 (100.0 g, 571 mmol, 1.0 equiv) in DMSO (600 mL, 6 vol, Finar) was charged with IBX (243 g, 868 mmol, 1.5 equiv, Quiver Technologies) portionwise over 30 min at room temperature, and was stirred for 5 h. The progress of the reaction was monitored by TLC (9:1 $CH_2Cl_2$: MeOH). After the completion of the reaction, the mixture was diluted with DI water (4000 mL). The solid was filtered and washed with DI water (1000 mL). The filtrate was extracted with ethyl acetate (2×1000 m, MSN). The combined organic layers were washed with saturated $NaHCO_3$ (1×1000 mL) and DI water (1000 mL), dried over anhydrous $Na_2SO_4$, and evaporated under vacuum to afford 21 (71 g, 70%) as a yellow liquid.

Scheme 4
Preparation of the Hydrochloride Salt of (2S,2'S)-N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2,6-diaminohexanamide)- Compound 30:

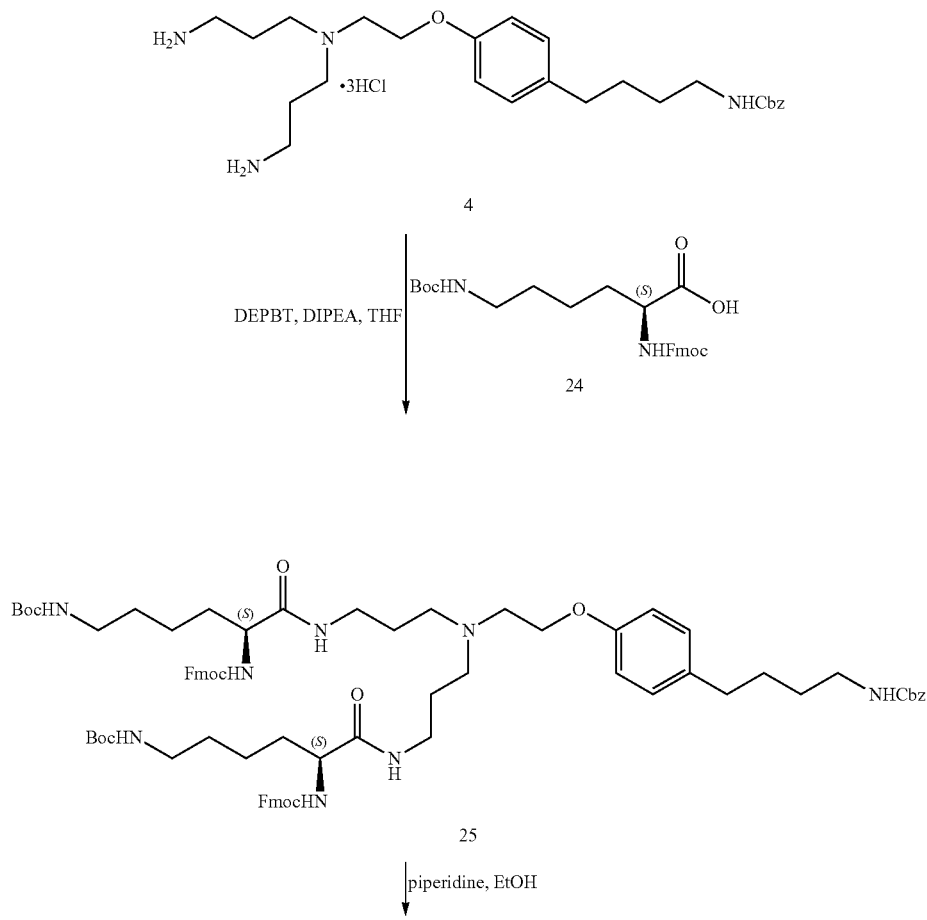

-continued
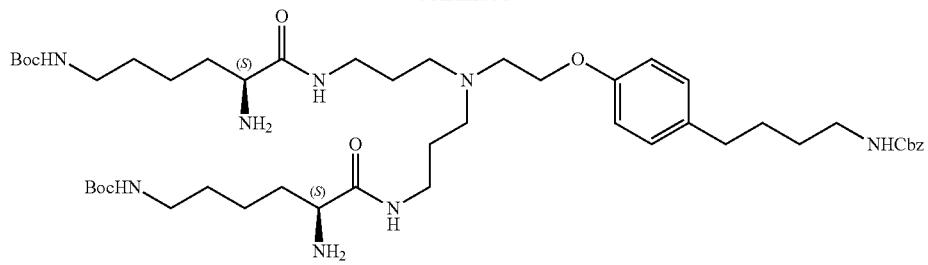
26
↓ Boc₂O, NaHCO₃, MeOH, H₂O
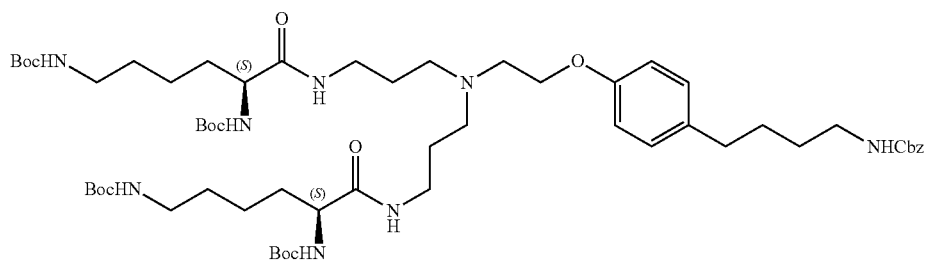
27
↓ Pd/C, H₂, AcOH/EtOH
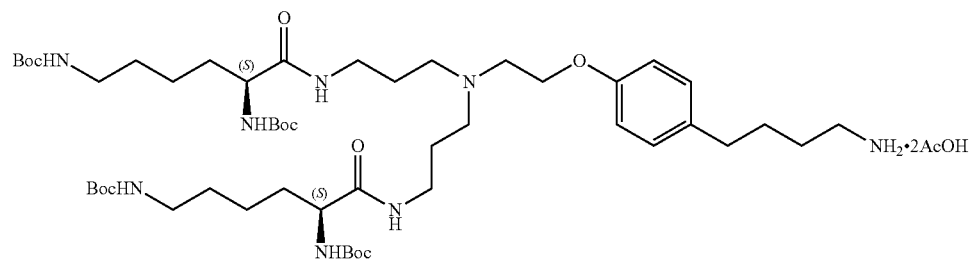
28
↓ DIPEA, EtOH
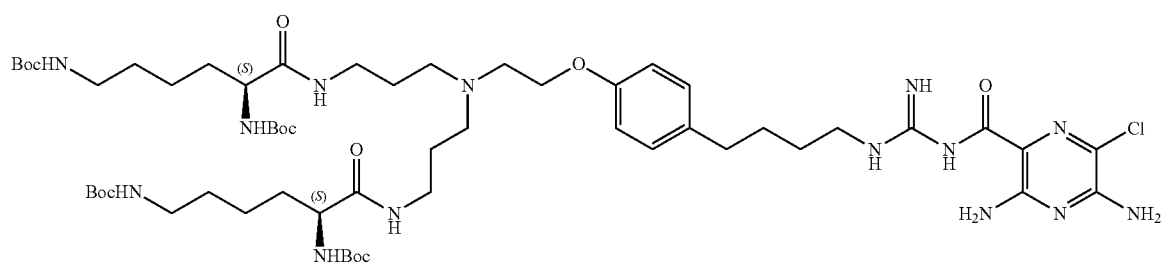
29

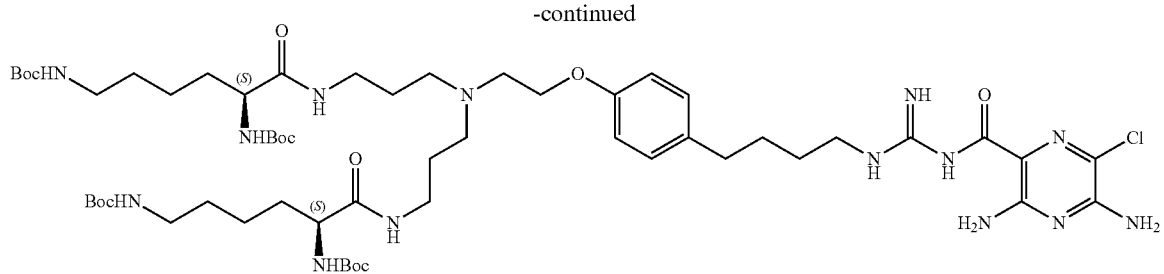

29

↓ 4N aq HCl, EtOH

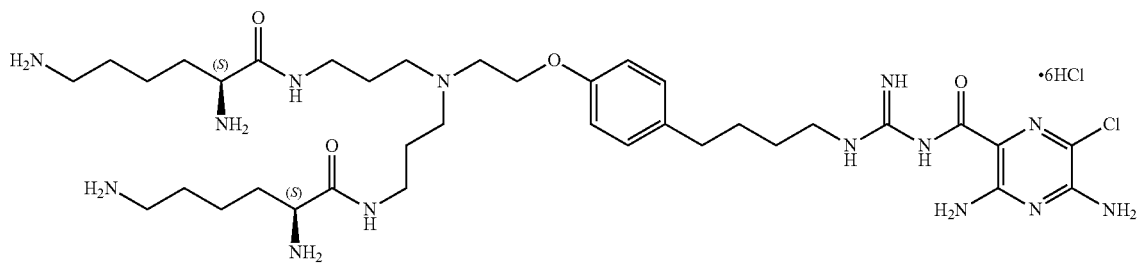

30

Preparation of Compound 25

A solution of amino acid 24 (1.80 g, 3.94 mmol) in THF (50 mL) was charged with DEPBT (1.23 g, 4.14 mmol) and DIPEA (1.27 g, 9.85 mmol). The reaction mixture was stirred at room temperature for 1 h and bis-amine 4 (900 mg, 1.97 mmol) was added. The resulting mixture was stirred at room temperature for 16 h and 40° C. for 8 h. The solvent was removed and the residue was purified by column chromatography (silica gel, 5:1 $CH_2Cl_2$/EtOAc) to afford amide 3 (1.63 g, mixture with compound 25 as a yellow solid, which was used directly in the next step.

Preparation of Compound 26

A solution of compound 25 (100 mg, mixture) in EtOH (3.0 mL) was charged with piperidine (1.0 mL). The reaction mixture was stirred at room temperature for 3 h. After the solvent was removed, the residue was precipitated from hexanes, washed with 1 N NaOH, and azeotroped with MeOH to afford compound 26 (40.0 mg, 36% over 2 steps) as a white solid: $^1$H NMR (300 MHz, $CD_3OD$) δ 7.32-7.27 (m, 5H), 7.06 (d, J=8.1 Hz, 2H), 6.82 (d, J=8.1 Hz, 2H), 5.05 (s, 2H), 4.04 (t, J=5.4 Hz, 2H), 3.34-3.19 (m, 5H), 3.11 (t, J=6.9 Hz, 2H), 3.04-2.98 (m, 5H), 2.85 (t, J=5.7 Hz, 2H), 2.62-2.52 (m, 6H), 1.75-1.28 (m, 20H), 1.42 (s, 18H).

Preparation of Compound 27

A solution of compound 26 (300 mg, 0.329 mmol) in MeOH (10 mL) and water (5.0 mL) was charged with $NaHCO_3$ (56.0 mg, 0.666 mmol) and $Boc_2O$ (56.0 mg, 0.394 mmol). The reaction mixture was stirred for 4 h at room temperature. After the solvent was removed, the residue was washed with water and azeotroped with MeOH to afford compound 27 (303 mg, 83%) as a colorless oil: $^1$H NMR (300 MHz, $CD_3OD$) δ 7.33-7.29 (m, 5H), 7.06 (d, J=8.4 Hz, 2H), 6.82 (d, J=8.4 Hz, 2H), 5.05 (s, 2H), 4.04 (t, J=5.1 Hz, 2H), 3.94-3.93 (br s, 2H), 3.37-3.22 (m, 4H), 3.14-3.11 (m, 2H), 3.09-2.98 (m, 4H), 2.90-2.86 (m, 2H), 2.61-2.52 (m, 6H), 1.69-1.29 (m, 20H), 1.42 (s, 36H).

Preparation of Compound 28

A suspension of compound 27 (300 mg, 0.269 mmol) and 10% Pd/C (150 mg) in EtOH (4.0 mL) and AcOH (0.5 mL) was subjected to hydrogenation conditions (1 atm) for 4 h at room temperature. The reaction mixture was filtered through celite and washed with EtOH. The filtrate was concentrated and washed with MTBE to afford compound 28 (285 mg, 96%) as a colorless oil: $^1$H NMR (300 MHz, $CD_3OD$) δ 7.12 (d, J=8.4 Hz, 2H), 6.87 (d, J=8.4 Hz, 2H), 4.12 (br s, 2H), 3.93 (br s, 2H), 3.40-3.30 (m, 4H), 3.07-2.91 (m, 8H), 2.78-2.61 (m, 6H), 1.93 (s, 6H), 1.77-1.42 (m, 20H), 1.42 (s, 36H).

Preparation of Compound 29

A solution of compound 28 (280 mg, 0.213 mmol) and methyl 3,5-diamino-6-chloropyrazine-2-carbonylcarbamimidothioate hydroiodic acid salt (7, 132 mg, 0.339 mmol) in EtOH (5.0 mL) was charged with DIPEA (220 mg, 1.70 mmol) at room temperature. The reaction mixture was heated at 70° C. for 2 h, cooled to room temperature, and concentrated in vacuum. The residue was purified by column chromatography (silica gel, 10:1 $CH_2Cl_2$/MeOH, 5:1:0.1 $CHCl_3$/MeOH/$NH_4OH$) to afford compound 29 (189 mg, 63%) as a yellow solid: $^1$H NMR (400 MHz, CD$_3$OD) δ 7.10 (d, J=8.4 Hz, 2H), 6.84 (d, J=8.4 Hz, 2H), 4.03 (t, J=5.6 Hz, 2H), 3.95 (br s, 2H), 3.34-3.29 (m, 6H), 3.00 (t, J=6.8 Hz, 4H), 2.84 (br s, 2H), 2.61-2.56 (m, 6H), 1.70-1.42 (m, 20H), 1.42 (s, 36H).

Preparation of the Hydrochloride Salt of (2S,2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2,6-diaminohexanamide) (Compound 30)

A solution of compound 29 (188 mg, 0.157 mmol) in EtOH (2.0 mL) was charged with 4 N aqueous HCl (6.0 mL) at room temperature and the reaction mixture was stirred for 4 h at room temperature. The reaction mixture was concentrated in vacuum and the residue was recrystallized from EtOH/H$_2$O and lyophilized to afford hydrochloric acid salt 30 (140 mg, 87%) as a yellow hygroscopic solid: $^1$H NMR (400 MHz, D$_2$O) δ 7.22 (d, J=8.4 Hz, 2H), 6.91 (d, J=8.4 Hz, 2H), 4.28 (br s, 2H), 3.90 (t, J=6.8 Hz, 2H), 3.61 (br s, 2H), 3.36-3.23 (m, 10H), 2.94 (t, J=7.6 Hz, 4H), 2.59 (br s, 2H), 1.98-1.87 (m, 4H), 1.85-1.82 (m, 4H), 1.66-1.62 (m, 8H), 1.40-1.38 (m, 4H).

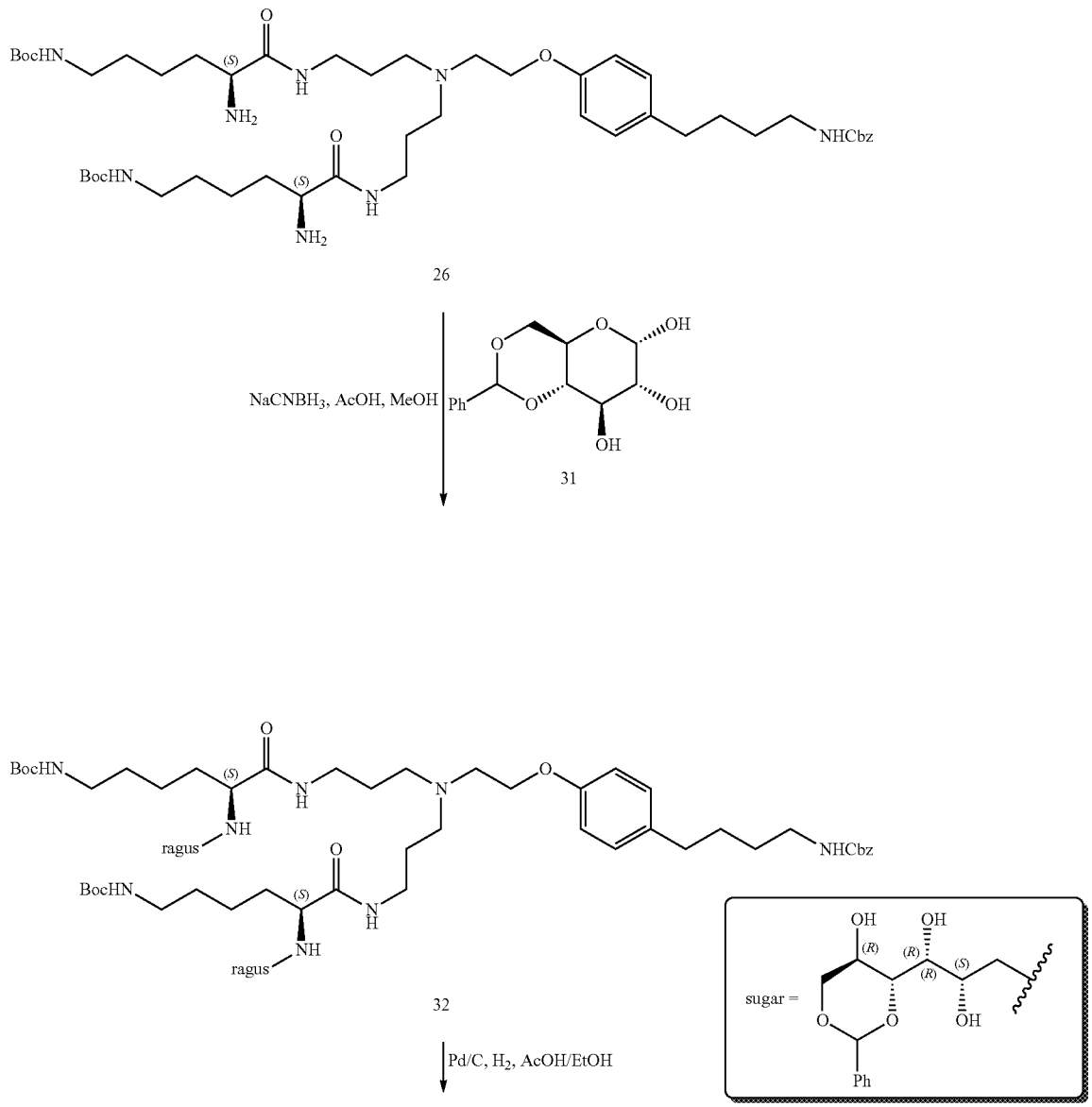

Scheme 5. Preparation of (S,R,R,R,2S,2'S)-N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(6-amino-2-((2S,3R,4R,5R)-2,3,4,5,6-pentahydroxyhexylamino)hexanamide)-35

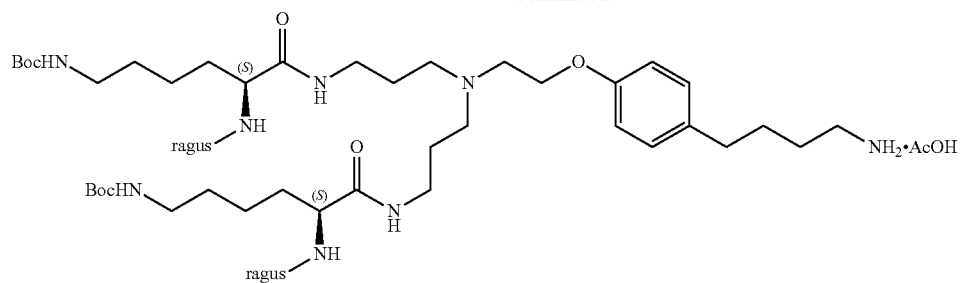
33
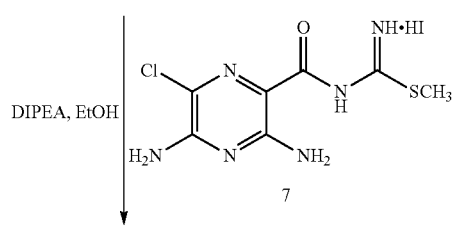
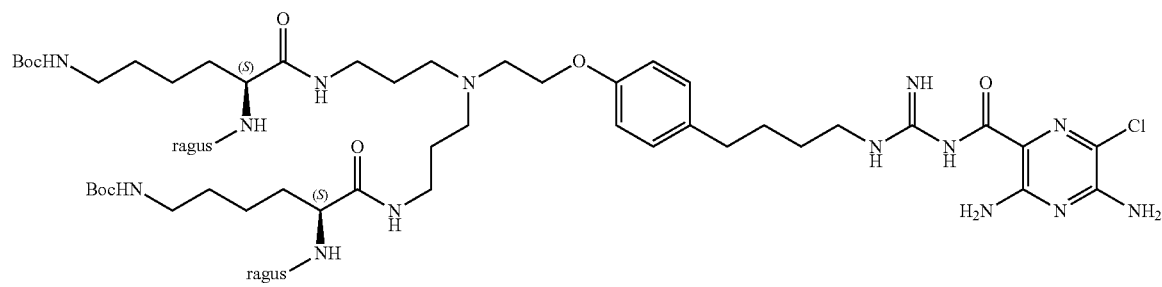
34
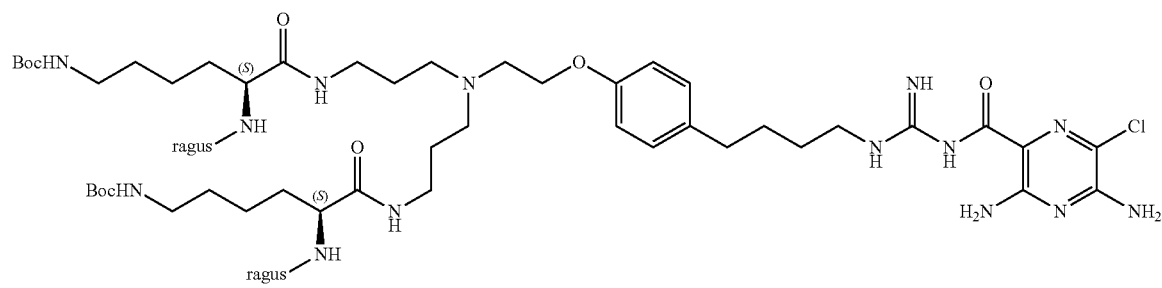
34
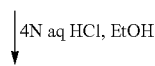

-continued

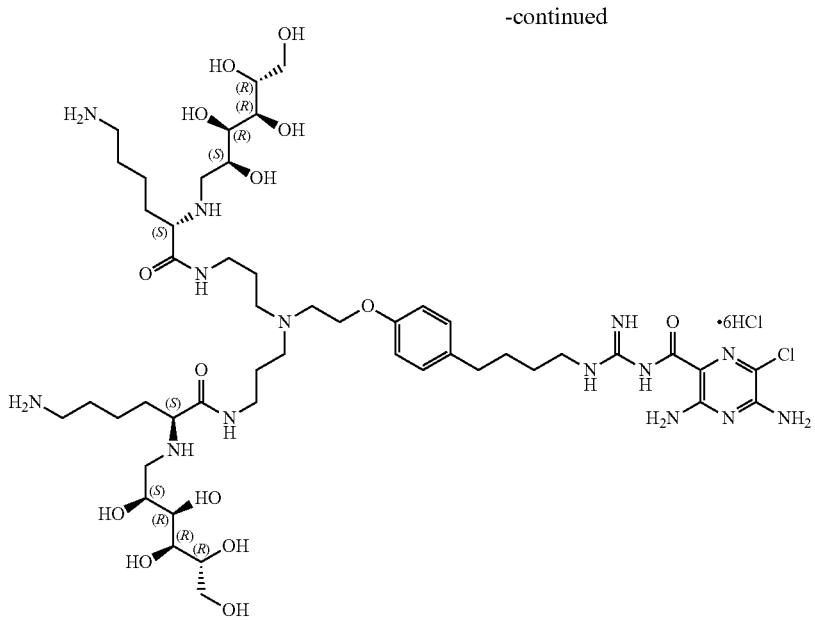

35

Preparation of Compound 32

A solution of compound 26 (180 mg, 0.197 mmol) in MeOH (5.0 mL) was charged with compound 31 (132 mg, 0.493 mmol) and AcOH (60 mg, 0.985 mmol). The reaction mixture was stirred at room temperature for 20 min and NaCNBH$_3$ (57.3 mg, 0.788 mmol) was added. After the reaction mixture was stirred at room temperature for 16 h, the solvent was removed in vacuum. The residue was washed with saturated Na$_2$CO$_3$, azeotroped with MeOH, and purified by column chromatography (silica gel, 10:1 CH$_2$Cl$_2$/MeOH, 5:1:0.1 CHCl$_3$/MeOH/NH$_4$OH) to afford compound 32 (183 mg, mixture) as a colorless oil, which was used directly in the next step.

Preparation of Compound 33

A suspension of compound 32 (180 mg, 0.127 mmol) and 10% Pd/C (100 mg) in EtOH (5.0 mL) and AcOH (1.0 mL) was subjected to hydrogenation conditions (1 atm) for 36 h at room temperature. The reaction mixture was filtered through celite and washed with EtOH. The filtrate was concentrated and washed with MTBE to afford compound 33 (129 mg, 46% over 2 steps) as a colorless oil: $^1$H NMR (300 MHz, CD$_3$OD) δ 7.47-7.45 (m, 4H), 7.33-7.31 (m, 6H), 7.12 (d, J=8.4 Hz, 2H), 6.86 (d, J=8.4 Hz, 2H), 5.53 (s, 2H), 4.24-4.21 (m, 2H), 4.07-3.86 (m, 6H), 3.74-3.53 (m, 4H), 3.34-2.53 (m, 16H), 1.90-1.30 (m, 20H), 1.42 (s, 36H).

Preparation of Compound 34

A solution of compound 33 (127 mg, 0.0834 mmol) and methyl 3,5-diamino-6-chloropyrazine-2-carbonylcarbamimidothioate hydroiodic acid salt (7, 59 mg, 0.150 mmol) in EtOH (5.0 mL) was charged with DIPEA (108 mg, 0.839 mmol) at room temperature. The reaction mixture was heated at 70° C. for 2 h, cooled to room temperature, and concentrated in vacuum. The residue was purified by column chromatography (silica gel, 10:1 CH$_2$Cl$_2$/MeOH, 8:2:0.2 CHCl$_3$/MeOH/NH$_4$OH) to afford compound 34 (81 mg, 65%) as a yellow solid: $^1$H NMR (300 MHz, CD$_3$OD) δ 7.43-7.40 (m, 4H), 7.31-7.30 (m, 6H), 7.10 (d, J=8.7 Hz, 2H), 6.83 (d, J=8.7 Hz, 2H), 5.47 (s, 2H), 4.23-4.20 (m, 2H), 3.99-3.87 (m, 8H), 3.68-3.53 (m, 4H), 3.34-3.15 (m, 4H), 3.05-2.95 (m, 10H), 2.81-2.51 (m, 10H), 1.66-1.32 (m, 20H), 1.42 (s, 36H).

Preparation the Hydrochloride Salt of (S,R,R,R,2S,2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(6-amino-2-((2S,3R,4R,5R)-2,3,4,5,6-pentahydroxyhexylamino) hexanamide)—(Compound 35)

A solution of compound 34 (80.0 mg, 0.0535 mmol) in EtOH (1.0 mL) was charged with 4 N aqueous HCl (3.0 mL) at room temperature and the reaction mixture was stirred for 4 h at room temperature. The reaction mixture was concentrated in vacuum and the residue was purified by reverse-phase column chromatography and lyophilized to afford hydrochloric acid salt 35 (39.0 mg, 55%) as a yellow hygroscopic solid: $^1$H NMR (400 MHz, D$_2$O) δ 7.23 (d, J=8.4 Hz, 2H), 6.92 (d, J=8.4 Hz, 2H), 4.29 (br s, 2H), 4.08-4.03 (m, 2H), 3.90 (t, J=6.8 Hz, 2H), 3.76-3.59 (m, 12H), 3.38-3.18 (m, 12H), 3.10-2.93 (m, 6H), 2.60 (br s, 2H), 2.10-1.91 (m, 8H), 1.67-1.64 (m, 8H), 1.40-1.36 (m, 4H). HRMS calculated for C$_{48}$H$_{88}$ClN$_{14}$O$_{14}$ [M+H]$^+$, 1119.6287. found 1119.6316. Elemental analysis: % calculated C, 43.07; H, 7.00; N, 14.65. found C, 38.78; H, 7.09; N, 13.03.

Scheme 6. Preparation of the Hydrochloride Salt of (S,R,R,R,2S,2'S)-N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(6-guanidino-2-((2S,3R,4R,5R)-2,3,4,5,6-pentahydroxyhexylamino)hexanamide)-Compound 42
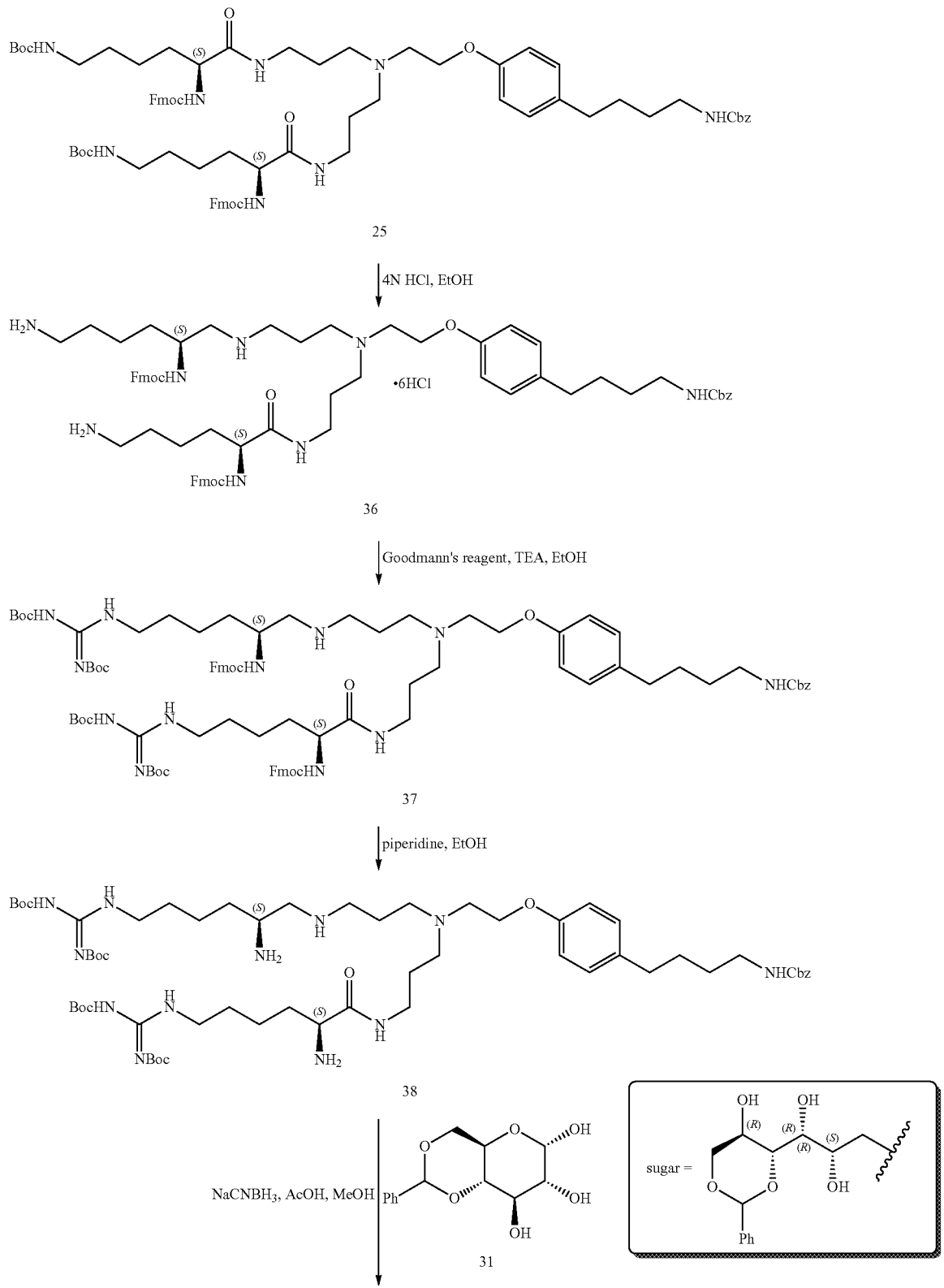

-continued
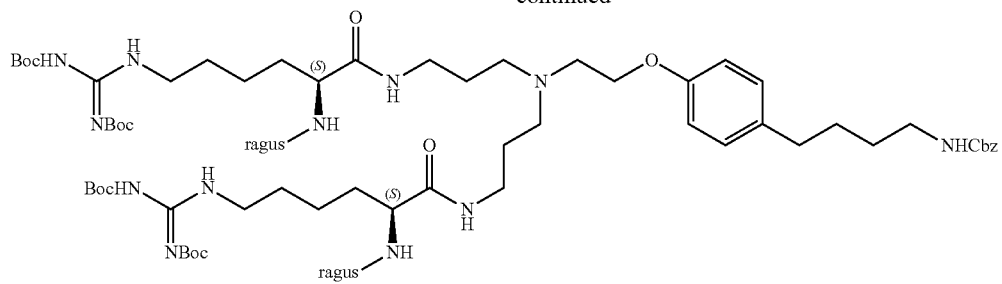
39
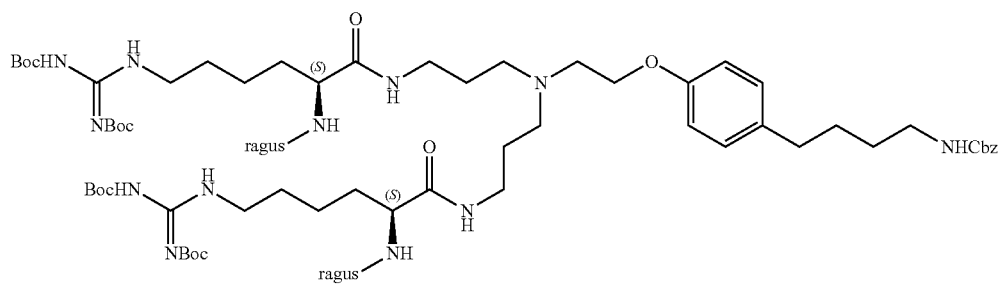
39
↓ Pd/C, H₂, AcOH/EtOH
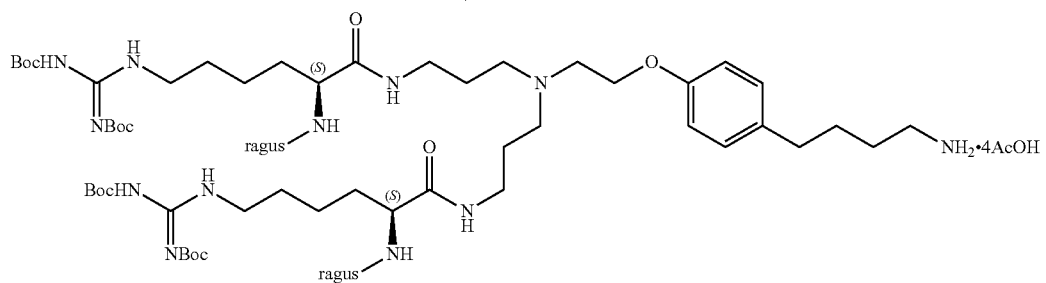
40
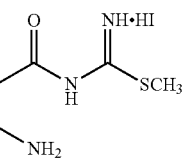
7
DIPEA, EtOH
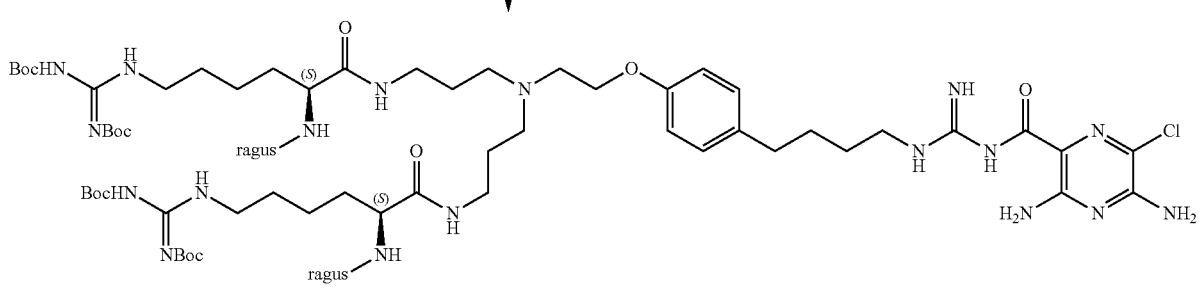
41
1. TFA, CH₂Cl₂
2. 4N aq HCl

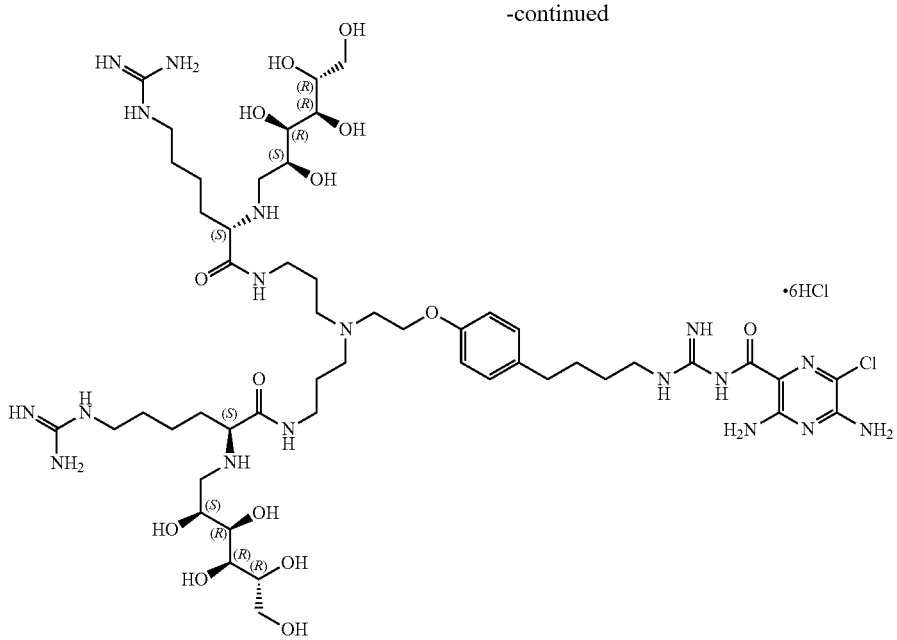

42

Preparation of Compound 36

A solution of compound 25 (2.19 g, 1.61 mmol) in EtOH (50 mL) was charged with 4 N HCl in dioxane (10 mL) and the reaction mixture was stirred for 3 h at room temperature. The reaction mixture was concentrated to afford hydrochloric acid salt 36 (1.88 g, 92%) as a yellow oil: $^1$H NMR (300 MHz, CD$_3$OD) δ 7.78-7.75 (m, 4H), 7.62-7.60 (m, 4H), 7.39-7.25 (m, 13H), 6.96 (d, J=8.1 Hz, 2H), 6.82 (d, J=8.1 Hz, 2H), 5.04 (s, 2H), 4.37-4.15 (m, 12H), 3.73-3.06 (m, 8H), 2.99-2.81 (m, 6H), 2.50-2.46 (m, 2H), 1.94-1.17 (m, 20H).

Preparation of Compound 37

A solution of compound 36 (1.86 g, 1.46 mmol) in EtOH (80 mL) was charged with Goodmann's reagent (1.26 g, 3.23 mmol) and TEA (1.18 g, 11.6 mmol). The reaction mixture was stirred at 0° C. for 2 h and at room temperature for 3 h. After the solvent was removed, the residue was purified by column chromatography (silica gel, 20:1 CH$_2$Cl$_2$/MeOH) to afford compound 37 (1.54 g, 64%) as a white semisolid: $^1$H NMR (300 MHz, CD$_3$OD) δ 7.78-7.75 (m, 4H), 7.59-7.57 (m, 4H), 7.37-7.23 (m, 13H), 6.97 (d, J=8.1 Hz, 2H), 6.73 (d, J=8.1 Hz, 2H), 5.04 (s, 2H), 4.36-3.95 (m, 12H), 3.30-3.06 (m, 10H), 2.58-2.46 (m, 6H), 1.66-1.28 (m, 20H), 1.43 (s, 36H).

Preparation of Compound 38

A solution of compound 37 (1.63 g, 0.99 mmol) in EtOH (24 mL) was charged with piperidine (8.0 mL). The reaction mixture was stirred at room temperature for 16 h. After the solvent was removed, the residue was precipitated from MTBE/hexanes to afford compound 38 (1.01 g, 85%) as an off-white solid: $^1$H NMR (300 MHz, CD$_3$OD) δ 7.33-7.32 (m, 5H), 7.06 (d, J=8.4 Hz, 2H), 6.82 (d, J=8.4 Hz, 2H), 5.05 (s, 2H), 4.02 (br s, 2H), 3.59-2.99 (m, 12H), 2.85 (br s, 2H), 2.62-2.54 (m, 6H), 1.71-1.28 (m, 20H), 1.43 (s, 36H).

Preparation of Compound 39

A solution of compound 38 (120 mg, 0.100 mmol) in MeOH (5.0 mL) was charged with compound 31 (67 mg, 0.250 mmol), AcOH (30 mg, 0.500 mmol), and NaCNBH$_3$ (29 mg, 0.400 mmol). After the reaction mixture was stirred at room temperature for 16 h, the solvent was removed in vacuum. The residue was purified by column chromatography (silica gel, 20:1 CH$_2$Cl$_2$/MeOH, 10:1:0.1 CHCl$_3$/MeOH/NH$_4$OH) to afford compound 39 (101 mg, 61%) as a white semisolid: $^1$H NMR (300 MHz, CD$_3$OD) δ 7.47-7.44 (m, 4H), 7.32-7.30 (m, 11H), 7.06 (d, J=8.4 Hz, 2H), 6.82 (d, J=8.4 Hz, 2H), 5.48 (s, 2H), 5.05 (s, 2H), 4.23-4.20 (m, 2H), 4.01-3.85 (m, 8H), 3.71-3.58 (m, 6H), 3.29-3.07 (m, 10H), 2.85-2.53 (m, 12H), 1.71-1.50 (m, 20H), 1.47 (s, 18H), 1.47 (s, 18H).

Preparation of Compound 40

A suspension of compound 39 (518 mg, 0.304 mmol) and 10% Pd/C (250 mg) in EtOH (15 mL) and AcOH (3.0 mL) was subjected to hydrogenation conditions (1 atm) for 36 h at room temperature. The reaction mixture was filtered through celite and washed with EtOH. The filtrate was concentrated, neutralized with 1 N Na$_2$CO$_3$, and purified by column chromatography (silica gel, 10:1 CH$_2$Cl$_2$/MeOH, 5:1:0.1 CHCl$_3$/MeOH/NH$_4$OH) to afford compound 40 (283 mg, 54%) as a colorless oil: $^1$H NMR (300 MHz, CD$_3$OD) δ 7.47-7.45 (m, 4H), 7.31-7.29 (m, 6H), 7.10 (d, J=8.4 Hz, 2H), 6.85 (d, J=8.4 Hz, 2H), 5.49 (s, 2H), 4.25-4.20 (m, 2H), 4.03-3.89 (m, 8H), 3.71-3.58 (m, 6H), 3.29-3.07 (m, 10H), 2.85-2.53 (m, 12H), 1.95 (s, 12H), 1.64-1.19 (m, 56H).

Preparation of Compound 41

A solution of compound 40 (283 mg, 0.156 mmol) and methyl 3,5-diamino-6-chloropyrazine-2-carbonylcarbamimidothioate hydroiodic acid salt (7, 98 mg, 0.250 mmol) in t-BuOH (10 mL) was charged with DIPEA (161 mg, 1.25 mmol) at room temperature. The reaction mixture was heated at 70° C. for 2 h, cooled to room temperature, and concentrated in vacuum. The residue was purified by column chromatography (silica gel, 10:1 CH$_2$Cl$_2$/MeOH, 8:1:0.1 CHCl$_3$/MeOH/NH$_4$OH) to afford compound 41 (130 mg, 41%) as a yellow solid: $^1$H NMR (400 MHz, CD$_3$OD) δ 7.45-7.44 (m, 4H), 7.32-7.30 (m, 6H), 7.09 (d, J=8.4 Hz, 2H), 6.83 (d, J=8.4 Hz, 2H), 5.47 (s, 2H), 4.23-4.20 (m, 2H), 4.00-3.85 (m, 8H), 3.68-3.58 (m, 6H), 3.29-3.07 (m, 10H), 2.81-2.53 (m, 12H), 1.69-1.13 (m, 20H), 1.50 (s, 18H), 1.45 (s, 18H).

Preparation of the Hydrochloride Salt of ((S,R,R,R,2S,2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(6-guanidino-2-((2S,3R,4R,5R)-2,3,4,5,6-pentahydroxyhexylamino)hexanamide)—Compound 42

A solution of compound 41 (152 mg, 0.0853 mmol) in CH$_2$Cl$_2$ (6.0 mL) was charged with TFA (2.0 mL) and the reaction mixture was stirred for 2 h at room temperature. After the solvent was removed, 4 N HCl (5.0 mL) was charged to the residue and the reaction mixture was stirred for 4 h at room temperature. After the solvent was removed, the residue was purified by preparative HPLC and lyophilized to afford hydrochloric acid salt 42 (39 mg, 38%) as a yellow hygroscopic solid: $^1$H NMR (400 MHz, D$_2$O) δ 7.21 (d, J=8.4 Hz, 2H), 6.91 (d, J=8.4 Hz, 2H), 4.28 (br s, 2H), 4.08-4.04 (m, 2H), 3.90 (t, J=6.8 Hz, 2H), 3.77-3.59 (m, 12H), 3.30-3.06 (m, 18H), 2.59 (br s, 2H), 2.03-2.01 (m, 4H), 1.87-1.85 (m, 4H), 1.66 (br s, 4H), 1.54-1.51 (m, 4H), 1.35-1.31 (m, 4H). HRMS calculated for C$_{50}$H$_{92}$ClN$_{18}$O$_{14}$ [M+H]$^+$, 1203.6723. found 1203.6818.

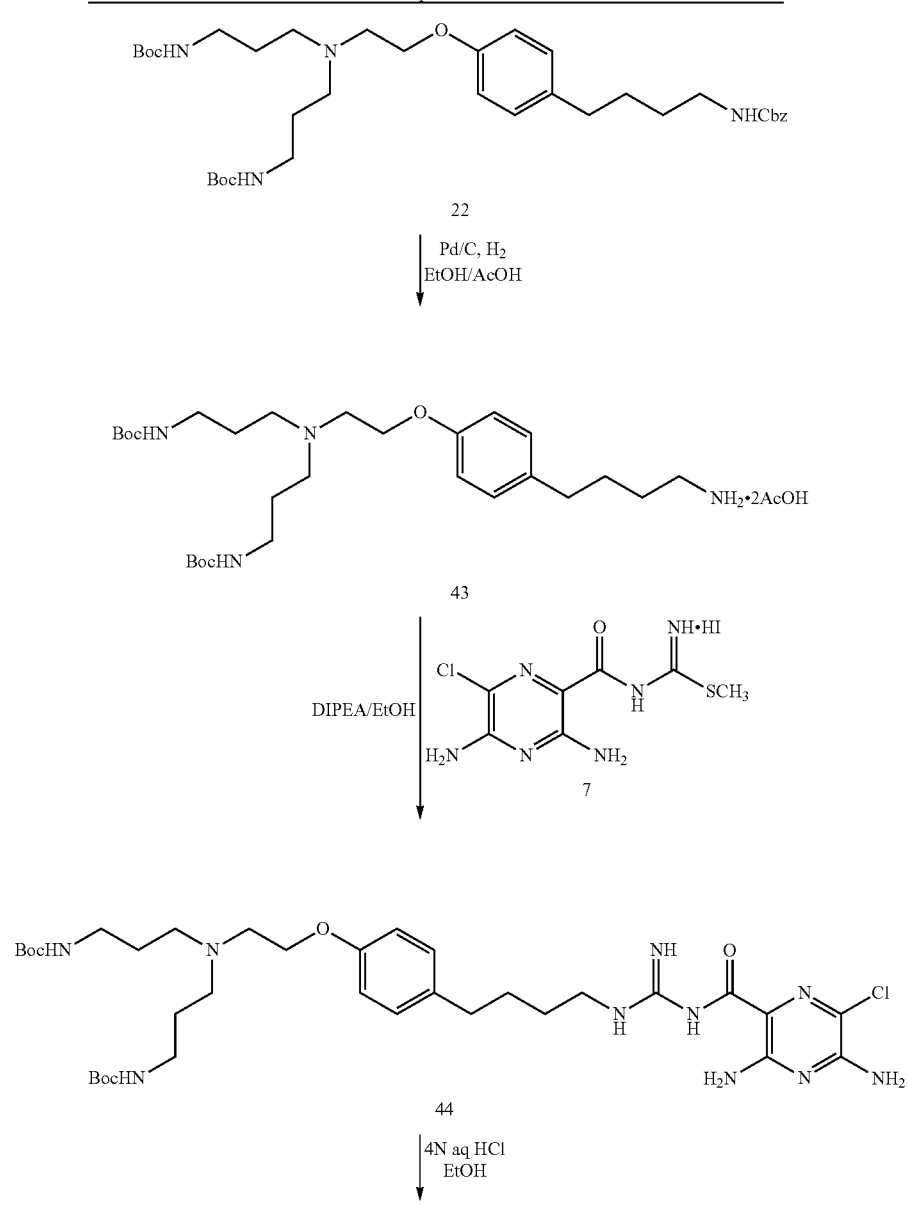

Scheme 7. The Preparation of the Hydrochloride Salt of 3,5-diamino-N-(N-(4-(4-(2-(bis(3-aminopropyl)amino)ethoxy)phenyl)butyl)carbamimidoyl)-6-chloropyrazine-2-carboxamide-Compound 45

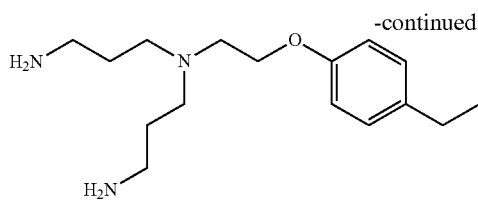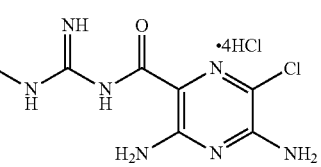

45

Preparation of Compound 43

A suspension of compound 22 (7.00 g, 10.7 mmol) and 10% Pd/C (3.00 g) in EtOH/AcOH (70 mL/2.0 mL) was subjected to hydrogenation conditions (1 atm) for 6 h at room temperature. The reaction mixture was filtered through celite and washed with EtOH. The filtrate was concentrated in vacuum to afford acetic salt 43 (7.00 g, crude) as an off-white solid. The crude product was used directly in the next step. $^1$H NMR (400 MHz, CDCl$_3$) 7.13 (d, J=8.4 Hz, 2H), 6.81 (d, J=8.4 Hz, 2H), 4.09 (t, J=5.2 Hz, 2H), 3.16-3.10 (m, 4H), 3.01 (t, J=5.2 Hz, 2H), 2.89 (t, J=6.8 Hz, 2H), 2.73 (t, J=6.8 Hz, 4H), 2.56 (t, J=6.8 Hz, 2H), 1.75-1.63 (m, 8H), 1.67-1.65 (m, 6H), 1.42 (s, 18H).

Preparation of Compound 44

A solution of amine salt 43 (7.00 g, crude) and methyl 3,5-diamino-6-chloropyrazine-2-carbonylcarbamimidothioate hydroiodic acid salt (7, 5.41 g, 14.4 mmol) in EtOH (70 mL) was charged with DIPEA (14.0 g, 108 mmol) at room temperature. The reaction mixture was heated at 70° C. in a sealed tube for 2 h, cooled to room temperature, and concentrated in vacuum. The residue was purified by column chromatography (silica gel, 80:18:2 CHCl$_3$/CH$_3$OH/NH$_4$OH) to afford guanidine 44 (3.00 g, 38% over 2 steps) as a yellow solid: $^1$H NMR (400 MHz, CD$_3$OD) 7.10 (d, J=8.4 Hz, 2H), 6.85 (d, J=8.4 Hz, 2H), 4.02 (t, J=5.6 Hz, 2H), 3.08 (t, J=6.8 Hz, 4H), 2.83 (t, J=5.6 Hz, 2H), 2.61-2.55 (m, 6H), 1.68-1.63 (m, 8H), 1.40 (s, 18H).

Preparation of the Hydrochloride Salt of 3,5-diamino-N—(N-(4-(4-(2-(bis(3-aminopropyl)amino)ethoxy)phenyl)butyl)carbamimidoyl)-6-chloropyrazine-2-carboxamide—Compound 45

4 N HCl in water (20.0 mL) and ethanol (10.0 mL) was charged with compound 44 (1.80 g, 2.45 mmol) and the reaction mixture was stirred at room temperature for 5 h. The solvent was removed and the mixture was purified by reverse-phase column to give compound 45 (1.30 g, 78%) as a yellow solid: $^1$H NMR (400 MHz, D$_2$O) 7.20 (d, J=8.8 Hz, 2H), 6.91 (d, J=8.8 Hz, 2H), 4.30 (t, J=4.4 Hz, 2H), 3.66 (t, J=4.4 Hz, 2H), 3.37 (t, J=8.0 Hz, 4H), 3.25 (t, J=6.4 Hz, 2H), 3.05 (t, J=8.0 Hz, 4H), 2.57 (d, J=6.4 Hz, 2H), 2.19-2.11 (m, 4H), 1.63 (br s, 4H).

Preparation of 3,5-diamino-N—(N-(4-(4-((R)-11-amino-17-(3-((R)-2-amino-6-guanidinohexanamido)propyl)-5-imino-3,12-dioxo-2-oxa-4,6,13,17-tetraazanonadecan-19-yloxy)phenyl)butyl)carbamimidoyl)-6-chloropyrazine-2-carboxamide-Compound 46 was isolated as a byproduct of the preparation of Compound 9. $^1$H NMR (300 MHz, D$_2$O) δ 7.26 (d, J=8.4 Hz, 2H), 6.91 (d, J=8.4 Hz, 2H), 4.40 (br s, 2H), 3.88-3.85 (m, 2H), 3.79 (br s, 2H), 3.34-3.33 (m, 10H), 3.15 (s, 3H), 3.12 (t, J=6.6 Hz, 4H), 2.63 (br s, 2H), 2.06-2.04 (m, 4H), 1.83-1.78 (m, 4H), 1.69 (br s, 4H), 1.57-1.50 (m, 4H), 1.38-1.33 (m, 4H).

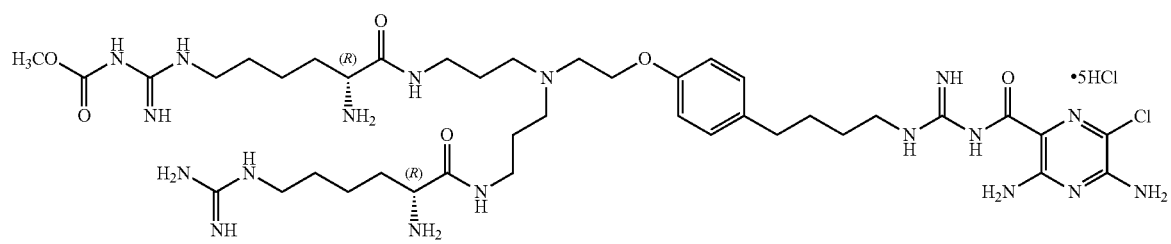

46

Scheme 8. The Preparation of the Hydrochloride Salt of (S)-3,5-diamino-N-(N-(4-(4-(2-((3-(2-amino-6-guanidinohexanamido)propyl)(3-aminopropyl)amino)ethoxy)phenyl)butyl)carbamimidoyl)-6-chloropyrazine-2-carboxamide-Compound 51
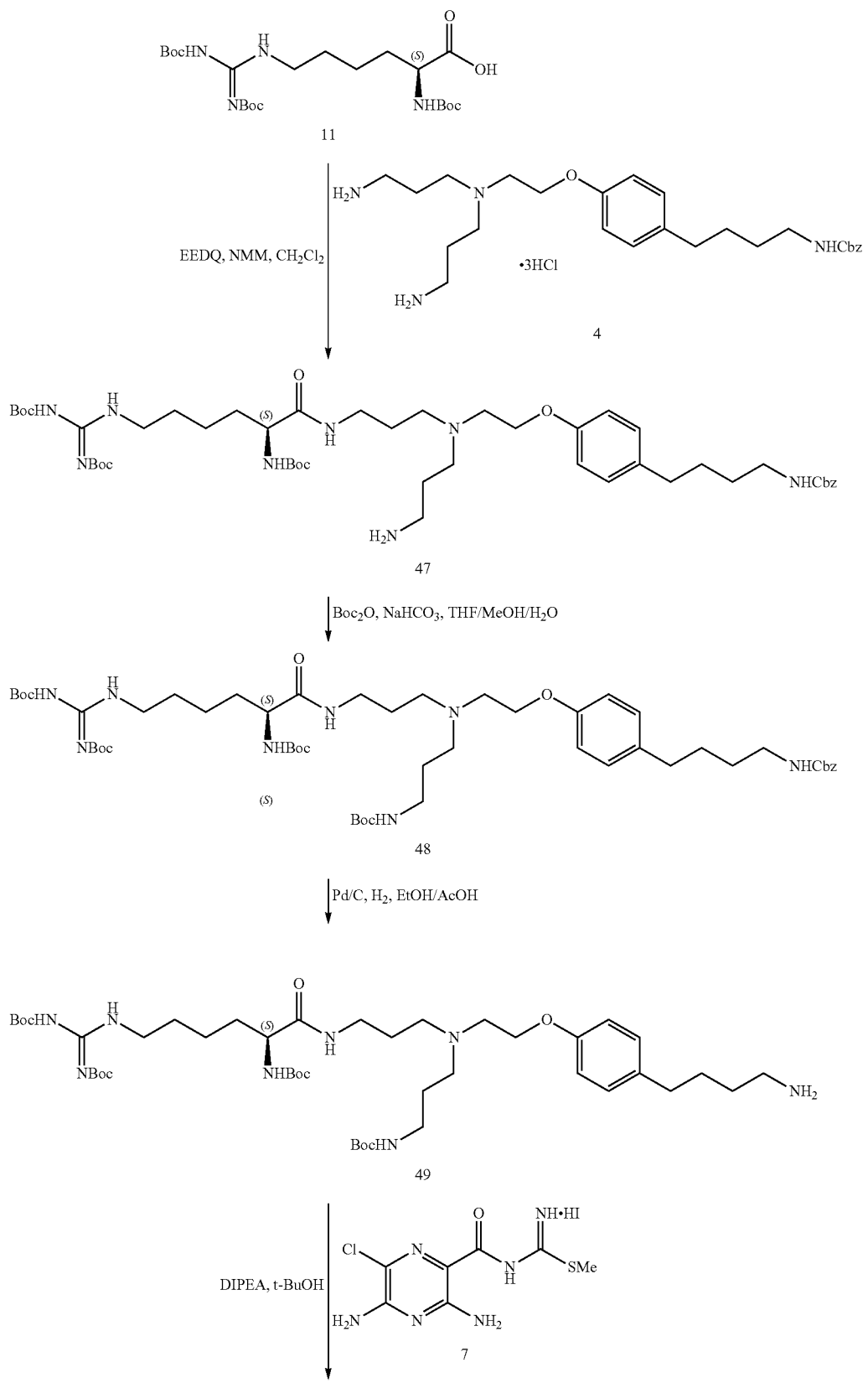

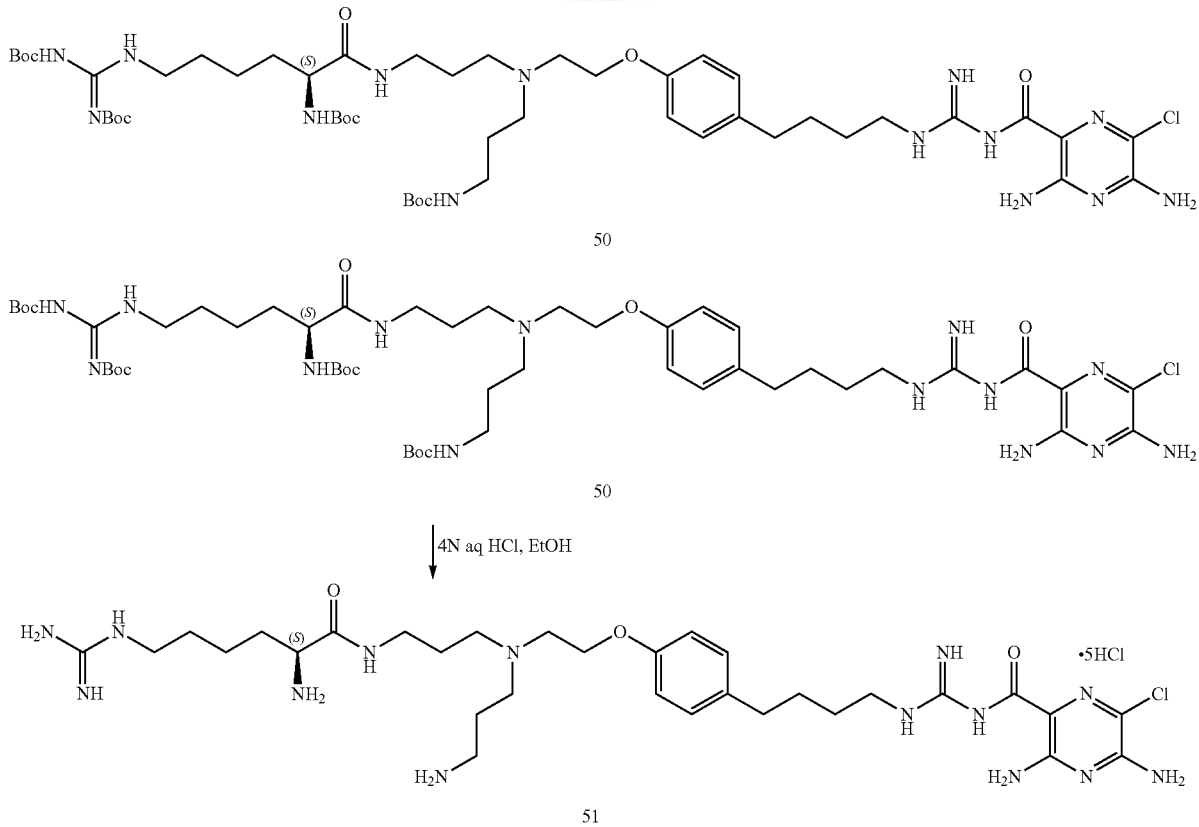

Preparation of Compound 47

A solution of amino acid 11 (750 mg, 1.53 mmol) in $CH_2Cl_2$ (30 mL) was charged with EEDQ (890 mg, 2.97 mmol), bis-amine 4 (1.73 g, 3.06 mmol) and NMM (2.40 g, 23.7 mmol). The reaction mixture was stirred at 0° C. for 6 h and at room temperature for 24 h. Additional amino acid 11 (750 mg, 1.53 mmol) and EEDQ (890 mg, 2.97 mmol) were added and the resulting mixture was stirred at room temperature for 24 h. The solvent was removed and the residue was purified by column chromatography (silica gel, 10:1 $CH_2Cl_2$/MeOH) to afford compound 47 (620 mg, mixture with compound 11) as a yellow solid, which was used directly in the next step.

Preparation of Compound 48

A solution of compound 47 (850 mg, mixture with compound 11) in THF (6.0 mL), MeOH (6.0 mL), and water (2.0 mL) was charged with $NaHCO_3$ (462 mg, 5.52 mmol) and $Boc_2O$ (250 mg, 1.14 mmol). The reaction mixture was stirred for 6 h at room temperature. After the solvent was removed, the residue was partitioned between $CH_2Cl_2$ (20 mL) and water (20 mL). The aqueous layer was separated and extracted with $CH_2Cl_2$ (20 mL). The combined organic extracts were dried over $Na_2SO_4$, concentrated, and purified by column chromatography (silica gel, 10:1 $CH_2Cl_2$/MeOH) to afford compound 48 (460 mg, 11% over 2 steps) as a white solid: $^1H$ NMR (300 MHz, $CD_3OD$) δ 7.33-7.32 (m, 5H), 7.06 (d, J=8.4 Hz, 2H), 6.83 (d, J=8.4 Hz, 2H), 5.05 (s, 2H), 4.06 (t, J=5.7 Hz, 2H), 3.95 (br s, 1H), 3.34-3.23 (m, 4H), 3.14-3.07 (m, 4H), 2.92 (br s, 2H), 2.66-2.52 (m, 6H), 1.86-1.54 (m, 14H), 1.51 (s, 9H), 1.46 (s, 9H), 1.42 (s, 9H), 1.40 (s, 9H).

Preparation of Compound 49

A suspension of compound 48 (460 mg, 0.448 mmol) and 10% Pd/C (230 mg) in EtOH (15 mL) was subjected to hydrogenation conditions (1 atm) for 3 h at room temperature. The reaction mixture was filtered through celite and washed with EtOH. The filtrate was concentrated and purified by column chromatography (silica gel, 10:1 $CH_2Cl_2$/MeOH) to afford compound 49 (342 mg, 86%) as a white solid: $^1H$ NMR (300 MHz, $CD_3OD$) δ 7.09 (d, J=8.1 Hz, 2H), 6.85 (d, J=8.1 Hz, 2H), 4.03 (t, J=5.4 Hz, 2H), 3.95 (br s, 1H), 3.34-3.24 (m, 4H), 3.08 (d, J=6.6 Hz, 2H), 2.88-2.84 (m, 4H), 2.59-2.52 (m, 6H), 1.64-1.57 (m, 14H), 1.52 (s, 9H), 1.46 (s, 9H), 1.43 (s, 9H), 1.41 (s, 9H).

Preparation of Compound 50

A solution of amine 49 (342 mg, 0.383 mmol) and methyl 3,5-diamino-6-chloropyrazine-2-carbonylcarbamimidothioate hydroiodic acid salt (7, 238 mg, 0.611 mmol) in t-BuOH (15 mL) was charged with DIPEA (392 mg, 3.04 mmol) at room temperature. The reaction mixture was heated at 70° C. for 2 h, cooled to room temperature, and concentrated in vacuum. The residue was purified by column chromatography (silica gel, 10:1 $CH_2Cl_2$/MeOH, 5:1:0.1 $CHCl_3$/MeOH/$NH_4OH$) to afford compound 50 (236 mg, 56%) as a yellow solid: $^1H$ NMR (300 MHz, $CD_3OD$) δ 7.09 (d, J=7.2 Hz, 2H), 6.85 (d, J=7.2 Hz, 2H), 4.03 (d, J=5.1 Hz, 2H), 3.95 (br s, 1H), 3.31-3.25 (m, 6H), 3.08 (t, J=6.3 Hz, 2H), 2.84 (t, J=4.8 Hz, 2H), 2.60-2.56 (m, 6H), 1.67-1.54 (m, 14H), 1.51 (s, 9H), 1.46 (s, 9H), 1.42 (s, 9H), 1.40 (s, 9H).

Preparation of the Hydrochloride Acid Salt of (S)-3,5-diamino-N—(N-(4-(4-(2-((3-(2-amino-6-guanidinohexanamido)propyl)(3-aminopropyl)amino)ethoxy)phenyl)butyl)carbamimidoyl)-6-chloropyrazine-2-carboxamide—Compound 51

A solution of compound 50 (235 mg, 0.212 mmol) in EtOH (1.5 mL) was charged with 4 N aqueous HCl (5.0 mL) at room temperature, and the reaction mixture was stirred for 4 h at room temperature. The reaction mixture was concentrated in vacuum and the residue was purified by reverse-phase column chromatography and lyophilized to afford hydrochloric acid salt 51 (145 mg, 76%) as a yellow hygroscopic solid: $^1$H NMR (400 MHz, D$_2$O) δ 7.22 (d, J=8.4 Hz, 2H), 6.91 (d, J=8.4 Hz, 2H), 4.29 (t, J=4.8 Hz, 2H), 3.88 (t, J=6.8 Hz, 2H), 3.63 (t, J=4.4 Hz, 2H), 3.35-3.28 (m, 8H), 3.09-3.03 (m, 2H), 2.59 (br s, 2H), 2.17-2.12 (m, 2H), 2.03-1.97 (m, 2H), 1.83-1.79 (m, 2H), 1.66 (br s, 4H), 1.53-1.49 (m, 2H), 1.34-1.32 (m, 2H). HRMS calculated for C$_{31}$H$_{54}$ClN$_{14}$O$_3$ [M+H]$^+$, 705.4186. found 705.4216.

Preparation of the Hydrochloride Salt of (S,2S,2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-((S)-2,6-diaminohexanamido)hexanamide)

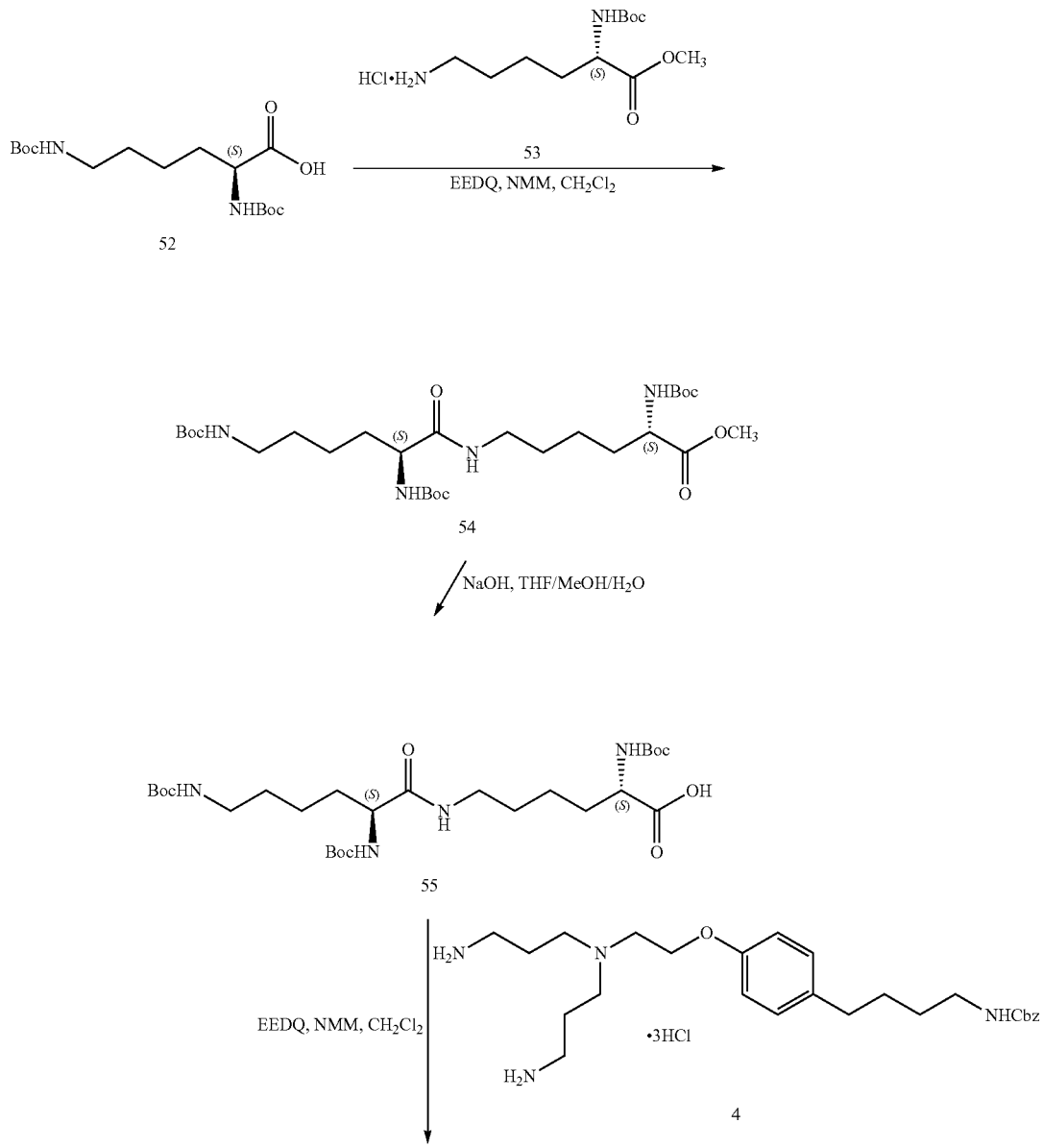

Scheme 9

-continued
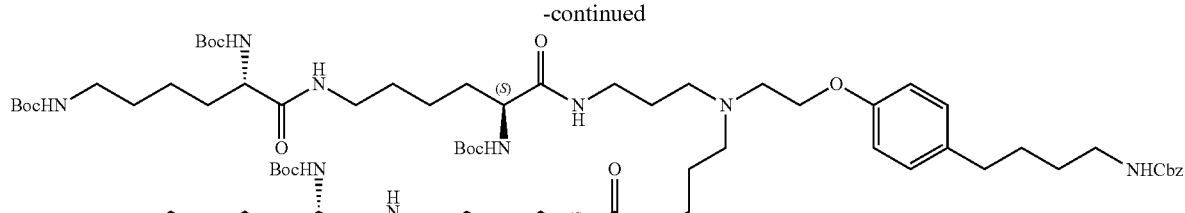
56
↓ Pd/C, H₂, EtOH/AcOH
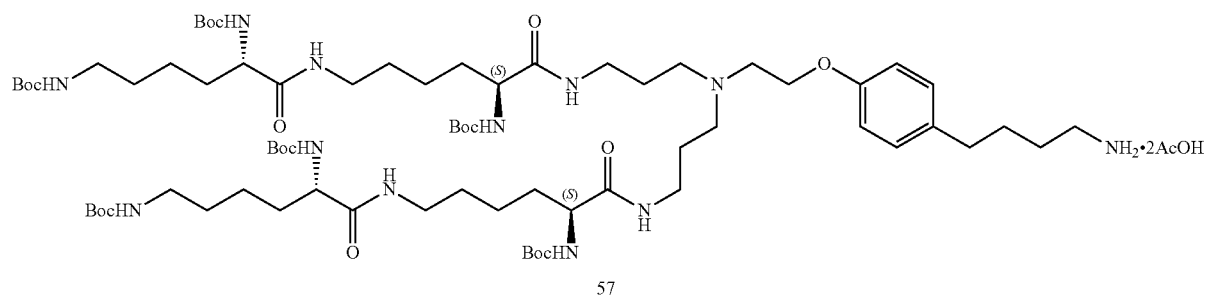
57
↓ DIPEA, t-BuOH
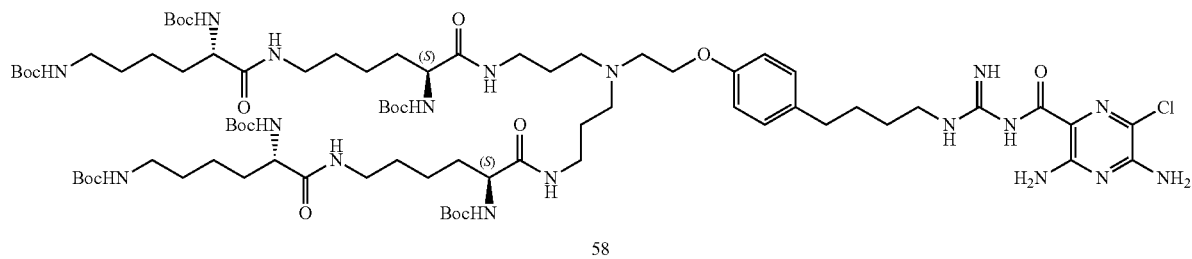
58
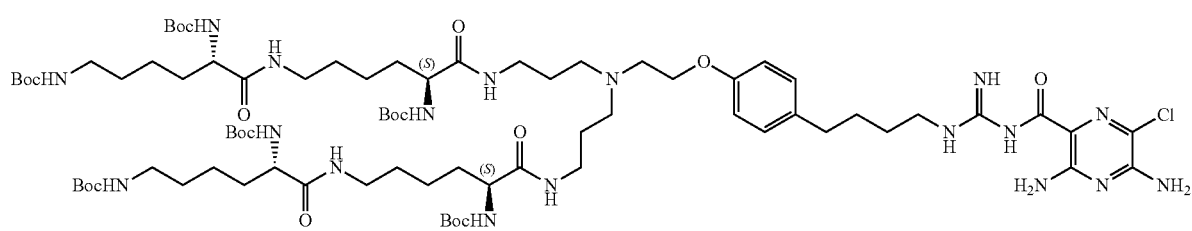
58
↓ 4N aq HCl, EtOH

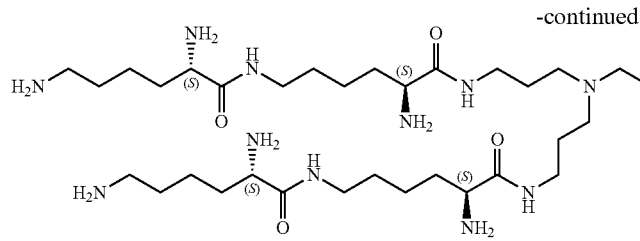
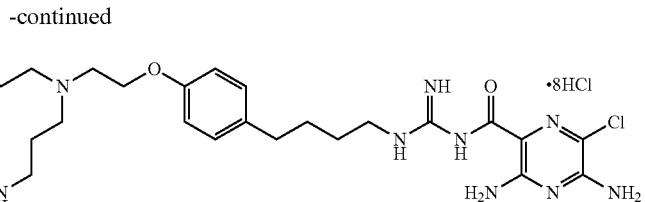

59

Preparation of Compound 54

A solution of amino acid 52 (2.00 g, 5.77 mmol) in $CH_2Cl_2$ (40 mL) was charged with EEDQ (2.07 g, 6.92 mmol), compound 53 (1.71 g, 5.77 mmol), and NMM (1.74 g, 17.3 mmol). The reaction mixture was stirred at room temperature for 16 h. The solvent was removed and the residue was purified by column chromatography (silica gel, 10:1 $CH_2Cl_2$/EtOAc, 10:1 $CH_2Cl_2$/MeOH) to afford compound 54 (2.80 g, 82%) as a colorless oil: $^1H$ NMR (300 MHz, $CD_3OD$) δ 4.08-4.04 (m, 1H), 3.96-3.94 (m, 1H), 3.70 (s, 3H), 3.21-3.15 (m, 2H), 3.02 (t, J=6.6 Hz, 2H), 1.73-1.47 (m, 12H), 1.46 (s, 27H).

Preparation of Compound 55

A solution of compound 54 (24.8 g, 42.0 mmol) in THF (200 mL), MeOH (200 mL), and $H_2O$ (60 mL) was charged with NaOH (16.8 g, 420 mmol). The reaction mixture was stirred at room temperature for 3 h. The solvent was removed and water (300 mL) was charged to the residue. After the pH was adjusted to 5 with 1 N HCl, the resulting solid was filtered out and dried to afford compound 55 (22.5 g, 93%) as an orange solid: $^1H$ NMR (400 MHz, $CD_3OD$) δ 4.06-4.02 (m, 1H), 3.96-3.94 (m, 1H), 3.70 (s, 3H), 3.21-3.18 (m, 1H), 3.02 (t, J=6.8 Hz, 2H), 1.80-1.53 (m, 12H), 1.43 (s, 27H).

Preparation of Compound 56

A solution of amino acid 55 (2.54 g, 4.41 mmol) in $CH_2Cl_2$ (80 mL) was charged with EEDQ (1.58 g, 5.28 mmol), compound 4 (1.25 g, 2.20 mmol), and NMM (3.55 g, 35.2 mmol). The reaction mixture was stirred at room temperature for 16 h. The solvent was removed and the residue was purified by column chromatography (silica gel, 10:1 $CH_2Cl_2$/EtOAc, 10:1 $CH_2Cl_2$/MeOH) to afford compound 56 (2.40 g, 75%) as a colorless oil: $^1H$ NMR (300 MHz, $CD_3OD$) δ 7.32-7.28 (m, 5H), 7.06 (d, J=8.4 Hz, 2H), 6.82 (d, J=8.4 Hz, 2H), 5.05 (s, 2H), 4.04-3.95 (m, 6H), 3.24-2.99 (m, 14H), 2.87 (br s, 2H), 2.63-2.52 (m, 6H), 1.72-1.42 (m, 32H), 1.47 (s, 54H).

Preparation of Compound 57

A suspension of compound 56 (2.40 g, 1.52 mmol) and 10% Pd/C (1.20 g) in EtOH (50 mL) and AcOH (2.0 mL) was subjected to hydrogenation conditions (1 atm) for 6 h at room temperature. The reaction mixture was filtered through celite and washed with EtOH. The filtrate was concentrated and washed with MTBE to afford compound 57 (2.13 g, 90%) as a colorless oil: $^1H$ NMR (300 MHz, $CD_3OD$) δ 7.12 (d, J=8.4 Hz, 2H), 6.90 (d, J=8.4 Hz, 2H), 4.19 (br s, 2H), 3.94-3.85 (m, 4H), 3.34-2.92 (m, 20H), 2.62 (t, J=6.6 Hz, 2H), 1.95 (s, 6H), 1.90-1.50 (m, 32H), 1.47 (s, 54H).

Preparation of Compound 58

A solution of amine 37 (2.12 g, 1.36 mmol) and methyl 3,5-diamino-6-chloropyrazine-2-carbonylcarbamimidothioate hydroiodic acid salt (7, 638 mg, 1.63 mmol) in EtOH (80 mL) was charged with DIPEA (1.41 g, 10.8 mmol) at room temperature. The reaction mixture was heated at 70° C. for 2 h, cooled to room temperature, and concentrated in vacuum. The residue was purified by column chromatography (silica gel, 10:1 $CH_2Cl_2$/MeOH, 5:1:0.1 $CHCl_3$/MeOH/$NH_4OH$) to afford compound %8 (1.21 g, 54%) as a yellow solid: $^1H$ NMR (400 MHz, $CD_3OD$) δ 7.10 (d, J=8.4 Hz, 2H), 6.85 (d, J=8.4 Hz, 2H), 4.13 (t, J=5.2 Hz, 2H), 3.94-3.85 (m, 4H), 3.34-3.10 (m, 10H), 3.01 (t, J=6.8 Hz, 4H), 2.89 (br s, 2H), 2.62 (t, J=6.4 Hz, 6H), 1.92-1.47 (m, 32H), 1.43 (s, 54H).

Preparation of Compound 59—The Hydrochloride Salt of (S,2S,2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-((S)-2,6-diaminohexanamido)hexanamide)

A solution of compound 58 (360 mg, 0.218 mmol) in EtOH (2.0 mL) was charged with 4 N aqueous HCl (6.0 mL) at room temperature and the reaction mixture was stirred for 6 h at room temperature. The reaction mixture was concentrated in vacuum and the residue was purified by reverse-phase column chromatography and lyophilized to afford hydrochloric acid salt 59 (117 mg, 41%) as a yellow hygroscopic solid: $^1H$ NMR (400 MHz, $D_2O$) δ 7.22 (d, J=8.4 Hz, 2H), 6.91 (d, J=8.4 Hz, 2H), 4.28 (br s, 2H), 3.90-3.86 (m, 4H), 3.60 (br s, 2H), 3.37-3.15 (m, 14H), 2.60 (br s, 2H), 2.00-1.96 (m, 4H), 1.85-1.79 (m, 8H), 1.68-1.64 (m, 8H), 1.49-1.32 (m, 12H). HRMS calculated for $C_{48}H_{88}ClN_{18}O_6$ $[M+H]^+$, 1047.6817. found 1047.6831.

Preparation of the Hydrochloride Salt of (S,S,2S, 2'S)—N,N'-(3,3'-(2-(4-(4-(3-(3,5-diamino-6-chloro-pyrazine-2-carbonyl)guanidino)butyl)phenoxy)ethylazanediyl)bis(propane-3,1-diyl))bis(2-amino-6-((S)-2-amino-6-((S)-2,6-diaminohexanamido)hexanamido)hexanamide)
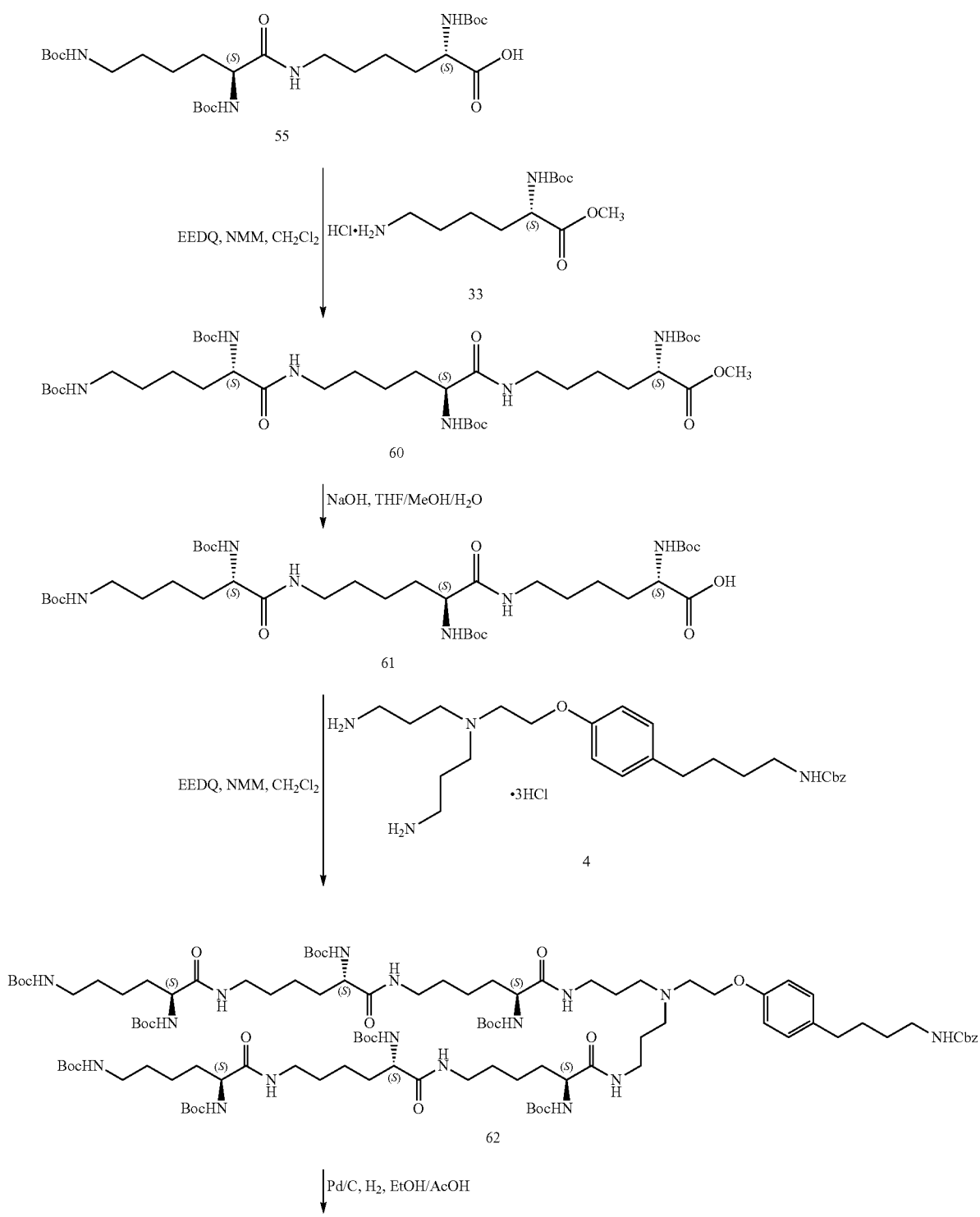
Scheme 10

155 -continued 156
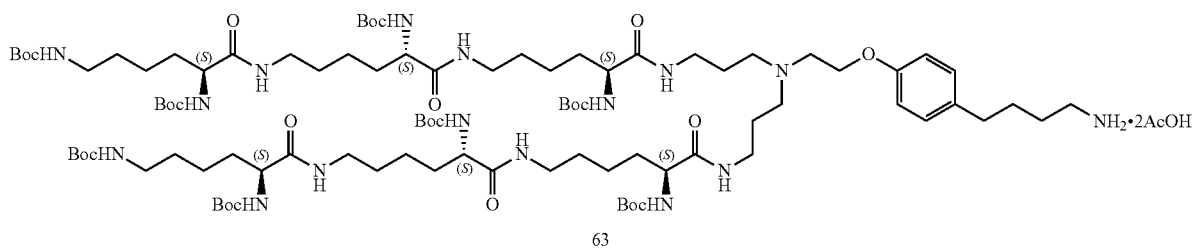
63
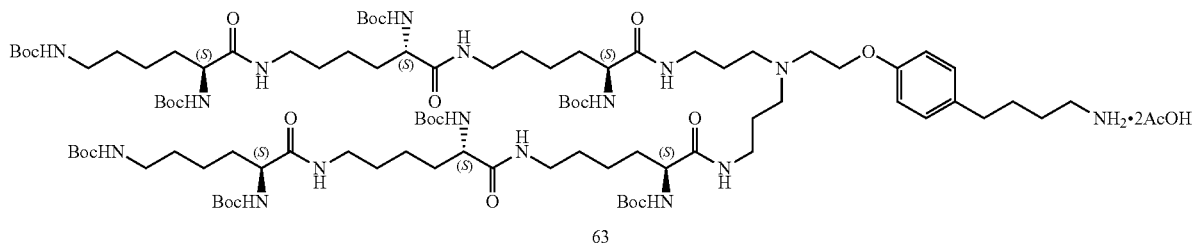
63
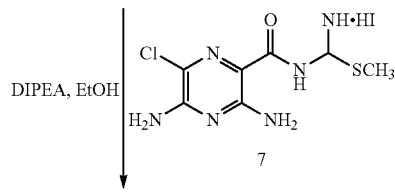
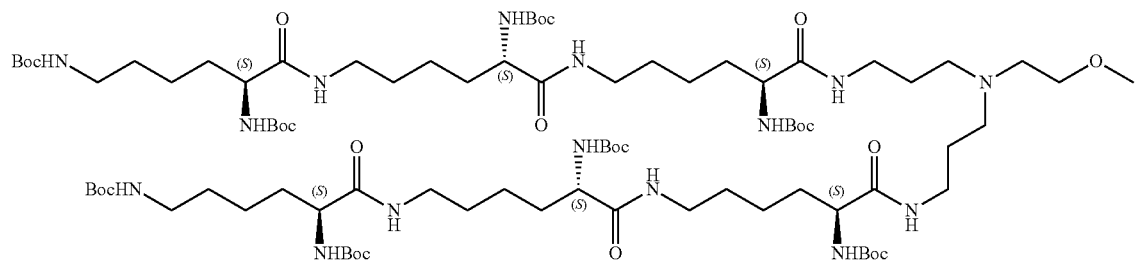
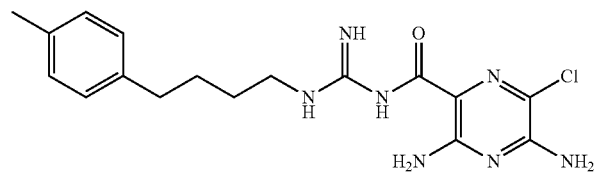
64
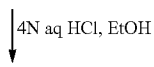
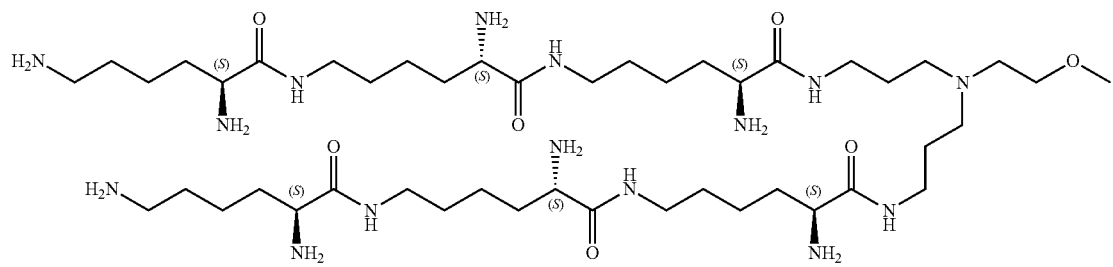

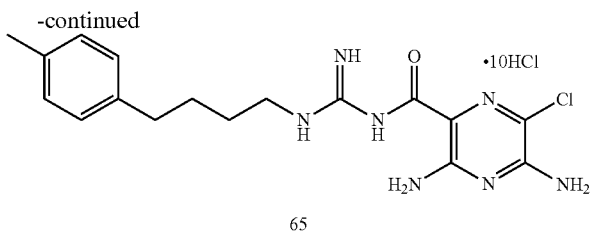

65

Preparation of Compound 60

A solution of amino acid 55 (12.0 g, 20.8 mmol) in CH$_2$Cl$_2$ (300 mL) was charged with EEDQ (7.40 g, 25.0 mmol), compound 33 (6.20 g, 20.8 mmol), and NMM (6.30 g, 62.4 mmol). The reaction mixture was stirred at room temperature for 16 h. The solvent was removed and the residue was purified by column chromatography (silica gel, 10:1 CH$_2$Cl$_2$/EtOAc, 10:1 CH$_2$Cl$_2$/MeOH) to afford compound 40 (13.1 g, 77%) as a yellow oil: $^1$H NMR (300 MHz, CD$_3$OD) δ 4.08 (br s, 1H), 3.94 (br s, 2H), 3.70 (s, 3H), 3.21-3.15 (m, 4H), 3.02 (t, J=6.6 Hz, 2H), 1.70-1.47 (m, 18H), 1.43 (s, 36H).

Preparation of Compound 61

A solution of compound 60 (13.0 g, 15.9 mmol) in THF (100 mL), MeOH (100 mL), and H$_2$O (35 mL) was charged with NaOH (3.20 g, 80.0 mmol). The reaction mixture was stirred at room temperature for 4 h. The solvent was removed and water (300 mL) was charged to the residue. After the pH was adjusted to 5 with 1 N HCl, the resulting solid was filtered out and dried to afford compound 61 (12.1 g, 95%) as an orange solid: $^1$H NMR (300 MHz, CD$_3$OD) δ 4.03 (br s, 1H), 3.94 (br s, 2H), 3.70 (s, 3H), 3.29-3.14 (m, 4H), 3.02 (t, J=6.6 Hz, 2H), 1.70-1.47 (m, 18H), 1.43 (s, 36H).

Preparation of Compound 62

A solution of amino acid 61 (500 mg, 0.622 mmol) in CH$_2$Cl$_2$ (15 mL) was charged with EEDQ (223 mg, 0.746 mmol), compound 4 (176 mg, 0.311 mmol), and NMM (502 mg, 4.97 mmol). The reaction mixture was stirred at room temperature for 16 h. The solvent was removed and the residue was purified by column chromatography (silica gel, 10:1 CH$_2$Cl$_2$/EtOAc, 10:1 CH$_2$Cl$_2$/MeOH) to afford compound 62 (290 mg, 46%) as a colorless oil: $^1$H NMR (400 MHz, CD$_3$OD) δ 7.33-7.29 (m, 5H), 7.12 (d, J=8.4 Hz, 2H), 6.91 (d, J=8.4 Hz, 2H), 5.05 (s, 2H), 4.32 (br s, 2H), 3.94-3.84 (m, 6H), 3.57 (br s, 2H), 3.32-3.00 (m, 22H), 2.57 (t, J=7.2 Hz, 2H), 1.70-1.47 (m, 44H), 1.47 (s, 72H).

Preparation of Compound 63

A suspension of compound 62 (2.20 g, 1.08 mmol) and 10% Pd/C (1.10 g) in EtOH (50 mL) was subjected to hydrogenation conditions (1 atm) for 6 h at room temperature. The reaction mixture was filtered through celite and washed with EtOH. The filtrate was concentrated to afford compound 63 (1.87 g, 91%) as a white solid: $^1$H NMR (300 MHz, CD$_3$OD) δ 7.16 (d, J=8.4 Hz, 2H), 6.93 (d, J=8.4 Hz, 2H), 4.30 (br s, 2H), 3.91-3.83 (m, 6H), 3.52 (br s, 2H), 3.17-2.94 (m, 22H), 2.62 (s, 2H), 1.98-1.47 (m, 44H), 1.47 (s, 72H).

Preparation of Compound 64

A solution of amine 43 (1.86 g, 0.980 mmol) and methyl 3,5-diamino-6-chloropyrazine-2-carbonylcarbamimidothioate hydroiodic acid salt (7, 455 mg, 1.17 mmol) in EtOH (20 mL) was charged with DIPEA (1.01 g, 7.78 mmol) at room temperature. The reaction mixture was heated at 70° C. for 2 h, cooled to room temperature, and concentrated in vacuum. The residue was purified by column chromatography (silica gel, 10:1 CH$_2$Cl$_2$/MeOH, 5:1:0.1 CHCl$_3$/MeOH/NH$_4$OH) to afford compound 64 (1.26 g, 61%) as a yellow solid: $^1$H NMR (300 MHz, CD$_3$OD) δ 7.11 (d, J=8.7 Hz, 2H), 6.84 (d, J=8.7 Hz, 2H), 4.05-3.95 (br s, 8H), 3.34-3.07 (m, 14H), 3.02 (t, J=6.6 Hz, 4H), 2.85 (t, J=5.4 Hz, 2H), 2.62-2.57 (m, 6H), 1.69-1.47 (m, 44H), 1.43 (s, 72H).

Preparation of the Hydrochloride Salt of (S,S,2S,2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-((S)-2-amino-6-((S)-2,6-diaminohexanamido)hexanamido)hexanamide)—Compound 65

A solution of compound 64 (1.25 g, 0.661 mmol) in EtOH (5.0 mL) was charged with 4 N aqueous HCl (15 mL) at room temperature and the reaction mixture was stirred for 4 h at room temperature. The reaction mixture was concentrated in vacuum, and the residue was purified by reverse-phase column chromatography and lyophilized to afford hydrochloric acid salt 65 (681 mg, 62%) as a yellow hygroscopic solid: $^1$H NMR (400 MHz, D$_2$O) δ 7.22 (d, J=8.4 Hz, 2H), 6.91 (d, J=8.4 Hz, 2H), 4.28 (br s, 2H), 3.91-3.87 (m, 6H), 3.60 (br s, 2H), 3.37-3.17 (m, 18H), 2.97-2.93 (m, 4H), 2.59 (br s, 2H), 2.01-1.96 (m, 4H), 1.84-1.79 (m, 12H), 1.68-1.64 (m, 8H), 1.52-1.32 (m, 20H). HRMS calculated for C$_{60}$H$_{112}$ClN$_{22}$O$_8$ [M+H]$^+$, 1303.8717. found 1303.8708.

10. Preparation of the Hydrochloride Salt of N,N'-((7S,19S)-7,19-diamino-13-(2-(4-(4-(3-(3,5-diamino-6-chloropyrazine-2-carbonyl)guanidino)butyl)phenoxy)ethyl)-1,25-diimino-8,18-dioxo-2,9,13,17,24-pentaazapentacosane-1,25-diyl)dibenzamide
Scheme 11
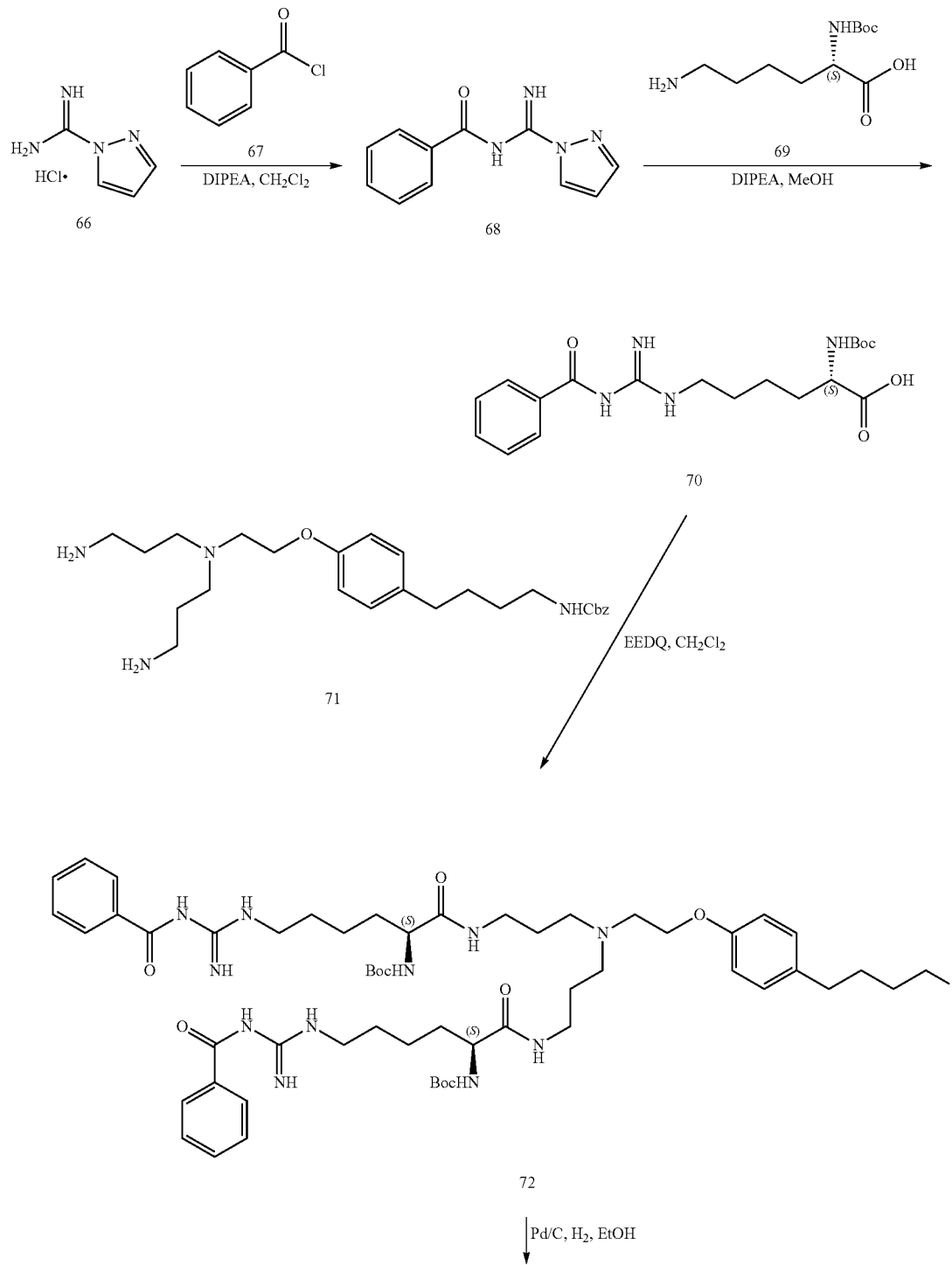

-continued
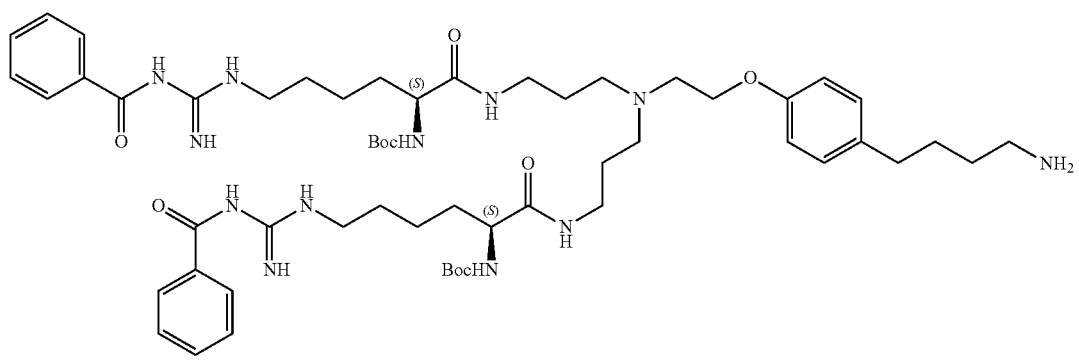
73
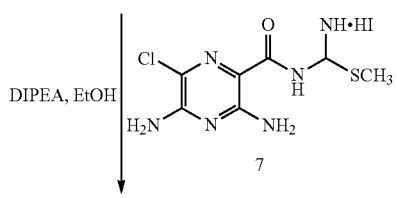
DIPEA, EtOH
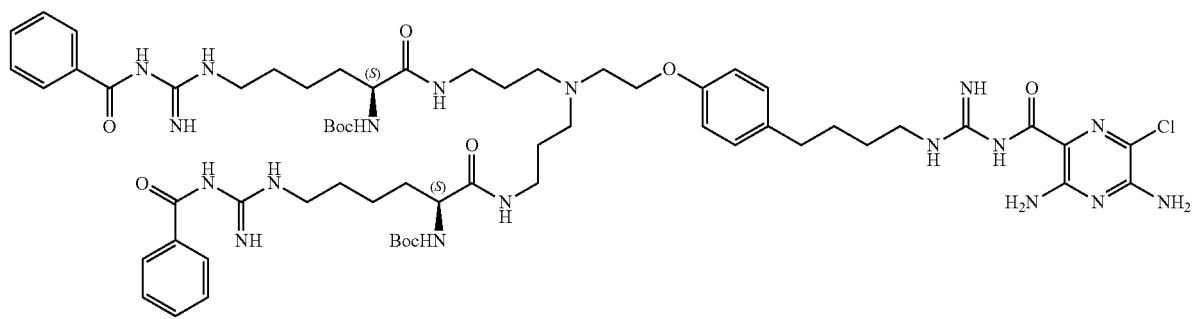
74
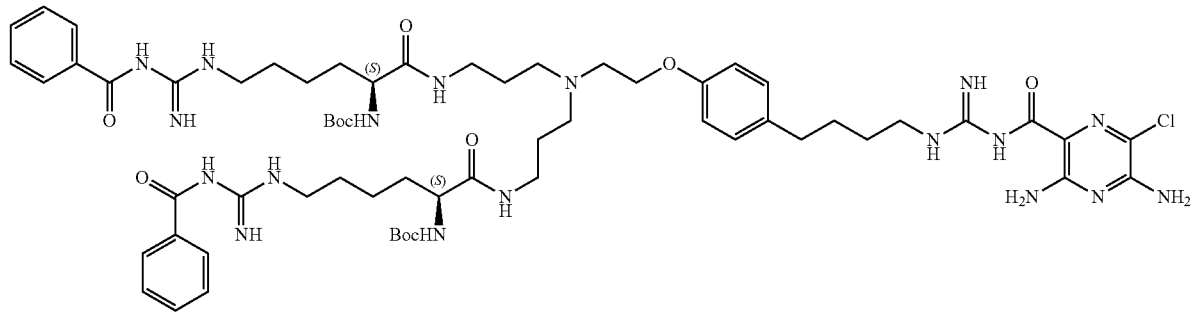
74
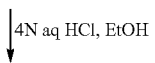
4N aq HCl, EtOH

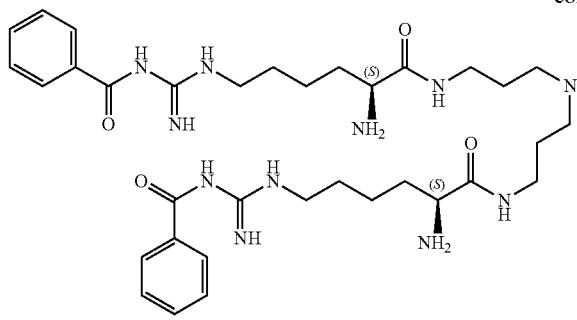 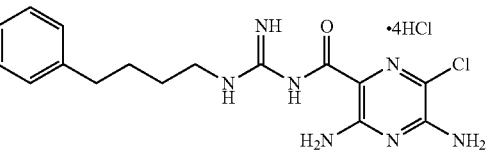

Preparation of Compound 68

A solution of compound 66 (300 mg, 2.05 mmol) and DIPEA (2.10 g, 16.4 mmol) in CH$_2$Cl$_2$ (6.0 mL) was charged with compound 67 (316 mg, 2.25 mmol). The reaction mixture was stirred at room temperature for 24 h. Water (20 mL) was added, and the aqueous layer was extracted with CH$_2$Cl$_2$ (20 mL) The combined organic extracts were dried over Na$_2$SO$_4$, concentrated, and purified by column chromatography (silica gel, 10:1 CH$_2$Cl$_2$/MeOH) to afford compound 68 (340 mg, 78%) as a white solid: $^1$H NMR (300 MHz, CDCl$_3$) δ 10.0 (br s, 1H), 8.64 (d, J=2.7 Hz, 1H), 8.30 (dd, J=0.9, 8.1 Hz, 2H), 7.74 (d, J=0.9 Hz, 1H), 7.53-7.45 (m, 3H), 6.48 (dd, J=1.8, 2.7 Hz, 1H).

Preparation of Compound 70

A solution of compound 69 (200 mg, 0.813 mmol) in MeOH (8.0 mL) was charged with compound 68 (174 mg, 0.813 mmol) and DIPEA (419 mg, 3.25 mmol). The reaction mixture was stirred at room temperature for 16 h. Additional 68 (35 mg, 0.162 mmol) was charged and the reaction mixture was stirred at room temperature for 5 h. After the solvent was removed, the residue was purified by column chromatography (silica gel, 10:1 CH$_2$Cl$_2$/MeOH) to afford compound 70 (246 mg, 78%) as a white solid: $^1$H NMR (300 MHz, CD$_3$OD) δ 8.00-7.98 (m, 2H), 7.65-7.53 (m, 3H), 4.03 (br s, 1H), 3.34-3.29 (m, 2H), 1.85-1.49 (m, 6H), 1.42 (s, 9H).

Preparation of Compound 72

A solution of amino acid 70 (200 mg, 0.509 mmol) in CH$_2$Cl$_2$ (5.0 mL) was charged with EEDQ (305 mg, 1.02 mmol) and compound 71 (116 mg, 0.255 mmol). The reaction mixture was stirred at room temperature for 30 h. Additional 70 (40 mg, 0.118 mmol) was charged and the reaction mixture was stirred at room temperature for 6 h. The solvent was removed and the residue was purified by column chromatography (silica gel, 10:1 CH$_2$Cl$_2$/MeOH) to afford compound 72 (197 mg, 64%) as a colorless oil: $^1$H NMR (400 MHz, CD$_3$OD) δ 8.04 (br s, 4H), 7.45-7.28 (m, 11H), 7.05 (d, J=8.4 Hz, 2H), 6.82 (d, J=8.4 Hz, 2H), 5.05 (s, 2H), 4.04-3.98 (m, 4H), 3.24-3.23 (m, 8H), 3.09 (t, J=6.8 Hz, 2H), 2.92 (br s, 2H), 2.65 (br s, 4H), 2.52 (t, J=7.6 Hz, 2H), 1.72-1.46 (m, 20H), 1.41 (s, 18H).

Preparation of Compound 73

A suspension of compound 72 (195 mg, 0.162 mmol) and 10% Pd/C (100 mg) in EtOH (5.0 mL) was subjected to hydrogenation conditions (1 atm) for 4 h at room temperature. The reaction mixture was filtered through celite and precipitated from MTBE/hexanes. The filtrate was concentrated to afford compound 73 (149 mg, 86%) as a white solid: $^1$H NMR (400 MHz, CD$_3$OD) δ 8.05 (br s, 4H), 7.45-7.34 (m, 6H), 7.08 (d, J=8.4 Hz, 2H), 6.82 (d, J=8.4 Hz, 2H), 4.00-3.98 (m, 4H), 3.34-3.23 (m, 8H), 2.81-2.79 (m, 4H), 2.55 (br s, 6H), 1.64-1.42 (m, 20H), 1.41 (s, 18H).

Preparation of Compound 74

A solution of amine 73 (145 mg, 0.135 mmol) and methyl 3,5-diamino-6-chloropyrazine-2-carbonylcarbamimidothioate hydroiodic acid salt (7, 64 mg, 0.162 mmol) in EtOH (3.0 mL) was charged with DIPEA (88 mg, 0.675 mmol) at room temperature. The reaction mixture was heated at 70° C. for 2 h, cooled to room temperature, and concentrated in vacuum. The residue was purified by column chromatography (silica gel, 10:1 CH$_2$Cl$_2$/MeOH, 5:1:0.1 CHCl$_3$/MeOH/NH$_4$OH) to afford compound 74 (104 mg, 60%) as a yellow solid: $^1$H NMR (400 MHz, CD$_3$OD) δ 8.05 (br s, 4H), 7.42-7.33 (m, 6H), 7.08 (d, J=8.4 Hz, 2H), 6.82 (d, J=8.4 Hz, 2H), 4.00-3.98 (m, 4H), 3.34-3.23 (m, 10H), 2.80-2.79 (m, 2H), 2.58-2.53 (m, 6H), 1.68-1.61 (m, 20H), 1.41 (s, 18H).

The preparation of the Hydrochloride salt of N,N'-((7S,19S)-7,19-diamino-13-(2-(4-(4-(3-(3,5-diamino-6-chloropyrazine-2-carbonyl)guanidino)butyl)phenoxy)ethyl)-1,25-diimino-8,18-dioxo-2,9,13,17,24-pentaazapentaco sane-1,25-diyl)dibenzamide—Compound 75

A solution of compound 74 (1.02 g, 0.794 mmol) in EtOH (20 mL) was charged with 4 N aqueous HCl (20 mL) at room temperature and the reaction mixture was stirred for 4 h at room temperature. The reaction mixture was concentrated in vacuum and the residue was purified by reverse-phase column chromatography and lyophilized to afford hydrochloric acid salt 75 (511 mg, 52%) as a yellow hygroscopic solid: $^1$H NMR (300 MHz, D$_2$O) δ 7.73 (d, J=7.5 Hz, 2H), 7.55 (t, J=7.5 Hz, 2H), 7.55 (t, J=7.5 Hz, 4H), 7.13 (d, J=8.7 Hz, 2H), 6.82 (d, J=8.7 Hz, 2H), 4.13 (br s, 2H), 3.85 (t, J=6.6 Hz, 2H), 3.47 (br s, 2H), 3.23-3.19 (m, 14H), 2.49 (br s, 2H), 1.91-1.75 (m, 8H), 1.58-1.52 (m, 8H), 1.37-1.32 (m, 4H). HRMS calculated for C$_{52}$H$_{76}$ClN$_{18}$O$_6$ [M+H]$^+$, 1083.5878. found 1083.5884.

Preparation of the Hydrochloride Salt of (2S,2'S,2"S, 2'''S)—N,N,N",N'''-(3,3',", 3'''-(3,3'-(2-(4-(4-(3-(3,5-diamino-6-chloropyrazine-2-carbonyl)guanidino) butyl)phenoxy)ethylazanediyl)bis(propane-3,1-diyl)) bis(azanetriyl)tetrakis(propane-3,1-diyl))tetrakis(2-amino-6-guanidinohexanamide)—Compound 82
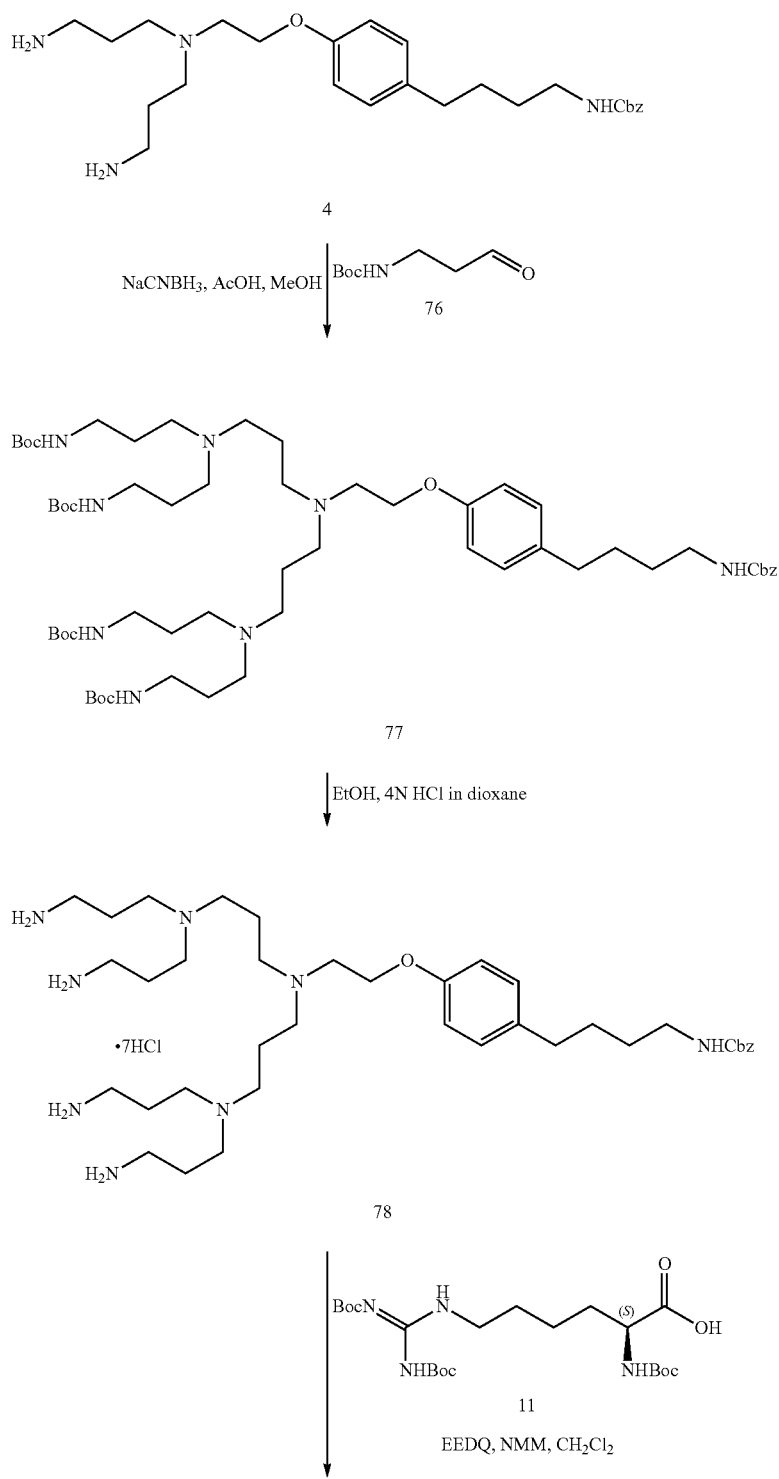
Scheme 12

-continued
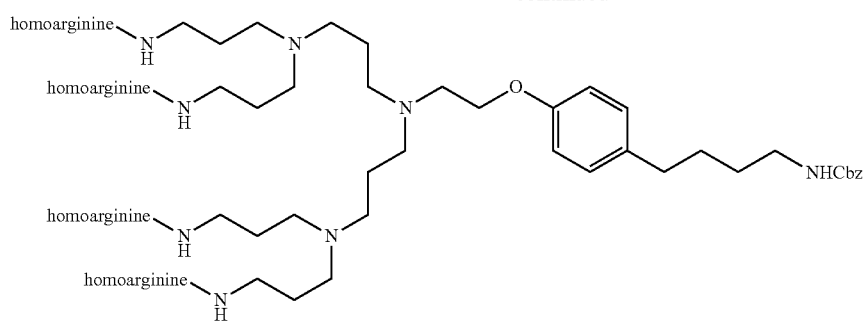
79
Pd/C, H₂
EtOH, AcOH
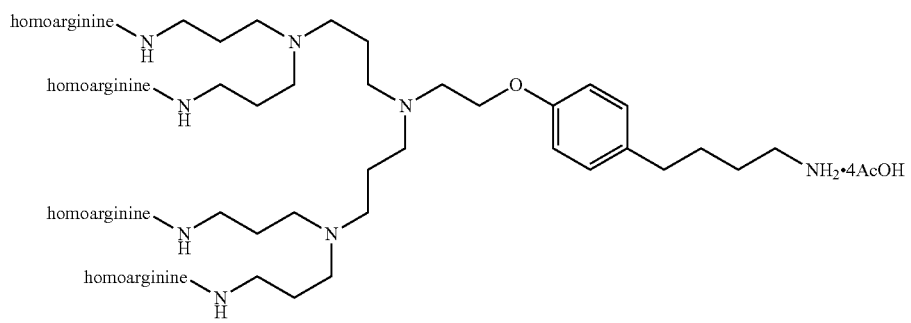
80
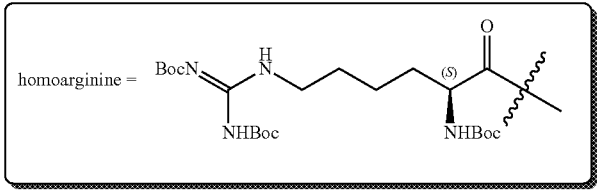
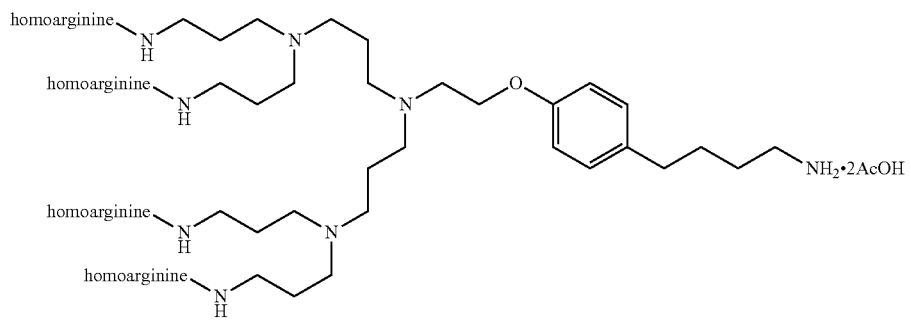
80
DIPEA, t-BuOH
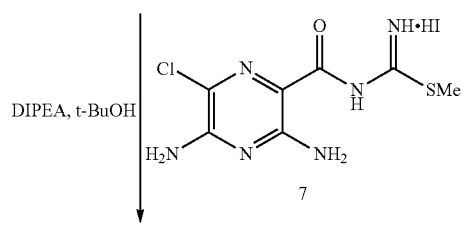
7

Preparation of Compound 77

A solution of compound 4 (100 mg, 0.219 mmol) in MeOH (4.0 mL) was charged with compound 76 (227 mg, 1.37 mmol), NaCNBH$_3$ (128 mg, 1.76 mmol), and AcOH (132 mg, 2.20 mmol). The reaction mixture was stirred at room temperature for 16 h. Additional compound 76 (151 mg, 0.876 mmol), NaCNBH$_3$ (79.8 mg, 1.10 mmol), and AcOH (79 mg, 1.31 mmol) were added, and the resulting mixture was stirred at room temperature for 24 h. The solvent was removed and the residue was purified by column chromatography (silica gel, 20:1 CH$_2$Cl$_2$/MeOH) to afford compound 77 (63 mg, 27%) as a colorless oil: $^1$H NMR (300 MHz, CD$_3$OD) δ 7.32-7.31 (m, 5H), 7.12 (d, J=8.4 Hz, 2H), 6.86 (d, J=8.4 Hz, 2H), 5.05 (s, 2H), 4.10 (d, J=4.5 Hz, 2H), 3.34-3.11 (m, 22H), 2.95 (br s, 2H), 2.78-2.75 (m, 4H), 2.57 (d, J=7.8 Hz, 2H), 1.98-1.83 (m, 10H), 1.60-1.49 (m, 6H), 1.43 (s, 36H).

Preparation of Compound 78

A solution of compound 77 (502 mg, 0.463 mmol) in EtOH (5.0 mL) was charged with 4 N aqueous HCl (5.0 mL) at room temperature and the reaction mixture was stirred for 4 h at room temperature. The reaction mixture was concentrated in vacuum and the residue was precipitated from MTBE to afford compound 78 (374 mg, 86%) as a colorless oil: $^1$H NMR (400 MHz, CD$_3$OD) δ 7.34-7.29 (m, 5H), 7.13 (d, J=7.6 Hz, 2H), 7.00 (d, J=7.6 Hz, 2H), 5.06 (s, 2H), 4.45 (br s, 2H), 3.81-3.48 (m, 20H), 3.13-3.10 (m, 10H), 2.59-2.43 (m, 5H), 2.26 (br s, 7H), 1.64-1.44 (m, 4H).

Preparation of Compound 79

A solution of amino acid 11 (104 mg, 0.213 mmol) in CH$_2$Cl$_2$ (5.0 mL) was charged with EEDQ (127 mg, 0.426 mmol), compound 78 (50.0 mg, 0.0530 mmol), and NMM (108 mg, 1.06 mmol). The reaction mixture was stirred at room temperature for 4 days. The solvent was removed and the residue was purified by column chromatography (silica gel, 10:1 CH$_2$Cl$_2$/MeOH, 5:1:0.1 CHCl$_3$/MeOH/NH$_4$OH) to afford compound 79 (52 mg, 38%) as a colorless oil: $^1$H NMR (300 MHz, CD$_3$OD) δ 7.32-7.29 (m, 5H), 7.11 (d, J=7.8 Hz, 2H), 6.86 (d, J=7.8 Hz, 2H), 5.06 (s, 2H), 4.14-3.96 (m, 6H), 3.30-2.80 (m, 22H), 2.67-2.45 (m, 16H), 1.90-1.20 (m, 148H).

Preparation of Compound 80

A suspension of compound 79 (320 mg, 0.124 mmol) and 10% Pd/C (160 mg) in EtOH (10 mL) and AcOH (1.0 mL)

was subjected to hydrogenation conditions (1 atm) for 16 h at room temperature. The reaction mixture was filtered through celite and washed with EtOH. The filtrate was concentrated and precipitated from MTBE/hexanes to afford compound 80 (285 mg, 87%) as a colorless oil: $^1$H NMR (300 MHz, CD$_3$OD) δ 7.14 (d, J=8.4 Hz, 2H), 6.89 (d, J=8.4 Hz, 2H), 4.11-3.79 (m, 6H), 3.35-2.66 (m, 38H), 1.90-1.20 (m, 148H).

Preparation of Compound 81

A solution of amine 80 (280 mg, 0.104 mmol) and methyl 3,5-diamino-6-chloropyrazine-2-carbonylcarbamimidothioate hydroiodic acid salt (7, 49.0 mg, 0.125 mmol) in t-BuOH (10 mL) was charged with DIPEA (103 mg, 0.795 mmol) at room temperature. The reaction mixture was heated at 70° C. for 2 h, cooled to room temperature, and concentrated in vacuum. The residue was purified by column chromatography (silica gel, 10:1 CH$_2$Cl$_2$/MeOH, 5:1:0.1 CHCl$_3$/MeOH/ NH$_4$OH) to afford compound 81 (112 mg, 40%) as a yellow solid: $^1$H NMR (300 MHz, CD$_3$OD) δ 7.11 (d, J=8.4 Hz, 2H), 6.83 (d, J=8.4 Hz, 2H), 4.03 (br s, 6H), 3.30-3.07 (m, 20H), 2.88 (br s, 2H), 2.60-2.48 (m, 16H), 1.65-1.23 (m, 148H).

Preparation of the Hydrochloride Salt of (2S,2'S,2"S, 2'''S)—N,N',N'',N'''-(3,3',", 3'''-(3,3'-(2-(4-(4-(3-(3,5-diamino-6-chloropyrazine-2-carbonyl)guanidino) butyl)phenoxy)ethylazanediyl)bis(propane-3,1-diyl)) bis(azanetriyl)tetrakis(propane-3,1-diyl))tetrakis(2-amino-6-guanidinohexanamide)—Compound 82

A solution of compound 81 (15.0 mg, 0.00567 mmol) in EtOH (2.0 mL) was charged with 4 N aqueous HCl (2.0 mL) at room temperature and the reaction mixture was stirred for 4 h at room temperature. The reaction mixture was concentrated in vacuum, and the residue was purified by reverse-phase column chromatography and lyophilized to afford hydrochloric acid salt 82 (3.95 mg, 37%) as a yellow hygroscopic solid: $^1$H NMR (400 MHz, D$_2$O) δ 7.24 (d, J=8.4 Hz, 2H), 6.96 (d, J=8.4 Hz, 2H), 4.34 (br s, 2H), 3.93 (d, J=6.8 Hz, 2H), 3.64 (br s, 2H), 3.38-3.11 (m, 34H), 2.60 (br s, 2H), 2.21-2.17 (m, 4H), 2.02-1.79 (m, 16H), 1.66-1.54 (m, 12H), 1.41-1.28 (m, 8H). HRMS calculated for C$_{64}$H$_{124}$ClN$_{30}$O$_6$ [M+H]$^+$, 1444.0003. found 1444.0054.

Preparation of the Hydrochloride Salt of 3,5-diamino-N—(N-(4-(4-(2-((3-((R)-2-amino-6-guanidinohexanamido)propyl)(3-((S)-2-amino-6-guanidinohexanamido)propyl)amino)ethoxy)phenyl)butyl) carbamimidoyl)-6-chloropyrazine-2-carboxamide—Compound 90

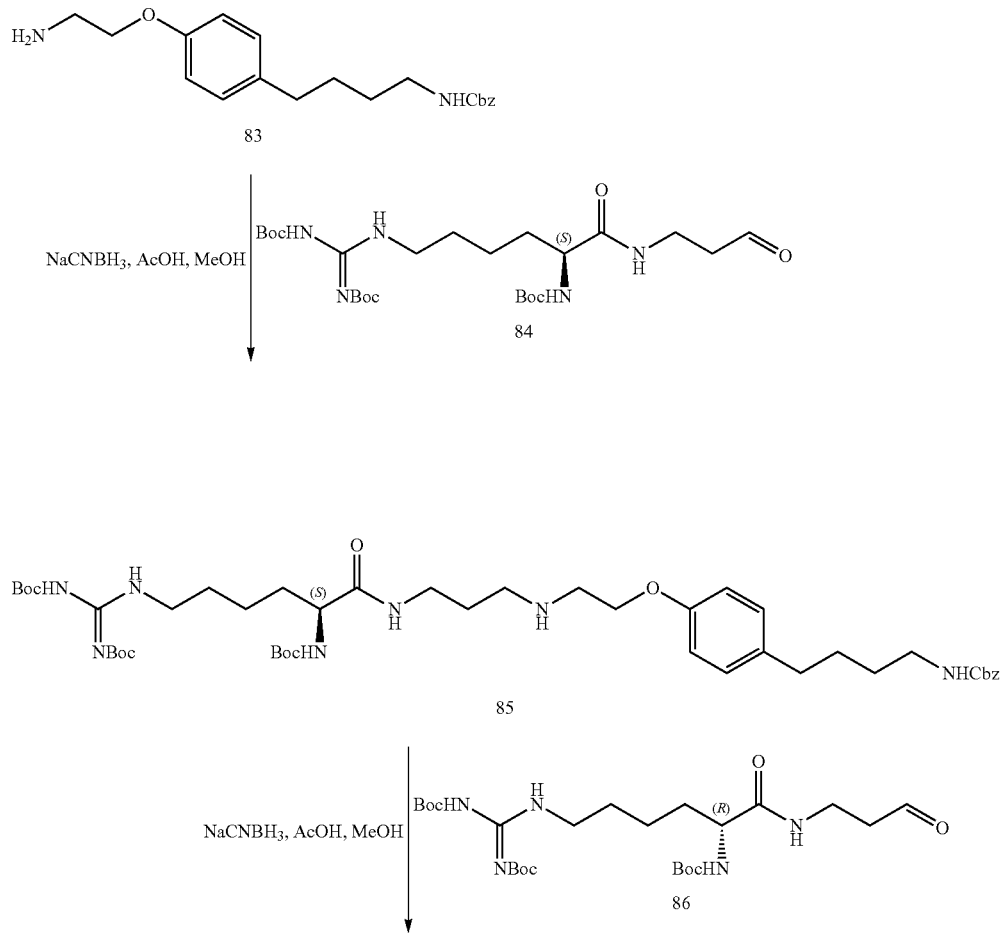

Scheme 13

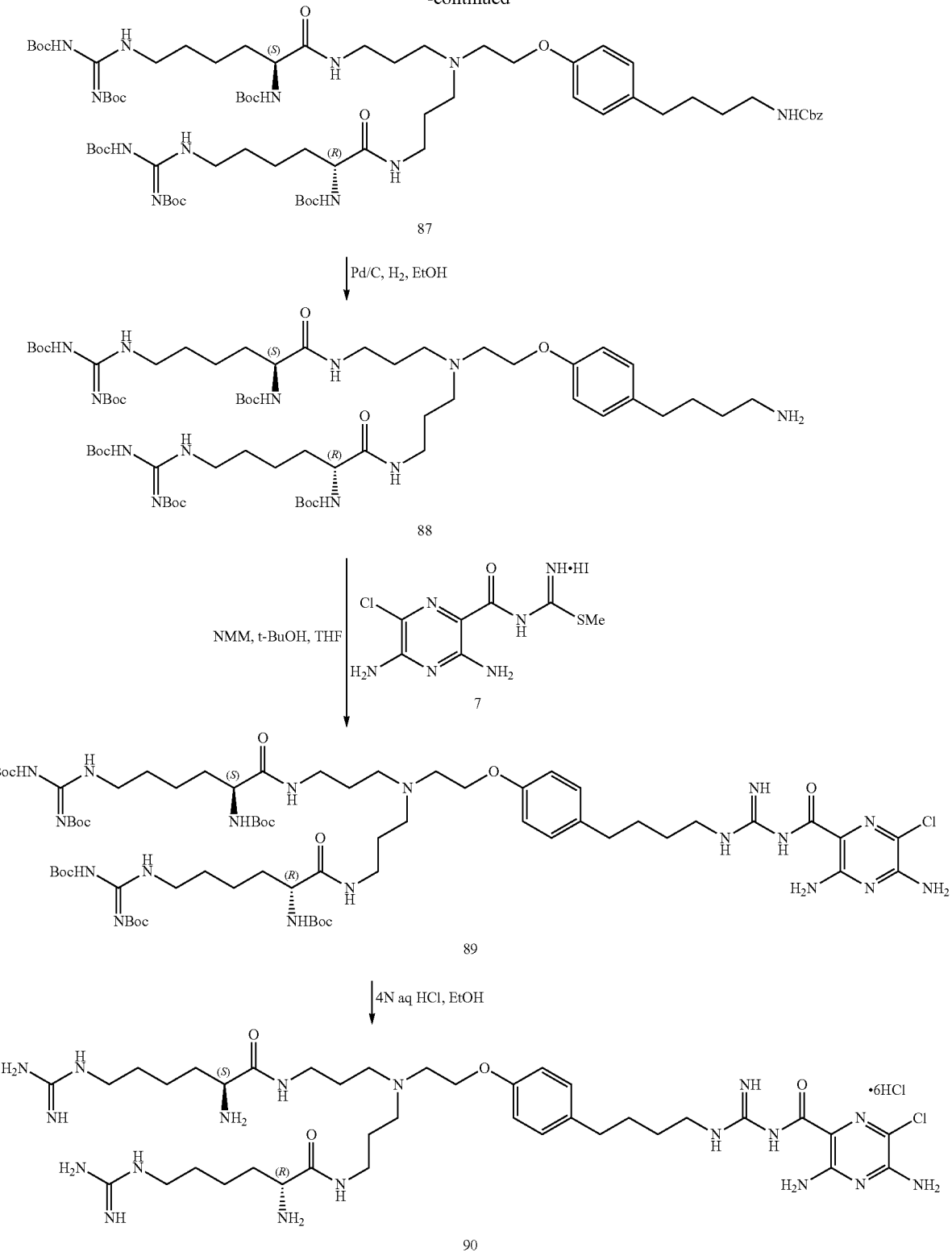

Preparation of Compound 85

A solution of amine 83 (1.19 g, 3.47 mmol) and compound 84 (1.90 g, 3.49 mmol) in MeOH (60 mL) was charged with NaCNBH₃ (510 mg, 7.00 mmol) and AcOH (630 mg, 10.5 mmol). The reaction mixture was stirred at room temperature for 16 h. After the solvent was removed, the residue was washed with 1 N Na₂CO₃ (100 mL), dissolved in CH₂Cl₂ (200 mL), and washed with water (100 mL) and brine (100 mL) The organic layer was evaporated to dryness and the residue was purified by column chromatography (silica gel, 20:1 CH$_2$Cl$_2$/MeOH) to afford compound 85 (1.58 g, 52%) as a colorless oil: $^1$H NMR (300 MHz, DMSO-d$_6$) δ 8.27 (br s, 1H), 7.83 (br s, 1H), 7.38-7.26 (m, 5H), 7.06 (d, J=8.4 Hz, 2H), 6.82 (d, J=8.4 Hz, 2H), 6.77 (br s, 1H), 5.76 (br s, 3H), 4.99 (s, 2H), 3.94 (br s, 2H), 3.83 (br s, 1H), 3.27-3.22 (m, 2H), 3.16-2.98 (m, 4H), 2.83 (br s, 2H), 1.55-1.48 (m, 5H), 1.46 (s, 1H), 1.38 (s, 10H), 1.36 (s, 10H).

Preparation of Compound 87

A solution of compound 85 (1.18 g, 1.36 mmol) and compound 86 (1.10 g, 2.03 mmol) in MeOH (20 mL) was charged with NaCNBH$_3$ (297 mg, 4.08 mmol) and AcOH (326 mg, 5.44 mmol). The reaction mixture was stirred at room temperature for 16 h. Additional compound 86 (1.10 g, 2.03 mmol), NaCNBH$_3$ (297 mg, 4.08 mmol), and AcOH (326 mg, 5.44 mmol) were added. The reaction mixture continued to stir at room temperature for 16 h. After the solvent was removed, the residue was washed with 1 N Na$_2$CO$_3$ (100 mL), dissolved in CH$_2$Cl$_2$ (200 mL), and washed with water (100 mL) and brine (100 mL). The organic layer was evaporated to dryness and the residue was purified by column chromatography (silica gel, 20:1 CH$_2$Cl$_2$/MeOH) to afford compound 87 (2.12 g, mixture) as a colorless oil, which was used directly in the next step.

Preparation of Compound 88

A suspension of compound 87 (2.12 g, mixture) and 10% Pd/C (1.00 g) in EtOH (30 mL) was subjected to hydrogenation conditions (1 atm) for 4 h at room temperature. The reaction mixture was filtered through celite and washed with EtOH. The filtrate was concentrated and purified by column chromatography (silica gel, 20:1 CH$_2$Cl$_2$/MeOH, 8:1:0.1 CHCl$_3$/MeOH/NH$_4$OH) to afford compound 88 (732 mg, 43% over 2 steps) as a colorless oil: $^1$H NMR (300 MHz, CD$_3$OD) δ 7.09 (d, J=8.4 Hz, 2H), 6.84 (d, J=8.4 Hz, 2H), 4.05-3.95 (m, 4H), 3.27-3.21 (m, 4H), 2.88-2.83 (m, 4H), 2.62-2.56 (m, 6H), 1.77-1.55 (m, 15H), 1.51 (s, 18H), 1.46 (s, 18H), 1.43 (s, 18H).

Preparation of Compound 89

A solution of amine 88 (710 mg, 0.562 mmol) and methyl 3,5-diamino-6-chloropyrazine-2-carbonylcarbamimidothioate hydroiodic acid salt (7, 261 mg, 0.675 mmol) in t-BuOH (15 mL) was charged with DIPEA (359 mg, 2.81 mmol) at room temperature. The reaction mixture was heated at 70° C. for 2 h, cooled to room temperature, and concentrated in vacuum. The residue was purified by column chromatography (silica gel, 10:1 CH$_2$Cl$_2$/MeOH, 10:1:0.1 CHCl$_3$/MeOH/NH$_4$OH) to afford compound 89 (350 mg, 43%) as a yellow solid: $^1$H NMR (300 MHz, CD$_3$OD) δ 7.10 (d, J=8.6 Hz, 2H), 6.84 (d, J=8.6 Hz, 2H), 4.08-3.98 (m, 4H), 3.76-3.67 (m, 1H), 2.86 (br s, 3H), 2.63-2.58 (m, 6H), 1.73-1.64 (m, 10H), 1.62-1.56 (m, 4H), 1.51 (s, 19H), 1.46 (s, 18H), 1.42 (s, 18H).

Preparation of the Hydrochloride Salt of 3,5-di-amino-N—(N-(4-(4-(2-((3-((R)-2-amino-6-guanidinohexanamido)propyl)(3-((S)-2-amino-6-guanidinohexanamido)propyl)amino)ethoxy)phenyl)butyl)carbamimidoyl)-6-chloropyrazine-2-carboxamide—Compound 90

A solution of compound 89 (230 mg, 0.156 mmol) in EtOH (1.0 mL) was charged with 4 N aqueous HCl (10 mL) at room temperature and the reaction mixture was stirred for 4 h at room temperature. The reaction mixture was concentrated in vacuum and the residue was purified by reverse-phase column chromatography and lyophilized to afford hydrochloric acid salt 90 (59 mg, 35%) as a yellow hygroscopic solid: $^1$H NMR (400 MHz, D$_2$O) δ 7.21 (d, J=8.4 Hz, 2H), 6.91 (d, J=8.4 Hz, 2H), 4.19 (br s, 2H), 3.77 (t, J=6.4 Hz, 2H), 3.46 (br s, 2H), 3.25-3.21 (m, 8H), 3.13 (br s, 4H), 3.02 (t, J=7.0 Hz, 4H), 2.53 (br s, 2H), 1.93-1.86 (m, 4H), 1.75-1.70 (m, 4H), 1.60 (br s, 4H), 1.49-1.42 (m, 4H), 1.30-1.22 (m, 4H). HRMS calculated for C$_{38}$H$_{68}$ClN$_{18}$O$_4$ [M+H]$^+$, 875.5354. found 875.5372. Elemental analysis: % calculated C, 41.71; H, 6.72; N, 23.04. found C, 38.03; H, 5.80; N, 20.40.

Preparation the Hydrochloride Salt of (S)-3,5-di-amino-N—(N-(4-(4-(2-(3-(2-amino-6-guanidinohexanamido)propylamino)ethoxy)phenyl)butyl)carbamimidoyl)-6-chloropyrazine-2-carboxamide—Compound 94

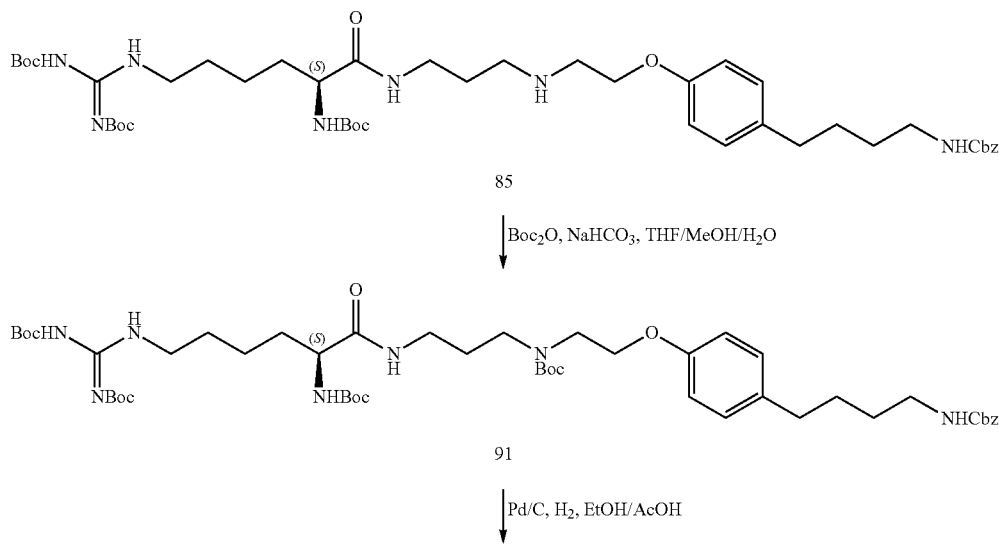

Scheme 14

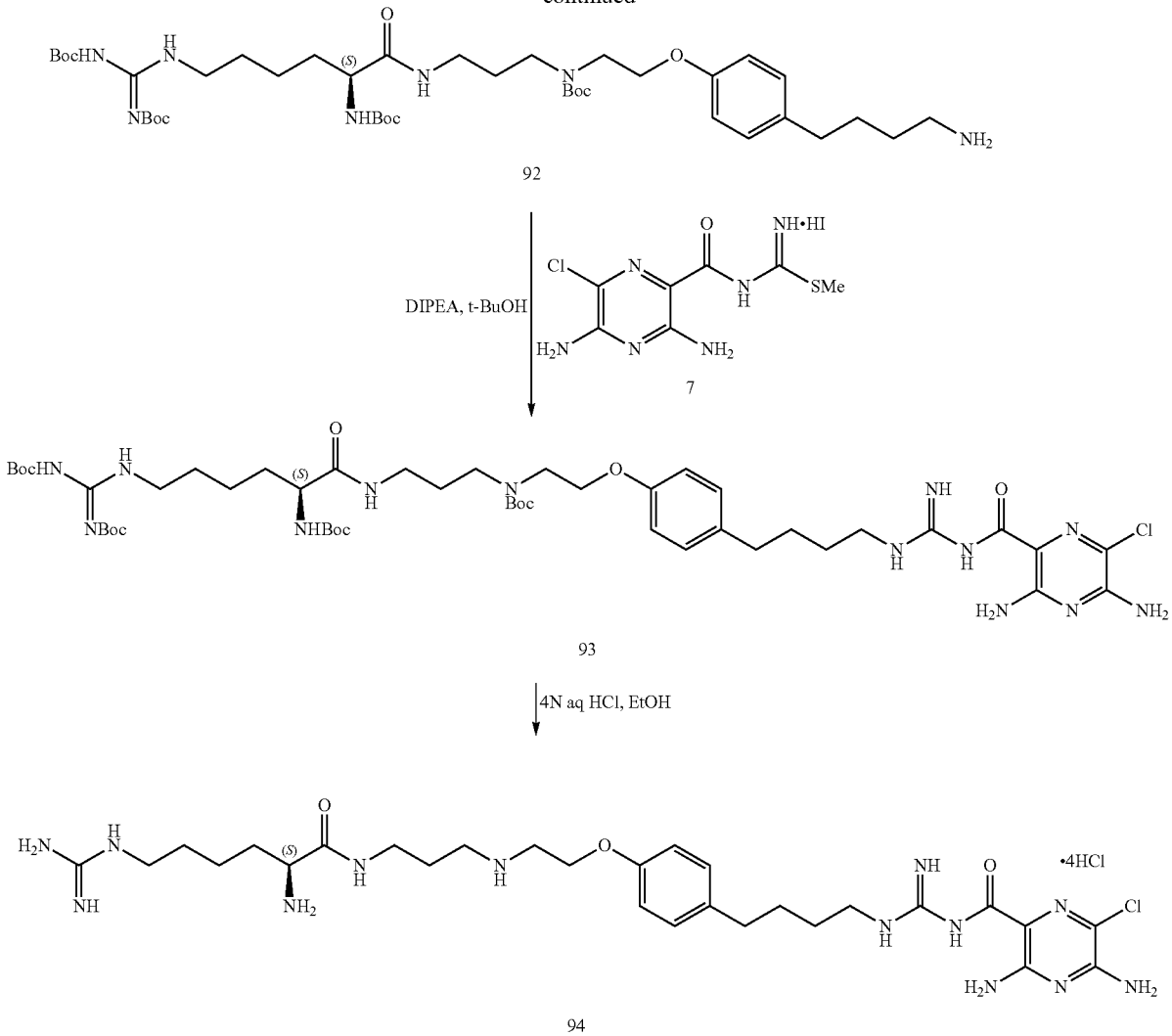

Preparation of Compound 91

A solution of compound 85 (400 mg, 0.460 mmol) in THF (6.0 mL), MeOH (6.0 mL), and water (2.0 mL) was charged with NaHCO$_3$ (116 mg, 1.38 mmol) and Boc$_2$O (120 mg, 0.550 mmol). The reaction mixture was stirred for 3 h at room temperature. After the solvent was removed, the residue was partitioned between CH$_2$Cl$_2$ (20 mL) and water (10 mL). The aqueous layer was separated and extracted with CH$_2$Cl$_2$ (20 mL). The combined organic extracts were dried over Na$_2$SO$_4$, concentrated, and purified by column chromatography (silica gel, 10:1 CH$_2$Cl$_2$/MeOH), to afford compound 91 (379 mg, 85%) as a white solid: $^1$H NMR (300 MHz, CD$_3$OD) δ 7.32-7.28 (m, 5H), 7.05 (d, J=8.6 Hz, 2H), 6.80 (d, J=8.6 Hz, 2H), 5.05 (s, 2H), 4.10-4.04 (m, 2H), 3.95 (br s, 1H), 3.57 (t, J=5.6 Hz, 2H), 3.23-3.09 (m, 4H), 2.54 (t, J=7.2 Hz, 2H), 1.77 (br s, 2H), 1.62-1.52 (m, 4H), 1.51 (s, 11H), 1.45-1.42 (m, 28H).

Preparation of Compound 92

A suspension of compound 91 (375 mg, 0.387 mmol) and 10% Pd/C (200 mg) in EtOH (15 mL) was subjected to hydrogenation conditions (1 atm) for 2 h at room temperature. The reaction mixture was filtered through celite and washed with EtOH. The filtrate was concentrated to afford compound 92 (297 mg, 92%) as a white solid: $^1$H NMR (300 MHz, CD$_3$OD) δ 7.09 (d, J=8.4 Hz, 2H), 6.82 (d, J=8.4 Hz, 2H), 4.05 (br s, 2H), 3.99-3.94 (m, 1H), 3.57 (t, J=5.2 Hz, 2H), 3.25-3.19 (m, 2H), 2.71 (t, J=6.8 Hz, 2H), 2.57 (t, J=7.2 Hz, 2H), 1.76 (br s, 3H), 1.65-1.54 (m, 5H), 1.51 (s, 10H), 1.47-1.45 (m, 18H), 1.42 (s, 10H).

Preparation of Compound 93

A solution of amine 92 (295 mg, 0.353 mmol) and methyl 3,5-diamino-6-chloropyrazine-2-carbonylcarbamimidothioate hydroiodic acid salt (7, 165 mg, 0.424 mmol) in t-BuOH (20 mL) was charged with DIPEA (227 mg, 1.76 mmol) at room temperature. The reaction mixture was heated at 70° C. for 2 h, cooled to room temperature, and concentrated in vacuum. The residue was purified by column chromatography (silica gel, 10:1 CH$_2$Cl$_2$/MeOH, 10:1:0.1 CHCl$_3$/MeOH/NH$_4$OH) to afford compound 93 (244 mg, 66%) as a yellow solid: $^1$H NMR (300 MHz, CD$_3$OD) δ 7.10 (d, J=8.4 Hz, 2H), 6.82 (d, J=8.4 Hz, 2H), 4.07-4.04 (m, 2H), 3.98-3.93 (m, 1H), 3.57 (t, J=5.6 Hz, 2H), 3.25-3.17 (m, 3H), 2.62 (br s, 2H), 1.77-1.56 (m, 8H), 1.51 (s, 9H), 1.46 (s, 18H), 1.42 (s, 10H).

Preparation the Hydrochloride Salt of (S)-3,5-diamino-N—(N-(4-(4-(2-(3-(2-amino-6-guanidinohexanamido)propylamino)ethoxy)phenyl)butyl)carbamimidoyl)-6-chloropyrazine-2-carboxamide—Compound 94

A solution of compound 73 (238 mg, 0.227 mmol) in EtOH (3.0 mL) was charged with 4 N aqueous HCl (10 mL) at room temperature and the reaction mixture was stirred for 4 h at room temperature. The reaction mixture was concentrated in vacuum, and the residue was purified by reverse-phase column chromatography and lyophilized to afford hydrochloric acid salt 74 (96 mg, 53%) as a yellow hygroscopic solid: $^1$H NMR (400 MHz, D$_2$O) δ 7.20 (d, J=8.6 Hz, 2H), 6.91 (d, J=8.6 Hz, 2H), 4.21 (br s, 2H), 3.82 (br s, 1H), 3.42 (t, J=4.8 Hz, 2H), 3.34-3.28 (m, 4H), 3.13-3.08 (m, 4H), 2.59 (br s, 2H), 1.92 (t, J=7.6 Hz, 2H), 1.78 (br s, 2H), 1.66 (br s, 4H), 1.56-1.50 (m, 2H), 1.37-1.31 (m, 2H). HRMS calculated for C$_{28}$H$_{47}$ClN$_{13}$O$_3$ [M+H]$^+$, 648.3608. found 648.3619. Elemental analysis: % calculated C, 42.35; H, 6.35; N, 22.32. found C, 37.84; H, 6.57; N, 20.29.

Preparation of the Hydrochloride Salt of (S,S,2S,2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-((S)-2-amino-6-((S)-2-amino-6-guanidinohexanamido)hexanamido)hexanamide)

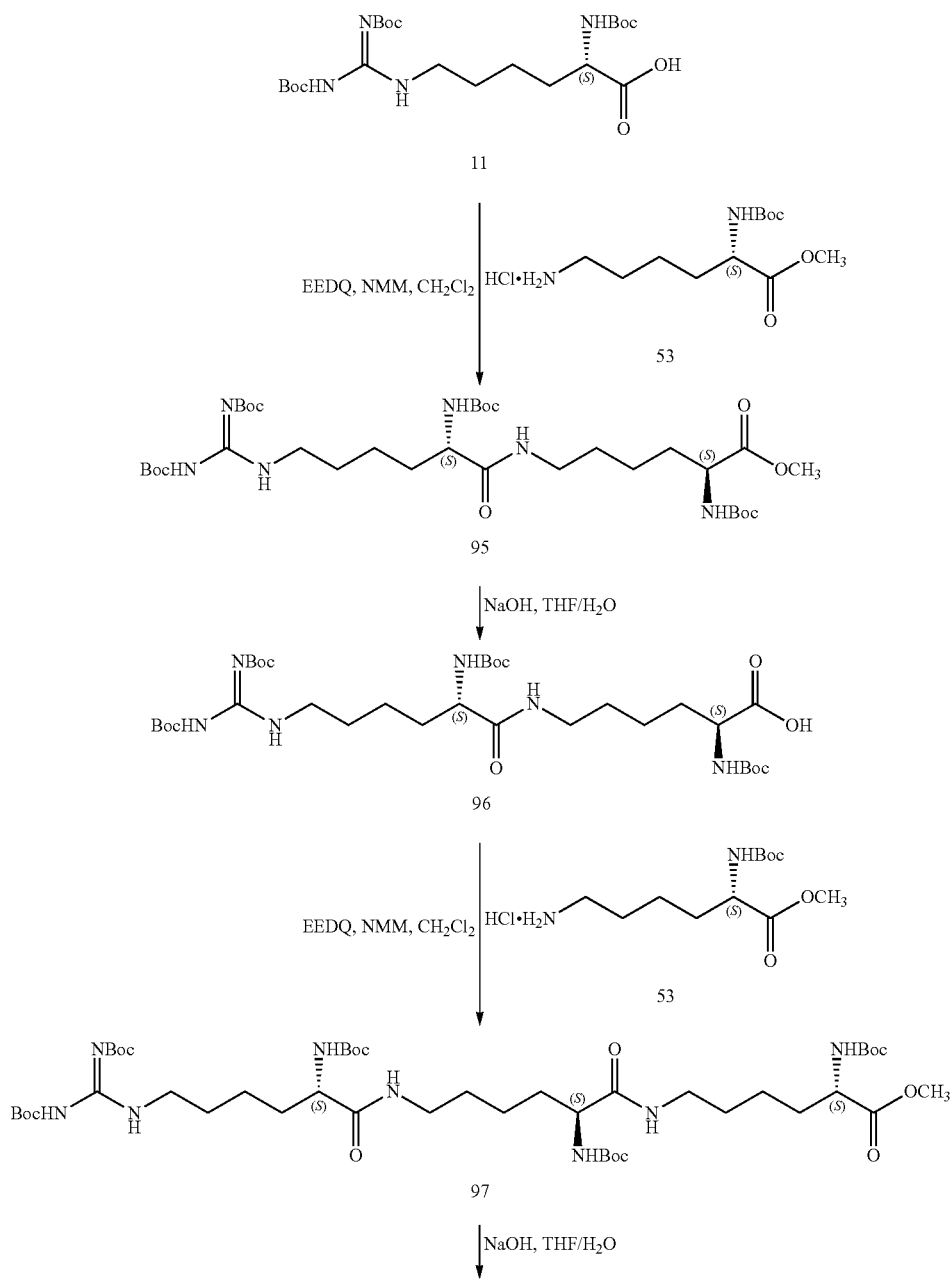

-continued
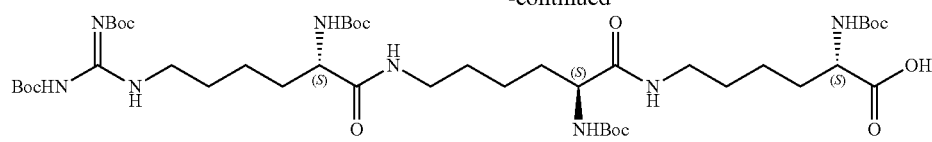
98
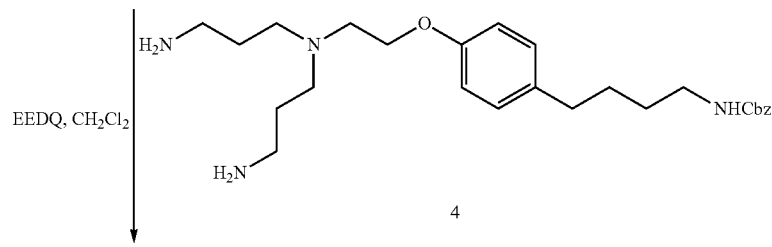
4
EEDQ, CH$_2$Cl$_2$
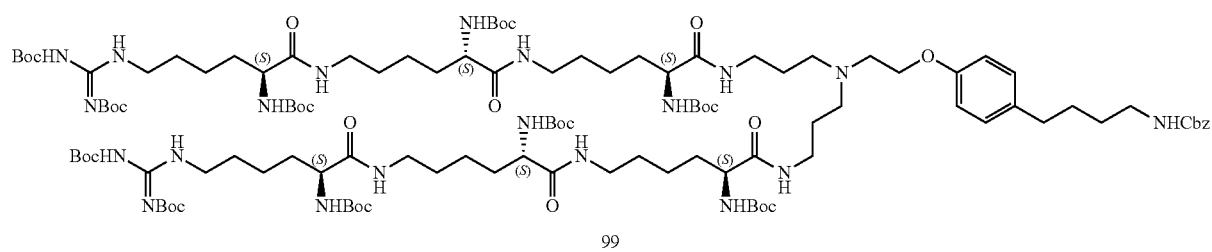
99
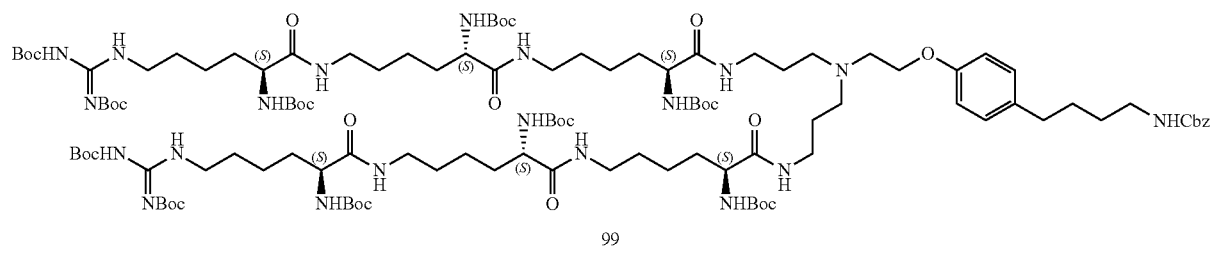
99
Pd/C, H$_2$, t-BuOH, THF
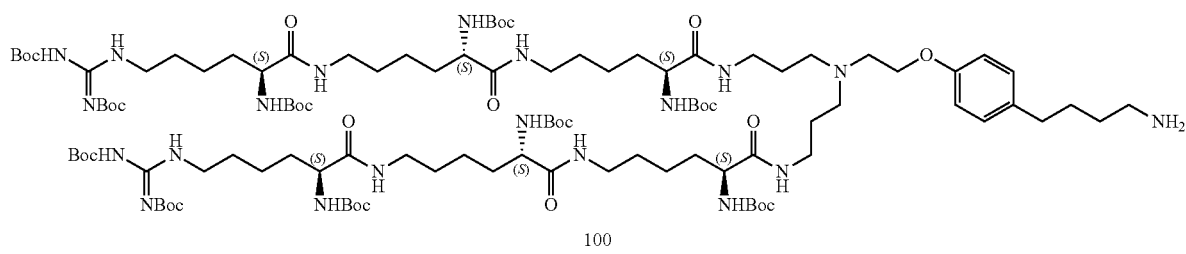
100
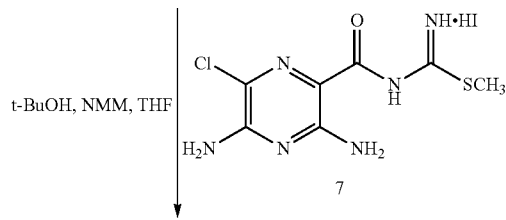
7
t-BuOH, NMM, THF

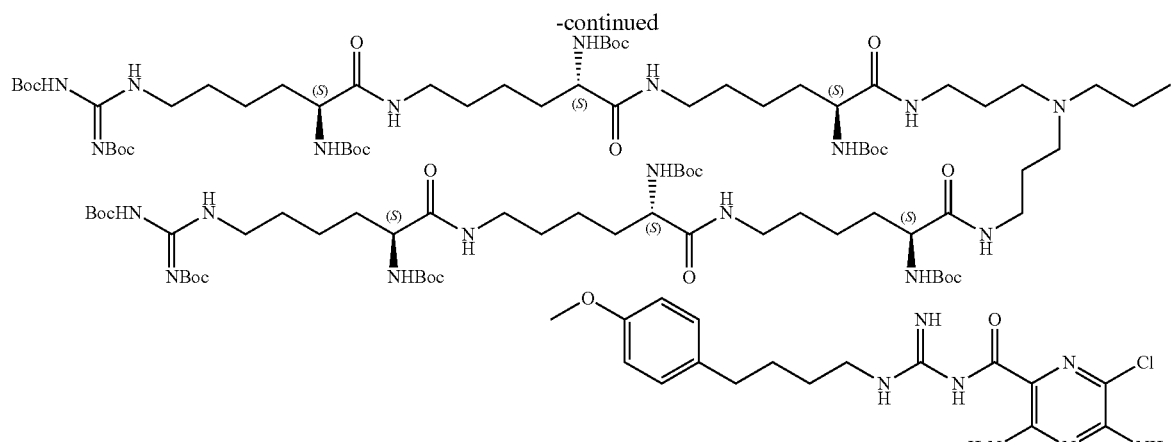

-continued

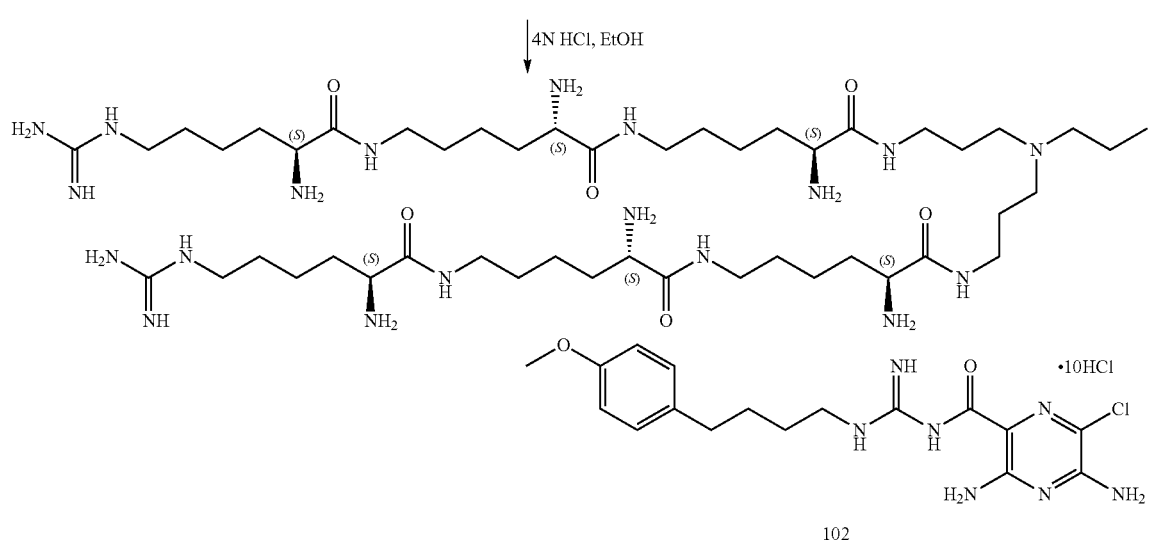

Preparation of Compound 95

A stirred solution of amino acid 11 (4.00 g, 8.19 mmol) in $CH_2Cl_2$ (100 mL) was charged with EEDQ (2.42 g, 9.83 mmol) and NMM (2.50 g, 24.5 mmol). The reaction mixture was stirred at room temperature for 10 min and amine 53 (2.12 g, 8.19 mmol) was added. The resulting mixture was stirred at room temperature for 16 h. The solvent was removed and the residue was purified by column chromatography (silica gel, 10:1 $CH_2Cl_2$/EtOAc, 10:1 $CH_2Cl_2$/MeOH) to afford amide 75 (3.80 g, 74%) as a white solid: $^1$H NMR (300 MHz, $CDCl_3$) δ 11.48 (s, 1H), 8.32 (t, J=5.2 Hz, 1H), 6.36 (br s, 1H), 5.23-5.14 (m, 2H), 4.28-4.19 (m, 1H), 4.06-3.97 (m, 1H), 3.73 (s, 3H). 3.42-3.15 (m, 4H), 1.90-1.69 (m, 6H), 1.67-1.55 (m, 4H), 1.49 (s, 18H), 1.47 (s, 9H), 1.43 (s, 9H), 1.41-1.36 (m, 4H).

Preparation of Compound 96

A solution of methyl ester 95 (3.80 g, 5.20 mmol) in THF/$H_2O$ (50 mL/10 mL) was charged with NaOH (416 mg, 10.41 mmol) and the reaction mixture was stirred at room temperature for 3 h. After completion of the reaction, the mixture was concentrated under reduced pressure and the pH was adjusted to 9 with 1 N NaOH. The aqueous solution was washed with EtOAc (2×150 mL) and the pH was adjusted to 5. The suspension was partitioned between $CH_2Cl_2$ (200 mL) and water (200 mL). The aqueous layer was separated and extracted with $CH_2Cl_2$ (2×200 mL) The combined organic extracts were dried over $Na_2SO_4$ and concentrated to afford compound 96 (crude, 3.30 g, 89%) as a white solid, which was used directly in the next step.

Preparation of Compound 97

A stirred solution of amino acid 96 (crude, 3.30 g, 4.60 mmol) in $CH_2Cl_2$ (100 mL) was charged with EEDQ (1.36 g, 5.53 mmol) and NMM (1.40 g, 13.8 mmol). The reaction mixture was stirred at room temperature for 10 min and amine 53 (1.20 g, 4.60 mmol) was added. The resulting mixture was stirred at room temperature for 16 h. The solvent was removed and the residue was purified by column chromatography (silica gel, 10:1 $CH_2Cl_2$/EtOAc, 10:1 $CH_2Cl_2$/MeOH) to afford compound 77 (3.51 g, 80%) as a white solid: $^1$H NMR (300 MHz, $CDCl_3$) δ 11.47 (s, 1H), 8.30 (t, J=4.8 Hz, 1H), 6.40 (br s, 2H), 5.41-5.32 (m, 1H), 5.25-5.12 (m, 2H), 4.23 (br s, 1H), 4.11-3.96 (m, 3H), 3.42-3.36 (m, 2H), 3.25-3.15 (m, 4H), 1.87-1.74 (m, 4H), 1.54-1.46 (m, 23H), 1.46-1.40 (m, 30H), 1.39-1.31 (m, 6H).

Preparation of Compound 98

A solution of methyl ester 97 (3.51 g, 3.66 mmol) in THF/H$_2$O (50 mL/10 mL) was charged with NaOH (293 mg, 7.32 mmol) and the reaction mixture was stirred at room temperature for 3 h. After completion of the reaction, the mixture was concentrated under reduced pressure and the pH was adjusted to 9 with 1 N NaOH. The aqueous solution was washed with EtOAc (2×150 mL) and the pH was adjusted to 5. The suspension was partitioned between CH$_2$Cl$_2$ (200 mL) and water (200 mL). The aqueous layer was separated and extracted with CH$_2$Cl$_2$ (2×200 mL). The combined organic extracts were dried over Na$_2$SO$_4$ and concentrated to afford compound 98 (3.00 g, 88%) as a white solid: $^1$H NMR (400 MHz, CDCl$_3$) δ 8.34 (br s, 1H), 6.93 (br s, 1H), 6.61 (br s, 1H), 5.51-5.40 (m, 3H), 4.28 (br s, 1H), 4.14-4.04 (m, 3H), 3.76-3.16 (m, 6H), 1.87-1.75 (m, 7H), 1.65-1.51 (m, 5H), 1.49 (s, 9H), 1.48 (s, 9H), 1.44 (s, 9H), 1.42 (s, 18H), 1.39-1.26 (m, 6H).

Preparation of Compound 99

A stirred solution of compound 4 (free base, 500 mg, 1.09 mmol) in CH$_2$Cl$_2$ (50 mL) was charged with EEDQ (1.21 g, 4.93 mmol) and amino acid 98 (2.57 g, 2.72 mmol). The resulting mixture was stirred at room temperature for 16 h. Additional amino acid 98 (515 mg, 0.545 mmol) and EEDQ (270 mg, 1.09 mmol) were added. The resulting mixture was stirred at room temperature for 6 h. The solvent was removed and the residue was purified by column chromatography (silica gel, 10:1 CH$_2$Cl$_2$/EtOAc, 10:1 CH$_2$Cl$_2$/MeOH) to afford amide 99 (1.42 g, 70%) as a white solid: $^1$H NMR (400 MHz, CD$_3$OD) δ 7.33-7.27 (m, 4H), 7.06 (d, J=8.2 Hz, 2H), 6.82 (d, J=8.2 Hz, 2H), 5.05 (s, 2H), 4.05-3.96 (m, 10H), 3.68 (t, J=4.2 Hz, 1H), 3.34 (t, J=7.0 Hz, 4H), 3.24-3.10 (m, 16H), 2.88-2.83 (m, 2H), 2.61-2.52 (m, 6H), 2.43 (br s, 1H), 1.74-1.66 (m, 12H), 1.63-1.54 (m, 14H), 1.51 (s, 25H), 1.46 (s, 25H), 1.44 (s, 20H), 1.43 (s, 20H), 1.42 (s, 20H).

Preparation of Compound 100

A stirred solution of compound 99 (300 mg 0.129 mmol) in t-BuOH (10 mL) and THF (2.0 mL) was charged with 10% Pd/C (150 mg) and the mixture was subjected to hydrogenation conditions (1 atm) for 16 h at room temperature. After completion of the reaction, the mixture was filtered through celite and washed with THF. The filtrate was concentrated under reduced pressure to afford compound 100 (260 mg, 92%) as a brown solid: $^1$H NMR (400 MHz, CD$_3$OD): δ 7.09 (d, J=8.8 Hz, 2H), 6.84 (d, J=8.8 Hz, 2H), 4.03-3.96 (m, 8H), 3.35-3.12 (m, 14H), 2.90-2.83 (m, 4H), 2.60-2.57 (m, 6H), 1.70-1.31 (m, 154H).

Preparation of Compound 101

A stirred solution of compound 100 (1.43 g, 0.650 mmol) was charged with methyl (3,5-diamino-6-chloropyrazine-2-carbonyl)carbamimidothioate hydroiodide 7 (253 mg, 0.650 mmol) and NMM (332 mg, 3.28 mmol) in t-BuOH (60 mL) and THF (12 mL) The reaction mixture was stirred for 4 h at 60° C. and at 70° C. for 1 h. After completion of the reaction, the mixture was concentrated under reduced pressure and purified by column chromatography (silica gel, 10:1 CH$_2$Cl$_2$/MeOH, 5:1:0.1 CHCl$_3$/MeOH/NH$_4$OH) to afford compound 101 (1.24 g, 79%) as a yellow solid: $^1$H NMR (300 MHz, CD$_3$OD): δ 7.14 (d, J=7.8 Hz, 2H), 6.90 (d, J=7.8 Hz, 2H), 4.20 (br s, 2H), 3.98-3.89 (m, 6H), 3.79-3.74 (m, 2H), 3.34-3.07 (m, 12H), 2.84-2.77 (m, 4H), 2.66-2.56 (m, 6H), 1.70-1.31 (m, 154H).

Preparation of the Hydrochloride Salt of (S,S,2S, 2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-((S)-2-amino-6-((S)-2-amino-6-guanidinohexanamido)hexanamido)hexanamide)—Compound 102

A solution of compound 81 (1.40 g, 0.50 mmol) in EtOH (30 mL) was charged with 4 N aqueous HCl (100 mL) and the reaction mixture was stirred for 4 h at room temperature. The reaction mixture was concentrated and fresh 4 N aqueous HCl was added. After stirring for 4 h at room temperature, the reaction mixture was concentrated in vacuum and the residue was purified by reverse-phase column chromatography and lyophilized to afford hydrochloric acid salt 82 (450 mg, 62%) as a yellow hygroscopic solid: $^1$H NMR (400 MHz, D$_2$O) δ 7.22 (d, J=8.8 Hz, 2H), 6.92 (d, J=8.8 Hz, 2H), 4.29 (br s, 2H), 3.91-3.88 (m, 6H), 3.60 (br s, 2H), 3.39-3.11 (m, 23H), 2.60 (br s, 2H), 2.01-1.97 (m, 4H), 1.86-1.78 (m, 13H), 1.67-1.46 (m, 17H), 1.40-1.32 (m, 12H).

Preparation of the Hydrochloride Salt of (S,2S, 2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-((S)-2-amino-6-guanidinohexanamido)hexanamide)—Compound 106

Scheme 16

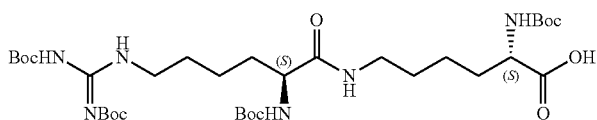

96

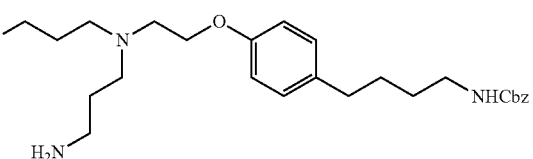

4

EEDQ, CH$_2$Cl$_2$

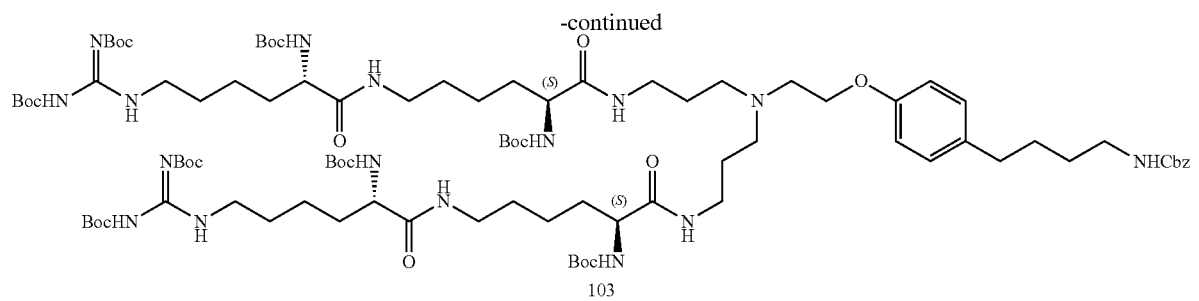
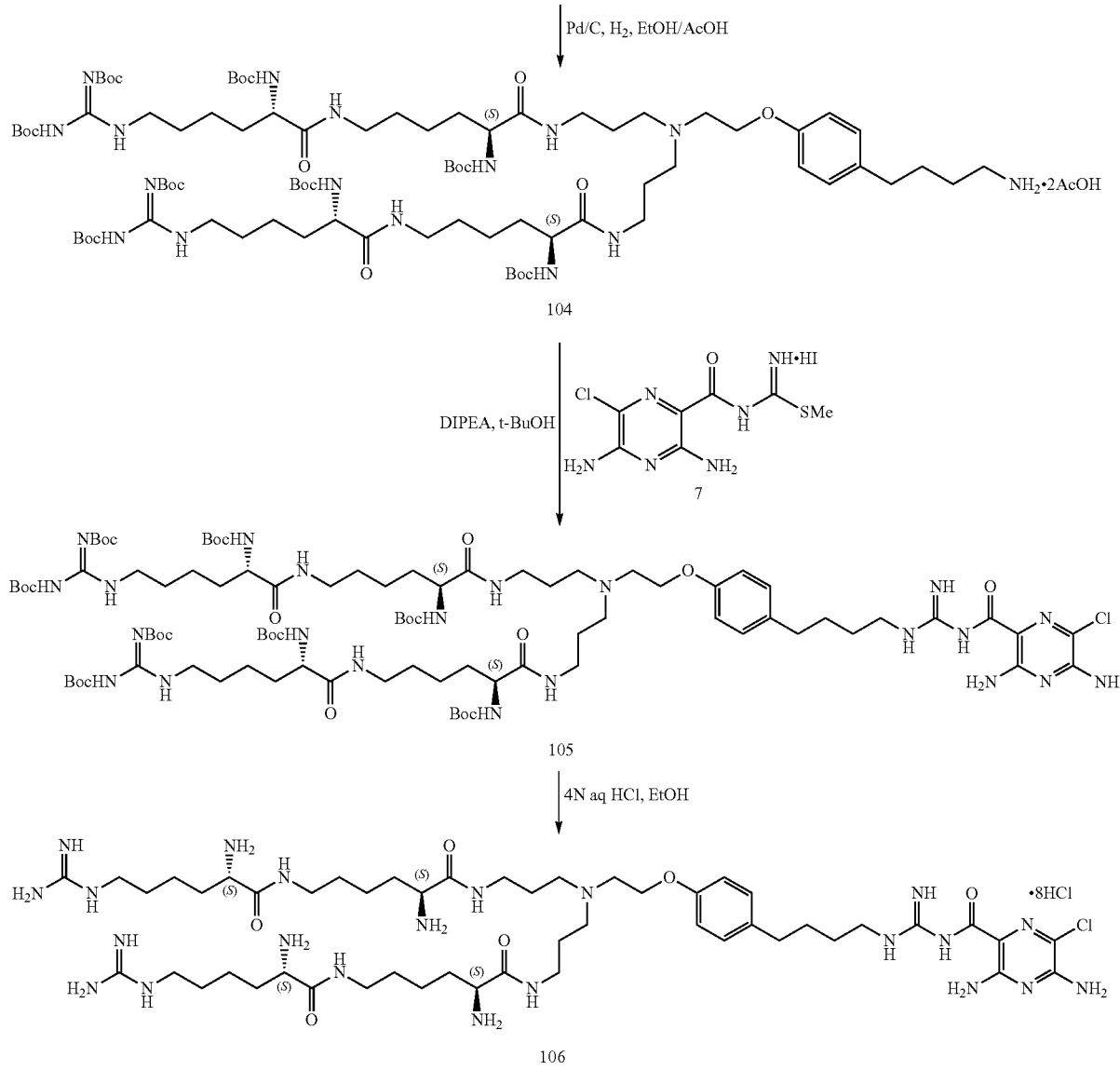

Preparation of Compound 103

A solution of amino acid 96 (100 mg, 0.139 mmol) in CH$_2$Cl$_2$ (5.0 mL) was charged with EEDQ (84 mg, 0.280 mmol) and compound 4 (free base, 32.0 mg, 0.0701 mmol). The reaction mixture was stirred at room temperature for 16 h. The solvent was removed and the residue was purified by column chromatography (silica gel, 10:1 CH$_2$Cl$_2$/MeOH) to afford compound 103 (78.0 mg, 61%) as a white solid: $^1$H NMR (300 MHz, CD$_3$OD) δ 7.33-7.28 (m, 5H), 7.07 (d, J=8.4 Hz, 2H), 6.84 (d, J=8.4 Hz, 2H), 5.05 (s, 2H), 4.08-3.95 (m, 6H), 3.29-3.21 (m, 4H), 3.19-3.06 (m, 7H), 2.95 (br s, 2H), 2.68 (br s, 3H), 2.54 (t, J=6.8 Hz, 2H), 1.77-1.55 (m, 17H), 1.51 (s, 21H), 1.46 (s, 18H), 1.43 (s, 18H), 1.42 (s, 18H).

Preparation of Compound 104

A suspension of compound 103 (736 mg, 0.397 mmol) and 10% Pd/C (380 mg) in EtOH (15 mL) was subjected to hydrogenation conditions (1 atm) for 6 h at room temperature.

The reaction mixture was filtered through celite and washed with EtOH. The filtrate was concentrated and precipitated from MTBE/hexanes to afford compound 104 (627 mg, 92%) as a white solid: $^1$H NMR (300 MHz, CD$_3$OD) δ 7.09 (d, J=8.6 Hz, 2H), 6.84 (d, J=8.6 Hz, 2H), 4.05-3.93 (m, 6H), 3.27-3.06 (m, 6H), 2.85 (t, J=7.6 Hz, 4H), 2.58 (br s, 6H), 1.73-1.54 (m, 20H), 1.51 (s, 21H), 1.46 (s, 19H), 1.43 (s, 22H), 1.42 (s, 18H).

Preparation of Compound 105

A solution of amine 104 (624 mg, 0.363 mmol) and methyl 3,5-diamino-6-chloropyrazine-2-carbonylcarbamimidothioate hydroiodic acid salt (7, 169 mg, 0.436 mmol) in t-BuOH (15 mL) was charged with DIPEA (235 mg, 1.81 mmol) at room temperature. The reaction mixture was heated at 70° C. for 2 h, cooled to room temperature, and concentrated in vacuum. The residue was purified by column chromatography (silica gel, 20:1 CH$_2$Cl$_2$/MeOH) to afford compound 105 (350 mg, 50%) as a yellow solid: $^1$H NMR (300 MHz, CD$_3$OD) δ 7.10 (d, J=8.6 Hz, 2H), 6.84 (d, J=8.6 Hz, 2H), 4.02-3.95 (m, 6H), 3.23-3.06 (m, 5H), 2.84 (br s, 2H), 2.58 (br s, 6H), 1.71-1.54 (m, 20H), 1.51 (s, 21H), 1.46 (s, 20H), 1.43 (s, 22H), 1.42 (s, 18H).

Preparation of the Hydrochloride Salt of (S,2S, 2'S)—N,N'-(3,3'-(2-(4-(4-(3-(3,5-diamino-6-chloropyrazine-2-carbonyl)guanidino)butyl)phenoxy)ethylazanediyl)bis(propane-3,1-diyl))bis(2-amino-6-((S)-2-amino-6-guanidinohexanamido)hexanamide)—Compound 106

A solution of compound 105 (347 mg, 0.179 mmol) in CH$_2$Cl$_2$ (10 mL) was charged with TFA (5.0 mL) at room temperature and the reaction mixture was stirred for 2 h at room temperature. The reaction mixture was concentrated in vacuum and twice azeotroped with 1 N aqueous HCl. The residue was purified by reverse-phase column chromatography and lyophilized to afford hydrochloric acid salt 106 (155 mg, 61%) as a yellow hygroscopic solid: $^1$H NMR (400 MHz, D$_2$O) δ 7.22 (d, J=8.4 Hz, 2H), 6.91 (d, J=8.4 Hz, 2H), 4.28 (br s, 2H), 3.90-3.86 (m, 4H), 3.60 (br s, 2H), 3.35-3.11 (m, 18H), 2.60 (br s, 2H), 2.00-1.95 (m, 4H), 1.84-1.79 (m, 8H), 1.67 (br s, 4H), 1.57-1.47 (m, 8H), 1.37-1.32 (m, 8H). HRMS calculated for C$_{50}$H$_{92}$ClN$_{22}$O$_6$ [M+H]$^+$, 1131.7253. found 1131.7297.

Preparation of the Hydrochloride Salt of (2R,2'R)—N,N'-(3,3'-(2-(6-(4-(3-(3,5-diamino-6-chloropyrazine-2-carbonyl)guanidino)butyl)naphthalen-2-yloxy)ethylazanediyl)bis(propane-3,1-diyl))bis(2-amino-6-guanidinohexanamide)—Compound 116

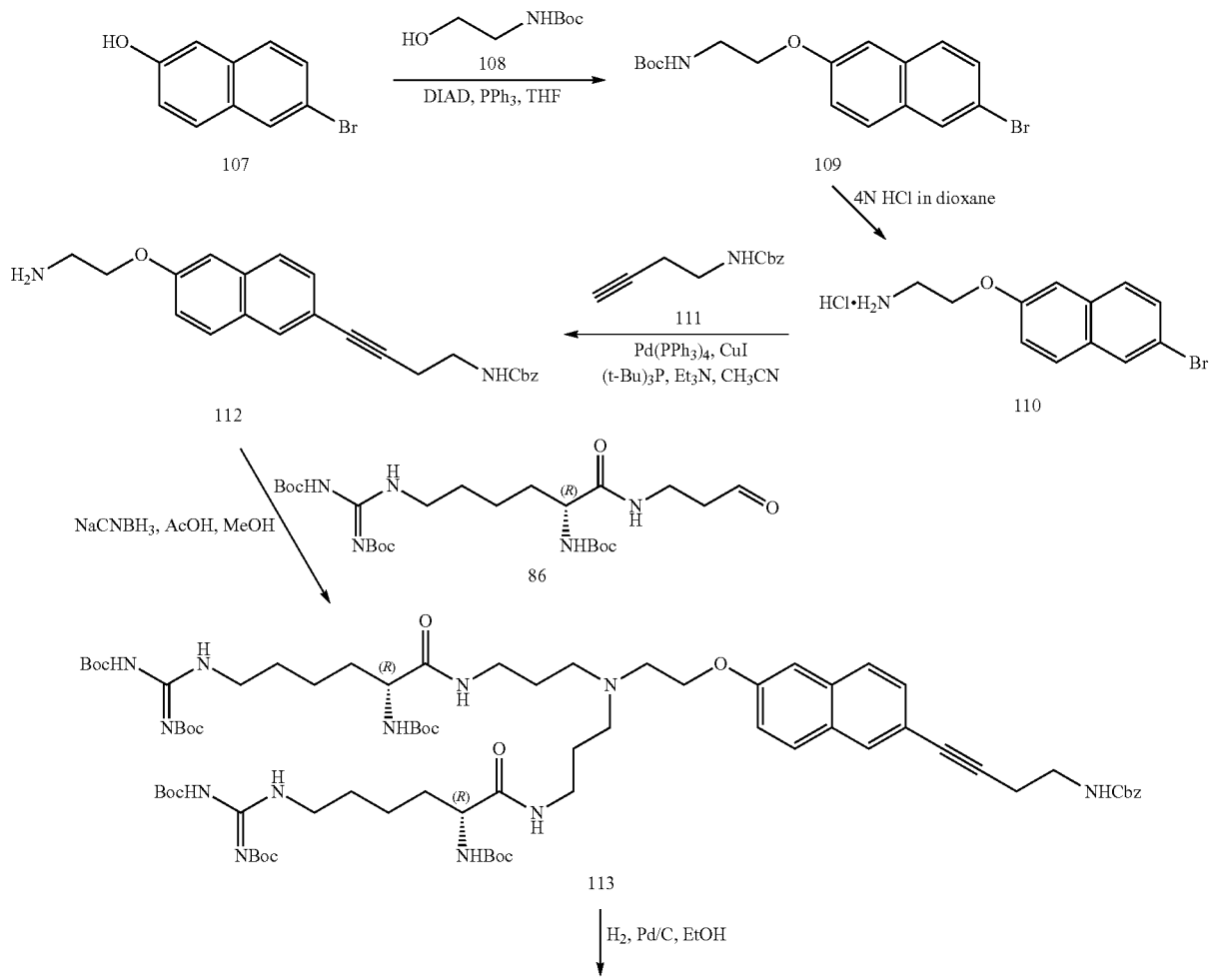

Scheme 17

-continued

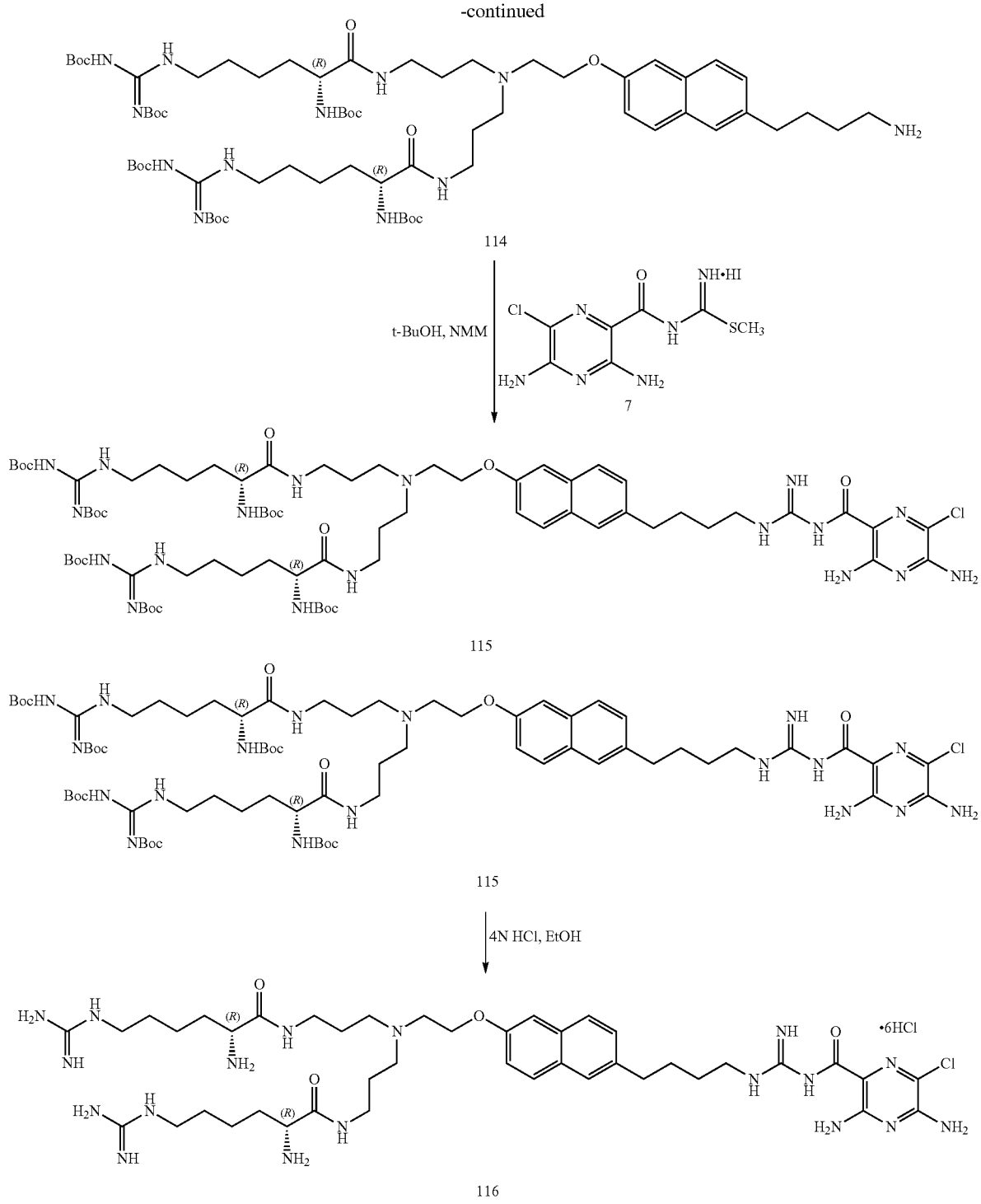

Preparation of Compound 109

A stirred solution of compound 107 (5.00 g, 22.5 mmol) in dry $CH_2Cl_2$ (100 mL) was charged with compound 108 (4.30 g, 27.1 mmol), $Ph_3P$ (7.10 g, 27.1 mmol), and DIAD (5.40 g, 27.1 mmol) at 0° C. The reaction mixture was warmed to room temperature and stirred for 4 h. After completion of the reaction, the mixture was diluted with $CH_2Cl_2$ and washed with 1 N $NaHCO_3$, water, and brine. The organic layer was concentrated under reduced pressure and purified by column chromatography (silica gel, 80:20 hexanes/EtOAc) to afford compound 109 (5.50 g, 67%) as an off-white solid: ESI-MS m/z 366 $[C_{17}H_{20}BrNO_3+H]^+$.

Preparation of Compound 110

Compound 109 (5.50 g, 15.1 mmol) was dissolved in 4 N HCl in dioxane (50 mL) at room temperature and the solution was stirred for 3 h. After concentration, the residue was suspended in MTBE (50 mL) and stirred for 0.5 h. The solid was filtered out to afford hydrochloric acid salt 110 (3.20 g, 82%) as a white solid: ¹H NMR (300 MHz, CD₃OD) δ 7.99 (br s, 1H), 7.77-7.70 (m, 2H), 7.55-7.51 (m, 1H), 7.33-7.26 (m, 2H), 4.36 (t, J=4.8 Hz, 2H), 3.43 (t, J=4.8 Hz, 2H).

Preparation of Compound 112

A stirred solution of compound 110 (3.20 g, 12.1) in anhydrous CH₃CN (150 mL) was charged with TEA (4.8 g, 48.3 mmol), 10% (t-Bu)₃P in hexanes (0.48 g, 2.42 mmol), compound 111 (3.68 g, 18.1 mmol), and CuI (114 mg, 0.6 mmol) at room temperature. The resulting mixture was degassed with argon for 10 min and Pd(PPh₃)₄ (1.40 g, 1.21 mmol) was added rapidly in one portion. After degassing with argon for 5 min, the mixture was refluxed for 4 h. The reaction mixture was concentrated under vacuum and the residue was purified by column chromatography (silica gel, 80:20 hexanes/EtOAc) to afford compound 112 (2.80 g, 61%) as a brown solid: ¹H NMR (400 MHz, CD₃OD) δ 7.80 (br s, 1H), 7.67 (t, J=8.2 Hz, 2H), 7.37-7.16 (m, 8H), 5.09 (s, 2H), 4.14 (t, J=5.2 Hz, 2H), 3.37 (t, J=6.8 Hz, 2H), 3.09 (br s, 2H), 2.60 (t, J=6.8 Hz, 2H).

Preparation of Compound 113

A stirred solution of compound 112 (1.00 g, 2.57 mmol) in MeOH (80 mL) was charged with NaCNBH₃ (480 mg, 7.71 mmol), acetic acid (0.6 g, 10.28 mmol), and aldehyde 86 (3.50 g, 6.44 mmol). The reaction mixture was stirred at room temperature for 6 h. After completion of the reaction, the mixture was concentrated under reduced pressure. The residue was partitioned between EtOAc (300 mL) and saturated NaHCO₃ (200 mL) The aqueous layer was separated and extracted with EtOAc (2×300 mL). The combined organic extracts were dried over Na₂SO₄, concentrated, and purified by column chromatography (silica gel, 10:1 CH₂Cl₂/CH₃OH) to afford compound 113 (2.50 g, 68%) as a yellow solid: ¹H NMR (400 MHz, DMSO-d₆) δ 11.49 (s, 2H), 8.31-8.22 (m, 3H), 7.79-7.73 (m, 4H), 7.52 (t, J=5.8 Hz, 1H), 7.38-7.28 (m, 7H), 7.17-7.14 (m, 1H), 6.73 (d, J=8.2 Hz, 2H), 5.04 (s, 2H), 4.11 (t, J=5.8 Hz, 2H), 3.83 (t, J=5.8 Hz, 2H), 3.41-3.36 (m, 1H), 3.27-3.21 (m, 7H), 3.12-3.06 (m, 5H), 2.82 (t, J=5.6 Hz, 2H), 2.58 (t, J=6.8 Hz, 2H), 1.54-1.50 (m, 8H), 1.47-1.43 (m, 30H), 1.39-1.33 (m, 48H), 1.29-1.23 (m, 6H).

Preparation of Compound 114

A stirred solution of compound 113 (2.50 g, 1.73 mmol) in EtOH (50 mL) was charged with 10% Pd/C (250 mg) and was subjected to hydrogenation conditions (1 atm) for 12 h at room temperature. The reaction mixture was filtered through celite and washed with EtOH. The filtrate was concentrated under reduced pressure and purified by column chromatography (silica gel, 10:1 CH₂Cl₂/CH₃OH) to afford compound 114 (1.20 g, 55%) as a brown solid: ¹H NMR (400 MHz, CD₃OD) δ 7.69-7.66 (m, 2H), 7.55 (br s, 1H), 7.30-7.26 (m, 1H), 7.21 (br s, 1H), 7.12-7.09 (m, 1H), 4.17 (t, J=5.6 Hz, 2H), 3.98 (br s, 2H), 3.37-3.32 (m, 2H), 2.93 (t, J=5.6 Hz, 2H), 2.79-2.71 (m, 4H), 2.62 (t, J=6.6 Hz, 4H), 1.76-1.65 (m, 9H), 1.63-1.55 (m, 6H), 1.52-1.50 (m, 25H), 1.46-1.45 (m, 23H), 1.43-1.42 (m, 25H).

Preparation of Compound 115

A stirred solution of compound 114 (240 mg, 0.18 mmol) in t-BuOH (5 mL) and THF (1 mL) was charged with methyl (3,5-diamino-6-chloropyrazine-2-carbonyl)carbamimidothioate hydroiodide 7 (71 mg, 0.18 mmol) and NMM (0.9 g, 0.9 mmol). The reaction mixture was stirred for 4 h at 60° C. After concentration, the residue was purified by column chromatography (silica gel, 10:1 CH₂Cl₂/MeOH, 5:1:0.1 CHCl₃/MeOH/NH₄OH) to afford compound 115 (140 mg, 46%) as a yellow solid: ¹H NMR (400 MHz, CD₃OD) δ 7.69-7.62 (m, 2H), 7.56 (br s, 1H), 7.36-7.29 (m, 1H), 7.20 (br s, 1H), 7.11-7.08 (m, 1H), 4.17 (t, J=5.6 Hz, 2H), 3.97 (br s, 2H), 3.69-3.63 (m, 1H), 2.93 (t, J=5.4 Hz, 2H), 2.81 (t, J=7.2 Hz, 2H), 2.62 (t, J=6.8 Hz, 4H), 1.86-1.79 (m, 2H), 1.74-1.69 (m, 8H), 1.60-1.29 (m, 66H).

Preparation of the Hydrochloride Salt of (2R,2'R)—N,N'-(3,3'-(2-(6-(4-(3-(3,5-diamino-6-chloropyrazine-2-carbonyl)guanidino)butyl)naphthalen-2-yloxy)ethylazanediyl)bis(propane-3,1-diyl))bis(2-amino-6-guanidinohexanamide)—Compound 116

A solution of compound 115 (140 mg, 0.091 mmol) in EtOH (1.0 mL) was charged with 4 N aqueous HCl (5.0 mL) and the reaction mixture was stirred for 3 h at room temperature. After concentration, the residue was purified by reverse-phase column chromatography and lyophilized to afford hydrochloric acid salt 116 (40 mg, 47%) as a yellow hygroscopic solid: ¹H NMR (400 MHz, D₂O) δ 7.72-7.65 (m, 3H), 7.39 (d, J=9.2 Hz, 1H), 7.12 (br s, 1H), 6.99-6.96 (m, 1H), 4.31 (br s, 2H), 3.79-3.74 (m, 2H), 3.61-3.57 (m, 2H), 3.33-3.20 (m, 10H), 2.90 (t, J=7.4 Hz, 4H), 2.74 (t, J=5.2 Hz, 2H), 2.10-1.94 (m, 4H), 1.85-1.65 (m, 9H), 1.38-1.31 (m, 4H), 1.25-1.19 (m, 4H).

Preparation of Hydrochloride Salt of (2R,2'R)—N,N'-(3,3'-(2-(4-(4-(3-(3,5-diamino-6-chloropyrazine-2-carbonyl)guanidino)butyl)naphthalen-1-yloxy)ethylazanediyl)bis(propane-3,1-diyl))bis(2-amino-6-guanidinohexanamide)—Compound 124

Scheme 18

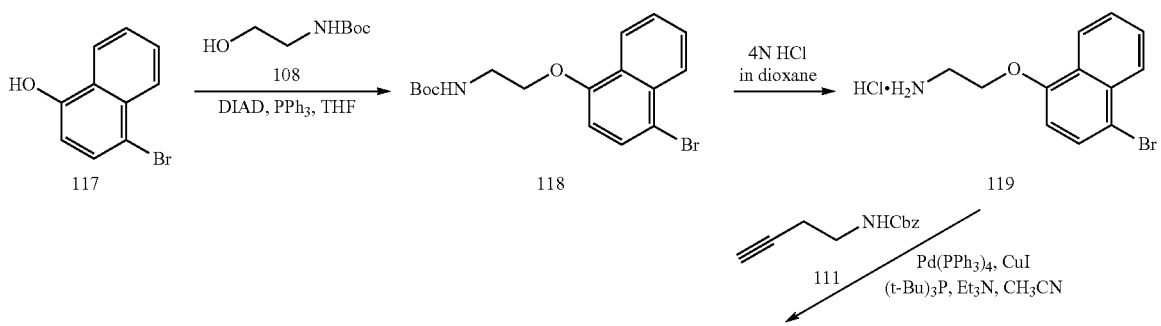

-continued
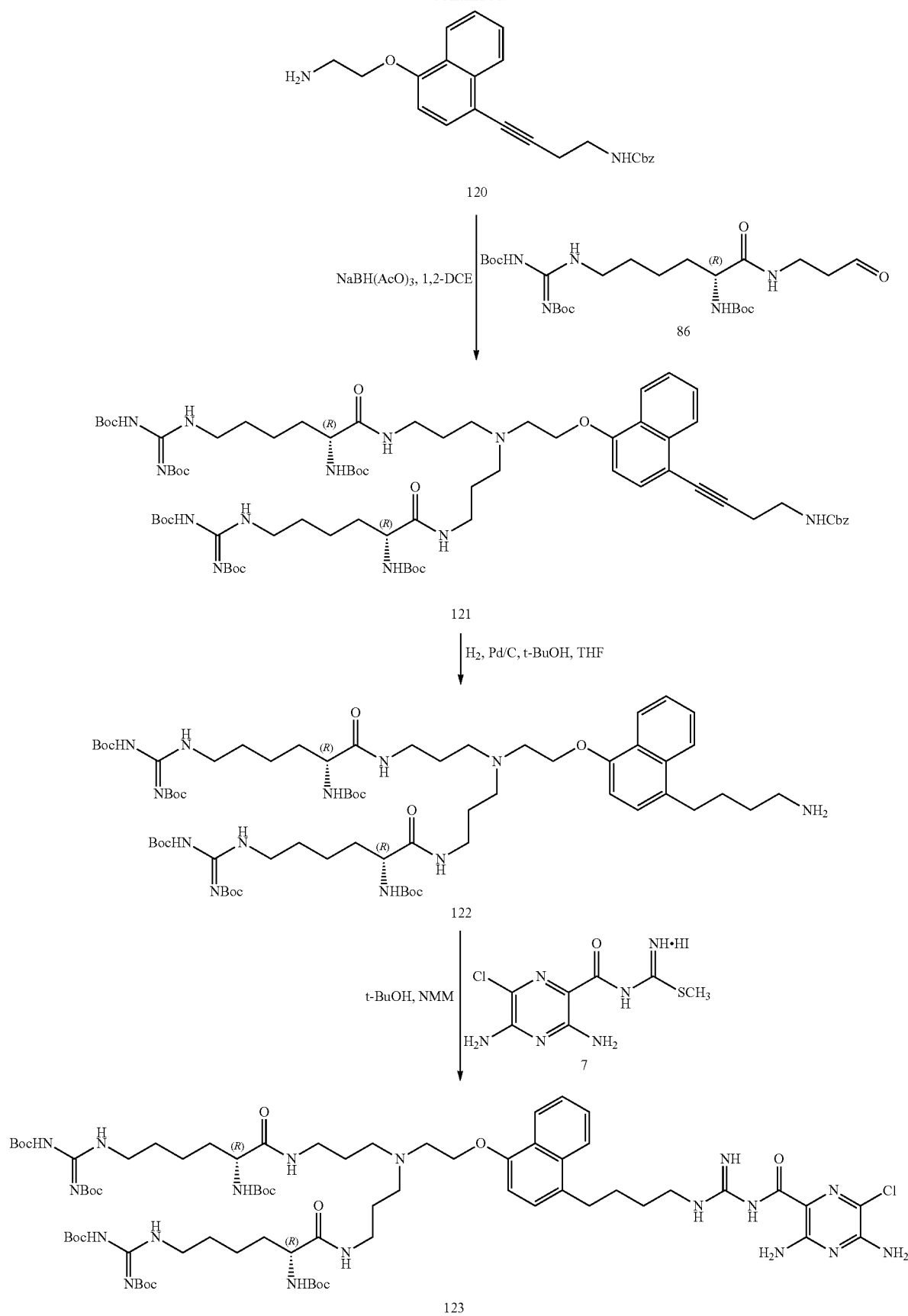

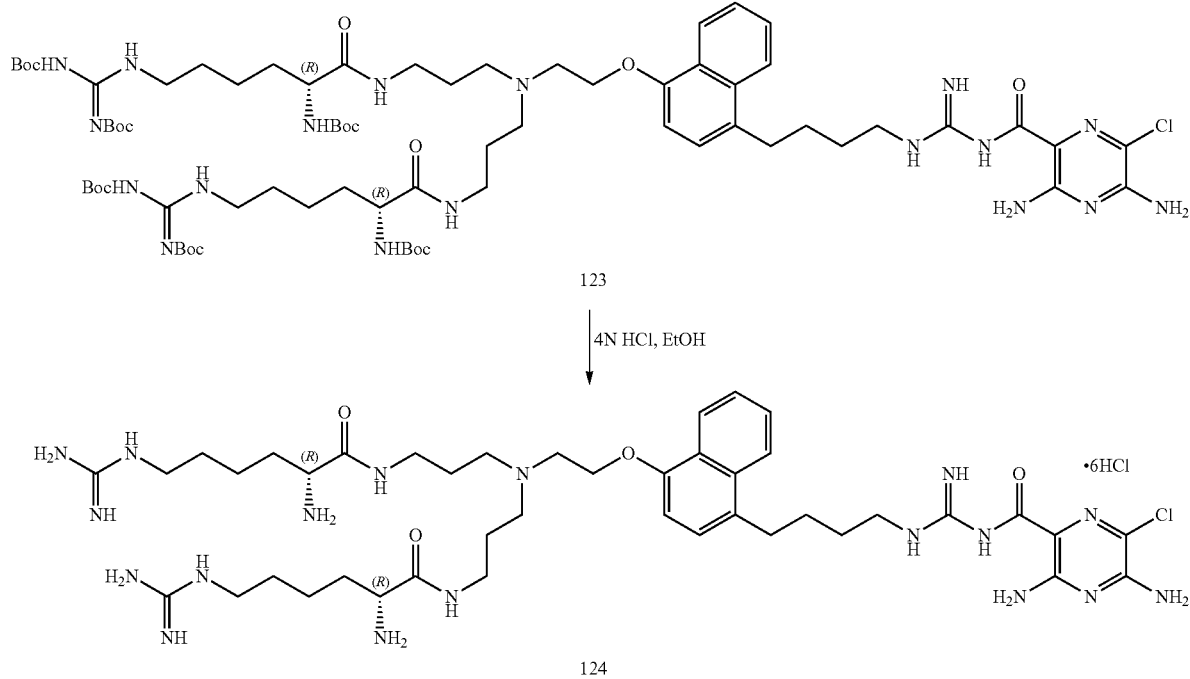

Preparation of Compound 118

A stirred solution of compound 117 (5.00 g, 22.5 mmol) in dry $CH_2Cl_2$ (100 mL) was charged with compound 108 (4.30 g, 27.1 mmol), $Ph_3P$ (7.10 g, 27.1 mmol), and DIAD (5.40 g, 27.1 mmol) at 0° C. The reaction mixture was warmed to room temperature and stirred for 4 h. After completion of the reaction, the mixture was diluted with $CH_2Cl_2$ and washed with 1 N $NaHCO_3$, water, and brine. The organic layer was concentrated under reduced pressure and purified by column chromatography (silica gel, 80:20 hexanes/EtOAc) to afford compound 118 (5.40 g, 66%) as an off-white solid: ESI-MS m/z 366 $[C_{17}H_{20}BrNO_3+H]^+$.

Preparation of Compound 119

Compound 118 (5.40 g, 14.8 mmol) was dissolved in 4 N HCl in dioxane (50 mL) at room temperature and the solution was stirred for 3 h. After concentration, the residue was suspended in MTBE (50 mL) and stirred for 0.5 h. The solid was filtered to afford hydrochloric acid salt 119 (3.40 g, 87%) as a white solid: $^1$H NMR (400 MHz, $CD_3OD$) 8.46-8.44 (m, 1H), 8.17-8.14 (m, 1H), 7.73-7.56 (m, 3H), 6.91 (d, J=8.2 Hz, 1H), 4.42 (t, J=5.2 Hz, 2H), 3.53 (t, J=5.2 Hz, 2H).

Preparation of Compound 120

A stirred solution of compound 119 (3.40 g, 12.8) in anhydrous $CH_3CN$ (150 mL) was charged with TEA (5.1 g, 51.3 mmol), 10% $(t-Bu)_3P$ in hexanes (0.51 g, 2.56 mmol), compound 111 (3.90 g, 19.2 mmol), and CuI (121 mg, 0.64 mmol) at room temperature. The resulting mixture was degassed with argon for 10 min and $Pd(PPh_3)_4$ (1.48 g, 1.28 mmol) was added rapidly in one portion. After degassing with argon for 5 min, the resulting mixture was refluxed for 4 h. The reaction mixture was concentrated under vacuum and the residue was purified by column chromatography (silica gel, 80:20 hexanes/EtOAc) to afford compound 120 (3.20 g, 65%) as a brown solid: $^1$H NMR (400 MHz, $CD_3OD$) δ 8.41-8.39 (m, 1H), 8.26 (d, J=7.4 Hz, 1H), 7.57-7.50 (m, 3H), 7.34-7.24 (m, 5H), 6.92 (d, J=7.8 Hz, 1H), 5.09 (s, 2H), 4.43 (t, J=5.2 Hz, 2H), 3.53 (t, J=5.2 Hz, 2H), 3.43 (t, J=6.8 Hz, 2H), 2.75 (t, J=6.8 Hz, 2H).

Preparation of Compound 121

A stirred solution of compound 120 (500 mg, 1.29 mmol) in 1,2-DCE was charged with $NaBH(AcO)_3$ (815 mg, 3.86 mmol) and aldehyde 86 (1.40 g, 2.58 mmol). The reaction mixture was stirred at room temperature for 3 h. Additional $NaBH(AcO)_3$ (270 mg, 1.29 mmol) and aldehyde 86 (140 mg, 0.258 mmol) were added and the reaction mixture was stirred for 3 h at room temperature. After concentration, the residue was partitioned between $CH_2Cl_2$ (300 mL) and saturated $NaHCO_3$ (200 mL). The aqueous layer was separated and extracted with $CH_2Cl_2$ (2×100 mL). The combined organic extracts were dried over $Na_2SO_4$ and concentrated to afford compound 121 (crude, 1.20 g) as a white solid, which was used directly in the next step.

Preparation of Compound 122

A stirred solution of compound 121 (crude, 1.20 g) in t-BuOH (60 mL) and THF (12 mL) was charged with 10% Pd/C (600 mg). The suspension was subjected to hydrogenation conditions (1 atm) for 26 h at room temperature. The reaction mixture was filtered through celite and washed with THF. Fresh 10% Pd/C (600 mg) was added to the filtrate and the suspension was subjected to hydrogenation conditions (1 atm) for 24 h. The reaction mixture was filtered through celite and washed with THF. The filtrate was concentrated under reduced pressure to afford compound 122 (crude, 900 mg) as a brown solid, which was used directly in the next step.

Preparation of Compound 123

A stirred solution of compound 122 (crude, 900 mg) in t-BuOH (50 mL) was charged with methyl (3,5-diamino-6- chloropyrazine-2-carbonyl)carbamimidothioate hydroiodide 7 (316 mg, 0.82 mmol) and NMM (1.70 g, 3.4 mmol). The reaction mixture was stirred for 4 h at 60° C., 2 h at 65° C., and 1 h at 70° C. After concentration, the residue was purified by column chromatography (silica gel, 10:1 CH$_2$Cl$_2$/MeOH, 5:1:0.1 CHCl$_3$/MeOH/NH$_4$OH) to afford compound 123 (310 mg, 17% over 3 steps) as a yellow solid: $^1$H NMR (300 MHz, CD$_3$OD) δ 8.24 (d, J=7.6 Hz, 1H), 7.99 (d, J=8.4 Hz, 1H), 7.53-7.40 (m, 2H), 7.24 (d, J=7.8 Hz, 1H), 6.85 (d, J=7.8 Hz, 1H), 4.23 (t, J=5.4 Hz, 2H), 3.96 (br s, 2H), 3.10-3.01 (m, 4H), 2.67 (t, J=6.4 Hz, 4H), 1.82-1.68 (m, 11H), 1.51 (s, 26H), 1.45 (s, 26H), 1.41 (s, 22H).

Preparation of Hydrochloride Salt of (2R,2'R)—N,N'-(3,3'-(2-(4-(4-(3-(3,5-diamino-6-chloropyrazine-2-carbonyl)guanidino)butyl)naphthalen-1-yloxy)ethylazanediyl)bis(propane-3,1-diyl))bis(2-amino-6-guanidinohexanamide)—Compound 124

A solution of compound 103 (310 mg, 0.203 mmol) in EtOH (2.0 mL) was charged with 4 N aqueous HCl (15.0 mL) and the reaction mixture was stirred for 5 h at room temperature. The reaction mixture was concentrated in vacuum, and the residue was purified by reverse-phase column chromatography and lyophilized to afford hydrochloric acid salt 104 (95 mg, 41%) as a yellow hygroscopic solid: $^1$H NMR (400 MHz, D$_2$O) δ 8.07 (d, J=8.6 Hz, 1H), 7.97 (d, J=8.2 Hz, 1H), 7.58 (t, J=7.4 Hz, 1H), 7.42 (t, J=7.4 Hz, 1H), 7.33 (d, J=7.8 Hz, 1H), 6.91 (d, J=7.8 Hz, 1H), 4.50 (br s, 2H), 3.79 (t, J=6.6 Hz, 4H), 3.37-3.29 (m, 8H), 3.22 (t, J=5.8 Hz, 2H), 3.03 (t, J=6.2 Hz, 2H), 2.92 (t, J=7.2 Hz, 4H), 2.08-2.01 (m, 4H), 1.88-1.64 (m, 8H), 1.38-1.31 (m, 4H), 1.24-1.18 (m, 4H).

Preparation of Hydrochloride Salt of (2R,2'R)—N,N'-(3,3'-(2-(4-(4-(3-(3,5-diamino-6-chloropyrazine-2-carbonyl)guanidino)butyl)-5,6,7,8-tetrahydronaphthalen-1-yloxy)ethylazanediyl)bis(propane-3,1-diyl))bis(2-amino-6-guanidinohexanamide) Compound 133

Scheme 19

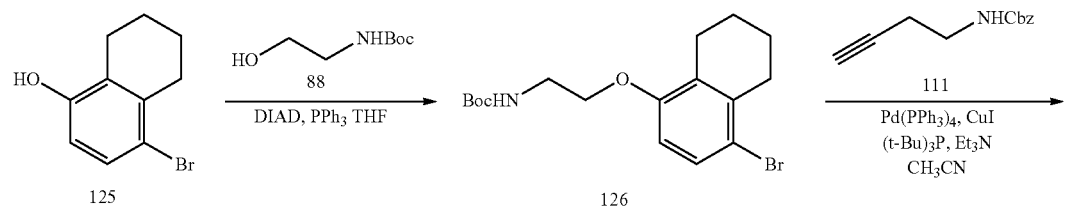

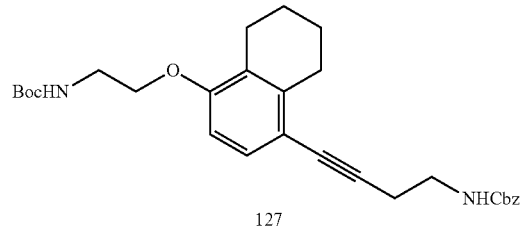

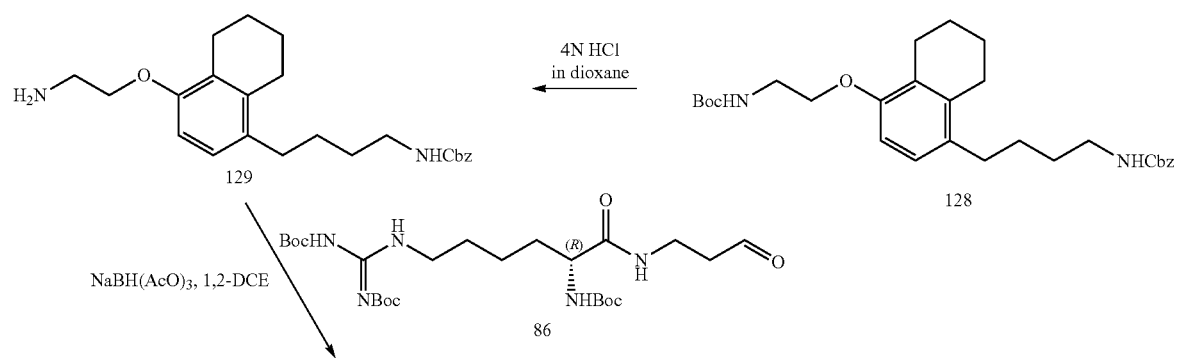

-continued
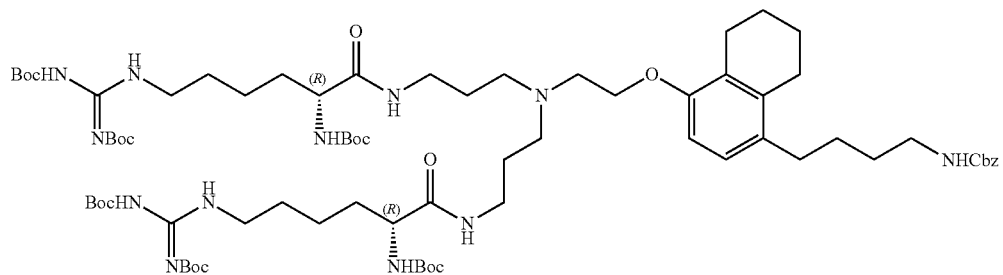
130
↓ H₂, Pd/C, t-BuOH, THF
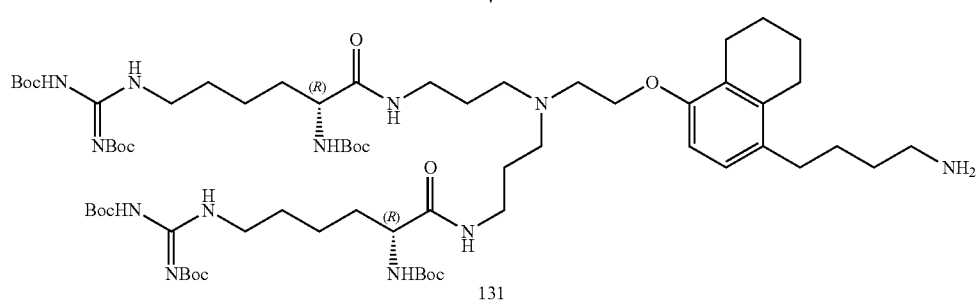
131
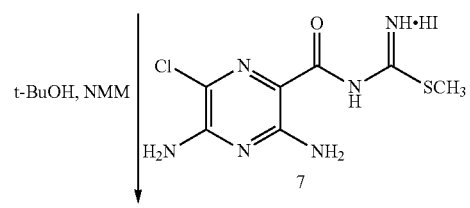
↓ t-BuOH, NMM
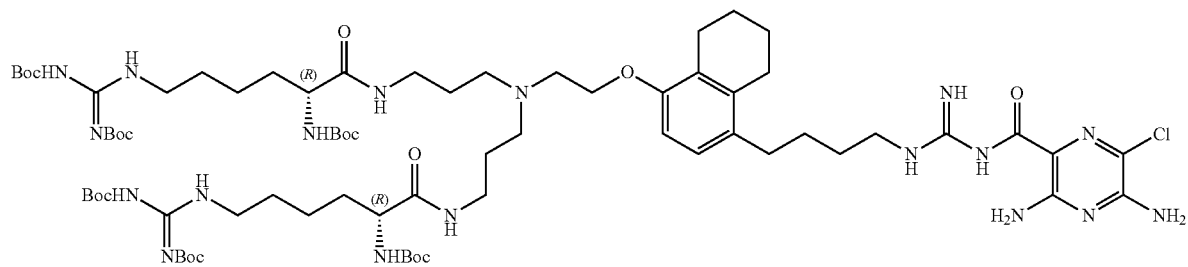
132
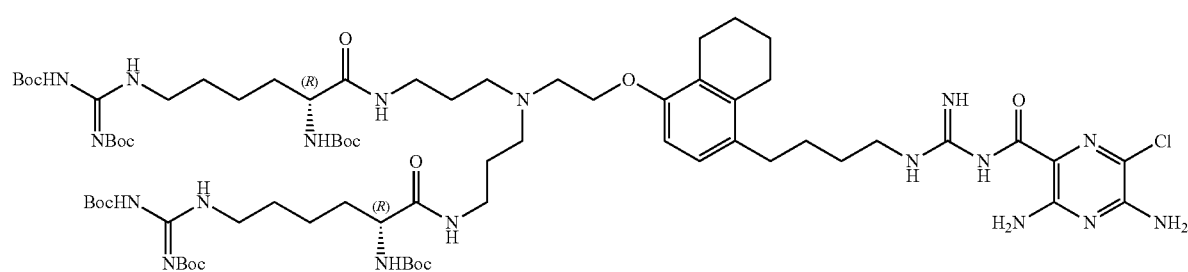
132
↓ 4N HCl, EtOH

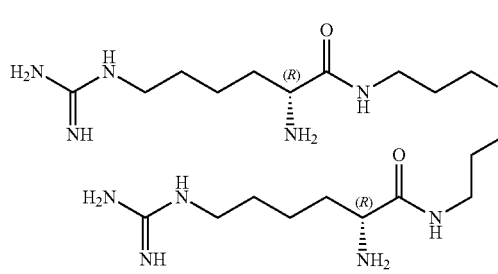 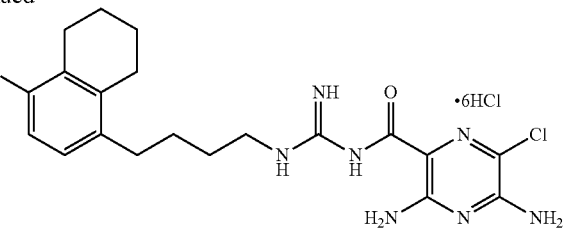

133

Preparation of Compound 126

A stirred solution of compound 125 (6.00 g, 26.4 mmol) in dry CH$_2$Cl$_2$ (150 mL) was charged with compound 108 (4.68 g, 29.0 mmol), Ph$_3$P (8.30 g, 31.6 mmol), and DIAD (6.38 g, 31.6 mmol) at 0° C. The reaction mixture was warmed to room temperature and stirred for 4 h. After completion of the reaction, the mixture was diluted with CH$_2$Cl$_2$ and washed with 1 N NaHCO$_3$, water, and brine. The organic layer was concentrated under reduced pressure and purified by column chromatography (silica gel, 80:20 hexanes/EtOAc) to afford compound 126 (6.10 g, 63%) as a white solid: $^1$H NMR (300 MHz, DMSO-d$_6$) δ 7.32 (d, J=8.6 Hz, 1H), 6.93 (t, J=5.4 Hz, 1H), 6.72 (d, J=8.6 Hz, 1H), 3.91 (t, J=5.8 Hz, 2H), 3.30 (t, J=5.6 Hz, 2H), 2.62-2.56 (m, 4H), 1.72-1.63 (m, 4H), 1.37 (s, 9H).

Preparation of Compound 127

A stirred solution of compound 126 (4.00 g, 10.8) in anhydrous CH$_3$CN (150 mL) was charged with TEA (4.36 g, 43.2 mmol), 10% (t-Bu)$_3$P in hexanes (0.43 g, 2.16 mmol), compound 111 (3.28 g, 16.2 mmol), and CuI (102 mg, 0.54 mmol) at room temperature. The resulting mixture was degassed with argon for 10 min and Pd(PPh$_3$)$_4$ (1.24 g, 1.08 mmol) was added rapidly in one portion. After degassing with argon for 5 min, the resulting mixture was refluxed for 16 h. The reaction mixture was concentrated under vacuum and the residue was purified by column chromatography (silica gel, 80:20 hexanes/EtOAc) to afford compound 127 (2.90 g, 54%) as a brown solid: $^1$H NMR (300 MHz, CDCl$_3$) δ 7.36-7.30 (m, 6H), 7.23-7.16 (m, 1H), 6.55 (d, J=8.4 Hz, 1H), 5.11 (s, 2H), 3.98 (t, J=4.8 Hz, 2H), 3.56-3.50 (m, 2H), 3.48-3.39 (m, 2H), 2.79 (br s, 2H), 2.67-2.61 (m, 4H), 1.76-1.72 (m, 4H), 1.45 (s, 9H).

Preparation of Compound 128

A stirred solution of compound 127 (4.10 g, 8.33 mmol) in EtOH (200 mL) was charged with 10% Pd/C (410 mg) and the resulting mixture was subjected to hydrogenation conditions (1 atm) for 24 h at room temperature. The reaction mixture was filtered through celite and washed with EtOH. After concentration, the residue was dissolved in dioxane (50 mL) and H$_2$O (50 mL) CbzCl (2.11 g, 12.4 mmol) was added dropwise at room temperature and the reaction mixture was stirred for 4 h. After concentration, the residue was dissolved in CH$_2$Cl$_2$ and washed with 1 N NaHCO$_3$, water, and brine. The organic layer was concentrated to afford compound 128 (crude, 2.50 g) as a brown solid, which was used directly in the next step.

Preparation of Compound 129

Compound 128 (crude, 2.50 g) was dissolved in 4 N HCl in dioxane (50 mL) at room temperature and the solution was stirred for 3 h. After concentration, the residue was neutralized with 1 N Na$_2$CO$_3$ and extracted with CH$_2$Cl$_2$. The organic layer was concentrated and purified by column chromatography (silica gel, 10:1 CH$_2$Cl$_2$/MeOH) to afford compound 129 (1.10 g, 34% over 3 steps) as a brown oil: $^1$H NMR (300 MHz, CDCl$_3$) δ 7.36-7.26 (m, 5H), 6.89 (d, J=8.2 Hz, 1H), 6.60 (d, J=8.2 Hz, 1H), 5.11 (s, 2H), 3.94 (t, J=5.2 Hz, 2H), 3.28-3.21 (m, 2H), 3.07 (t, J=5.2 Hz, 2H), 2.68-2.64 (m, 4H), 2.54-2.51 (m, 2H), 1.78-1.73 (m, 4H), 1.58-1.54 (m, 4H).

Preparation of Compound 130

A stirred solution of compound 129 (1.00 g, 2.52 mmol) in 1,2-DCE (80 mL) was charged with NaBH(AcO)$_3$ (1.59 g, 7.57 mmol) and aldehyde 86 (2.73 g, 5.04 mmol). The reaction mixture was stirred at room temperature for 3 h. Additional NaBH(AcO)$_3$ (530 mg, 2.52 mmol) and aldehyde 86 (820 mg, 1.51 mmol) were added and the reaction mixture was stirred for 3 h at room temperature. After concentration, the residue was partitioned between CH$_2$Cl$_2$ (300 mL) and saturated NaHCO$_3$ (200 mL). The aqueous layer was separated and extracted with CH$_2$Cl$_2$ (2×100 mL). The combined organic extracts were dried over Na$_2$SO$_4$ and concentrated to afford compound 130 (crude, 1.90 g), which was used directly in the next step.

Preparation of Compound 131

A stirred solution of compound 130 (crude, 2.10 g) in t-BuOH (60 mL) and THF (20 mL) was charged with 10% Pd/C (1.10 g). The suspension was subjected to hydrogenation conditions (1 atm) for 16 h at room temperature. The reaction mixture was filtered through celite and washed with THF. The filtrate was concentrated under reduced pressure to afford compound 131 (1.20 g crude) as a brown solid, which was used directly in the next step.

Preparation of Compound 132

A stirred solution of compound 131 (400 mg, 0.303 mmol) in t-BuOH (20 mL) and THF (4.0 mL) was charged with methyl (3,5-diamino-6-chloropyrazine-2-carbonyl)carbamimidothioate hydroiodide 7 (117 mg, 0.303 mmol) and NMM (152 mg, 1.51 mmol). The reaction mixture was stirred for 4 h at 60° C., 2 h at 65° C., and 1 h at 70° C. After concentration, the residue was purified by column chromatography (silica gel, 10:1 CH$_2$Cl$_2$/MeOH, 5:1:0.1 CHCl$_3$/MeOH/NH$_4$OH) to afford compound 132 (800 mg, 17% over 3 steps) as a yellow solid: ESI-MS m/z 765 [C$_{72}$H$_{121}$ClN$_{18}$O$_{16}$+2H]$^{2+}$.

Preparation of Hydrochloride Salt of (2R,2'R)—N, N'-(3,3'-(2-(4-(4-(3-(3,5-diamino-6-chloropyrazine-2-carbonyl)guanidino)butyl)-5,6,7,8-tetrahydronaphthalen-1-yloxy)ethylazanediyl)bis(propane-3,1-diyl))bis(2-amino-6-guanidinohexanamide) Compound 133

A solution of compound 132 (800 mg, 0.52 mmol) in EtOH (1.0 mL) was charged with 4 N HCl (5.0 mL) and the reaction mixture was stirred for 4 h at room temperature. The reaction mixture was concentrated and the residue was redissolved in fresh 4 N HCl (5.0 mL). The reaction mixture was stirred for 4 h at room temperature. After concentration, the residue was purified by reverse-phase column chromatography and lyophilized to afford hydrochloric acid salt 133 (180 mg, 42%) as a yellow hygroscopic solid: $^1$H NMR (400 MHz, D$_2$O) δ 7.04 (d, J=8.4 Hz, 1H), 6.74 (d, J=8.4 Hz, 1H), 4.26 (br s, 2H), 3.88 (t, J=6.8 Hz, 2H), 3.63 (br s, 2H), 3.32-3.27 (m, 10H), 3.06 (t, J=6.8 Hz, 4H), 2.65-2.50 (m, 6H), 2.02-1.95 (m, 4H), 1.82-1.59 (m, 10H), 1.54-1.47 (m, 4H), 1.36-1.30 (m, 4H).

Preparation of the Hydrochloride Salt of (2S,2'S)—N,N'-(3,3'-(3-(4-((S)-2-amino-3-(4-(4-(3-(3,5-diamino-6-chloropyrazine-2-carbonyl)guanidino)butyl)phenyl)propanamido)phenyl)propylazanediyl)bis(propane-3,1-diyl))bis(2-amino-6-guanidinohexanamide)—Compound 145

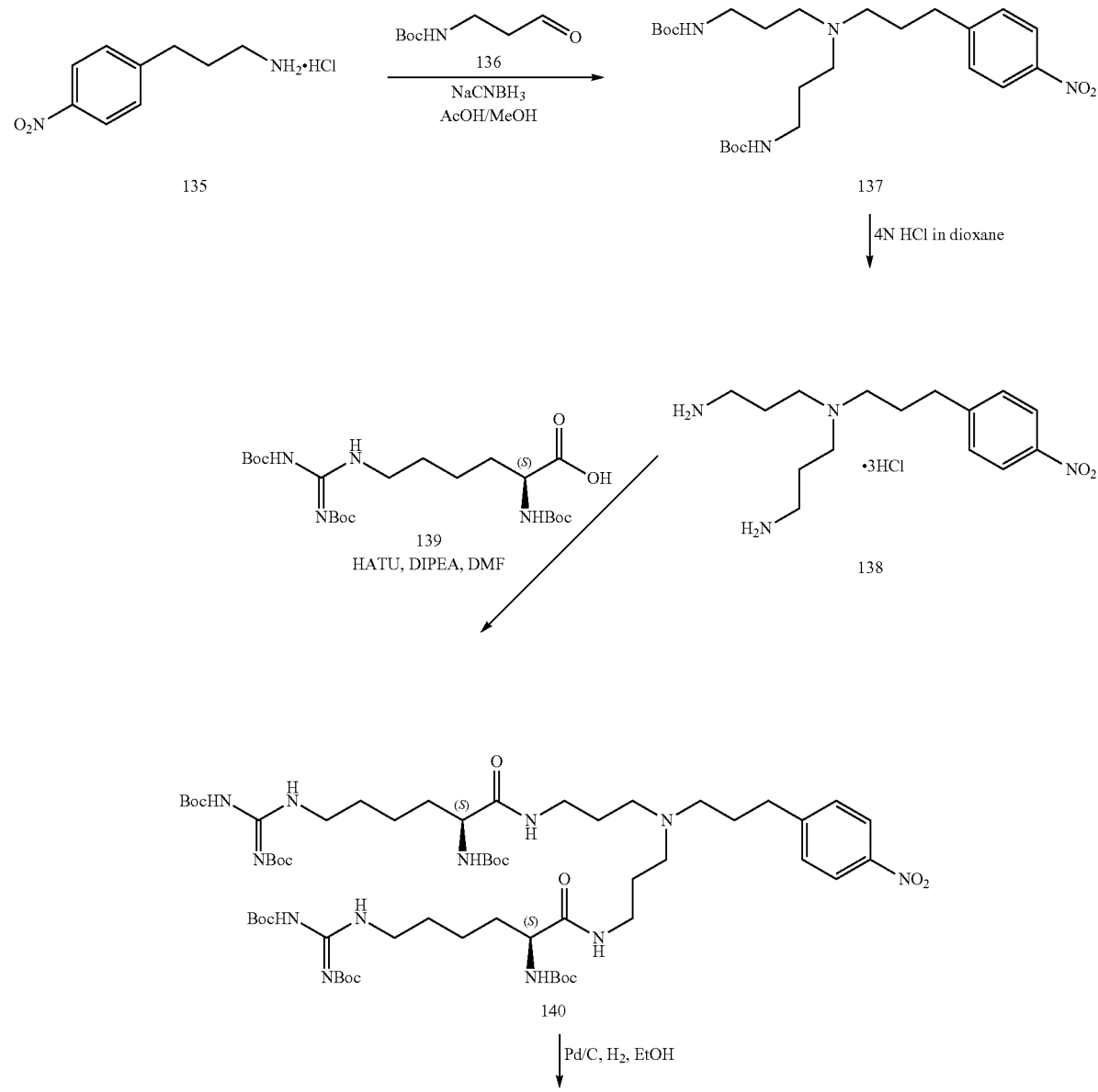

-continued
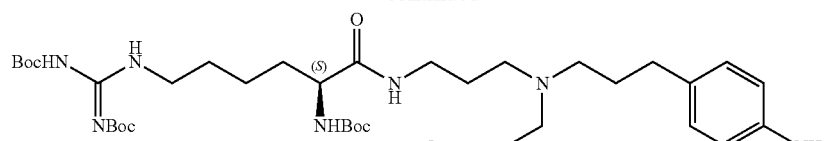
141
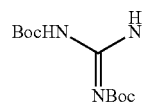
16
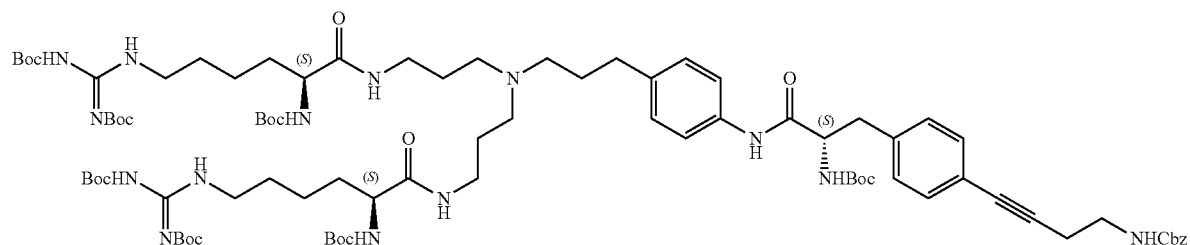
142
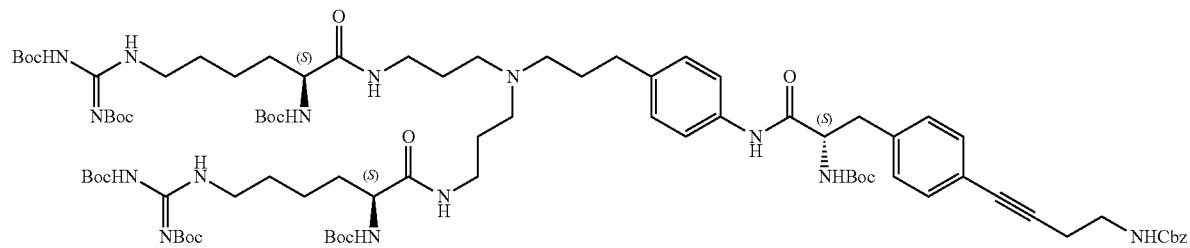
142
Pd/C, H₂, EtOH
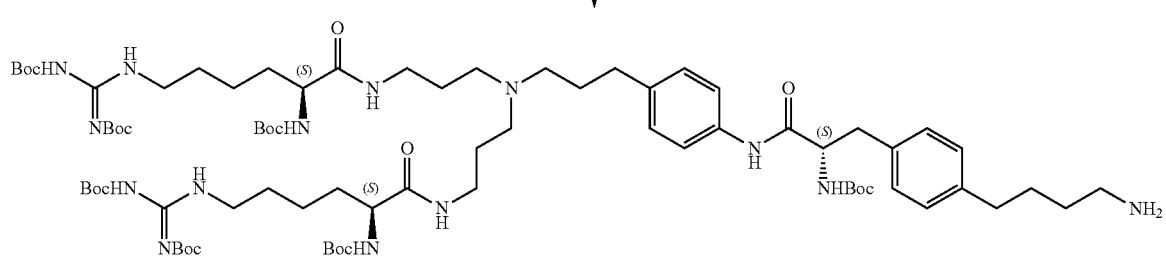
143
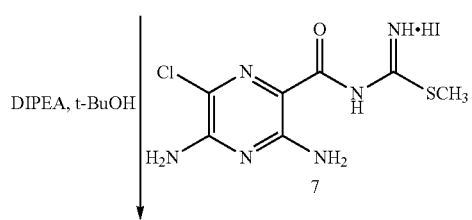
7
DIPEA, t-BuOH

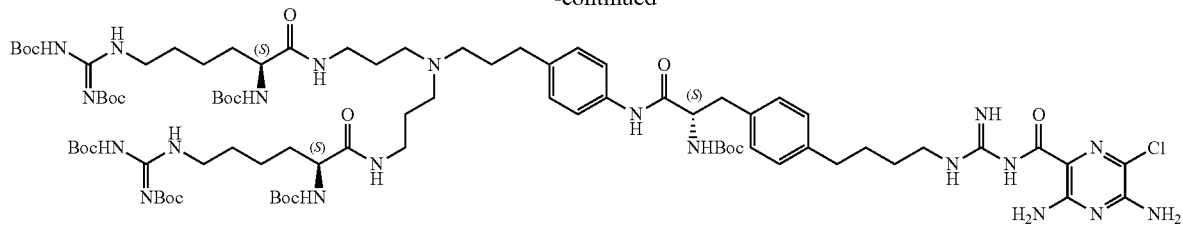

144

↓ 4N aq HCl, EtOH

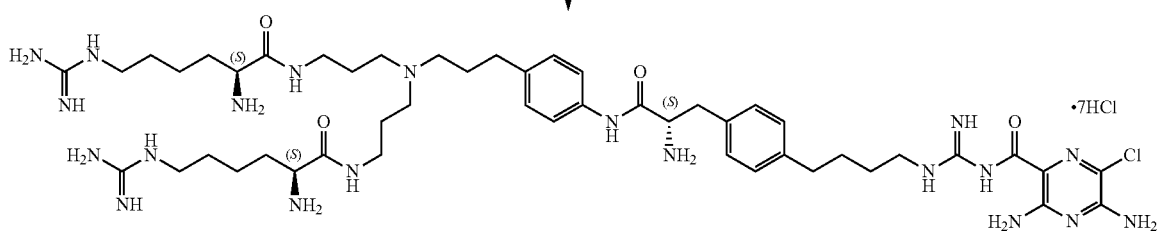

145

Preparation of Compound 137

A solution of compound 135 (2.00 g, 9.26 mmol) in MeOH (10 mL) was charged with NaCNBH$_3$ (2.00 g, 27.7 mmol) followed by AcOH (1.60 g, 27.7 mmol) and compound 136 (4.79 g, 27.7 mmol). The reaction mixture was stirred at room temperature for 24 h. Additional NaCNBH$_3$ (2.00 g, 27.7 mmol), AcOH (1.60 g, 27.7 mmol), and compound 136 (3.20 g, 18.5 mmol) were added. After stirring at room temperature for 16 h, the solvent was removed. The residue was washed with 1 N Na$_2$CO$_3$ (30 mL) and purified by column chromatography (silica gel, 10:1 CH$_2$Cl$_2$/MeOH) to afford compound 137 (2.00 g, 44%) as a yellow oil: $^1$H NMR (400 MHz, CDCl$_3$) δ 8.17 (d, J=8.6 Hz, 2H), 7.39 (d, J=8.6 Hz, 2H), 5.10 (br s, 2H), 3.22-3.18 (m, 4H), 2.93 (br s, 5H), 2.81 (t, J=7.4 Hz, 2H), 2.03 (br s, 2H), 1.85 (br s, 5H), 1.42 (s, 18H).

Preparation of Compound 138

Compound 137 (2.00 g, 4.04 mmol) was dissolved in 4 N HCl in dioxane (100 mL) at room temperature and the reaction mixture was stirred at room temperature for 2 h. After the solvent was removed, the residue was washed with hexanes to afford compound 138 (1.20 g, 76%) as a white solid: $^1$H NMR (400 MHz, CD$_3$OD) δ 8.19 (d, J=8.6 Hz, 2H), 7.57 (d, J=8.6 Hz, 2H), 3.69-3.62 (m, 1H), 3.36-3.32 (m, 4H), 3.08 (t, J=7.6 Hz, 4H), 2.90 (t, J=7.6 Hz, 2H), 2.23-2.15 (m, 6H).

Preparation of Compound 140

A solution of compound 138 (100 mg, 0.248 mmol) in DMF (5.0 mL) was charged with HATU (208 mg, 0.546 mmol) followed by compound 139 (242 mg, 0.496 mmol) and DIPEA (128 mg, 0.992 mmol) at room temperature. After stirring at room temperature for 6 h, the solvent was removed and the residue was purified by column chromatography (silica gel, 15:1 CH$_2$Cl$_2$/MeOH) to afford compound 140 (90.0 mg, 29%) as a white solid: $^1$H NMR (400 MHz, CD$_3$OD) δ 8.17 (d, J=8.6 Hz, 2H), 7.49 (d, J=8.6 Hz, 2H), 3.95-3.92 (m, 2H), 3.75-3.69 (m, 1H), 3.35-3.32 (m, 4H), 3.26-3.19 (m, 4H), 2.81 (br s, 4H), 1.98 (br s, 2H), 1.79-1.70 (m, 6H), 1.64-1.54 (m, 8H), 1.51 (br s, 24H), 1.46-1.42 (m, 48H), 1.38-1.34 (m, 11H).

Preparation of Compound 141; SG-DVR-A-105

A suspension of compound 140 (100 mg, 0.081 mmol) and 10% Pd/C (50 mg) in EtOH (10 mL) was subjected to hydrogenation conditions (1 atm) for 8 h at room temperature. The reaction mixture was filtered through celite and washed with EtOH. The filtrate was concentrated and the residue was purified by column chromatography (silica gel, 10:1 CH$_2$Cl$_2$/MeOH) to afford compound 141 (70 mg, 72%) as a white solid: $^1$H NMR (300 MHz, CD$_3$OD) δ 6.97 (d, J=8.2 Hz, 2H), 6.67 (d, J=8.2 Hz, 2H), 3.94-3.90 (m, 2H), 3.74-3.68 (m, 1H), 3.28-3.19 (m, 4H), 3.07 (br s, 6H), 2.58 (t, J=7.4 Hz, 2H), 1.98-1.94 (m, 2H), 1.87-1.78 (m, 4H), 1.74-1.56 (m, 8H), 1.52 (s, 24H), 1.46 (s, 22H), 1.44 (s, 24H), 1.38-1.35 (m, 9H).

Preparation of Compound 142

A solution of compound 141 (150 mg, 0.124 mmol) in DMF (4.0 mL) was charged with HATU (52 mg, 0.137 mmol) followed by compound 16 (58 mg, 0.124 mmol) and DIPEA (63 mg, 0.496 mmol) at room temperature. After stirring at room temperature for 8 h, the solvent was removed and the residue was purified by column chromatography (silica gel, 15:1 CH$_2$Cl$_2$/MeOH) to afford compound 142 (130 mg, 63%) as a white solid: $^1$H NMR (400 MHz, CD$_3$OD) δ 7.40 (d, J=8.6 Hz, 2H), 7.34-7.25 (m, 7H), 7.17 (t, J=8.4 Hz, 4H), 5.08 (s, 2H), 4.39 (br s, 1H), 3.96-3.93 (m, 2H), 3.35-3.31 (m, 8H), 3.24-3.19 (m, 5H), 3.12-3.07 (m, 1H), 2.94-2.89 (m, 1H), 2.80-2.73 (m, 3H), 2.62-2.52 (m, 5H), 1.94-1.86 (m, 2H), 1.73 (br s, 6H), 1.61-1.54 (m, 7H), 1.51 (br s, 21H), 1.45 (br s, 44H), 1.38-1.34 (m, 15H).

Preparation of Compound 143

A suspension of compound 142 (1.18 g, 0.713 mmol) and 10% Pd/C (120 mg) in EtOH (10 mL) was subjected to hydrogenation conditions (1 atm) for 8 h at room temperature. The reaction mixture was filtered through celite and washed with EtOH. The filtrate was concentrated to afford compound 143 (680 mg, 62%) as a brown solid: ESI MS m/z 762 $[C_{77}H_{130}N_{14}O_{17}+2H]^{2+}$.

Preparation of Compound 144

A solution of compound 143 (100 mg, 0.065 mmol) and methyl 3,5-diamino-6-chloropyrazine-2-carbonylcarbamimidothioate hydroiodic acid salt (7, 30 mg, 0.078 mmol) in t-BuOH (10 mL) was charged with DIPEA (66 mg, 0.520 mmol) at room temperature. The reaction mixture was heated at 70° C. for 3 h and 80° C. for 2 h, cooled to room temperature, and concentrated in vacuum. The residue was purified by column chromatography (silica gel, 10:1 $CH_2Cl_2$/MeOH, 4:1:0.1 $CHCl_3$/MeOH/$NH_4OH$) to afford compound 144 (40 mg, 35%) as a yellow solid: $^1$H NMR (300 MHz, $CD_3OD$) δ 7.38 (d, J=8.2 Hz, 2H), 7.18-7.09 (m, 6H), 4.38 (br s, 1H), 3.99 (br s, 2H), 3.63-3.53 (m, 1H), 3.36 (br s, 3H), 3.22 (br s, 4H), 3.11-3.07 (m, 1H), 2.92-2.85 (m, 1H), 2.74 (t, J=7.2 Hz, 2H), 2.63-2.58 (m, 4H), 2.46 (br s, 6H), 1.79-1.70 (m, 4H), 1.62-1.55 (m, 13H), 1.51 (s, 19H), 1.46 (s, 9H), 1.43 (s, 20H), 1.38 (s, 9H).

Preparation of the Hydrochloride Salt of (2S,2'S)—N,N'-(3,3'-(3-(4-((S)-2-amino-3-(4-(4-(3-(3,5-diamino-6-chloropyrazine-2-carbonyl)guanidino)butyl) phenyl)propanamido)phenyl)propylazanediyl)bis (propane-3,1-diyl))bis(2-amino-6-guanidinohexanamide)—Compound 145

A solution of compound 144 (250 mg, 0.144 mmol) in EtOH (3.0 mL) was charged with 4 N aqueous HCl (25 mL) and the reaction mixture was stirred for 6 h at room temperature. The reaction mixture was concentrated in vacuum, and the residue was purified by reverse-phase column chromatography and lyophilized to afford hydrochloric acid salt 145 (70 mg, 38%) as a yellow hygroscopic solid: $^1$H NMR (400 MHz, $D_2O$) δ 7.23 (d, J=8.4 Hz, 2H), 7.17 (d, J=8.4 Hz, 4H), 7.11 (d, J=8.4 Hz, 2H), 4.26-4.23 (m, 1H), 3.92 (t, J=6.8 Hz, 2H), 3.35-3.28 (m, 2H), 3.27-3.18 (m, 5H), 3.16-3.09 (m, 11H), 2.65-2.57 (m, 4H), 1.97-1.78 (m, 10H), 1.70-1.63 (m, 2H), 1.60-1.51 (m, 6H), 1.39-1.33 (m, 4H). HRMS calculated for $C_{48}H_{80}ClN_{20}O_4$ $[M+H]^+$, 1035.6354. found 1035.6375

All of the references cited above are incorporated herein by reference. In the event of a conflict between the foregoing description and a reference, the description provided herein controls.

What is claimed is:
1. A compound represented by formula (I):

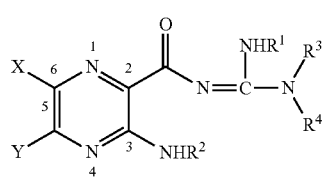

(I)

and racemates, enantiomers, diastereomers, tautomers, polymorphs, pseudopolymorphs and pharmaceutically acceptable salts, thereof, wherein:
X is hydrogen, halogen, trifluoromethyl, lower alkyl, unsubstituted or substituted phenyl, lower alkyl-thio, phenyl-lower alkyl-thio, lower alkyl-sulfonyl, or phenyl-lower alkyl-sulfonyl;
Y is hydrogen, hydroxyl, mercapto, lower alkoxy, lower alkyl-thio, halogen, lower alkyl, unsubstituted or substituted mononuclear aryl, or —$N(R^2)_2$;
$R^1$ is hydrogen or lower alkyl;
each $R^2$ is, independently, —$R^7$, —$(CH_2)_m$—$OR^8$, —$(CH_2)_m$—$NR^7R^{10}$, —$(CH_2)_n(CHOR^8)(CHOR^8)_n$—$CH_2OR^8$, —$(CH_2CH_2O)_m$—$R^8$, —$(CH_2CH_2O)_m$—$CH_2CH_2NR^7R^{10}$, —$(CH_2)_n$—C(=O)$NR^7R^{10}$, —$(CH_2)_n$—$(Z)_g$—$R^7$, —$(CH_2)_m$—$NR^{10}$—$CH_2(CHOR^8)(CHOR^8)_n$—$CH_2OR^8$, —$(CH_2)_n$—$CO_2R^7$, or

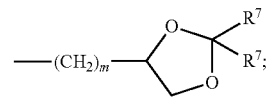

$R^3$ and $R^4$ are each, independently, hydrogen, lower alkyl, hydroxyl-lower alkyl, phenyl, (phenyl)-lower alkyl, (halophenyl)-lower alkyl, ((lower-alkyl)phenyl)-lower-alkyl, ((lower-alkoxy)phenyl)-lower-alkyl, (naphthyl)-lower-alkyl, or (pyridyl)-lower-alkyl, or a group represented by formula A or formula B, with the proviso that at least one of $R^3$ and $R^4$ is a group represented by the formula A or formula B;

—$(C(R^L)_2)_o$-x-$(C(R^L)_2)_p A^1$     formula A:

—$(C(R^L)_2)_o$-x-$(C(R^L)_2)_p A^2$     formula B:

$A^1$ is a $C_6$-$C_{15}$-membered aromatic carbocycle substituted with at least one $R^5$ and the remaining substituents are $R^6$;
$A^2$ is a six to fifteen-membered aromatic heterocycle substituted with at least one $R^5$ and the remaining substituents are $R^6$ wherein said aromatic heterocycle comprises 1-4 heteroatoms selected from the group consisting of O, N, and S;
each $R^L$ is, independently, —$R^7$, —$(CH_2)_n$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

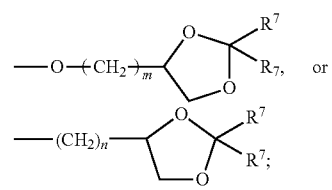

each o is, independently, an integer from 0 to 10;
each p is, independently, an integer from 0 to 10;

with the proviso that the sum of o and p in each contiguous chain is from 1 to 10;

each x is, independently, O, $NR^{10}$, C(=O), CHOH, C(=N—$R^{10}$), $CHNR^7R^{10}$, or a single bond;

each $R^5$ is, independently, -Link-$(CH_2)_m$-CAP, -Link-$(CH_2)_n(CHOR^8)(CHOR^8)_n$-CAP, -Link-$(CH_2CH_2O)_m$—$CH_2$-CAP, -Link-$(CH_2CH_2O)_m$—$CH_2CH_2$-CAP, -Link-$(CH_2)_m$—$(Z)_g$-CAP, -Link-$(CH_2)_n(Z)_g$—$(CH_2)_m$-CAP, -Link-$(CH_2)_n$—$NR^{13}$—$CH_2(CHOR^8)(CHOR^8)_n$-CAP, -Link-$(CH_2)_n$—$(CHOR^8)_mCH_2$—$NR^{13}$—$(Z)_g$-CAP, -Link-$(CH_2)_n NR^{13}$—$(CH_2)_m(CHOR^8)_mCH_2NR^{13}$—$(Z)_g$-CAP, -Link-$(CH_2)_m$—$(Z)_g$—$(CH_2)_m$-CAP, -Link-NH—C(=O)—NH—$(CH_2)_m$-CAP, -Link-$(CH_2)_m$—C(=O)$NR^{13}$—$(CH_2)_m$-CAP, -Link-$(CH_2)_n$—$(Z)_g$—$(CH_2)_m$—$(Z)_g$-CAP, or -Link-$Z_g$—$(CH_2)_m$-Het-$(CH_2)_m$-CAP;

each $R^6$ is, independently, $R^5$, —$R^7$, —$OR^{11}$, —$N(R^7)_2$, —$(CH_2)_m$—$OR^8$, —O—$(CH_2)_m$—$OR^8$, —$(CH_2)_n$—$NR^7R^{10}$, —O—$(CH_2)_m$—$NR^7R^{10}$, —$(CH_2)_n(CHOR^8)(CHOR^8)_n$—$CH_2OR^8$, —O—$(CH_2)_m(CHOR^8)(CHOR^8)_n$—$CH_2OR^8$, —$(CH_2CH_2O)_m$—$R^8$, —O—$(CH_2CH_2O)_m$—$R^8$, —$(CH_2CH_2O)_m$—$CH_2CH_2NR^7R^{10}$, —O—$(CH_2CH_2O)_m$—$CH_2CH_2NR^7R^{10}$, —$(CH_2)_n$—C(=O)$NR^7R^{10}$, —O—$(CH_2)_m$—C(=O)$NR^7R^{10}$, —$(CH_2)_n$—$(Z)_g$—$R^7$, —O—$(CH_2)_m$—$(Z)_g$—$R^7$, —$(CH_2)_n$—$NR^{10}$—$CH_2(CHOR^8)(CHOR^8)_n$—$CH_2OR^8$, —O—$(CH_2)_m$—$NR^{10}$—$CH_2(CHOR^8)(CHOR^8)_n$—$CH_2OR^8$, —$(CH_2)_n$—$CO_2R^7$, —O—$(CH_2)_m$—$CO_2R^7$, —$OSO_3H$, —O-glucuronide, —O-glucose,

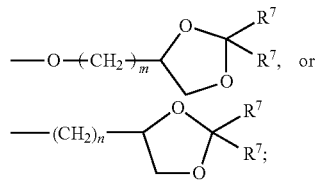

wherein when two $R^6$ are —$OR^{11}$ and are located adjacent to each other on the aromatic carbocycle or aromatic heterocycle, the two $OR^{11}$ may form a methylenedioxy group;

each $R^7$ is, independently, hydrogen, lower alkyl, phenyl, substituted phenyl or —$CH_2(CHOR^8)_m$—$CH_2OR^8$;

each $R^8$ is, independently, hydrogen, lower alkyl, —C(=O)—$R^{11}$, glucuronide, 2-tetrahydropyranyl, or

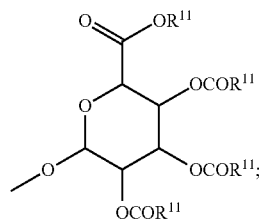

each $R^9$ is, independently, —$CO_2R^7$, —$CON(R^7)_2$, —$SO_2CH_3$, —C(=O)$R^7$, —$CO_2R^{13}$, —$CON(R^{13})_2$, —$SO_2CH_2R^{13}$, or —C(=O)$R^{13}$;

each $R^{10}$ is, independently, —H, —$SO_2CH_3$, —$CO_2R^7$, —C(=O)$NR^7R^9$, —C(=O)$R^7$, or —$CH_2$—$(CHOH)_n$—$CH_2OH$;

each Z is, independently, —(CHOH)—, —C(=O)—, —($CHNR^7R^{10}$)—, —(C=$NR^{10}$)—, —$NR^{10}$—, —$(CH_2)_n$—, —($CHNR^{13}R^{13}$)—, —(C=$NR^{13}$)—, or —$NR^{13}$—;

each $R^{11}$ is, independently, hydrogen, lower alkyl, phenyl lower alkyl or substituted phenyl lower alkyl;

each $R^{12}$ is, independently, —$SO_2CH_3$, —$CO_2R^7$, —C(=O)$NR^7R^9$, —C(=O)$R^7$, —$CH_2(CHOH)_n$—$CH_2OH$, —$CO_2R^7$, —C(=O)$NR^7R^7$, or —C(=O)$R^7$;

each $R^{13}$ is, independently, hydrogen, —$OR^7$, $R^{10}$, $R^{11}$ or $R^{12}$;

each g is, independently, an integer from 1 to 6;

each m is, independently, an integer from 1 to 7;

each n is, independently, an integer from 0 to 7;

each -Het- is, independently, —N($R^7$)—, —N($R^{10}$)—, —S—, —SO—, —$SO_2$—; —O—, —$SO_2NH$—, —$NHSO_2$—, —$NR^7CO$—, —$CONR^7$—, —N($R^{13}$)—, —$SO_2NR^{13}$—, —$NR^{13}CO$—, or —$CONR^{13}$—;

each Link is, independently, —O—, —$(CH_2)_n$—, —O$(CH_2)_m$—, —$NR^{13}$—C(=O)—$NR^{13}$—, —$NR^{13}$—C(=O)—$(CH_2)_m$—, —C(=O)$NR^{13}$—$(CH_2)_m$—, —$(CH_2)_n$—$(Z)_g$—$(CH_2)_n$—, —S—, —SO—, —$SO_2$—, —$SO_2NR^7$—, —$SO_2NR^{10}$—, or -Het-;

each CAP is

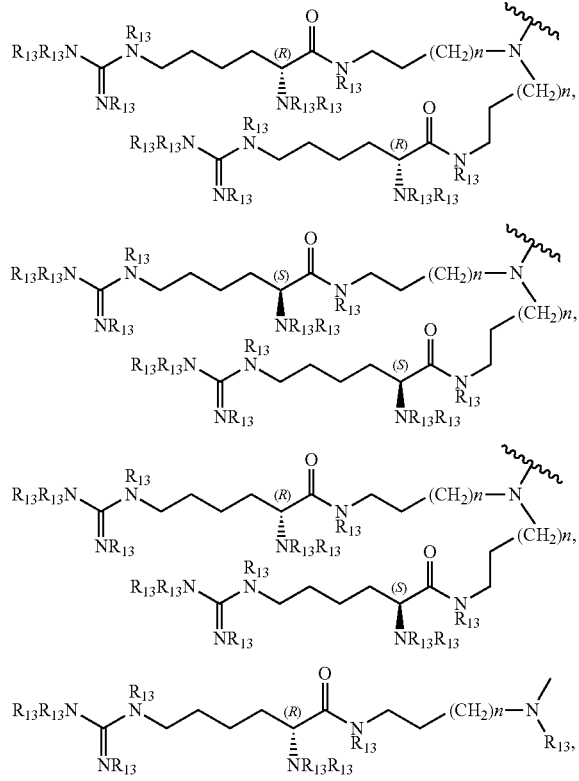

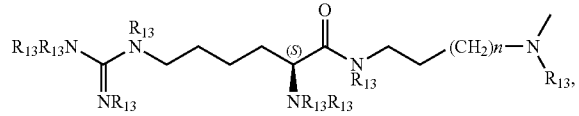

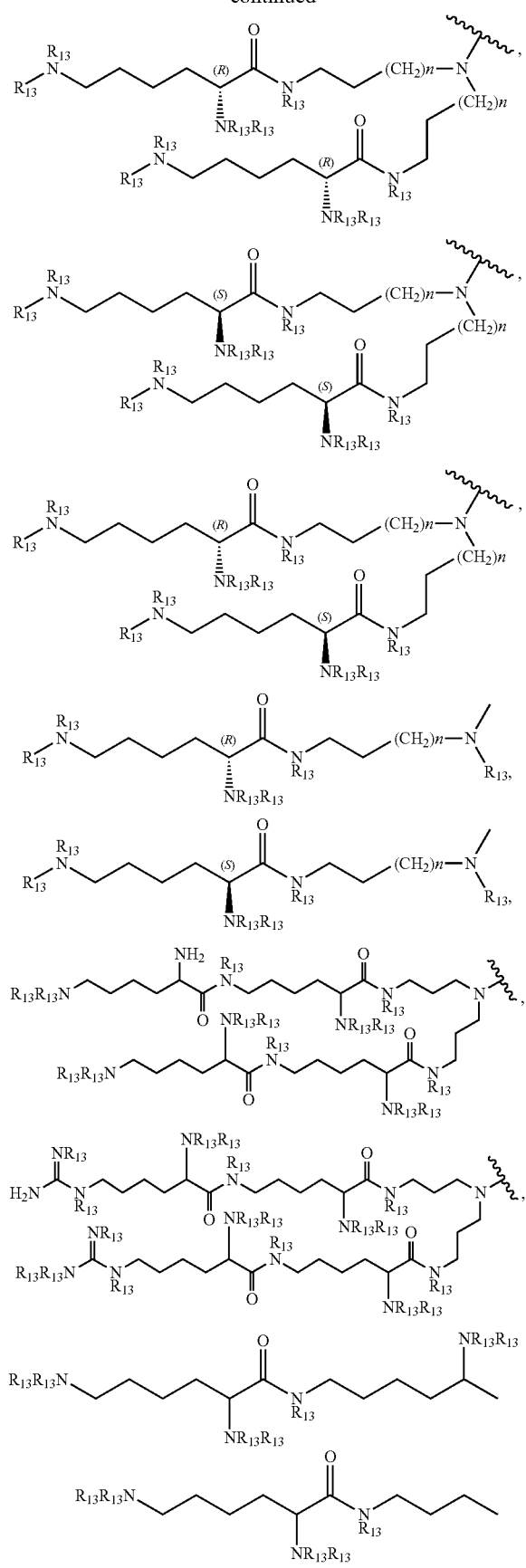
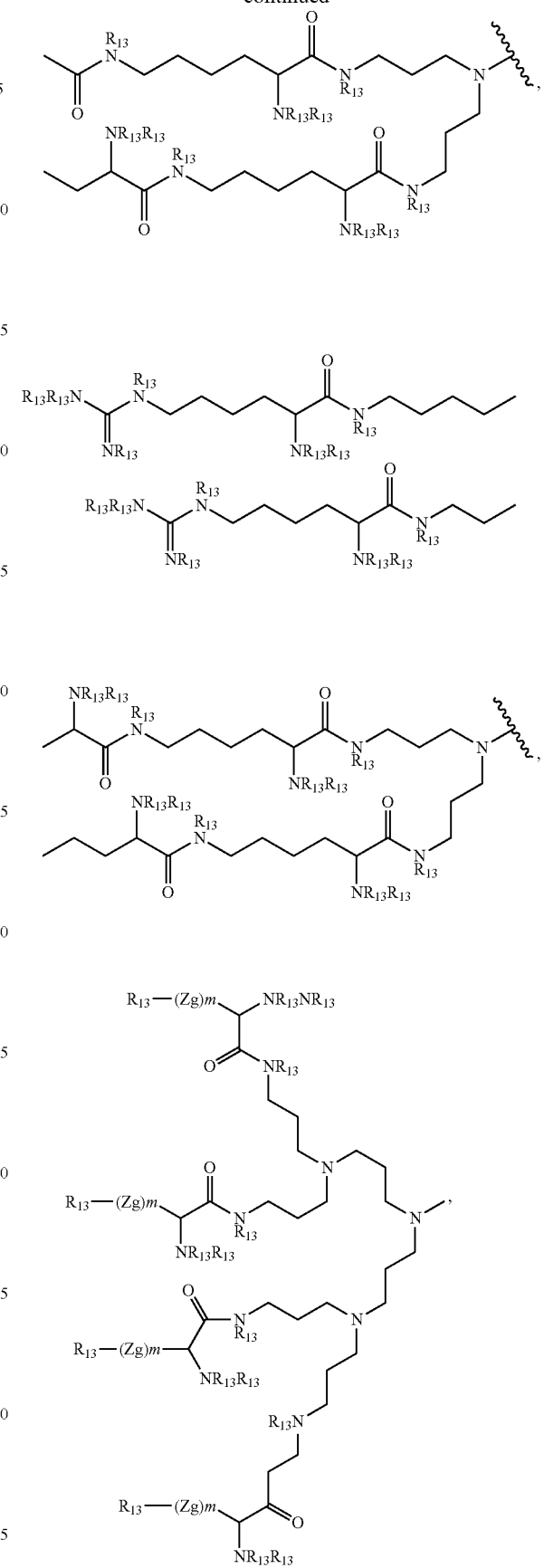

217
-continued

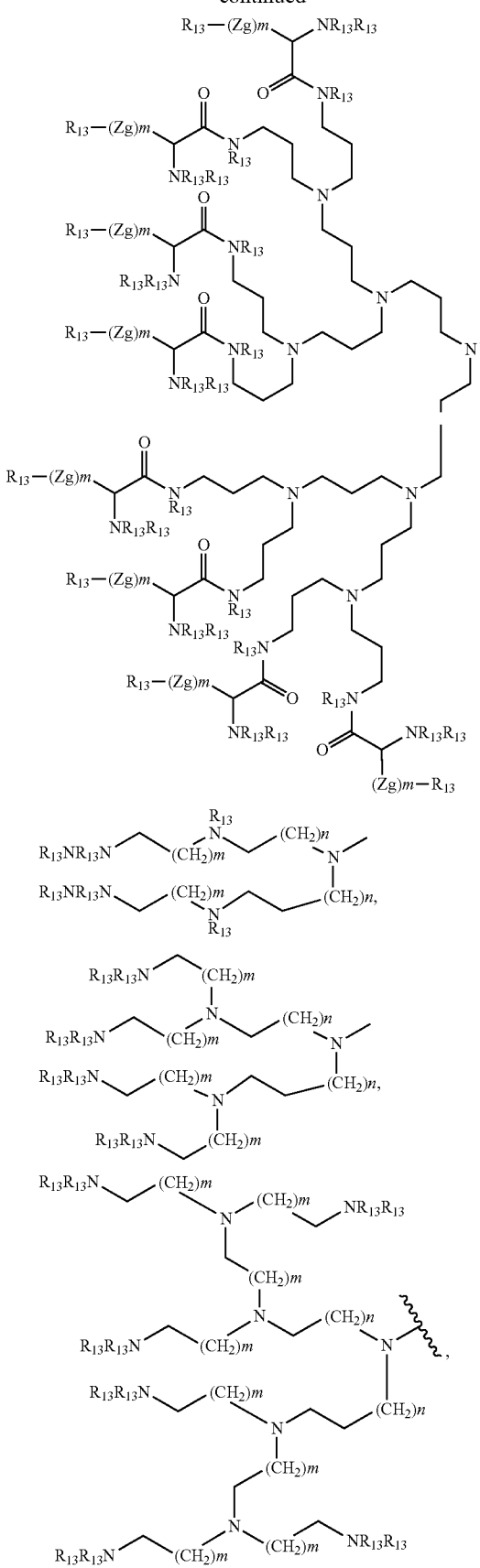

218
-continued

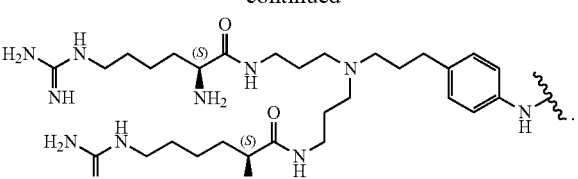

2. The compound according to claim 1, which is represented by formula II or formula III:

formula II

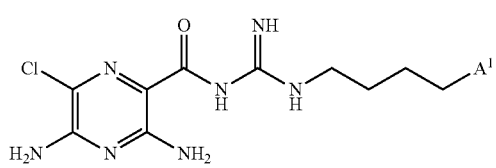

formula III

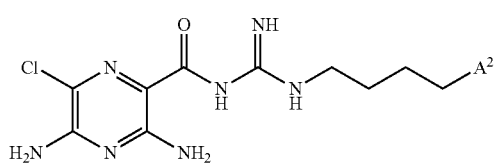

and racemates, enantiomers, diastereomers, tautomers, polymorphs, pseudopolymorphs and pharmaceutically acceptable salts, thereof.

3. The compound according to claim 1, wherein the $C_6$-$C_{15}$-membered aromatic carbocycle of $A^1$ is selected from -phenyl, napthalenyl, 1,2-dihydronapthalenyl, and 1,2,3,4-tetrahydronapthalenyl.

4. The compound according to claim 1, wherein $A^1$ is

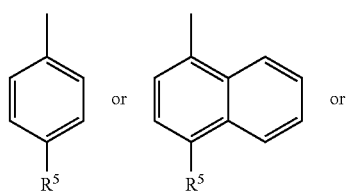

or

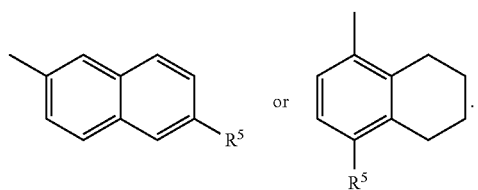

5. The compound according to claim 1, wherein $R^5$ is represented by one of the following formulas:
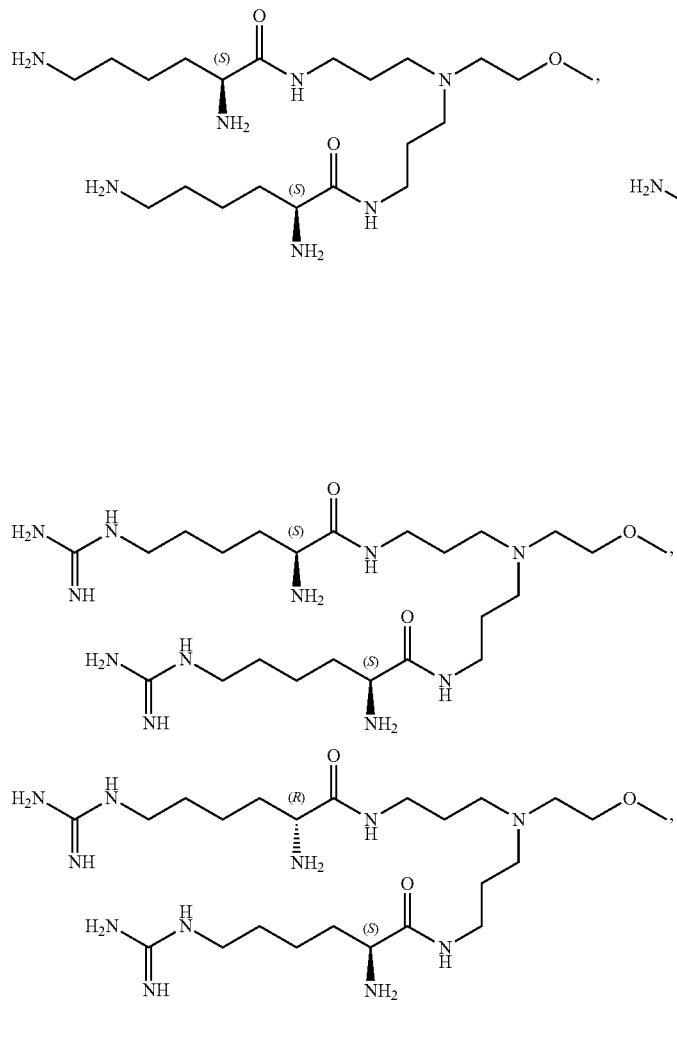
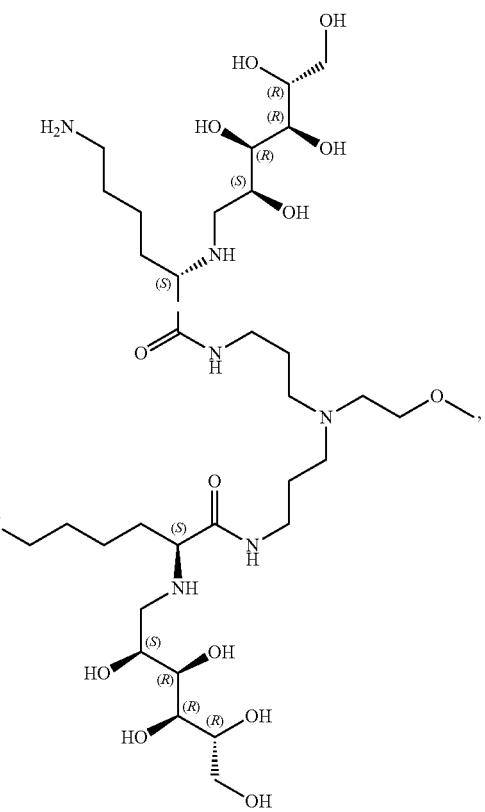
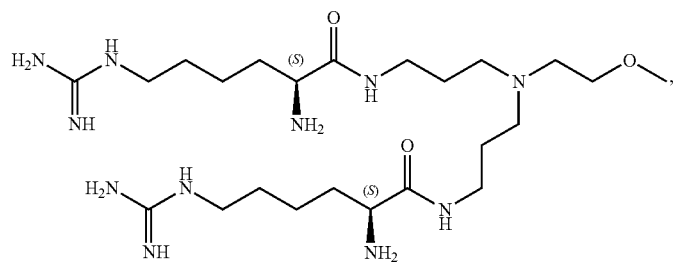

-continued
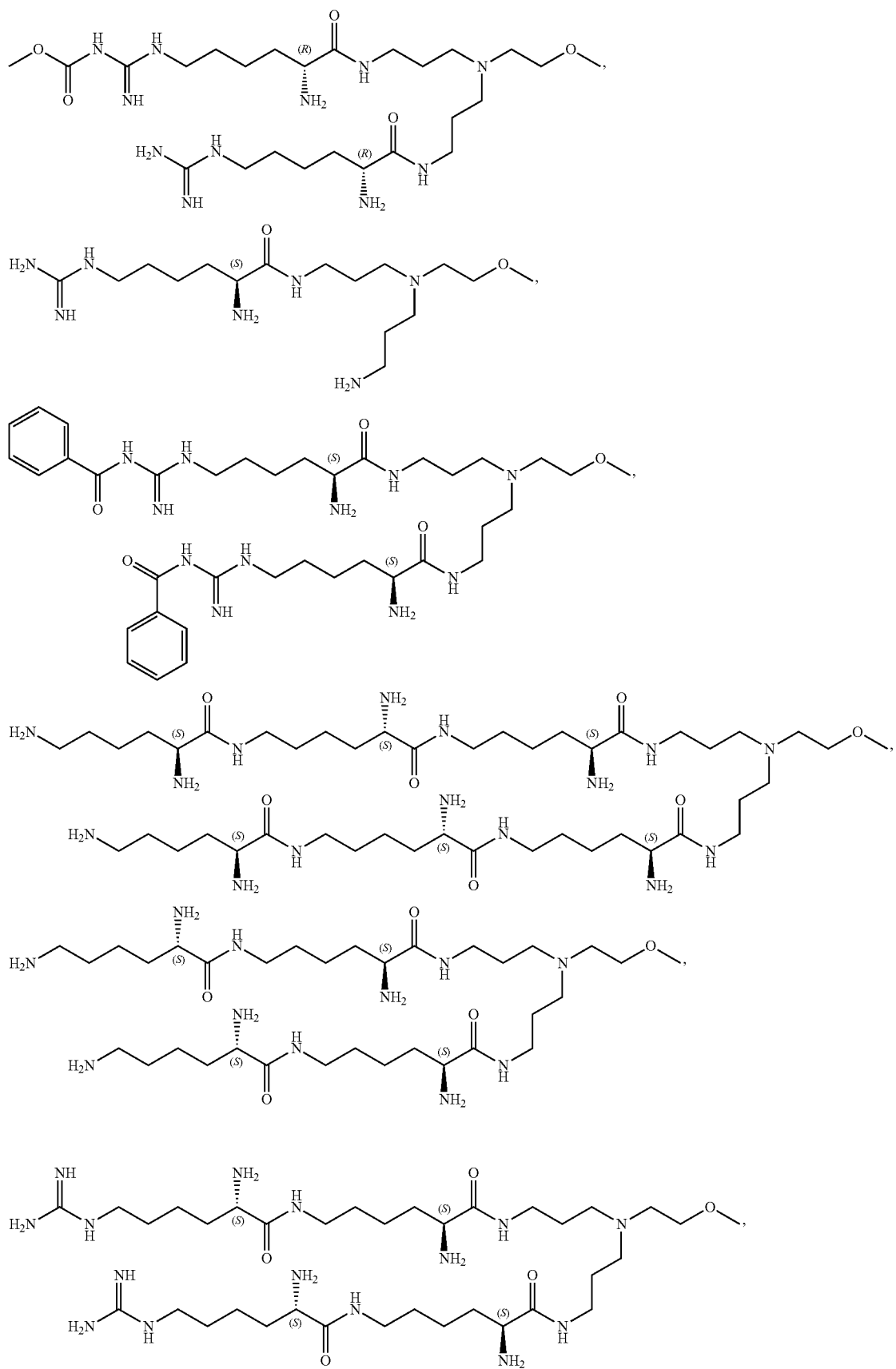

223                                   224
-continued
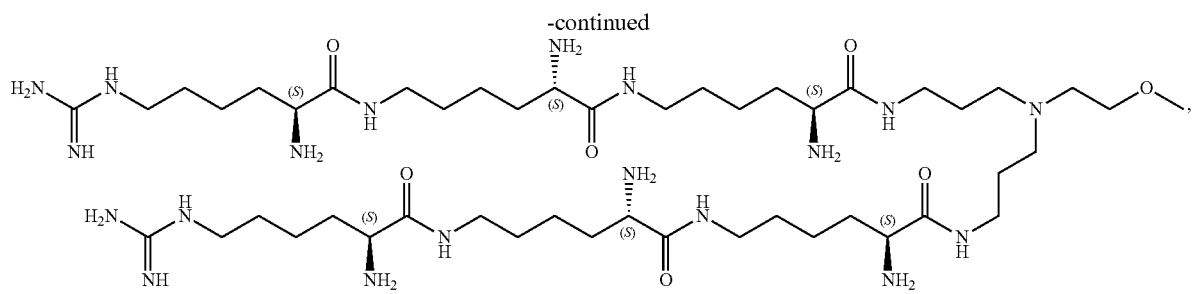
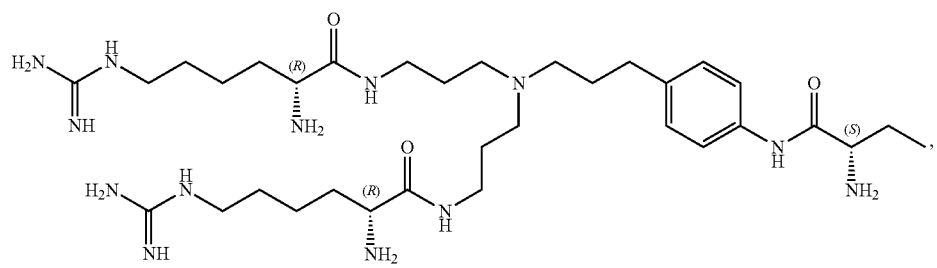
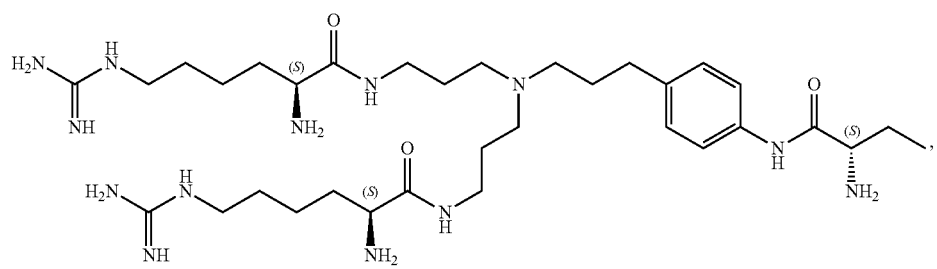
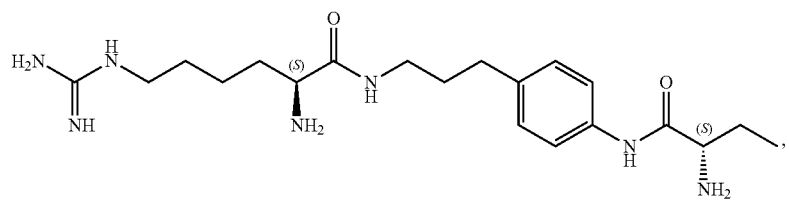
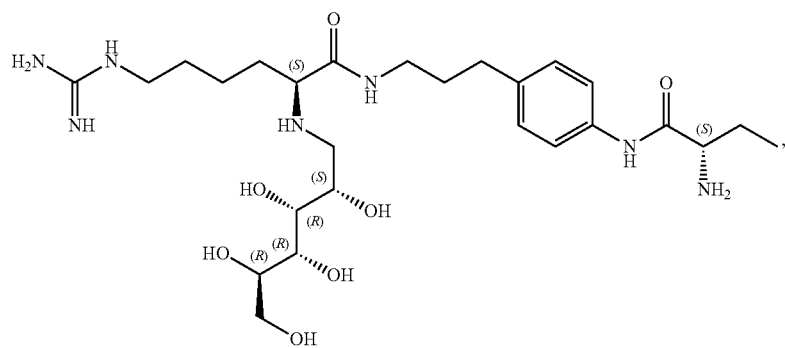

-continued
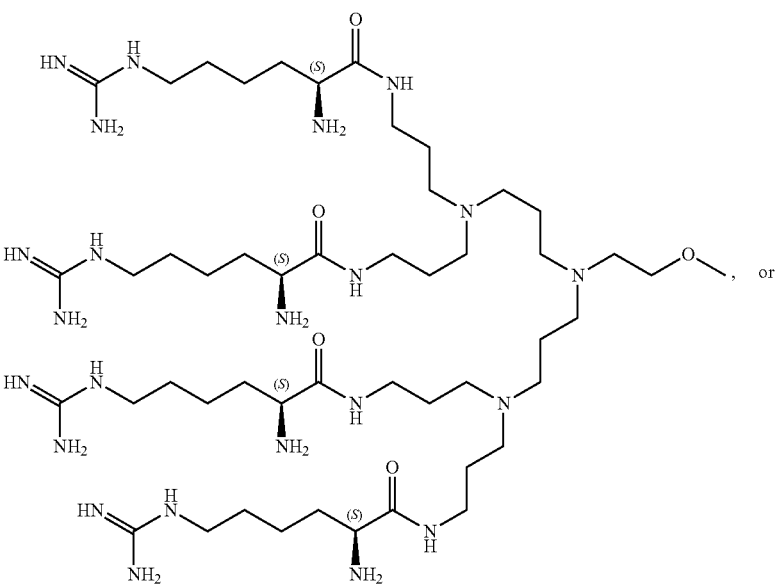
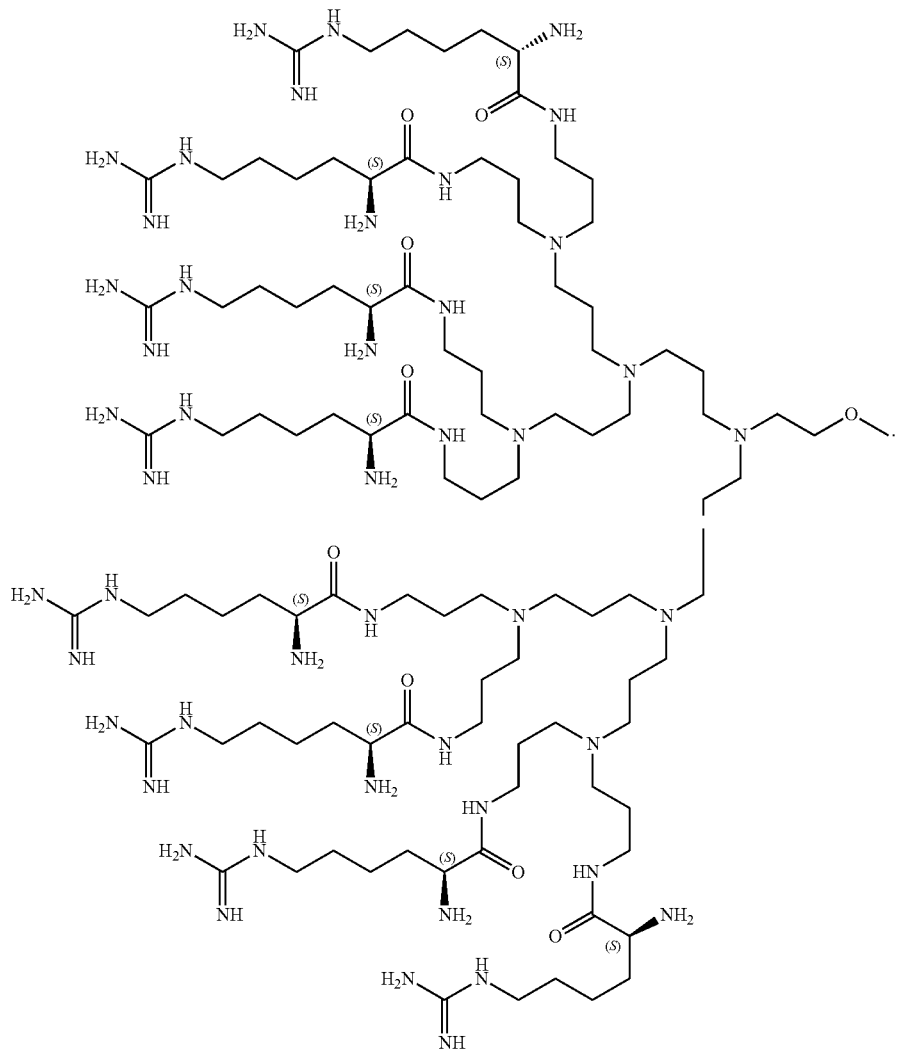

6. A compound represented by one of the following formulas:
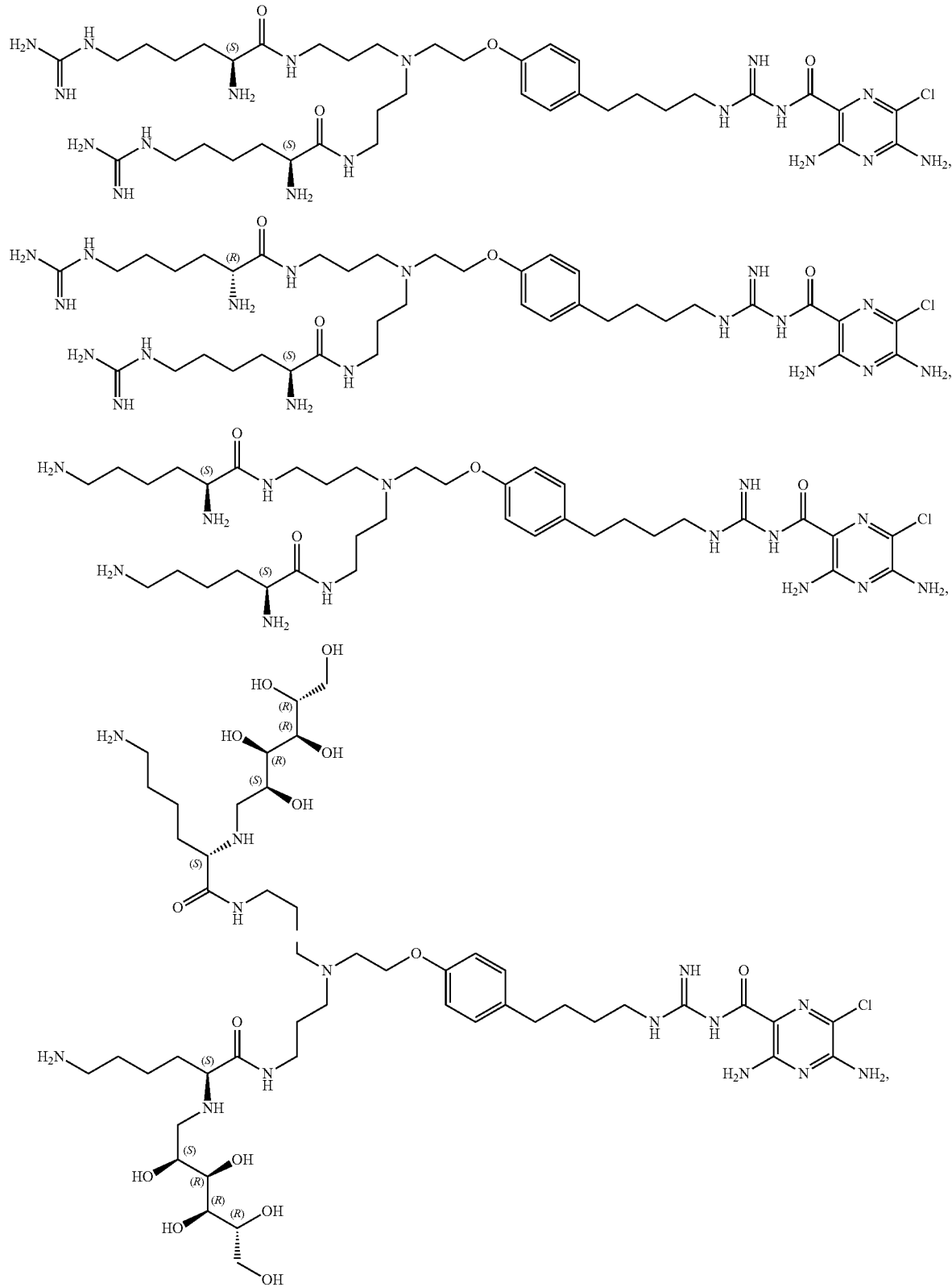

229
230
-continued
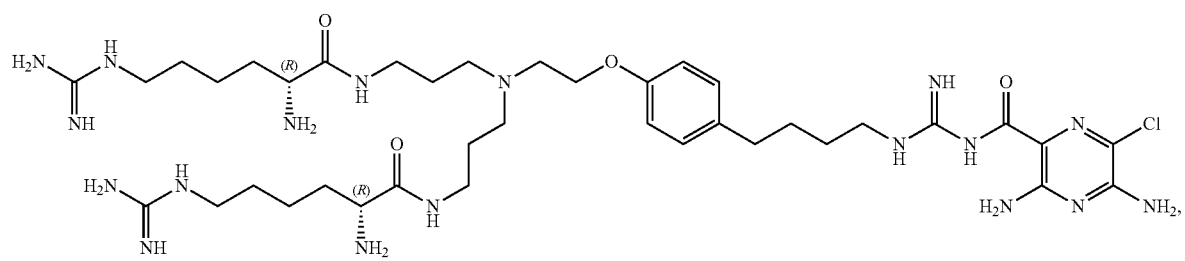
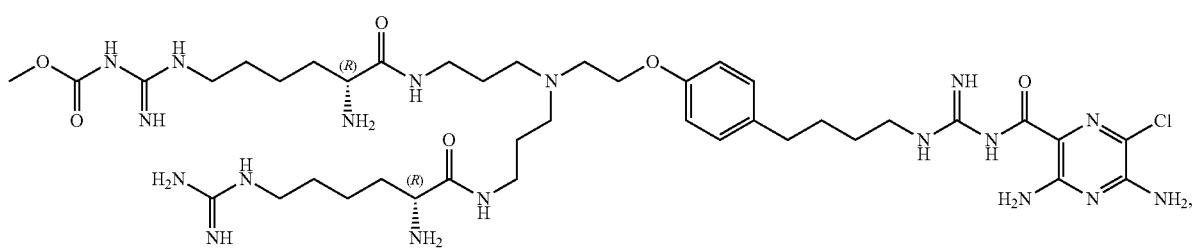
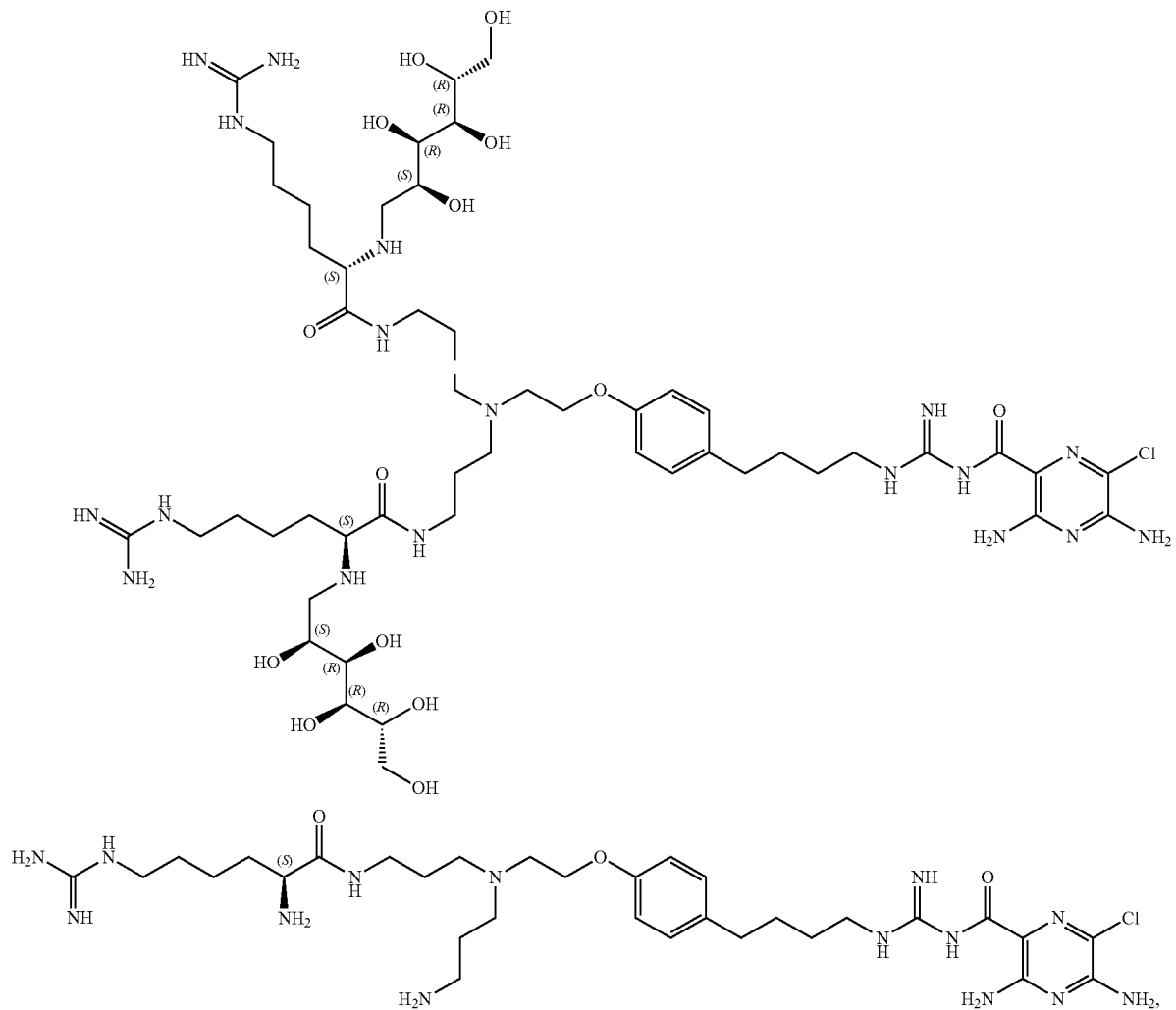

-continued
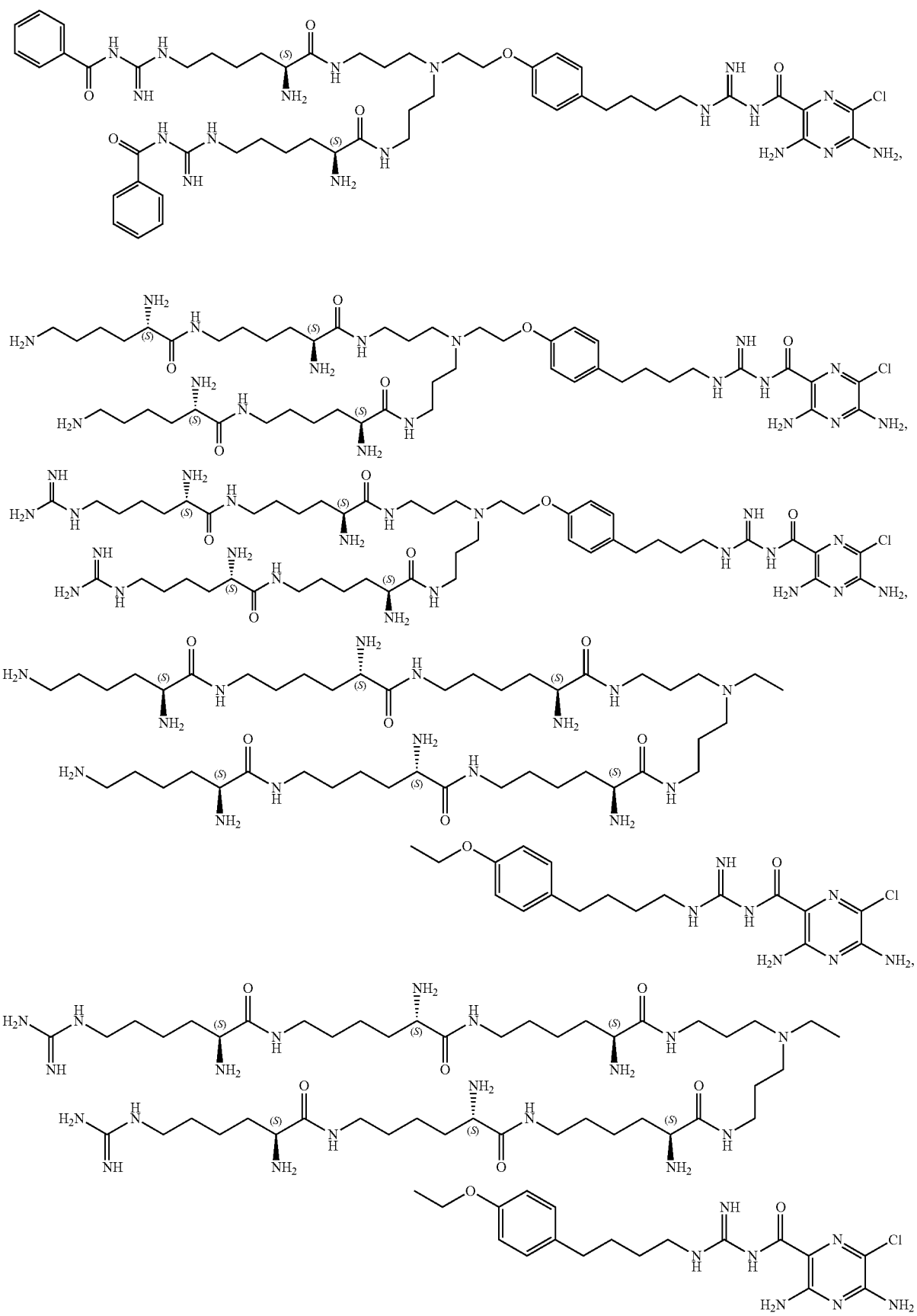

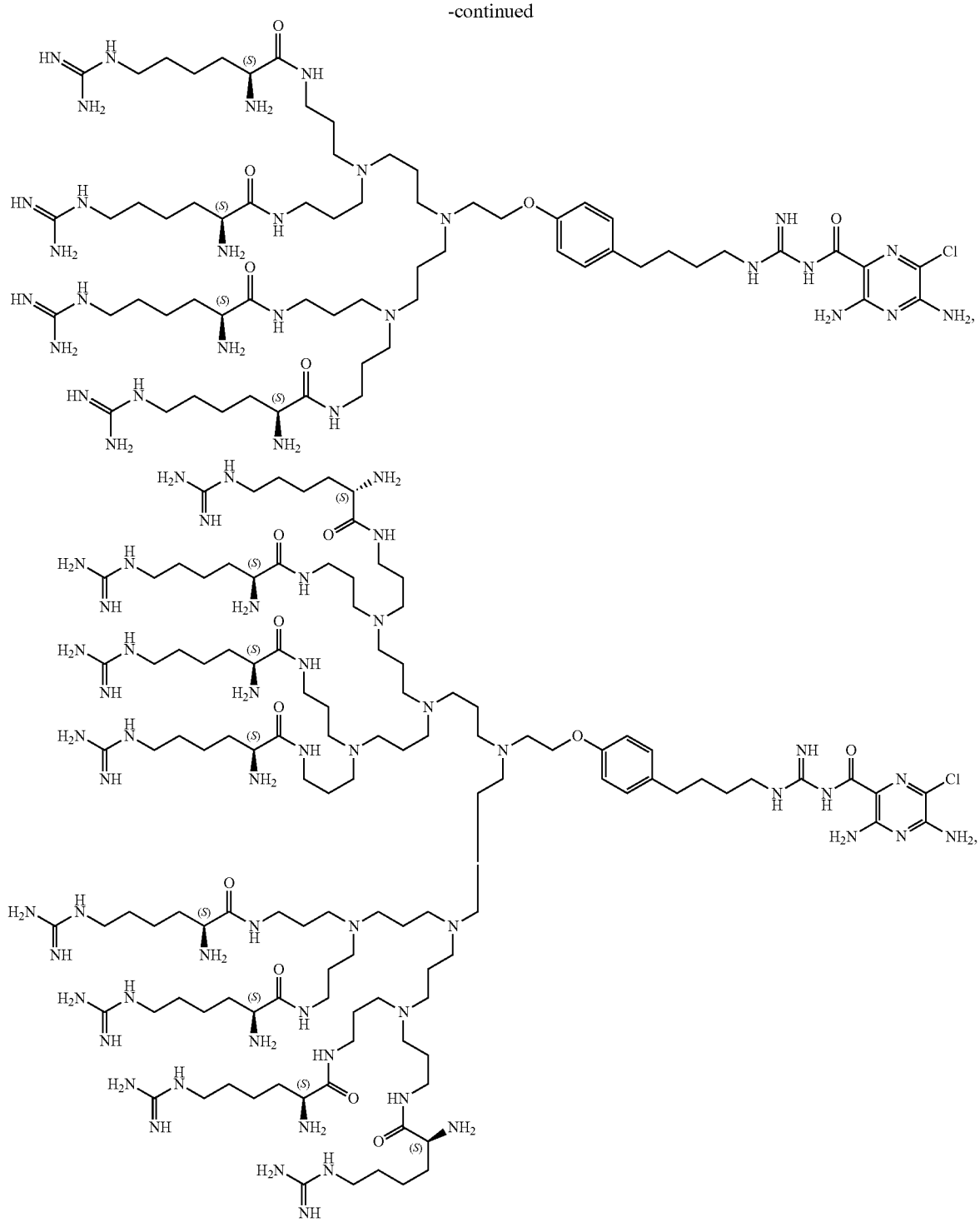

or a pharmaceutically active salt thereof.

7. A pharmaceutical composition comprising a pharmaceutically effective amount of a compound according to claim 1, or a pharmaceutically acceptable salt thereof, and a pharmaceutically acceptable carrier or excipient.

8. The pharmaceutical composition according to claim 7, wherein the compound is
(2R,2'R)—N,N'-(3,3'-(2-(4-(4-(3-(3,5-diamino-6-chloro-pyrazine-2-carbonyl)guanidino) butyl)phenoxy)ethylazanediyl)bis(propane-3,1-diyl))bis(2-amino-6-guanidinohexanamide), or a pharmaceutically acceptable salt thereof.

9. The composition according to claim 7, wherein said composition is a solution for administration by eye drops.

10. A method for blocking sodium channels in a human comprising administering to said human an effective amount of a compound according to claim 1, or a pharmaceutically acceptable salt thereof.

11. A method for promoting hydration of mucosal surfaces or restoring mucosal defense in a human comprising administering to said human an effective amount of a compound according to claim 1, or a pharmaceutically acceptable salt thereof.

12. A method of treating dry eye, treating Sjogren's disease-associated dry eye, treating eye inflammation caused by dry eye, promoting ocular hydration, promoting corneal hydration, treating chronic bronchitis, treating bronchiectasis, treating cystic fibrosis, treating sinusitis, treating vaginal dryness, promoting mucus clearance in mucosal surfaces, treating Sjogren's disease, treating distal intestinal obstruction syndrome, treating dry skin, treating esophagitis, treating dry mouth, treating nasal dehydration, treating ventilator-induced pneumonia, treating asthma, treating primary ciliary dyskinesia, treating otitis media, inducing sputum for diagnostic purposes, treating chronic obstructive pulmonary disease, treating emphysema, treating pneumonia, treating constipation, treating chronic diverticulitis, treating rhinosinusitis, comprising:
administering an effective amount of the compound according to claim 1 to a subject in need thereof.

13. A method of treating a disease ameliorated by increased mucociliary clearance and mucosal hydration comprising administering to a subject in need of increased mucociliary clearance and mucosal hydration an effective amount of an osmolyte and the compound according to claim 1.

14. The method according to claim 12, wherein the disease is one or more conditions selected from the group consisting of dry eye, chronic bronchitis, bronchiectasis, cystic fibrosis, sinusitis, vaginal dryness, Sjogren's disease, distal intestinal obstruction syndrome, dry skin, esophagitis, dry mouth, nasal dehydration, asthma, primary ciliary dyskinesia, otitis media, chronic obstructive pulmonary disease, emphysema, pneumonia, diverticulitis, rhinosinusitis, and airborne infections.

15. A composition, comprising:
(a) a compound or a pharmaceutically acceptable salt thereof according to claim 1 and
(b) an osmolotically active compound.

16. The composition according to claim 7, further comprising a pharmaceutically effective amount of a therapeutically active agent selected from anti-inflammatory agents, anticholinergic agents, β-agonists, P2Y2 receptor agonists, peroxisome proliferator-activated receptor agonists, kinase inhibitors, antiinfective agents and antihistamines.

17. A compound according to claim 1, or a pharmaceutically acceptable salt thereof, for use in treating dry eye, treating Sjogren's disease-associated dry eye, treating eye inflammation caused by dry eye, promoting ocular hydration, promoting corneal hydration, treating chronic bronchitis, treating bronchiectasis (including bronchiectasis due to conditions other than cystic fibrosis), treating cystic fibrosis, treating sinusitis, treating vaginal dryness, promoting mucus clearance in mucosal surfaces, treating Sjogren's disease, treating distal intestinal obstruction syndrome, treating dry skin, treating esophagitis, treating dry mouth, treating nasal dehydration (including nasal dehydration is brought on by administering dry oxygen to the subject), treating ventilator-induced pneumonia, treating asthma, treating primary ciliary dyskinesia, treating otitis media, inducing sputum for diagnostic purposes, treating chronic obstructive pulmonary disease, treating emphysema, treating pneumonia, treating constipation, treating chronic diverticulitis, or treating rhinosinusitis in a human in need thereof.

18. The method according to claim 10, wherein the compound is:

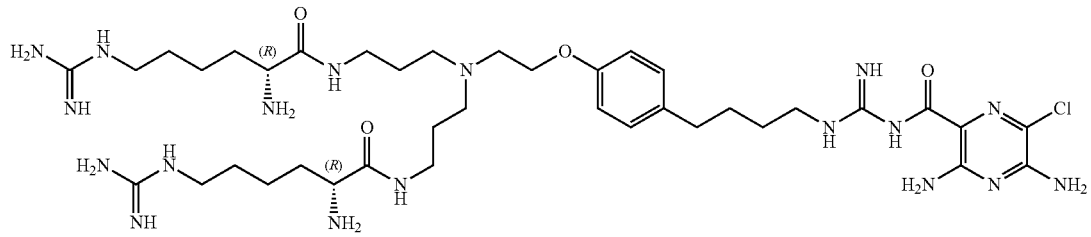

or a pharmaceutically acceptable salt thereof.

19. The hydrochloride salt of:

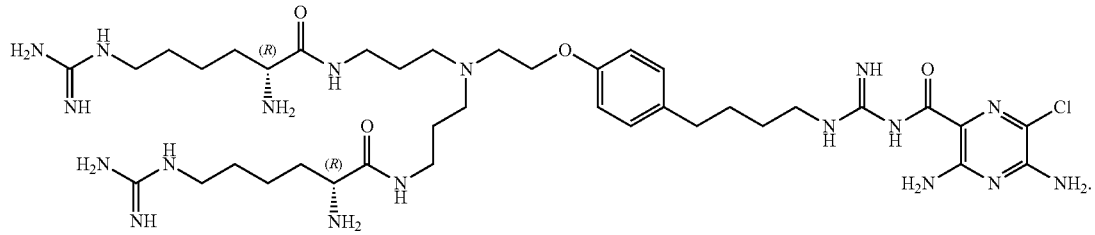

* * * * *